(12) United States Patent
Schaefer et al.

(10) Patent No.: US 8,445,530 B2
(45) Date of Patent: May 21, 2013

(54) ACYLAMINO-SUBSTITUTED FUSED CYCLOPENTANECARBOXYLIC ACID DERIVATIVES AND THEIR USE AS PHARMACEUTICALS

(71) Applicant: Sanofi, Paris (FR)

(72) Inventors: Matthias Schaefer, Frankfurt am Main (DE); Josef Pernerstorfer, Frankfurt am Main (DE); Dieter Kadereit, Frankfurt am Main (DE); Hartmut Strobel, Frankfurt am Main (DE); Werngard Czechtizky, Frankfurt am Main (DE); L. Charlie Chen, Tucson, AZ (US); Alena Safarova, Tucson, AZ (US); Aleksandra Weichsel, Tucson, AZ (US); Marcel Patek, Tucson, AZ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/632,546

(22) Filed: Oct. 1, 2012

(65) Prior Publication Data

US 2013/0030008 A1    Jan. 31, 2013

Related U.S. Application Data

(63) Continuation of application No. 12/939,650, filed on Nov. 4, 2010, which is a continuation of application No. PCT/EP2009/002917, filed on Apr. 22, 2009.

(60) Provisional application No. 61/117,336, filed on Nov. 24, 2008.

(30) Foreign Application Priority Data

May 5, 2008 (EP) .................................... 08290427

(51) Int. Cl.
    A61K 31/381    (2006.01)
    A61K 31/435    (2006.01)
    C07D 333/78    (2006.01)
    C07D 221/04    (2006.01)

(52) U.S. Cl.
    USPC ............. 514/443; 514/279; 514/617; 549/57; 549/58; 546/112

(58) Field of Classification Search
    None
    See application file for complete search history.

(56) References Cited

U.S. PATENT DOCUMENTS

| | | | |
|---|---|---|---|
| 4,871,387 | A | 10/1989 | Sasse et al. |
| 6,358,960 | B1 | 3/2002 | Senokuchi et al. |
| 7,378,252 | B2 | 5/2008 | Kostenis |
| 2010/0130737 | A1 | 5/2010 | Itoh et al. |
| 2011/0152290 | A1 | 6/2011 | Schaefer et al. |

FOREIGN PATENT DOCUMENTS

| | | |
|---|---|---|
| EP | 1258484 A1 | 11/2002 |
| EP | 1533294 A1 | 5/2005 |
| EP | 1695955 A1 | 8/2006 |
| EP | 1849465 A1 | 10/2007 |
| EP | 1972615 A1 | 9/2008 |
| WO | WO 95/04045 | 2/1995 |
| WO | WO 99/49856 A2 | 10/1999 |
| WO | WO 02/04665 | 1/2002 |
| WO | WO 02/06232 A1 | 1/2002 |
| WO | WO 02/29001 | 4/2002 |
| WO | WO 03/062392 | 7/2003 |
| WO | WO 2004/011457 A1 | 2/2004 |
| WO | WO 2004/052921 A1 | 6/2004 |
| WO | WO 2005/009389 | 2/2005 |
| WO | WO 2005/021544 | 3/2005 |
| WO | WO 2005/115150 | 12/2005 |
| WO | WO 2005/115510 | 12/2005 |
| WO | WO 2006/044775 A2 | 4/2006 |
| WO | WO 2006/044975 | 4/2006 |
| WO | WO 2006/088246 | 8/2006 |
| WO | WO 2006/122788 | 11/2006 |
| WO | WO 2006/128184 | 11/2006 |
| WO | WO 2008/000409 A1 | 1/2008 |

OTHER PUBLICATIONS

U.S. Appl. No. 13/461,264, filed May 1, 2012, Pernerstorfer, et al.
Zwaagstra, M., E., et al., Synthesis and Structure-Activity Relationships of Carboxylated Chalcones: A Novel Series of CysLT1 (LTD4) Receptor Antagonists, J. Med. Chem., (1997), vol. 40, pp. 1075-1089.
Benati, L., et al., Radical Chain Reactions of a-Azido-B-Keto Esters with Tributyltin Hydride. A Novel Entry to Amides and Lactams Through Regiospecific Nitrogen Insertion, J. Org. Chem., (1999), vol. 64, pp. 7836-7841.
Borchardt, R. T., et al., Catechol O-Methyltransferase. 11. Inactivation by 5-Hydroxy-3-Mercapto-4-Methoxybenzoic Acid, J. Med. Chem., (1982), vol. 25, pp. 321-323.

(Continued)

*Primary Examiner* — Sreeni Padmanabhan
*Assistant Examiner* — Irina Neagu
(74) *Attorney, Agent, or Firm* — Jiang Lin

(57) ABSTRACT

The present invention relates to compounds of the formula I,

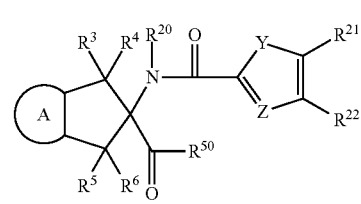

wherein A, Y, Z, $R^3$ to $R^6$, $R^{20}$ to $R^{22}$ and $R^{50}$ have the meanings indicated in the claims, which are valuable pharmaceutical active compounds. Specifically, they are inhibitors of the endothelial differentiation gene receptor 2 (Edg-2, EDG2), which is activated by lysophosphatidic acid (LPA) and is also termed as $LPA_1$ receptor, and are useful for the treatment of diseases such as atherosclerosis, myocardial infarction and heart failure, for example. The invention furthermore relates to processes for the preparation of the compounds of the formula I, their use and pharmaceutical compositions comprising them.

11 Claims, No Drawings

OTHER PUBLICATIONS

Boucharaba, A., et al., The Type 1 Lysophosphatidic Acid Receptor is a Target for Therapy in Bone Metastases, PNAS, (2006), vol. 103, No. 25, pp. 9643-9648.

Brault, S., et al., Lysophosphatidic Acid Induces Endothelial Cell Death by Modulating the Redox Environment, Am. J. Physiol. Regul. Integr Comp. Physiol., vol. 292, pp. R1174-R1183, (2007).

Canonne, P., et al., Reactions Selectives Des Organomagnesiens Avec Les Lactols et Les Lactones. Synthese Des Diols Prirnaires-Secondaires, Tetrahedron, vol. 44, No. 10, pp. 2903-2912, (1988).

Chattaway, F. D., et al., The Condensation of Chloral With Anisic Acid with p-Nitroanisole, and with 2:6-Dichloroquinol, J. Chemical Soc., (1928), pp. 2913-2918.

Chen, J., et al., Specific LPA Receptor Subtype Mediation of LPA-Induced Hypertrophy of Cardiac Myocytes and Involvement of Akt and NFkB Signal Pathways, Journal of Cellular Biochemistry, vol. 103, pp. 1718-1731, (2008).

Chen, J., et al., Specific Receptor Subtype Mediation of LPA-Induced Dual Effects in Cardiac Fibroblasts, FEBS Letters, vol. 580, (2006), pp. 4737-4745.

Chen, X., et. al., Serum Lysophosphatidic Acid Concentrations Measured by Dot Immunogold Filtration Assay in Patients with Acute Myocardial Infarction, Scand. J. Clin. Lab. Invest., vol. 63, pp. 497-504, (2003).

Chinchilla, R., et al., The Sonogashira Reaction: A Booming Methodology in Synthetic Organic Chemistry, Chem. Rev., vol. 107, pp. 874-922, (2007).

Cremers, B., et al., Modulation of Myocardial Contractility by Lysophosphatidic Acid (LPA), Journal of Molecular and Cellular Cardiology, vol. 35, (2003), pp. 71-80.

Guo, R., et al., Expression and Function of Lysophosphatidic Acid LPA1 Receptor in Prostate Cancer Cells, Endocrinology, vol. 147, No. 10, pp. 4883-4892.

Hilal-Dandan, R., et al., Lysophosphatidic Acid Induces Hypertrophy of Neonatal Cardiac Myocytes Via Activation of G1 and Rho, Journal of Molecular and Cellular Cardiology, vol. 36, (2004), pp. 481-493.

Hollingworth, G. J., et al., A Convenient Method for the Preparation of Aryl Cyclopropyl Ethers from Phenols, Tetrahedron Letters, vol. 40, (1999), pp. 2633-2636.

Inoue, M., et al., Initiation of Neuropathic Pain Requires Lysophosphatidic Acid Receptor Signaling, Nature Medicine, vol. 10, No. 7, pp. 712-718, (2004).

Ishii, L. et al., Lysophospholipid Receptors: Signaling and Biology, Annu. Rev. Biochem., vol. 73. pp. 321-354, (2004).

Jorgensen, M., et al., Efficient Synthesis of a-Aryl Esters by Room-Temperature Paliadium-Catalyzed Coupling of Aryl Halides With Ester Enolates, J. Am. Chem. Soc., vol. 124, (2002), pp. 12557-12565.

Kaneyuki, U., et al., Pitavastatin Inhibits Lysophosphatidic Acid-Induced Proliferation and Monocyte Chemoattractant Protein-1 Expression in Aortic Smooth Muscle Cells by Suppressing Rac-1-Mediated Reactive Oxygen Species Generation, Vasular Pharmacology, vol. 46, (2007). pp. 286-292.

Kanoh, S., et al., Unusual Cyclodimerization of Small Cyclic Ethers Via Neighboring Carbonyl-Group Participation and Cation Transfer, Tetrahedron, vol. 58, pp. 7065-7074, (2002).

Kerdesky, F. A. J., et al., 4-Hydroxythiazole Inhibitors of 5-Lipoxygenase, J. Med. Chem., (1991), vol. 34, pp. 2158-2165.

Kotha, S., et al., Synthesis of Indan-Based Unusual a-Amino Acid Derivatives Under Phase-Transfer Catalysis Conditions, J. Org. Chem., (2000), vol. 65, pp. 1359-1365.

Lee, H., et al., Lysophospholipids Increase ICAM-1 Expression in HUVEC Through a Gi- and NF-kB-Dependent Mechanism, Am. J. Physiol. Cell Physiol., vol. 287, C1657-C1666, (2004).

Linz, W., et al., Vasopeptidase Inhibition Prevents Target Organ Damage and Improves Survival in Spontaneously Hypertensive Rats, JRAAS, vol. 7, No. 3, pp. 155-161, (2006).

Lohmar, R., et al., Synthese Symmetrischer Ketone Unter Vemendung Von 2-Phenyl-2-Oxazolin-5-on, Chernische Berichte, (1980), vol. 113, No. 12, pp. 3706-3715.

Mitsunobu, O., et al., The Use of Diethyl Azodicarboxylate and Triphenylphosphine in Synthesis and Transformation of Natural Products, Synthesis, (1981), pp. 1-28.

Miyaura, et al, Palladium-Catalyzed Cross-Coupling Reactions of Organoboron Compounds, Chem Rev., 1995 (95) 7 pp. 2457-2483.

Nagano, T., et al., Preparation of 3',4'-Dihydraxy-6-Carboxyflavonol, J. Am. Chem. Soc., vol. 75, (1953), pp. 6237-6238.

Okusa, M. D., et al., Selective Blockade of Lysophosphatidic Acid LPA3 Receptors Reduces Murine Renal Ischernia-Reperfusion Injury, Am. J. Phsiol Renal Physiol, vol. 285, pp. F565-F574, (2003).

Palmetshofer, A., et al., Lysophosphatidic Acid Activates Nuclear Factor Kapppa B and Induces Proinflammatory Gene Expression in Endothelial Cells, Thromb. Haemost., vol. 82, pp. 1532-1537, (1999).

Pradere, J.-P., et al., LPA1 Receptor Activation Promotes Renal Interstitial Fibrosis, J. Am. Soc. Nephrol., vol. 18, pp. 3110-3118, (2007).

Rother, E., et al., Subtype-Selective Antagonists of Lysophosphatidic Acid Receptors Inhibit Platelet Activation Triggered by the Lipid Core of Atherosclerotic Plaques, Circulation, vol. 108, pp. 741-747, (2003).

Sano, T., et al., Multiple Mechanisms Linked to Platelet Activation Result in Lysophosphatidic Acid and Sphingosine 1-Phosphate Generation in Blood, The Journal of Biological Chemistry, vol. 277, No. 24, pp. 21197-21206, (2002).

Seewald, S., et al., Lysophosphatidic Acid and Intracellular Signalling in Vascular Smooth Muscle Cells, Atherosclerosis, vol. 130, (1997), pp. 121-131.

Shida, D., et al., Lysophosphatidic Acid (LPA) Enhances the Metastatic Potential of Human Colon Carcinoma DLD1 Cells Through LPA11, Cancer Research, vol. 63, pp. 1706-1711, (2003).

Siess, W., et al., Lysophosphatidic Acid Mediates the Rapid Activation of Platelets and Endothelial Cells by Mildly Oxidized Low Density Lipoprotein and Accumulates in Human Atherosclerotic Lesions, Proc. Natl. Acad. Sci. USA, vol. 96, pp. 6931-6936, (1999).

Tager, A. M., et al., The Lysophosphatidic Acid Receptor LPA1 Links Pulmonary Fibrosis to Lung Injury by Mediating Fibroblast Recruitment and Vascular Leak, Nat. Med., vol. 14, (2008), pp. 45-54.

Thompson, W. J., et al., A General Synthesis of 5-Arylnicotinates, J. Org. Chem., vol. 49, pp. 5237-5243, (1984).

Tiemann, F., et al., Abkommlinge der Dimethylprotocatechusaure und der Vanillinsaure (Monomethyl rotocatechusaure), Ber. dt. Chem. Ges., vol. 9, pp. 937-945, (1876).

Xing, Y., et al., Cell Density-Dependent Expression of EDG Family Receptors and Mesangial Cell Proliferation: Role in Lysophosphatidic Acid-Mediated Cell Growth, Am. J. Physiol Renal Physiol., vol. 287, pp. F1250-F1257. (2004).

Xu, Y.-J., et al., Stimulation of 90- and 70-kDa Ribosomal Protein S6 Kinases by Arginine Vasopressin and Lysophosphatidic Acid in Rat Cardiomyocytes, Biochemical Pharmacology, vol. 59, pp. 1163-1171, (2000).

Yoshida, K., et al., Vascular Remodeling Induced by Naturally Occurring Unsaturated Lysophosphatidic Acid in Vivo, Circulation, vol. 108, (2003), pp. 1746-1752.

Yoshiizumi, K., et al., Synthesis and Structure-Activity Relationships of 5,6,7,8-Tetrahydropyrido[3,4-b] Pyrazine-Based Hydroxamic Acids as HB-EGF Shedding Inhibitors, Bioorganic & Medicinal Chemistry, vol. 11, pp. 433-450, (2003).

Lohmar, R., et al., a-Amino Adds as Nucleophilic Acyl Equivalents. IV. Synthesis of Symmetrical Ketones by Means of 2-Phienyl-2-Oxazolin-5-One, Database Accession No. 1981:156251, CAPLUS (abstract).

International Search Report for WO2009/135590 dated Nov. 12, 2009.

Warm, et al., 74. Syntheses of (+)- and (−)-Methyl 8-Epinonactate and (+)- and (−) Methyl Nonactate1), Helvetica Chimica Acta, vol. 70, (1987), pp. 690-700.

Wheeler, et al., A Convenient and Efficient Synthesis of 1-Aminocyclopropanecarboxylic Acid (ACC), Synthetic Communications, vol. 18, No. 2, pp. 141-149. (1988).

Gorecka, et al., Deprotonation-Triggered Heavy-Halogen Migrations as a Key to the Structural Elaboration of 2,2-Difluoro-1,3-Benzodioxole, European Journal of Organic Chemistry, vol. 1, pp. 64-68, (2004).

Smith, et al., Total Synthesis of (+)-Jatropholones A and B: Exploitation of the High-Pressure Technique, J. Am. Chem. Soc., (1986), vol. 108, pp. 3040-3048.

Tsang, et al., Peptide Sweeteners 6. Structural Studies on the C-Terminal Amino Add of L-Aspartyl Dipeptide Sweeteners, J. Med. Chem., (1984), vol. 27, pp. 1663-1668.

Alonso, et al., Synthesis of 3- and 4-Substituted Cyclic a-Amino Acids Structurally Related to ACPD, Tetrahedron, vol. 51, No. 37, pp. 10259-10280, (1995).

Fohlisch, et al., Erzeugung and [4+3]-Cycloaddition von Cyclopentenylium-2-Olat aus 2-Chlorcyclopentanon unter Alkoholyse-Bedingungen, Chem. Ber., vol. 120, (1987), pp. 1951-1960.

Hammer, et al., Ruthenium(II) in Ring Closing Metathesis for the Stereoselective Preparation of Cyclic 1-Amino-1-Carboxylic Acids., Tetrahedron, vol. 53, No. 6, pp. 2309-2322, (1997).

Kline, et al., Potent, Novel in Vitro Inhibitors of the *Pseudomonas aeruginosa* Deacetylase LpxC, J. Med. Chem., vol. 45, pp. 3112-3129, (2002).

Munday, Amino-Acids of the Cyclohexane Series. Part I., J. Chem. Soc., (1961), pp. 4372-4379.

Oba, et al., Concise Synthetic Strategy Toward Cyclic a,a-Disubstituted a-Amino Acids Bearing a Beta-Nitrogen Atom: Chiral 1-Substituted 4-Aminopiperidine-4-Carboxylic Acids , Tetrahedron, vol. 61. (2005), pp. 593-598.

Pasto, et al., Reduction With Diirmide, Organic Reactions, vol. 40. (1991), pp. 91-107, 151-155.

Prelog, et al., Geometrisch Enantiomorphe Cyclobutan-Derivate, Helvetica Chimica Acta, vol. 65, No. 8, (1982), pp. 2622-2644.

Alfa Aesar, Peptide Reagents.

ACYLAMINO-SUBSTITUTED FUSED CYCLOPENTANECARBOXYLIC ACID DERIVATIVES AND THEIR USE AS PHARMACEUTICALS

This application is a Continuation of application Ser. No. 12/939,650, filed Nov. 4, 2010, which is a Continuation of International Application No. PCT/EP2009/002917, filed Apr. 22, 2009, which claims the benefit of U.S. Application No. 61/117,336, filed Nov. 24, 2008, all of which are incorporated herein by reference in their entireties.

The present invention relates to compounds of the formula I,

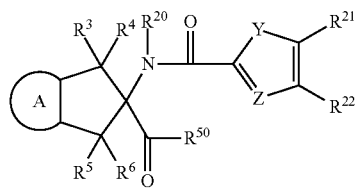

wherein A, Y, Z, $R^3$ to $R^6$, $R^{20}$ to $R^{22}$ and $R^{50}$ have the meanings indicated below, which are valuable pharmaceutical active compounds. Specifically, they are inhibitors of the endothelial differentiation gene receptor 2 (Edg-2, EDG2), which is activated by lysophosphatidic acid (LPA) and is also termed as $LPA_1$ receptor, and are useful for the treatment of diseases such as atherosclerosis, myocardial infarction and heart failure, for example. The invention furthermore relates to processes for the preparation of the compounds of the formula I, their use and pharmaceutical compositions comprising them.

LPA is a group of endogenous lysophospholipid derivatives including 1-oleoyl-sn-glycerol 3-phosphate, for example. LPA activates G-protein-coupled receptors (GPCR's) from the endothelial differentiation gene receptor family which belong to the lysophospholipid receptors. LPA signaling exerts a variety of pleiotropic biological responses on many different cell types which interfere with processes such as cell proliferation, cell growth, cell hypertrophy, re-differentiation, cell retraction, cell contraction, cell migration, cell survival or inflammation. The Edg receptor family, originally identified as a family of orphan GPCR's, currently comprises eight different members which were recently termed according to their respective ligand as LPA receptors or S1P receptors (sphingosine-1-phosphate receptors). According to the nomenclature of the International Union of Basic and Clinical Pharmacology (IUPHAR), LPA receptors Edg-2, Edg-4 and Edg-7 are now also termed as $LPA_1$, $LPA_2$ and $LPA_3$ receptor (cf. I. Ishii et al., Annu. Rev. Biochem. 73 (2004), 321-354).

LPA is generated mainly in the extracellular compartment by different pathways predominantly by the cancer cell motility factor autotaxin which was recently found to be identical with lysophospholipase D. LPA can also be generated by alternative routes involving phospholipase hydrolysis ($PLA_1$ and $PLA_2$) or other mechanisms such as de novo phospholipid synthesis. Although LPA, in contrast to other phospholipids, is highly soluble in water, in plasma it is carried by different binding proteins such as albumin and gelsolin which display a high affinity to LPA and from which it can be released. Under pathophysiological conditions, levels of LPA can be elevated to an undesirable amount and thus increase LPA-mediated signaling and lead to detrimental processes such as abnormal cell proliferation, for example. Blocking LPA signaling, for example by Edg-2 inhibitors, allows to prevent such processes.

For example, increased liberation of LPA was observed during platelet activation and blood clotting and at sites of inflammation (T. Sano et. al., J. Biol. Chem. 277 (2002), 21197-21206). After acute myocardial infarction (AMI) in humans, LPA serum levels were significantly raised in humans to about 6-fold higher concentrations, and LPA was regarded to be involved in the pathophysiological processes in the cardiovascular system related to AMI (X. Chen et al., Scand. J. Clin. Lab. Invest. 63 (2003), 497-503). The importance of LPA and its receptor Edg-2 for the pathophysiological processes after myocardial infarction such as cardiac remodeling and for the prevention of cardiac hypertrophy and heart failure was confirmed in further investigations (J. Chen et al., J. Cell. Biochem. 103 (2008), 1718-1731). LPA was shown to be generated during mild oxidation of low density lipoprotein (LDL) particles and to be accumulated in the lipid core of human atherosclerotic plaques (W. Siess et al., Proc. Natl. Acad. Sci. 96 (1999), 6931-6936). Furthermore, LPA was identified as an important bioactive component of mox-LDL (mildly oxidized low density lipoprotein) leading to platelet activation, and it was shown that the effects of LPA, moxLDL or lipid core extracts from human atherosclerotic plaques on platelet activation could be abrogated by the Edg-2/Edg-7 receptor inhibitor dioctanoylglycerol pyrophosphate DGPP(8:0), implicating a causative role of LPA-mediated Edg receptor signaling in platelet aggregation and usefulness of such LPA receptor inhibitors in the treatment of cardiovascular diseases (E. Rother et al., Circulation 108 (2003), 741-747).

Further findings underline the detrimental role of LPA during initiation and progression of cardiovascular diseases such as atherosclerosis, left ventricular remodeling and heart failure. LPA leads to pertussis toxin-sensitive, NFκB (nuclear factor kappa B)-mediated pro-inflammatory responses of endothelial cells including upregulation of chemokines like monocyte chemoattractant protein-1 (MCP-1) and interleukin-8 (IL8) (A. Palmetshofer et al., Thromb. Haemost. 82 (1999), 1532-1537) and exposure of endothelial cell adhesion molecules like E-selectin or intercellular adhesion molecule-1 (ICAM-1) (H. Lee et al., Am. J. Physiol. 287 (2004), C1657-C1666). Direct evidence for the involvement of Edg-2 receptors arises from recent studies which demonstrate that LPA induces oxidative stress in vascular smooth muscle cells and endothelial cells which was attenuated by pharmacological inhibition by DGPP(8:0) or THG1603, a specific Edg-2 receptor antagonist (U. Kaneyuki et al., Vascular Pharmacology 46 (2007), 286-292; S. Brault et al., Am. J. Physiol. Regul. Integr. Comp. Physiol. 292 (2007), R1174-R1183). In vascular smooth muscle cells, LPA leads to pertussis toxin-sensitive $Ca^{2+}$ release from internal stores, to activation of 42 kDa mitogen-activated protein kinase (p42MAPK) and to cell proliferation (S. Seewald et al., Atherosclerosis 130 (1997), 121-131). Intravascular injection of LPA was shown to induce neointima formation in vivo (K. Yoshida et al., Circulation 108 (2003), 1746-1752). On isolated adult cardiac myocytes, LPA leads to cellular hypertrophy and to activation of different kinases known to be relevant for a hypertrophic response (Y.-J. Xu et al., Biochemical Pharmacology 59 (2000), 1163-1171). Studies on neonatal myocytes confirmed a role of LPA in the induction of hypertrophy and revealed the relevance of a rho kinase-dependent pathway (R. Hilal-Dandan et al., J. Mol. Cell. Cardiol. 36 (2004), 481-493). The relevance of rho kinase underlines the involvement of the Edg-2 receptors which, in contrast to Edg-7 receptors, are coupled to $G_{\alpha 12/13}$ proteins. LPA furthermore attenuates the force of contraction in human myocardial ventricular and atrial preparations and impairs isoprenaline-induced fractional shortening of isolated adult rat ventricular myocytes. The latter effects were reverted after pre-incubation with pertussis toxin indicating the relevance of a GPCR-mediated and $G_{\alpha i/o}$-mediated pathway (B. Cremers et al., J. Mol. Cell. Cardiol. 35 (2003), 71-80). LPA was also found to lead to enhanced matrix generation and proliferation of cardiac fibroblasts (J. Chen et al., FEBS Letters 580 (2006), 4737-4745).

The importance of influencing Edg-2 receptor signaling and LPA-mediated effects for many diseases was confirmed by pharmacological approaches using specific tool compounds or Edg-2 receptor knock-out mice or by experimental silencing of the Edg-2 receptors. For example, the relevance of LPA-activated Edg receptors for renal diseases was demonstrated by different kinds of Edg-2/Edg-7 receptor inhibitors. In one approach, it was shown that the LPA-induced proliferative response of mesangial cells could be inhibited by the compound DGPP(8:0) (Y. Xing et al., Am. J. Physiol. Cell Physiol. 287 (2004), F1250-F1257). In another approach using the Edg-2/Edg-7 receptor inhibitor VPC12249 it was demonstrated in an in vivo model of mouse renal ischemia reperfusion that LPA displays a dual role in renoprotection. While Edg-4 receptor signaling was shown to be beneficial, Edg-2 and Edg-7 receptor signaling aggravated renal injury, most probably due to enhanced infiltration of leukocytes into the renal tissue, and should therefore be blocked for treating or preventing ischemia/reperfusion-induced acute renal failure (M. D. Okusa et al., Am. J. Physiol. Renal Physiol. 285 (2003), F565-F574). The crucial role of Edg-2 receptors in the development of tubulointerstitial fibrosis was confirmed in a model of unilateral ureteral obstruction (J. P. Pradere et al., J. Am. Soc. Nephrol. 18 (2007), 3110-3118). In this model, renal injury was attenuated in Edg-2 receptor knockout mice or by pharmacological treatment with the Edg-2/Edg-7 receptor inhibitor Ki16425. The impact of the LPA/Edg-2 receptor system in pulmonary fibrosis and vascular leakage was recently confirmed by the finding that the bioactive content of LPA was increased in bronchoalveolar fluid of humans suffering from idiopathic pulmonary fibrosis. Edg-2 receptor knock-out mice were protected from bleomycin-induced lung injury and vascular leakage, as compared to wild-type littermates (A. M. Tager et al., Nat. Med. 14 (2008), 45-54).

Direct involvement of Edg-2 receptors was recently demonstrated for the progression of bone metastasis in vivo. Progression was reduced under pharmacological treatment with the Edg-2/Edg-7 receptor inhibitor Ki16425 as well as after specific silencing of the Edg-2 receptors in the same order of magnitude (A. Boucharaba et al., Proc. Natl. Acad. Sci. 103 (2006), 9643-9648). The relevance of Edg-2 receptors was also shown in vitro with respect to prostate cancer cell proliferation and metastatic potential of human colon carcinoma cells (R. Guo et al., Endocrinology 147 (2006), 4883-4892; D. Shida et al., Cancer Res. 63 (2003), 1706-1711).

The relevance of LPA-mediated Edg-2 receptor signaling was also demonstrated in an in vivo model of neuropathic pain. Intrathecal injection of LPA mimicked behavioral, morphological and biochemical alterations similar to those observed after peripheral nerve injury. Non-redundant function of Edg-2 receptors was demonstrated in Edg-2 receptor deficient mice which did not develop signs of neuropathic pain after nerve injury. Therefore, Edg-2 receptor signaling is regarded as crucial in the initiation of neuropathic pain (M. Inoue et al., Nat. Med. 10 (2004), 712-718). Thus, it is evident that inhibition of the Edg-2 receptor and the effects of LPA by suitable inhibitors is an attractive approach for treating various diseases. Certain compounds which exhibit Edg-2 inhibitory activity, have already been described. For example, as compounds which are structurally related to LPA, the abovementioned compounds DGPP(8:0) or VPC12249 may be mentioned. In WO 02/29001 and WO 2005/115150 amino compounds comprising a phosphate group, phosphonate group or hydroxy group are described which have activity as agonists or antagonists of LPA receptors. LPA receptor antagonistic azole compounds which are characterized by a carbamate group in the 4-position of the azole ring, are described in EP 1258484. The use of azole compounds, further heterocycles and other compounds for modulating the Edg-2, Edg-3, Edg-4 and Edg-7 receptor is described in WO 03/062392. Compounds which have LPA receptor, especially Edg-2, antagonistic activity and which comprise a β-alanine moiety carrying a biphenyl-2-carbonyl group on the amino group, or an alcohol group and at least three cyclic groups, are described in EP 1533294 and EP 1695955, respectively. But there still is a need for further Edg-2 inhibitors which exhibit a favorable property profile and can be used in the treatment of diseases such as the above-mentioned ones and other diseases in which LPA signaling and Edg-2 receptors play a role. The present invention satisfies this need by providing the acylamino-substituted fused cyclopentanecarboxylic acid derivatives of the formula I defined below.

Certain acylamino-substituted fused cyclopentanecarboxylic acid derivatives which structurally differ from the compounds of the invention, have already been described, such as the compound 2-benzoylamino-indane-2-carboxylic acid in R. Lohmar et al., Chem. Ber. 113 (1980), 3706-3715. 2-Acylamino-indane-2-carboxylic acids which are characterized by an aryl or heteroaryl substituent on the benzene ring of the indane moiety and which control the function of the GPR34 receptor and thereby inhibit histamine release, have been described in WO 2006/088246 (EP 1849465), among them the compounds of the formula I in which the fused cyclopentane ring depicted in formula I together with ring A is an indane ring which carries a 4-chlorophenyl substituent in the 5-position, the groups $R^3$ to $R^6$ and $R^{20}$ are hydrogen, the group $R^{50}$ is hydroxy or ethoxy and the cyclic residue containing the groups Y, Z, $R^{21}$ and $R^{22}$ is 4-(2-methyl-1H-benzoimidazol-1-ylmethyl)-phenyl, which residue may also be designated as 4-(2-methyl-benzoimidazol-1-ylmethyl)-phenyl. The compounds of the formula I in which the fused cyclopentane ring depicted in formula I together with ring A is an unsubstituted indane ring, the groups $R^3$ to $R^6$ and $R^{20}$ are hydrogen, the group $R^{50}$ is hydroxy and the cyclic residue containing the groups Y, Z, $R^{21}$ and $R^{22}$ is 6,2',4'-trichlorobiphenyl-3-yl, 6-chloro-[1,1',4',1'']terphenyl-3-yl or 4-chloro-3-(2-phenylethynyl)-phenyl, have been described in WO 2006/044975 which relates to anti-tumor agents.

A subject of the present invention is a compound of the formula I, in any of its stereoisomeric forms or a mixture of stereoisomeric forms in any ratio, or a physiologically acceptable salt thereof, or a physiologically acceptable solvate of any of them,

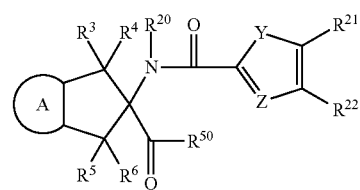

I wherein ring A is a 3-membered to 7-membered cycloalkane ring, a benzene ring, or a monocyclic 5-membered or 6-membered aromatic heterocyclic ring which comprises 1 or 2 identical or different hetero ring members chosen from the series consisting of N, N($R^0$), O and S, wherein the cycloalkane ring is optionally substituted by one or more identical or different substituents chosen from the series consisting of fluorine and ($C_1$-$C_4$)-alkyl, and the benzene ring and the heterocyclic rings are optionally substituted by one or more identical or different substituents chosen from the series consisting of halogen, $R^1$, HO—, $R^1$—O—, $R^1$—C(O)—O—, $R^1$—S(O)$_2$—O—, $R^1$—S(O)$_m$—, $H_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—CO(O)—, $H_2$N—C(O)—, $R^1$—NH—C(O)—, $R^1$—N($R^1$)—C(O)—, $H_2$N—S(O)$_2$—, $R^1$—NH—S(O)$_2$—, $R^1$—N($R^1$)—S(O)$_2$—, NC—, $O_2$N—, phenyl and Het;

Y is chosen from the series consisting of N($R^{10}$), S, O, C($R^{12}$)=C($R^{13}$), N=C($R^{14}$) and C($R^{15}$)=N;

Z is chosen from the series consisting of N and C($R^{16}$);

$R^0$ is chosen from the series consisting of hydrogen and $R^2$;

$R^1$, $R^2$, $R^{11}$, $R^{30}$, $R^{33}$, $R^{35}$, $R^{54}$, $R^{55}$, $R^{57}$ and $R^{58}$ are, independently of each other group $R^1$, $R^2$, $R^{11}$, $R^{30}$, $R^{33}$, $R^{35}$, $R^{54}$, $R^{55}$, $R^{57}$ and $R^{58}$, chosen from the series consisting of ($C_1$-$C_6$)-alkyl, ($C_2$-$C_6$)-alkenyl, ($C_2$-$C_6$)-alkynyl, ($C_3$-$C_7$)-cycloalkyl and ($C_3$-$C_7$)-cycloalkyl-($C_1$-$C_4$)-alkyl- which are all optionally substituted by one or more identical or different substituents $R^{70}$;

$R^3$ and $R^5$ are independently of each other chosen from the series consisting of hydrogen, ($C_1$-$C_4$)-alkyl, phenyl-($C_1$-$C_4$)-alkyl-, phenyl and hydroxy;

$R^4$ and $R^6$ are independently of each other chosen from the series consisting of hydrogen and ($C_1$-$C_4$)-alkyl;

$R^{10}$ is chosen from the series consisting of hydrogen and $R^{11}$;

$R^{12}$, $R^{13}$, $R^{14}$, $R^{15}$ and $R^{16}$ are independently of each other chosen from the series consisting of hydrogen, halogen, ($C_1$-$C_4$)-alkyl, ($C_1$-$C_4$)-alkyl-S(O)$_m$—, $H_2$N—, ($C_1$-$C_4$)-alkyl-NH—, ($C_1$-$C_4$)-alkyl-C(O)—, NC— and $O_2$N—;

$R^{20}$ is chosen from the series consisting of hydrogen and ($C_1$-$C_4$)-alkyl;

one of the groups $R^{21}$ and $R^{22}$ is a group of the formula II $$R^{24}\text{-}R^{23}\text{-} \qquad \text{II}$$

and the other of the groups $R^{21}$ and $R^{22}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, $H_2$N—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, $H_2$N—C(O)—, $R^{30}$—NH—C(O)—, $R^{30}$—N($R^{30}$)—C(O)—, $H_2$N—S(O)$_2$—, $R^{30}$—NH—S(O)$_2$—, $R^{30}$—N($R^{30}$)—S(O)$_2$—, NC—, $O_2$N— and Het$^1$;

$R^{23}$ is a direct bond or a chain consisting of 1 to 5 chain members of which 0, 1 or 2 chain members are identical or different hetero chain members chosen from the series consisting of N($R^{25}$), O, S, S(O) and S(O)$_2$, but two hetero chain members can be present in adjacent positions only if one of them is chosen from the series consisting of S(O) and S(O)$_2$ and the other is chosen from the series consisting of N($R^{25}$), O and S, and the other chain members are identical or different groups C($R^{26}$)($R^{26}$), wherein two adjacent groups C($R^{26}$)($R^{26}$) can be connected to each other by a double bond or a triple bond;

$R^{24}$ is chosen from the series consisting of hydrogen, $R^{31}$, HO—, $R^{31}$—O—, $R^{31}$—C(O)—O—, $R^{31}$—S(O)$_m$—, $H_2$N—, $R^{31}$—NH—, $R^{31}$—N($R^{31}$)—, $R^{31}$—C(O)—NH—, $R^{31}$—C(O)—N($R^{71}$)—, $R^{31}$—S(O)$_2$—NH—, $R^{31}$—S(O)$_2$—N($R^{71}$)—, $R^{31}$—C(O)—, HO—C(O)—, $R^{31}$—O—C(O)—, $H_2$N—C(O)—, $R^{31}$—NH—C(O)—, $R^{31}$—N($R^{31}$)—C(O)—, $H_2$N—S(O)$_2$—, $R^{31}$—NH—S(O)$_2$—, $R^{31}$—N($R^{31}$)—S(O)$_2$—, NC— and a 3-membered to 10-membered, monocyclic, bicyclic or tricyclic ring which is saturated or unsaturated and contains 0, 1, 2 or 3 identical or different hetero ring members chosen from the series consisting of N, N($R^{32}$), O, S, S(O) and S(O)$_2$, which ring is optionally substituted on ring carbon atoms by one or more identical or different substituents chosen from the series consisting of halogen, $R^{33}$, HO—, $R^{33}$—O—, $R^{33}$—C(O)—O—, $R^{33}$—S(O)$_2$—O—, $R^{33}$—S(O)$_m$—, $H_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, $H_2$N—S(O)$_2$—NH—, $R^{33}$—NH—S(O)$_2$—NH—, $R^{33}$—N($R^{33}$)—S(O)$_2$—NH—, $H_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, $R^{33}$—C(O)—, HO—C(O)—, $R^{33}$—O—C(O)—, $H_2$N—C(O)—, $R^{33}$—NH—C(O)—, $R^{33}$—N($R^{33}$)—C(O)—, $H_2$N—S(O)$_2$—, $R^{33}$—NH—S(O)$_2$—, $R^{33}$—N($R^{33}$)—S(O)$_2$—, NC—, $O_2$N—, oxo, phenyl and Het, provided that the total number of C, N, O and S atoms which is present in the two groups $R^{23}$ and $R^{24}$, is at least 5;

$R^{25}$ is chosen from the series consisting of hydrogen and ($C_1$-$C_4$)-alkyl;

$R^{26}$, independently of each other group $R^{26}$, is chosen from the series consisting of hydrogen, fluorine, ($C_1$-$C_4$)-alkyl and HO—, or two groups $R^{26}$ bonded to the same carbon atom together are oxo, or two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, N($R^{34}$), O, S, S(O) and S(O)$_2$, which ring is optionally substituted on ring carbon atoms by one more identical or different substituents chosen from the series consisting of fluorine and ($C_1$-$C_4$)-alkyl;

$R^{31}$ is chosen from the series consisting of ($C_1$-$C_6$)-alkyl, ($C_2$-$C_6$)-alkenyl and ($C_2$-$C_6$)-alkynyl which are all optionally substituted by one or more identical or different substituents $R^{70}$;

$R^{32}$ and $R^{34}$ are independently of each other chosen from the series consisting of hydrogen, $R^{35}$, $R^{35}$—S(O)$_2$—, $R^{35}$—C(O)—, $R^{35}$—O—C(O)—, phenyl and Het;

$R^{50}$ is chosen from the series consisting of $R^{51}$—O— and $R^{52}$—N($R^{53}$)—;

$R^{51}$ is chosen from the series consisting of hydrogen and $R^{54}$;

$R^{52}$ is chosen from the series consisting of hydrogen, $R^{55}$, NC— and $R^{56}$—S(O)$_2$—;

$R^{53}$ is chosen from the series consisting of hydrogen and $R^{57}$;

$R^{56}$ is chosen from the series consisting of $R^{58}$ and phenyl;

$R^{60}$, independently of each other group $R^{60}$, is chosen from the series consisting of hydrogen and ($C_1$-$C_4$)-alkyl;

$R^{70}$ is chosen from the series consisting of HO—, $R^{71}$—O—, $R^{71}$—C(O)—O—, $R^{71}$—S(O)$_m$—, $H_2$N—, $R^{71}$—NH—, $R^{71}$—N($R^{71}$)—, $R^{71}$—C(O)—NH—, $R^{71}$—C(O)—N($R^{71}$)—, $R^{71}$—S(O)$_2$—NH—, $R^{71}$—S(O)$_2$—N($R^{71}$)—, HO—C(O)—, $R^{71}$—O—C(O)—, $H_2$N—C(O)—, $R^{71}$—NH—C(O)—, $R^{71}$—N($R^{17}$)—C(O)—, $H_2$N—S(O)$_2$—, $R^{71}$—NH—S(O)$_2$—, $R^{71}$—N($R^{71}$)—S(O)$_2$—, NC—, oxo, phenyl and Het$^2$;

$R^{71}$, independently of each other group $R^{71}$, is chosen from ($C_1$-$C_4$)-alkyl, ($C_3$-$C_4$)-cycloalkyl and ($C_3$-$C_4$)-cycloalkyl-($C_1$-$C_2$)-alkyl-;

Het, independently of each other group Het, is a monocyclic 4-membered to 7-membered heterocyclic ring which comprises 1, 2 or 3 identical or different hetero ring members chosen from the series consisting of N, N($R^{60}$), O, S, S(O) and S(O)$_2$, which ring is saturated or unsaturated and is optionally substituted by one or more identical or different substituents chosen from the series consisting of halogen, (C$_1$-C$_4$)-alkyl and $R^{70}$;

Het$^1$ is a monocyclic 4-membered to 7-membered heterocyclic ring which comprises 1 or 2 identical or different hetero ring members chosen from the series consisting of N, N($R^{60}$), O, S, S(O) and S(O)$_2$, which ring is saturated and is optionally substituted by one or more identical or different substituents chosen from the series consisting of fluorine and (C$_1$-C$_4$)-alkyl;

Het$^2$ is a monocyclic 5-membered or 6-membered heterocyclic ring which comprises 1, 2 or 3 identical or different hetero ring members chosen from the series consisting of N, N($R^{60}$), O and S, which ring is aromatic and is optionally substituted by one or more identical or different substituents chosen from the series consisting of halogen, (C$_1$-C$_4$)-alkyl, (C$_1$-C$_4$)-alkyl-O— and NC—;

m, independently of each other number m, is an integer chosen from the series consisting of 0, 1 and 2;

phenyl, independently of each other group phenyl, is optionally substituted by one or more identical or different substituents chosen from the series consisting of halogen, (C$_1$-C$_4$)-alkyl, (C$_1$-C$_4$)-alkyl-O— and NC—, unless specified otherwise;

cycloalkyl, independently of each other group cycloalkyl, and independently of any other substituents on cycloalkyl, is optionally substituted by one or more identical or different substituents chosen from fluorine and (C$_1$-C$_4$)-alkyl;

alkyl, alkenyl and alkynyl, independently of each other group alkyl, alkenyl and alkynyl, and independently of any other substituents on alkyl, alkenyl and alkynyl, is optionally substituted by one or more fluorine substituents;

provided that the compound of the formula I is not 2-[(6,2',4'-trichlorobiphenyl-3-carbonyl)amino]indane-2-carboxylic acid, 2-[6-chloro-[1,1',4',1"]terphenyl-3-carbonyl)amino]indane-2-carboxylic acid, 2-(4-chloro-3-phenylethynyl-benzoylamino)-indane-2-carboxylic acid, 5-(4-chloro-phenyl)-2-[4-(2-methyl-1H-benzoimidazol-1-ylmethyl)-benzoylamino]-indane-2-carboxylic acid or 5-(4-chloro-phenyl)-2-[4-(2-methyl-1H-benzoimidazol-1-ylmethyl)-benzoylamino]-indane-2-carboxylic acid ethyl ester.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO-substituted alkyl group (hydroxyalkyl group). Depending on the respective definition, the number of carbon atoms in an alkyl group can be 1, 2, 3, 4, 5 or 6, or 1, 2, 3 or 4, or 1, 2 or 3, or 1 or 2, or 1. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Examples of alkyl-O— groups are methoxy, ethoxy, n-propoxy, isopropoxy, n-butoxy, isobutoxy, tert-butoxy, n-pentoxy. Examples of alkyl-S(O)$_m$— are methylsulfanyl-(CH$_3$—S—), methanesulfinyl-(CH$_3$—S(O)—), methanesulfonyl (CH$_3$—S(O)$_2$—), ethylsulfanyl-(CH$_3$—CH$_2$—S—), ethanesulfinyl-(CH$_3$—CH$_2$—S(O)—), ethanesulfonyl (CH$_3$—CH$_2$—S(O)$_2$—), 1-methylethylsulfanyl-((CH$_3$)$_2$CH—S—), 1-methylethanesulfinyl-((CH$_3$)$_2$CH—S(O)—), 1-methylethanesulfonyl ((CH$_3$)$_2$CH—S(O)$_2$—). In one embodiment of the invention the number m is chosen from 0 and 2, wherein all numbers m are independent of each other and can be identical or different. In another embodiment the number m in any of its occurrences is, independent of its meaning in other occurrences, 0. In another embodiment the number m in any of its occurrences is, independent of its meaning in other occurrences, 2.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. An alkyl group which is optionally substituted by one or more fluorine substituents can be unsubstituted, i.e. not carry fluorine substituents, or substituted, for example by 1, 2, 3, 4, 5, 6, 7, 8, 9, 10 or 11 fluorine substituents, or by 1, 2, 3, 4 or 5 fluorine substituents, which can be located in any positions. For example, in a fluoro-substituted alkyl group one or more methyl groups can carry three fluorine substituents each and be present as trifluoromethyl groups, and/or one or more methylene groups (CH$_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S(O)$_m$— groups are trifluoromethylsulfanyl-(CF$_3$—S—), trifluoromethanesulfinyl-(CF$_3$—S(O)—) and trifluoromethanesulfonyl (CF$_3$—S(O)$_2$—).

The above explanations with respect to alkyl groups apply correspondingly to unsaturated hydrocarbon residues, i.e. alkenyl groups, which in one embodiment of the invention contain one double bond, and alkynyl groups, which in one embodiment of the invention contain one triple bond. Thus, for example, alkenyl groups and alkynyl groups can likewise be linear or branched, and substituted alkenyl and alkynyl groups can be substituted in any positions, provided that the resulting compound is sufficiently stable and is suitable as a pharmaceutical active compound. Double bonds and triple bonds can be present in any positions. The number of carbon atoms in an alkenyl or alkynyl group can be 2, 3, 4, 5 or 6, for example 2, 3, 4 or 5. Examples of alkenyl and alkynyl are ethenyl (vinyl), prop-1-enyl, prop-2-enyl (allyl), but-2-enyl, 2-methylprop-2-enyl, 3-methylbut-2-enyl, hex-3-enyl, hex-4-enyl, 4-methylhex-4-enyl, prop-1-ynyl, prop-2-ynyl (propargyl), but-2-ynyl, but-3-ynyl, 4-methylpent-2-ynyl, hex-4-ynyl and hex-5-ynyl. In one embodiment of the invention, an alkenyl or alkynyl group contains at least three carbon atoms and is bonded to the remainder of the molecule via a carbon atom which is not part of a double bond or triple bond.

The above explanations with respect to alkyl groups apply correspondingly to alkanediyl groups (divalent alkyl groups) including chains of one or more groups C($R^{26}$)($R^{26}$) which latter groups as such and chains of such groups are alkanediyl groups in case $R^{26}$ is chosen from hydrogen and $(C_1-C_4)$-alkyl, or are substituted alkanediyl groups in case any of the groups $R^{26}$ has a meaning different from hydrogen and $(C_1-C_4)$-alkyl. Likewise, the alkyl part of a substituted alkyl group can also be regarded as an alkanediyl group. Thus, alkanediyl groups can also be linear or branched, the bonds to the adjacent groups can be located in any positions and can start from the same carbon atom or from different carbon atoms, and they can be substituted by fluorine substituents. Examples of alkanediyl groups are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$—, —$CH_2$—$C(CH_3)_2$—. Examples of fluoro-substituted alkanediyl groups, which can contain 1, 2, 3, 4, 5 or 6 fluorine substituents, for example, are —$CHF$—, —$CF_2$—, —$CF_2$—$CH_2$—, —$CH_2$—$CF_2$—, —$CF_2$—$CF_2$—, —$CF(CH_3)$—, —$C(CF_3)_2$—, —$C(CH_3)_2$—$CF_{2-3}$—$CF_2$—$C(CH_3)_2$—. Further, the above explanations apply correspondingly to divalent residues of unsaturated hydrocarbons, i.e. unsaturated alkanediyl groups such as alkenediyl groups and alkynediyl groups, which groups can occur in the group $R^{23}$ in case two adjacent groups $C(R^{26})(R^{26})$ are connected to each other by a double bond or triple bond and which groups in one embodiment of the invention contain one double bond or one triple bond, respectively, which can be present in any positions, and which groups are optionally substituted by fluorine substituents. Examples of such unsaturated divalent groups are —$CH=CH$—, —$CH_2$—$CH=CH$—, —$CH=CH$—$CH_2$—, —$CH_2$—$CH=CH$—$CH_2$—, —$C\equiv C$—, —$CH_2$—$C\equiv C$—, —$C\equiv C$—$CH_2$—, —$C(CH_3)_2$—$C\equiv C$—, —$C\equiv C$—$C(CH_3)_2$—, —$CH_2$—$C\equiv C$—$CH_2$—.

The number of ring carbon atoms in a $(C_3-C_7)$-cycloalkyl group can be 3, 4, 5, 6 or 7. Examples of cycloalkyl are cyclopropyl, cyclobutyl, cyclopentyl, cyclohexyl and cycloheptyl. Cycloalkyl groups which are optionally substituted by one or more $(C_1-C_4)$-alkyl substituents, can be unsubstituted, i.e. not carry alkyl substituents, or substituted, for example by 1, 2, 3 or 4 identical or different $(C_1-C_4)$-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl and 3,3,5,5-tetramethylcyclohexyl. Cycloalkyl groups which are optionally substituted by one or more fluorine substituents, can be unsubstituted, i.e. not carry fluorine substituents, or substituted, for example by 1, 2, 3, 4, 5, 6, 7, 8, 9, 10 or 11 fluorine substituents, or by 1, 2, 3, 4, 5 or 6 fluorine substituents. The fluorine substituents can be located in any positions of the cycloalkyl group and can also be located in an alkyl substituent on the cycloalkyl group. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl and 3,3,4,4,5,5-hexafluorocyclohexyl. Cycloalkyl groups can also be substituted simultaneously by fluorine and alkyl. Examples of the group $(C_3-C_7)$-cycloalkyl-$(C_1-C_4)$-alkyl- are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. The explanations with respect cycloalkyl groups apply correspondingly to unsaturated cycloalkyl groups such as cycloalkenyl groups which can occur in the group $R^{24}$ and which in one embodiment of the invention contain one double bond which can be present in any positions, and divalent cycloalkyl groups (cycloalkanediyl groups), which latter groups can occur in case two of the groups $R^{26}$ together with the comprised chain members form a ring. Likewise, the cycloalkyl part of a substituted cycloalkyl group can also be regarded as a cycloalkanediyl group. Thus, for example, the bonds through which a cycloalkanediyl group, such as a ring formed by two of the groups $R^{26}$ together with the comprised chain members, is connected to the adjacent groups, can be located in any positions and can start from the same ring carbon atom or from different ring carbon atoms.

In substituted phenyl groups, including phenyl groups which represent the 3-membered to 10-membered, monocyclic, bicyclic or tricyclic ring representing $R^{24}$, the substituents can be located in any positions. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. If a phenyl group carries four substituents, some of which can be fluorine atoms, for example, the substituents can be located in 2,3,4,5-position, the 2,3,4,6-position or 2,3,5,6-position. If a polysubstituted phenyl group or any other polysubstituted group such as a heteroaryl group carries different substituents, each substituent can be located in any suitable position, and the present invention comprises all positional isomers. The number of substituents in a substituted phenyl group can be 1, 2, 3, 4 or 5. In one embodiment of the invention, a substituted phenyl group, and likewise another substituted group such as a heteroaryl group, carries 1, 2 or 3, for example 1 or 2, identical or different substituents.

In heterocyclic groups, including the groups Het, Het$^1$ and Het$^2$ and heterocyclic rings which can be present in structural elements in the compounds of the formula I such as the ring A or the 3-membered to 10-membered ring representing $R^{24}$ or a ring formed by a group $R^{25}$ and a group $R^{26}$ together with the comprised chain members, for example, the hetero ring members specified in the respective definition can be present in any combination and located in any suitable ring positions, provided that the resulting group and the compound of the formula I are sufficiently stable and suitable as a pharmaceutical active compound. In one embodiment of the invention two oxygen atoms in any heterocyclic ring in the compounds of the formula I cannot be present in adjacent ring positions. In another embodiment two hetero ring members from the series consisting of O, S and N atoms carrying a hydrogen atom or a substituent, cannot be present in adjacent ring positions. Examples of such series are the hetero ring members O, S and N($R^{32}$), or O, S and N($R^{34}$), or O, S and N($R^{60}$). In another embodiment of the invention two hetero ring members from the series consisting of S(O) and S(O)$_2$ cannot be present in adjacent ring positions. In an aromatic heterocyclic ring the choice of hetero ring members and their positions is limited by the prerequisite that the ring is aromatic, i.e. it comprises a cyclic system of six delocalized pi electrons. The residue of a monocyclic, 5-membered or 6-membered, aromatic heterocyclic ring, which can occur in the groups Het, Het$^2$ and the 3-membered to 10 membered ring representing $R^{24}$, for example, can also be designated as monocyclic, 5-membered or 6-membered heteroaryl group. The ring nitrogen atom in such a heteroaryl group which carries the group $R^{32}$ or $R^{60}$, respectively, is the ring nitrogen atom in a 5-membered ring such as pyrrole, pyrazole, imidazole or triazole to which an exocyclic atom or group such as a hydrogen atom is bonded, and can be present once only in a 5-membered aromatic ring just as the hetero ring members O and S. Examples of rings from which such a heteroaryl group can be derived are pyrrole, furan, thiophene, imidazole, pyrazole, triazoles including [1,2,3]triazole and [1,2,4]triazole, oxazole ([1,3]oxazole), isoxazole ([1,2]oxazole), thiazole ([1,3]thiazole), isothiazole ([1,2]thiazole), oxadiazoles including [1,2,4]oxadiazole, [1,3,4]oxadiazole and [1,2,5]oxadiazole, thiadiazoles including [1,3,4]thiadiazole, pyridine, pyridazine, pyrimidine, pyrazine, triazines including [1,2,3]triazine, [1,2,4]triazine and [1,3,5]triazine. These explanations with respect to monocyclic, 5-membered or 6-membered heteroaryl groups apply correspondingly to the monocyclic, 5-membered or 6-membered, aromatic heterocyclic ring representing the ring A in formula I in which the ring nitrogen atom carrying the group $R^0$ can likewise be present once only in a 5-membered ring such as pyrrole, pyrazole or imidazole. Just so, the hetero ring members O and S can be present once only in the ring A. In one embodiment of the invention, a monocyclic, 5-membered or 6-membered heteroaryl group comprises one or two identical or different hetero ring members, in another embodiment of the invention such a heteroaryl group comprises one hetero ring member, which are defined as indicated, and in another embodiment of the invention such a heteroaryl is chosen from thiophenyl, thiazolyl and pyridinyl. A monocyclic, 5-membered or 6-membered heteroaryl group can be bonded via any ring carbon atom or, in the case of a 5-membered ring comprising a hetero ring member $N(R^{32})$ or $N(R^{60})$, via a ring nitrogen atom, wherein in the latter case the bond via which the heteroaryl group is attached to the remainder of the molecule, replaces the group $R^{32}$ or $R^{60}$. In one embodiment of the invention, a monocyclic, 5-membered or 6-membered heteroaryl group is bonded via a ring carbon atom. For example, a thiophenyl group (thienyl group) can be thiophen-2-yl (2-thienyl) or thiophen-3-yl (3-thienyl), furanyl can be furan-2-yl or furan-3-yl, pyridinyl (pyridyl) can be pyridin-2-yl, pyridin-3-yl or pyridin-4-yl, pyrazolyl can be 1H-pyrazol-3-yl, 1H-pyrazol-4-yl or 2H-pyrazol-3-yl, imidazolyl can be 1H-imidazol-1-yl, 1H-imidazol-2-yl, 1H-imidazol-4-yl or 3H-imidazolyl-4-yl, thiazolyl can be thiazol-2-yl, thiazol-4-yl or thiazol-5-yl.

In substituted monocyclic, 5-membered or 6-membered heteroaryl groups, the substituents can be located in any positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position. In one embodiment of the invention, a substituted monocyclic, 5-membered or 6-membered heteroaryl group is substituted by 1, 2 or 3, for example 1 or 2, identical or different substituents. Generally, besides optionally carrying the substituents indicated in the definition of the group, suitable ring nitrogen atoms in a monocyclic, 5-membered or 6-membered heteroaryl group as well as in other heterocyclic groups, for example in a 3-membered to 10-membered, monocyclic, bicyclic or tricyclic ring representing $R^{24}$ or in the aromatic ring A or the aromatic ring comprising the groups Y and Z which are depicted in formula I, for example the nitrogen atom in a pyridinyl group or a nitrogen atom in a [1,2,5]oxadiazolyl group, can also carry an oxido substituent —O⁻ and be present as an N-oxide.

The above explanations with respect to monocyclic, 5-membered or 6-membered aromatic heterocyclic groups apply correspondingly to the bicyclic aromatic heterocyclic groups discussed below which can occur in the 3-membered to 10-membered ring representing $R^{24}$ and which can also be designated as a bicyclic heteroaryl group.

Besides monocyclic, 5-membered or 6-membered, aromatic heterocyclic groups, the group Het comprises monocyclic, 4-membered to 7-membered, partially unsaturated, i.e. non-aromatic, heterocyclic groups and 4-membered to 7-membered, saturated, heterocyclic groups. 4-membered to 7-membered, saturated, heterocyclic groups are also comprised by the group $Het^1$. The rings of the groups Het and $Het^1$ thus can be 4-membered, 5-membered, 6-membered or 7-membered, for example 5-membered or 6-membered. In one embodiment of the invention, a partially unsaturated group Het comprises one or two, in another embodiment one, double bonds within the ring which can be present in any position. In one embodiment of the invention, a 4-membered group Het is saturated. In one embodiment of the invention, a group Het is a 4-membered to 7-membered saturated group or a 5-membered or 6-membered aromatic group, in another embodiment a group Het is a is a 4-membered to 7-membered saturated group, and in another embodiment a group Het is a 5-membered or 6-membered aromatic group. The groups Het and $Het^1$ can be bonded via any ring carbon atom or ring nitrogen atom. Examples of groups Het and $Het^1$ are azetidinyl including azetidin-1-yl, oxetanyl including oxetan-3-yl, tetrahydrofuranyl including tetrahydrofuran-2-yl and tetrahydrofuran-3-yl, tetrahydrothiophenyl including tetrahydrothiophen-2-yl and tetrahydrothiophen-3-yl, 1-oxo-tetrahydrothiophenyl including 1-oxo-tetrahydrothiophen-2-yl and 1-oxo-tetrahydrothiophen-3-yl, 1,1-dioxo-tetrahydrothiophenyl including 1,1-dioxo-tetrahydrothiophen-2-yl and 1,1-dioxo-tetrahydrothiophen-3-yl, pyrrolidinyl including pyrrolidin-1-yl, pyrrolidin-2-yl and pyrrolidin-3-yl, tetrahydropyranyl including tetrahydropyran-2-yl, tetrahydropyran-3-yl and tetrahydropyran-4-yl, tetrahydrothiopyranyl including tetrahydrothiopyran-2-yl, tetrahydrothiopyran-3-yl and tetrahydrothiopyran-4-yl, piperidinyl including piperidin-1-yl, piperidin-2-yl, piperidin-3-yl and piperidin-4-yl, 1,2,3,4-tetrahydropyridinyl including 1,2,3,4-tetrahydropyridin-1-yl, 1,2,3,6-tetrahydropyridinyl including 1,2,3,6-tetrahydropyridin-1-yl, oxepanyl including oxepan-2-yl, oxepan-3-yl and oxepan-4-yl, azepanyl including azepan-1-yl, azepan-2-yl, azepan-3-yl and azepan-4-yl, 1,3-dioxolanyl including 1,3-dioxolan-2-yl and 1,3-dioxolan-4-yl, imidazolidinyl including imidazolidin-1-yl, imidazolidin-2-yl and imidazolidin-4-yl, [1,3]oxazolidinyl including [1,3]oxazolidin-2-yl, [1,3]oxazolidin-3-yl, [1,3]oxazolidin-4-yl and [1,3]oxazolidin-5-yl, [1,3]thiazolidinyl including [1,3]thiazolidin-2-yl, [1,3]thiazolidin-3-yl, [1,3]thiazolidin-4-yl and [1,3]thiazolidin-5-yl, [1,3]dioxanyl including [1,3]dioxan-2-yl, [1,3]dioxan-4-yl and [1,3]dioxan-5-yl, [1,4]dioxanyl including [1,4]dioxan-2-yl, piperazinyl including piperazin-1-yl and piperazin-2-yl, morpholinyl including morpholin-2-yl, morpholin-3-yl and morpholin-4-yl, thiomorpholinyl including thiomorpholin-2-yl, thiomorpholin-3-yl and thiomorpholin-4-yl, 1-oxo-thiomorpholinyl including 1-oxo-thiomorpholin-2-yl, 1-oxo-thiomorpholin-3-yl and 1-oxo-thiomorpholin-4-yl, 1,1-dioxo-thiomorpholinyl including 1,1-dioxo-thiomorpholin-2-yl, 1,1-dioxo-thiomorpholin-3-yl and 1,1-dioxo-thiomorpholin-4-yl, [1,3]diazepanyl, [1,4]diazepanyl, [1,4]oxazepanyl or [1,4]thiazepanyl. Besides by oxo groups in the ring members S(O) and $S(O)_2$ and alkyl groups representing $R^{60}$, the groups Het and $Het^1$ are optionally substituted on ring carbon atoms by one or more, for example 1, 2, 3, 4 or 5, or 1, 2, 3 or 4, or 1, 2 or 3, identical or different substituents as indicated, which can be located in any positions.

The 3-membered to 10-membered, monocyclic, bicyclic or tricyclic ring which is saturated or unsaturated and which contains 0, 1, 2 or 3 identical or different hetero ring members chosen from the series consisting of N, N($R^{32}$), O, S, S(O) and S(O)$_2$, which ring can represent $R^{24}$, can comprise 3, 4, 5, 6, 7, 8, 9 or 10 ring members. In one embodiment of the invention, a bicyclic and tricyclic ring is fused or bridged. An unsaturated ring can be partially unsaturated and contain, for example, one or two double bonds within the ring, or, in the case of a monocyclic or bicyclic ring, be aromatic in one or both rings, and altogether the number of double bonds within an unsaturated ring can be one, two, three, four or five. In a bicyclic ring, the two individual rings can independently of each other be saturated or partially unsaturated or aromatic, and in a tricyclic ring the individual rings, independently of each other, can in particular be saturated or partially unsaturated. In one embodiment of the invention, a 3-membered or 4-membered ring is saturated. The 3-membered to 10-membered, monocyclic, bicyclic or tricyclic ring can be a carbocyclic ring, i.e. contain 0 (zero) hetero ring members, or a heterocyclic ring in which hetero ring members can be present as indicated above. In a bicyclic heterocyclic ring one or both individual rings can contain hetero ring members, and in a tricyclic ring one or more individual rings can contain hetero ring members. In case nitrogen atoms are present as hetero ring members in a bicyclic or tricyclic ring, they can also be present at a fusion position or a bridgehead position. The free bond via which the ring is bonded to the group $R^{23}$, can be located at any suitable ring carbon atom or ring nitrogen atom. In one embodiment of the invention the free bond is located at a ring carbon atom. In general, besides by oxo groups in the ring members S(O) and S(O)$_2$ and substituents $R^{32}$ on ring nitrogen atoms, the 3-membered to 10 membered ring is optionally substituted on ring carbon atoms by one or more, for example 1, 2, 3, 4 or 5, or 1, 2, 3 or 4, or 1, 2 or 3, identical or different substituents as indicated, which can be located in any positions.

The 3-membered to 10-membered, monocyclic, bicyclic or tricyclic ring comprises ($C_3$-$C_7$)-cycloalkyl groups, phenyl groups, and monocyclic, 5-membered or 6-membered aromatic heterocyclic groups and monocyclic 4-membered to 7-membered partially unsaturated and saturated groups as are comprised by the definitions of the groups Het, Het$^1$ and Het$^2$. All these groups thus are examples of the said 3-membered to 10-membered ring, and all explanations given above with respect to these groups apply correspondingly to the said 3-membered to 10-membered ring unless specified otherwise in the definition of the said 3-membered to 10-membered ring. Thus, for example, the substituents in these groups, such as in a phenyl group which represents the said 3-membered to 10-membered ring, or in a monocyclic 5-membered or 6-membered aromatic heterocyclic group representing the group Het or Het$^2$ which represents the said 3-membered to 10-membered ring, can then be as is specified in the definition of $R^{24}$. As further examples of cyclic groups which are comprised by the said 3-membered to 10-membered ring, ($C_5$-$C_7$)-cycloalkenyl groups, naphthalenyl groups and hydrogenated naphthalenyl groups, indenyl groups and hydrogenated indenyl groups, bicyclic heterocyclic groups, and bicycloalkyl, bicycloalkenyl and tricycloalkyl groups and hetero analogs thereof may be mentioned.

In a ($C_5$-$C_7$)-cycloalkenyl group representing $R^{24}$, the number of ring carbon atoms can be 5, 6 or 7. Examples of cycloalkenyl groups are cyclopentenyl including cyclopent-1-enyl, cyclopent-2-enyl and cyclopent-3-enyl, cyclohexyl including cyclohex-1-enyl, cyclohex-2-enyl and cyclohex-3-enyl, and cycloheptyl including cyclohept-1-enyl, cyclohept-2-enyl, cyclohept-3-enyl and cyclohept-4-enyl. Cycloalkenyl groups representing $R^{24}$ can be unsubstituted or substituted as indicated with respect to the 3-membered to 10-membered ring representing $R^{24}$, for example by one or more, or 1, 2, 3 or 4, or 1, 2 or 3, identical or different ($C_1$-$C_4$)-alkyl substituents, for example by methyl groups, which can be located in any positions. Examples of such alkyl-substituted cycloalkenyl groups are 1-methylcyclopent-2-enyl, 1-methylcyclopent-3-enyl, 2,3-dimethylcyclohex-2-enyl and 3,4-dimethylcyclohex-3-enyl. Cycloalkenyl groups also are optionally substituted by one or more fluorine substituents, i.e., they can be unsubstituted by fluorine and not carry any fluorine substituents, or substituted, for example by 1, 2, 3, 4, 5, 6 or 7, or by 1, 2, 3, 4 or 5, or by 1, 2, 3 or 4, fluorine substituents. Cycloalkenyl groups can also be substituted simultaneously by fluorine and alkyl. The fluorine atoms can be located in any positions of the cycloalkenyl group and can also be located in an alkyl substituent on the cycloalkenyl group. Examples of fluoro-substituted cycloalkyl groups are 1-fluorocyclohex-2-enyl, 1-fluorocyclohex-3-enyl and 4,4-difluorocyclohex-2-enyl.

Naphthalenyl groups (naphthyl groups) representing $R^{24}$ can be naphthalen-1-yl (1-naphthyl) and naphthalen-2-yl (2-naphthyl) groups, and are optionally substituted by one or more, for example by 1, 2, 3, 4 or 5, or by 1, 2 or 3, for example by 1 or 2, identical or different substituents as indicated above. The substituents in a substituted naphthalenyl group can be located in any positions, for example in the 2-position, 3-position, 4-position, 5-position, 6-position, 7-position or 8-position in the case of a monosubstituted naphthalen-1-yl group and in the 1-position, 3-position, 4-position, 5-position, 6-position, 7-position or 8-position in the case of a monosubstituted naphthalen-2-yl group. Likewise, in a naphthalenyl group which carries two or more substituents, the substituents can be located in the ring to which the remainder of the molecule is bonded, and/or in the other ring. Examples of hydrogenated naphthalenyl groups representing $R^{24}$ are dihydronaphthalenyl including 1,4-dihydronaphthalenyl, tetrahydronaphthalenyl including 1,2,3,4-tetrahydronaphthalenyl and 5,6,7,8-tetrahydronaphthalenyl, octahydronaphthalenyl including 1,2,3,4,5,6,7,8-octahydronaphthalenyl, and decahydronaphthalenyl. Hydrogenated naphthalenyl groups can be bonded to the remainder of the molecule via any ring carbon atom in a saturated or partially unsaturated or aromatic ring and are optionally substituted by one or more, for example by 1, 2, 3, 4 or 5, or by 1, 2 or 3, for example by 1 or 2, identical or different substituents as indicated above which can be located in any positions.

Indenyl groups representing $R^{24}$ can be 1H-inden-1-yl, 1H-inden-2-yl, 1H-inden-3-yl, 1H-inden-4-yl, 1H-inden-5-yl, 1H-inden-6-yl or 1H-inden-7-yl, for example, and are optionally substituted by one or more, for example by 1, 2, 3, 4 or 5, or by 1, 2 or 3, for example by 1 or 2, identical or different substituents as indicated above which can be located in any positions. Examples of hydrogenated indenyl groups representing $R^{24}$ are indanyl (2,3-dihydro-1H-indenyl) and octahydro-1H-indenyl, which can be bonded to the remainder of the molecule via any ring carbon atom in a saturated or partially unsaturated or aromatic ring, for example via the 1-position, 2-position, 4-position or 5-position in the case of an indanyl group, and are optionally substituted by one or more, for example by 1, 2, 3, 4 or 5, or by 1, 2 or 3, for example by 1 or 2, identical or different substituents as indicated above which can be located in any positions.

In one embodiment of the invention, bicyclic heterocyclic groups representing $R^{24}$ are fused bicyclic groups in which the two rings have a bond in common, and can be saturated, partially unsaturated or aromatic as indicated above with respect to the 3-membered to 10-membered ring representing $R^{24}$ in general. They can contain 1, 2, 3, 4 or 5 double bonds within the rings. Both of the rings can be saturated, or one of the rings can be saturated or partially unsaturated and the other ring partially unsaturated or aromatic, or both rings can be aromatic, i.e. comprise a cyclic system of six delocalized pi electrons. In one embodiment of the invention, both rings are aromatic or one of the rings is aromatic and the other ring is partially unsaturated and comprises at least one double bond due to the condensation to the aromatic ring. In one embodiment of the invention, a bicyclic heterocyclic group comprises 8, 9 or 10 ring members and two fused 5-membered rings or two fused 6-membered rings or a 6-membered ring fused to a 5-membered ring or a 7-membered ring fused to a 5-membered ring, in another embodiment 9 or 10 ring members and two fused 6-membered rings or a 6-membered ring fused to a 5-membered ring. Hetero ring members can be present in both rings of a bicyclic heterocyclic group or in one of the rings only and the other ring contain no hetero ring members. Ring nitrogen atoms can also be common to both rings. Besides being a hetero ring member in other 3-membered to 10-membered rings representing $R^{24}$ such as saturated rings, a ring nitrogen atom carrying a group $R^{32}$ can be the ring nitrogen atom in a fused 5-membered ring in an aromatic bicyclic heterocyclic group, such as in a fused pyrrole, pyrazole, imidazole or triazole, to which an exocyclic atom or group is bonded. Examples of rings from which a fused bicyclic heterocyclic group can be derived, are indole, isoindole, benzo[b]thiophene, benzofuran, benzo[1,3]dioxole ([1,3]benzodioxole, 1,2-methylenedioxybenzene), benzo[1,3]oxazole, benzo[1,3]thiazole, benzoimidazole, chromane, isochromane, benzo[1,4]dioxane ([1,4]benzodioxane, 1,2-ethylenedioxybenzene), quinoline, isoquinoline, cinnoline, quinazoline, quinoxaline, phthalazine, pyrroloazepines, imidazoazepines, thienothiophenes, thienopyrroles, thienopyridines, naphthyridines, and the respective rings in which one or some or all of the double bonds are hydrogenated, i.e. replaced with single bonds, such as 2,3-dihydro-1H-indole, 2,3-dihydro-1H-isoindole, 2,3-dihydrobenzofuran, 1,2,3,4-tetrahydroquinoline, 5,6,7,8-tetrahydroquinoline, decahydroquinoline, 1,2,3,4-tetrahydroisoquinoline, 5,6,7,8-tetrahydroisoquinoline, decahydroisoquinoline, for example. A bicyclic heterocyclic group can be bonded via any ring carbon atom or ring nitrogen atom. In one embodiment of the invention, a bicyclic heteroaromatic group is bonded via a ring carbon atom. For example, an indolyl group can be indol-1-yl, indol-2-yl, indol-3-yl, indol-4-yl, indol-5-yl, indol-6- or indol-7-yl, a benzoimidazolyl group can be 1H-benzoimidazol-1-yl, 1H-benzoimidazol-2-yl, 1H-benzoimidazol-4-yl, 1H-benzoimidazol-5-yl, 1H-benzoimidazol-6-yl or 1H-benzoimidazol-7-yl, a benzo[1,4]dioxanyl group can be benzo[1,4]dioxan-2-yl, benzo[1,4]dioxan-5-yl or benzo[1,4]dioxan-6-yl, a quinolinyl group (quinolyl group) can be quinolin-2-yl, quinolin-3-yl, quinolin-4-yl, quinolin-5-yl, quinolin-6-yl, quinolin-7-yl or quinolin-8-yl, an isoquinolinyl group can be isoquinolin-1-yl, isoquinolin-3-yl, isoquinolin-4-yl, isoquinolin-5-yl, isoquinolin-6-yl, isoquinolin-7-yl or isoquinolin-8-yl. In a substituted bicyclic heteroaromatic group, the substituents can be located in any desired positions such as, for example, in an indol-2-yl group in the 1-position and/or the 3-position and/or the 4-position and/or the 5-position and/or the 6-position and/or the 7-position, in an indol-5-yl group in the 1-position and/or the 2-position and/or the 3-position and/or the 4-position and/or the 6-position and/or the 7-position, in a 1H-benzoimidazol-2-yl group in the 1-position and/or the 4-position and/or the 5-position and/or the 6-position and/or the 7-position. Generally, besides the substituents indicated above, a bicyclic heterocyclic group can also carry on suitable ring nitrogen atoms in aromatic rings, for example the nitrogen atom in a quinolinyl group or isoquinolinyl group, an oxido substituent —O⁻ and be present as an N-oxide.

In one embodiment of the invention, bicycloalkyl, bicycloalkenyl and tricycloalkyl groups representing $R^{24}$ are bridged 6-membered to 10-membered, in another embodiment 7-membered to 10-membered, bicyclic and tricyclic groups which can contain carbon atoms only as ring members, i.e. they can be derived from carbocyclic bicycloalkanes, bicycloalkenes and tricycloalkanes, or which can also contain hetero ring members as indicated above, i.e. they can be derived from the respective heteroanalogous aza-, oxa- and thia-bicycloalkanes, -bicycloalkenes and -tricycloalkanes. If they contain hetero ring members, in one embodiment they contain one or two hetero ring members, in another embodiment one hetero ring member, for example ring members chosen from the series consisting of N, $N(R^{28})$ and O. The hetero ring members can be present in any desired positions in the bicyclic or tricyclic system including positions in the bridges and, in the case of nitrogen atoms, positions at the bridgeheads. Bicycloalkenyl and their hetero analogs can contain one or more double bonds within the rings. In one embodiment of the invention they contain one or two double bonds, in another embodiment one double bond, within the ring. Bicycloalkyl, bicycloalkenyl and tricycloalkyl can be bonded to the remainder of the molecule via any ring carbon atom or ring nitrogen atom. The free bond can be located in any stereochemical position, for example in an exo position or an endo position. Bicycloalkyl, bicycloalkenyl and tricycloalkyl and their hetero analogs are optionally substituted as indicated above, for example by substituents chosen from the series consisting of $(C_1-C_4)$-alkyl, $(C_2-C_5)$-alkenyl, HO—, HO—CH$_2$— (hydroxymethyl-) and oxo, in any positions. Examples of bicycloalkyl, bicycloalkenyl and tricycloalkyl groups and hetero analogs thereof are norbornyl (bicyclo[2.2.1]heptyl), bicyclo[3.1.1]heptyl, bicyclo[3.1.1]hept-2-enyl, bicyclo[2.2.2]octyl, bicyclo[2.2.2]oct-2-enyl, bicyclo[3.2.1]octyl, 7-azabicyclo[2.2.1]heptyl, 1-azabicyclo[2.2.2]octyl, bicyclo[2.2.2.]oct-2-en-yl, tricyclo[4.4.0.0$^{3,8}$]decyl), adamantyl (tricyclo[3.3.1.1$^{3,7}$]decyl), noradamantyl (tricyclo[3.3.1.0$^{3,7}$]nonyl), tricyclo[2.2.1.0$^{2,6}$]heptyl.

Halogen is fluorine, chlorine, bromine or iodine. In one embodiment of the invention, halogen is fluorine, chlorine or bromine, in another embodiment fluorine or chlorine.

An oxo group, i.e. a doubly bonded oxygen atom, when bonded to a carbon atom, replaces two hydrogen atoms on a carbon atom of the parent system. Thus, if a CH$_2$ group is substituted by oxo, it becomes a carbonyl group (C(O), C=O). An oxo group cannot occur as a substituent on a carbon atom in an aromatic ring such as in a phenyl group.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups, can all independently of each other have the S configuration or the R configuration. The invention relates to enantiomers, both the levorotatory and the dextrorotatory antipode, in enantiomerically pure form and essentially enantiomerically pure form and in the form of racemates and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form and in the form of mixtures of the cis isomer and the trans isomer in all ratios. Cis/trans isomerism can occur in substituted rings and on double bonds, for example. The preparation of individual stereoisomers, if desired, can be carried out by resolution of a mixture according to customary methods, for example, by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts, including pharmaceutically utilizable salts, of the compounds of the formula I generally comprise a nontoxic salt component. They can contain inorganic or organic salt components. Such salts can be formed, for example, from compounds of the formula I which contain an acidic group, for example a carboxylic acid group (hydroxycarbonyl group, HO—C(O)—), and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formula I with bases for the preparation of the salts are in general carried out according to customary procedures in a solvent or diluent. Examples of salts of acidic groups thus are sodium, potassium, magnesium or calcium salts or ammonium salts which can also carry one or more organic groups on the nitrogen atom. Compounds of the formula I which contain a basic, i.e. protonatable, group, for example an amino group or a basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formula I by reaction with an acid in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange. The present invention also comprises all solvates of the compounds of the formula I and their salts, including physiologically acceptable solvates, such as hydrates, i.e. adducts with water, and adducts with alcohols like ($C_1$-$C_4$)-alkanols, as well as active metabolites of compounds of the formula I and prodrugs of the compounds of the formula I, i.e. compounds which in vitro may not necessarily exhibit pharmacological activity but which in vivo are converted into pharmacologically active compounds of the formula I, for example compounds which are converted by metabolic hydrolysis into a compound of the formula I, such as compounds in which a carboxylic acid group is present in esterified form or in the form of an amide.

As indicated above, the hetero ring members in the ring A, which ring includes the two carbon atoms which also are part of the fused 5-membered ring depicted in formula I carrying the groups $R^3$ to $R^6$, can be present in any combination and can be located in any suitable position. For example, in the case of a pyridine ring or a thiophene representing A, the ring nitrogen atom or sulfur atom can be present in a position which is adjacent to the said 5-membered ring, or in a position which is not adjacent to the said 5-membered ring. In case the ring A is a 6-membered heterocyclic ring which comprises two hetero ring members N, for example, both hetero ring members can be present in the two positions adjacent to the said 5-membered ring and the 6-membered ring be a pyrazine ring, or one of them can be present in a position adjacent to the said 5-membered ring and the other in a non-adjacent position and the 6-membered ring be a pyrimidine ring or a pyridazine ring, or both hetero ring members can be present in non-adjacent positions and the 6-membered ring be a pyridazine ring. In one embodiment of the invention, the hetero ring members in a heterocyclic ring representing A are chosen from N and S, in another embodiment they are N. In one embodiment of the invention, a cycloalkane ring representing A is 5-membered, 6-membered or 7-membered, in another embodiment 5-membered or 6-membered, in another embodiment 6-membered, and the cycloalkane ring thus is a cyclopentane, cyclohexane or cycloheptane ring which can all be substituted as indicated. In one embodiment of the invention the ring A is a cyclohexane ring, a benzene ring, a pyridine ring, a pyrazine ring or a monocyclic 5-membered aromatic heterocyclic ring comprising 1 or 2 identical or different hetero ring members chosen from the series consisting of N, N($R^1$), O and S, for example 1 hetero ring member chosen from the series consisting of N($R^1$), O and S, such as a thiophene ring, which rings can all be optionally substituted as indicated. In another embodiment the ring A is a benzene ring, a pyridine ring, a pyrazine ring or a monocyclic 5-membered aromatic heterocyclic ring comprising 1 or 2 identical or different hetero ring members chosen from the series consisting of N, N($R^1$), O and S, for example 1 hetero ring member chosen from the series consisting of N($R^1$), O and S, such as a thiophene ring, which rings can all be optionally substituted as indicated. In another embodiment the ring A is a benzene ring or a monocyclic 5-membered aromatic heterocyclic ring comprising 1 or 2 identical or different hetero ring members chosen from the series consisting of N, N($R^1$), O and S, for example 1 hetero ring member chosen from the series consisting of N($R^1$), O and S, such as a thiophene ring, which rings can all be optionally substituted as indicated. In another embodiment the ring A is a benzene ring, a pyrazine ring or a thiophene ring, in another embodiment a benzene ring or a thiophene ring, which rings can all be optionally substituted as indicated. In another embodiment of the invention, the ring A is a benzene ring which is optionally substituted as indicated. In another embodiment of the invention, the ring A is a cycloalkane ring which is optionally substituted as indicated.

The number of the substituents which can optionally be present on the ring A, depends on the size and the kind of the ring A and the number of hetero ring members. In one embodiment of the invention the number of optional substituents is 1, 2, 3 or 4, in another embodiment 1, 2 or 3, in another embodiment 1 or 2, in another embodiment 1. For example, in the case of a benzene ring representing A, which ring can be unsubstituted or substituted, the number of optional substituents can be 1, 2, 3 or 4, or 1, 2 or 3, or 1 or 2, for example 1. In the case of a pyridine ring, the number of optional substituents can be 1, 2 or 3, or 1 or 2, for example 1, in the case of a pyrazine ring, it can be 1 or 2, for example 1, in the case of a thiophene ring it can be 1 or 2, for example 1, in the case of a thiazole ring it can be 1. In one embodiment of the invention, a cycloalkane ring representing A is not substituted by any substituents. In another embodiment of the invention the ring A is not substituted by any substituents and the ring carbon atoms thus carry hydrogen atoms. Substituents on the ring A can be present in any suitable position. In one embodiment of the invention, in compounds of the formula I in which the ring A is an optionally substituted benzene ring, the substituents which are optionally present in positions 5 and 6 of the indane ring comprising the said benzene ring representing A, are chosen from the series consisting of halogen, $R^1$, HO—, $R^1$—O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, H$_2$N—C(O)—, $R^1$—NH—C(O)—, $R^1$—N($R^1$)—C(O)—, H$_2$N—S(O)$_2$—, $R^1$—NH—S(O)$_2$—, $R^1$—N($R^1$)—S(O)$_2$—, NC— and O$_2$N—. In another embodiment of the invention, in compounds of the formula I in which the ring A is an optionally substituted benzene ring, the substituents which are optionally present in the ring A are chosen from the series consisting of halogen, $R^1$, HO—, $R^1$—O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, H$_2$N—C(O)—, $R^1$—NH—C(O)—, $R^1$—N($R^1$)—C(O)—, H$_2$N—S(O)$_2$—, $R^1$—NH—S(O)$_2$—, $R^1$—N($R^1$)—S(O)$_2$—, NC— and O$_2$N—. In another embodiment of the invention, the substituents in a benzene ring or a heterocyclic ring representing A are chosen from the series consisting of halogen, $R^1$, HO—, $R^1$—O—, $R^1$—O(O)—O—, $R^1$—S(O)$_2$—O—, $R^1$, —S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, H$_2$N—C(O)—, $R^1$—NH—C(O)—, $R^1$—N($R^1$)—C(O)—, H$_2$N—S(O)$_2$—, $R^1$—NH—S(O)$_2$—, $R^1$—N($R^1$)—S(O)$_2$—, NC— and O$_2$N—, in another embodiment from the series consisting of halogen, $R^1$, HO—, $R^1$—O—, $R^1$—O(O)—O—, $R^1$—S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, NC— and O$_2$N—, in another embodiment from the series consisting of halogen, $R^1$, $R^1$—O—, $R^1$—S(O)$_m$—, NC— and O$_2$N—, for example from the series consisting of halogen, (C$_1$—O$_4$)-alkyl, (C$_1$-C$_4$)-alkyl-O—, (C$_1$-C$_4$)-alkyl-S(O)$_m$—, NC— and O$_2$N—, in another embodiment from the series consisting of halogen, $R^1$, $R^1$—O—, $R^1$—S(O)$_m$— and NC—, for example from the series consisting of halogen, (C$_1$-C$_4$)-alkyl, (C$_1$-C$_4$)-alkyl-O—, (C$_1$—O$_4$)-alkyl-S(O)$_m$— and NC—, in another embodiment from the series consisting of halogen, $R^1$, $R^1$—O— and NC—, for example from the series consisting of halogen, (C$_1$-C$_4$)-alkyl, (C$_1$-C$_4$)-alkyl-O— and NC—, in another embodiment from the series consisting of halogen, $R^1$ and $R^1$—O—, for example from the series consisting of halogen, (C$_1$-C$_4$)-alkyl and (C$_1$-C$_4$)-alkyl-O—. In one embodiment of the invention the substituents in a benzene ring or a heterocyclic ring representing A are chosen from the series consisting of halogen and (C$_1$-C$_4$)-alkyl. In one embodiment of the invention, the number of nitro substituents (C$_2$N—) on the ring A is not greater than two, in another embodiment not greater than one. In one embodiment of the invention, the total number of nitro groups in a compound of the formula I is not greater than two.

In case the ring A is a benzene ring, the compounds of the formula I can also be represented by the formula Ia,

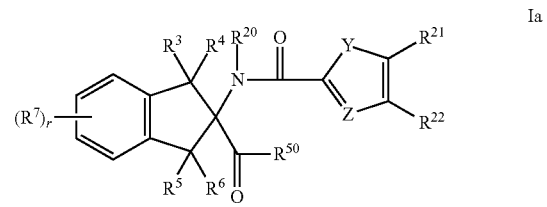

Ia wherein Y, Z, $R^3$ to $R^6$, $R^{20}$ to $R^{22}$ and $R^{50}$ are defined as in the compounds of the formula I, $R^7$ is defined as the substituents which are optionally present in a benzene ring representing the ring A in the compounds of the formula I, i.e. $R^7$ is chosen from the series consisting of halogen, $R^1$, HO—, $R^1$—O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, H$_2$N—C(O)—, $R^1$—NH—C(O)—, $R^1$—N($R^1$)—C(O)—, H$_2$N—S(O)$_2$—, $R^1$—NH—S(O)$_2$—, $R^1$—N($R^1$)—S(O)$_2$—, NC—, O$_2$N—, phenyl and Het, or from any of the other series of substituents indicated herein, for example from the series consisting of halogen, (C$_1$-C$_4$)-alkyl, (C$_1$-C$_4$)-alkyl-O—, (C$_1$-C$_4$)-alkyl-S(O)$_m$— and NC—, or from the series consisting of halogen and (C$_1$-C$_4$)-alkyl, and the number r is 0, 1, 2, 3 or 4, or is 0, 1, 2 or 3, or is 0, 1 or 2, or is 0 or 1. In one embodiment of the invention, the number r in the compounds of the formula Ia is 0, i.e. the benzene ring depicted in formula Ia does not carry a substituent $R^7$. The substituents $R^7$ can be present on any of the four carbon atoms of the benzene ring depicted in formula Ia which are not part of the fused 5-membered ring carrying the groups $R^3$ to $R^6$. All other such carbon atoms of the benzene ring which do not carry a substituent $R^7$, carry hydrogen atoms. I.e., in case the number r is 0, for example, the benzene ring carries four hydrogen atoms.

In a similar manner, in case the ring A is a pyridine ring, a pyridazine ring, a thiophene ring, or a cyclohexane ring, for example, the compounds of the formula I can be represented by the formulae Ib-1, Ib-2, Ic, Id-1, Id-2 and Ie,

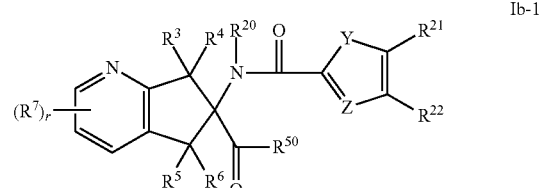

Ib-1

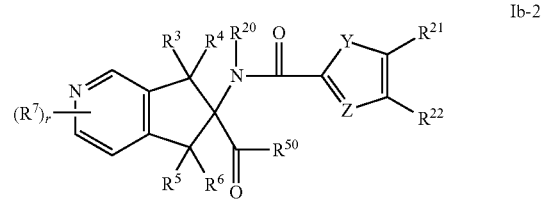

Ib-2

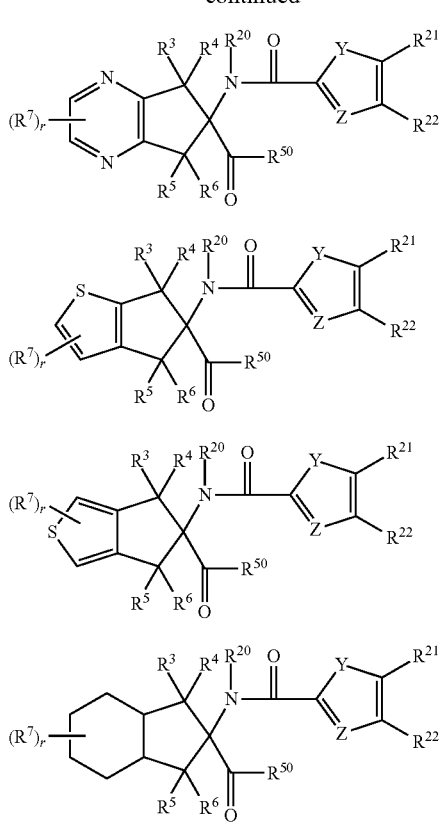

wherein Y, Z, $R^3$ to $R^6$, $R^{20}$ to $R^{22}$ and $R^{50}$ are defined as in the compounds of the formula I, $R^7$ is defined as the substituents which are optionally present in the ring A in the compounds of the formula I, i.e. in the case of the compounds of the formulae Ib-1, Ib-2, Ic, Id-1 and Id-2 $R^7$ is chosen from the series consisting of halogen, $R^1$, HO—, $R^1$—O—, $R^1$—C(O)—O—, $R^1$—S(O)$_2$—O—, $R^1$—S(O)$_m$—, $H_2N$—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, $H_2N$—C(O)—, $R^1$—NH—C(O)—, $R^1$—N($R^1$)—C(O)—, $H_2N$—S(O)$_2$—, $R^1$—NH—S(O)$_2$—, $R^1$—N($R^1$)—S(O)$_2$—, NC—, $O_2N$—, phenyl and Het, or from any of the other series of substituents indicated herein, for example from the series consisting of halogen, ($C_1$-$C_4$)-alkyl, ($C_1$-$C_4$)-alkyl-O—, ($C_1$-$C_4$)-alkyl-S(O)$_m$— and NC—, or from the series consisting of halogen and ($C_1$-$C_4$)-alkyl, and in the case of the compounds of the formula Ie $R^7$ is chosen from the series consisting of fluorine and ($C_1$-$C_4$)-alkyl, and the number r is 0, 1, 2 or 3, or is 0, 1 or 2, or is 0 or 1, in the case of the compounds of the formulae Ib-1 and Ib-2, and is or 0, 1 or 2, or is 0 or 1, in the case of the compounds of the formulae Ic, Id-1 and Id-2, and is 0, 1, 2, 3, 4, 5, 6, 7 or 8, or is 0, 1, 2, 3 or 4, or is 0, 1 or 2, for example, in the case of the compounds of the formula Ie. In one embodiment of the invention, the number r in the compounds of the formulae Ib-1, Ib-2, Ic, Id-1, Id-2 and Ie is 0, i.e. the pyridine ring, pyridazine ring, thiophene ring and cyclohexane ring depicted in the formulae do not carry a substituent $R^7$. The substituents $R^7$ can be present on any ring carbon atoms, in particular ring carbon atoms which are not part of the fused 5-membered ring carrying the groups $R^3$ to $R^6$. In positions on ring carbon atoms in which no substituent $R^7$ is present, hydrogen atoms are present.

In the group C($R^{12}$)=C($R^{13}$) representing the divalent group Y, the carbon atom carrying the group $R^{13}$ is bonded to the ring carbon atom carrying the group $R^{21}$ and the carbon atom carrying the group $R^{12}$ is bonded to the ring carbon atom carrying the group C(O)—N($R^{20}$). In the group N=C($R^{14}$), the carbon atom carrying the group $R^{14}$ is bonded to the ring carbon atom carrying the group $R^{21}$ and the nitrogen atom is bonded to the ring carbon atom carrying the group C(O)—N($R^{20}$). In the group C($R^{15}$)=N, the nitrogen atom is bonded to the ring carbon atom carrying the group $R^{21}$ and the carbon atom carrying the group $R^{15}$ is bonded to the ring carbon atom carrying the group C(O)—N($R^{20}$). In one embodiment of the invention, Y is chosen from the series consisting S, C($R^{12}$)=C($R^{13}$), N=C($R^{14}$) and C($R^{15}$)=N, in another embodiment from the series consisting S, C($R^{12}$)=C($R^{13}$) and C($R^{15}$)=N. In one embodiment of the invention Y is chosen from the series consisting of S and C($R^{12}$)=C($R^{13}$), in another embodiment from the series consisting of C($R^{12}$)=C($R^{13}$) and C($R^{15}$)=N. In another embodiment of the invention, Y is C($R^{12}$)=C($R^{13}$). In another embodiment of the invention, Y is C($R^{15}$)=N.

In one embodiment of the invention, the trivalent group Z is C($R^{16}$). In another embodiment Z is C($R^{16}$) and Y is chosen from the series consisting of S, C($R^{12}$)=C($R^{13}$) and C($R^{15}$)=N. In another embodiment Z is C($R^{16}$) and Y is chosen from the series consisting of S and C($R^{12}$)=C($R^{13}$). In another embodiment Z is C($R^{16}$) and Y is chosen from the series consisting of C($R^{15}$)=N and C($R^{12}$)=C($R^{13}$). In this latter embodiment, the aromatic ring in the compounds of the formula I comprising the ring members Y and Z is a pyridine ring or a benzene ring, respectively, and the compounds of the formula I are compounds of the formula If or of the formula Ig,

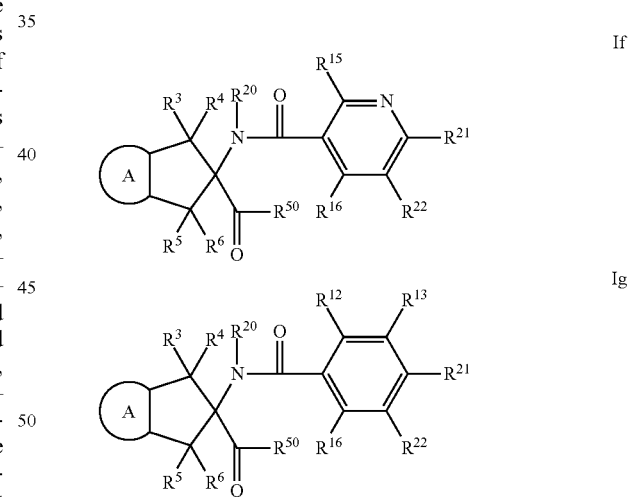

wherein A, $R^3$ to $R^6$, $R^{12}$, $R^{13}$, $R^{15}$, $R^{16}$, $R^{20}$ to $R^{22}$ and $R^{50}$ are defined as in the compounds of the formula I or have any of their other indicated meanings. In one embodiment of the invention the group Z is C($R^{16}$) and the group Y is S. In another embodiment of the invention the group Z is C($R^{16}$) and the group Y is C($R^{15}$)=N. In another embodiment of the invention the group Z is C($R^{16}$) and the group Y is C($R^{12}$)=C($R^{13}$), i.e., in this embodiment the compounds of the formula I are compounds of the formula Ig. In another embodiment of the invention, in the compounds of the formula Ia the group Z is C($R^{16}$) and the group Y is C($R^{12}$)=C($R^{13}$), i.e., compounds of this embodiment are compounds of the formula Ih,

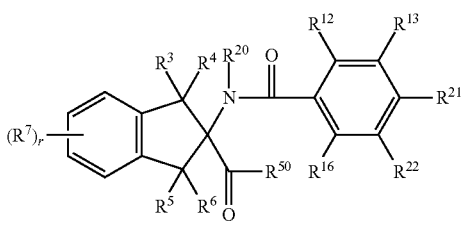

Ih wherein $R^3$ to $R^6$, $R^{12}$, $R^{13}$, $R^{16}$, $R^{20}$ to $R^{22}$ and $R^{50}$ are defined as in the compounds of the formula I or have any of their other indicated meanings. $R^7$ and r in the compounds of the formula Ih are defined as in the compounds of the formula Ia and, like in the compounds of the formula Ia, the substituents $R^7$ can be present on any of the four carbon atoms of the fused benzene ring depicted in formula Ih which are not part of the fused 5-membered ring carrying the groups $R^3$ to $R^6$, and all other such carbon atoms of the benzene ring which do not carry a substituent $R^7$ carry hydrogen atoms. All explanations on groups and all definitions and embodiments specified above or below with respect to the compounds of the formula I apply correspondingly to the compounds of all formulae which represent subgroups of the compounds of the formula I, including the compounds of the formulae Ia to Ih.

In one embodiment of the invention, $R^0$ is chosen from the series consisting of hydrogen and $(C_1-C_4)$-alkyl, in another embodiment from the series consisting of hydrogen and methyl. In one embodiment of the invention, $R^0$ is hydrogen. In another embodiment of the invention $R^0$ is $(C_1-C_4)$-alkyl, for example methyl.

In one embodiment of the invention, $R^1$, $R^2$, $R^{11}$, $R^{30}$, $R^{33}$, $R^{35}$, $R^{54}$, $R^{55}$, $R^{57}$ and $R^{58}$ are, independently of each other group $R^1$, $R^2$, $R^{11}$, $R^{30}$, $R^{33}$, $R^{35}$, $R^{54}$, $R^{55}$, $R^{57}$ and $R^{58}$, chosen from the series consisting of $(C_1-C_6)$-alkyl, $(C_2-C_4)$-alkenyl, $(C_2-C_4)$-alkynyl, $(C_3-C_7)$-cycloalkyl and $(C_3-C_7)$-cycloalkyl-$(C_1-C_2)$-alkyl-, in another embodiment from the series consisting of $(C_1-C_4)$-alkyl, $(C_2-C_4)$-alkenyl, $(C_2-C_4)$-alkynyl, $(C_3-C_7)$-cycloalkyl and $(C_3-C_7)$-cycloalkyl-$(C_1-C_2)$-alkyl-, in another embodiment from the series consisting of $(C_1-C_6)$-alkyl, $(C_3-C_7)$-cycloalkyl and $(C_3-C_7)$-cycloalkyl-$(C_1-C_2)$-alkyl-, in another embodiment from the series consisting of $(C_1-C_4)$-alkyl, $(C_3-C_7)$-cycloalkyl and $(C_3-C_7)$-cycloalkyl-$(C_1-C_2)$-alkyl-, in another embodiment from the series consisting of $(C_1-C_6)$-alkyl, $(C_3-C_7)$-cycloalkyl and $(C_3-C_7)$-cycloalkyl-$CH_2$-alkyl-, in another embodiment from the series consisting of $(C_1-C_6)$-alkyl and $(C_3-C_7)$-cycloalkyl, in another embodiment from the series consisting of $(C_1-C_4)$-alkyl and $(C_3-C_7)$-cycloalkyl, which are all optionally substituted by one or more identical or different substituents $R^{70}$, wherein in these groups besides any substituents $R^{70}$ one or more fluorine substituents are optionally present and in cycloalkyl groups one or more $(C_1-C_4)$-alkyl substituents are optionally present as applies to alkyl, alkenyl, alkynyl and cycloalkyl groups in general. In one embodiment of the invention $R^1$, $R^2$, $R^{11}$, $R^{30}$, $R^{33}$, $R^{35}$, $R^{54}$, $R^{55}$, $R^{57}$ and $R^{58}$ are, independently of each other group $R^1$, $R^2$, $R^{11}$, $R^{30}$, $R^{33}$, $R^{35}$, $R^{54}$, $R^{55}$, $R^{57}$ and $R^{58}$ are, independently of series consisting of $(C_1-C_6)$-alkyl, in another embodiment from the series consisting of $(C_1-C_4)$-alkyl, which are all optionally substituted by one or more identical or different substituents $R^{70}$. In one embodiment of the invention, $(C_3-C_7)$-cycloalkyl groups occurring in $R^1$, $R^2$, $R^{11}$, $R^{30}$, $R^{33}$, $R^{35}$, $R^{54}$, $R^{55}$, $R^{57}$ and $R^{58}$ are, independently of each other group $R^1$, $R^2$, $R^{11}$, $R^{30}$, $R^{33}$, $R^{35}$, $R^{54}$, $R^{55}$, $R^{57}$ and $R^{58}$, $(C_3-C_6)$-cycloalkyl, in another embodiment $(C_3-C_4)$-cycloalkyl, for example cyclopropyl, in another embodiment $(C_5-C_6)$-cycloalkyl, for example cyclohexyl. In one embodiment of the invention, the number of substituents $R^{70}$ in any of the groups $R^1$, $R^2$, $R^{11}$, $R^{30}$, $R^{33}$, $R^{35}$, $R^{54}$, $R^{55}$, $R^{57}$ and $R^{58}$ is, independently of each other group $R^1$, $R^2$, $R^{11}$, $R^{30}$, $R^{33}$, $R^{35}$, $R^{54}$, $R^{55}$, $R^{57}$ and $R^{58}$, 0, 1, 2, 3 or 4, in another embodiment 0, 1, 2 or 3, in another embodiment 0, 1 or 2, in another embodiment 0 or 1. In one embodiment of the invention, any of the groups $R^1$, $R^2$, $R^{11}$, $R^{30}$, $R^{33}$, $R^{35}$, $R^{54}$, $R^{55}$, $R^{57}$ and $R^{58}$, independently of each other group $R^1$, $R^2$, $R^{11}$, $R^{30}$, $R^{33}$, $R^{35}$, $R^{54}$, $R^{55}$, $R^{57}$ and $R^{58}$, does not carry a substituent $R^{70}$, but merely is optionally substituted by one or more fluorine substituents and, in the case of cycloalkyl groups, one or more $(C_1-C_4)$-alkyl substituents. In another embodiment of the invention, any of the groups $R^1$, $R^2$, $R^{11}$, $R^{30}$, $R^{33}$, $R^{35}$, $R^{54}$, $R^{55}$, $R^{57}$ and $R^{58}$, independently of each other group $R^1$, $R^2$, $R^{11}$, $R^{30}$, $R^{33}$, $R^{35}$, $R^{54}$, $R^{55}$, $R^{57}$ and $R^{58}$, does neither carry a substituent $R^{70}$ nor fluorine substituents nor, in the case of cycloalkyl groups, $(C_1-C_4)$-alkyl substituents.

In one embodiment of the invention, a phenyl-$(C_1-C_4)$-alkyl- group representing $R^3$ or $R^5$ is a benzyl group wherein the phenyl moiety is optionally substituted as indicated with respect to phenyl groups in general. In one embodiment of the invention, one of the groups $R^3$ and $R^5$ is chosen from the series consisting of hydrogen, $(C_1-C_4)$-alkyl, phenyl-$(C_1-C_4)$-alkyl-, phenyl and hydroxy and the other of the groups $R^3$ and $R^5$ is chosen from the series consisting of hydrogen, $(C_1-C_4)$-alkyl, phenyl-$(C_1-C_4)$-alkyl- and phenyl. In one embodiment of the invention, the groups $R^3$ and $R^5$ are independently of each other chosen from the series consisting of hydrogen, $(C_1-C_4)$-alkyl, phenyl-$(C_1-C_4)$-alkyl- and phenyl. In another embodiment, $R^3$ and $R^5$ are independently of each other chosen from the series consisting of hydrogen and $(C_1-C_4)$-alkyl, in another embodiment from the series consisting of hydrogen and methyl. In another embodiment, $R^3$ and $R^5$ are hydrogen.

In one embodiment of the invention, $R^4$ and $R^6$ are independently of each other chosen from the series consisting of hydrogen and methyl. In another embodiment, $R^4$ and $R^6$ are hydrogen.

In one embodiment of the invention, $R^3$ and $R^4$ are identical and are chosen from the series consisting of hydrogen and methyl, in another embodiment they both are hydrogen. In another embodiment, $R^5$ and $R^6$ are identical and are chosen from the series consisting of hydrogen and methyl, and in another embodiment they both are hydrogen. In another embodiment $R^3$, $R^4$, $R^5$ and $R^6$ are all identical and are chosen from the series consisting of hydrogen and methyl. In another embodiment $R^3$, $R^4$, $R^5$ and $R^6$ all are hydrogen.

In one embodiment of the invention, $R^{10}$ is chosen from the series consisting of hydrogen and methyl. In another embodiment $R^{10}$ is hydrogen. In another embodiment of the invention $R^{10}$ is $(C_1-C_4)$-alkyl, for example methyl.

In one embodiment of the invention, $R^{12}$, $R^{13}$, $R^{14}$, $R^{15}$ and $R^{16}$ are independently of each other chosen from the series consisting of hydrogen, halogen, $(C_1-C_4)$-alkyl, $(C_1-C_4)$-alkyl-O—, $(C_1-C_4)$-alkyl-S(O)$_m$—, $H_2N$—, $(C_1-C_4)$-alkyl-NH—, $(C_1-C_4)$-alkyl-N($(C_1-C_4)$-alkyl)-, NC— and $O_2N$—, in another embodiment from the series consisting of hydrogen, halogen, $(C_1-C_4)$-alkyl, $(C_1-C_4)$-alkyl-O—, NC— and $O_2N$—, in another embodiment from the series consisting of hydrogen, halogen, $(C_1-C_4)$-alkyl, $(C_1-C_4)$-alkyl-O— and $O_2N$—, in another embodiment from the series consisting of hydrogen, halogen, $(C_1-C_4)$-alkyl, $(C_1-C_4)$-alkyl-O— and NC—, in another embodiment from the series consisting of hydrogen, halogen, $(C_1-C_4)$-alkyl and $(C_1-C_4)$-alkyl-O—, in another embodiment from the series consisting of hydrogen, halogen and $(C_1-C_4)$-alkyl. In one embodiment of the invention, $R^{12}$ and $R^{13}$ are independently of each other chosen from the series consisting of hydrogen, halogen, $(C_1-C_4)$-alkyl, $(C_1-C_4)$-alkyl-O— and NC—, in another embodiment from the series consisting of hydrogen, halogen, $(C_1-C_4)$-alkyl and NC—, in another embodiment from the series consisting of hydrogen, halogen and NC—, in another embodiment from the series consisting of hydrogen and halogen, in another embodiment from the series consisting of hydrogen, chlorine and fluorine, in another embodiment from the series consisting of hydrogen and fluorine. In one embodiment of the invention, $R^{12}$ is hydrogen and $R^{13}$ is fluorine or $R^{12}$ is fluorine and $R^{13}$ is hydrogen. In another embodiment $R^{12}$ and $R^{13}$ are hydrogen. In one embodiment of the invention, $R^{14}$ and $R^{15}$ are independently of each other chosen from the series consisting of hydrogen, halogen, $(C_1-C_4)$-alkyl and $(C_1-C_4)$-alkyl-O—, in another embodiment from the series consisting of hydrogen, halogen and $(C_1-C_4)$-alkyl, in another embodiment from the series consisting of hydrogen and halogen, in another embodiment from the series consisting of hydrogen, chlorine and fluorine. In another embodiment of the invention, $R^{14}$ and $R^{15}$ are hydrogen. In one embodiment of the invention, $R^{16}$ is chosen from the series consisting of hydrogen, halogen, $(C_1-C_4)$-alkyl and $(C_1-C_4)$-alkyl-O—, in another embodiment from the series consisting of hydrogen, halogen and $(C_1-C_4)$-alkyl, in another embodiment from the series consisting of hydrogen and halogen, in another embodiment from the series consisting of hydrogen, chlorine and fluorine. In another embodiment of the invention, $R^{16}$ is hydrogen.

In one embodiment of the invention, $R^{20}$ is chosen from the series consisting of hydrogen and methyl. In another embodiment $R^{20}$ is hydrogen. In another embodiment $R^{20}$ is $(C_1-C_4)$-alkyl, for example methyl.

In one embodiment of the invention the group $R^{21}$ is a group of the formula II, i.e. of the formula $R^{24}-R^{23}$-, which is bonded to the remainder of the molecule through the moiety $R^{23}$ as is symbolized with respect to this group and in general by a terminal hyphen representing the free bond, and the group $R^{22}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, H$_2$N—, $R^{30}$—NH—, $R^{30}$—N(R$^{30}$)—, $R^{30}$—C(O)—NH—, $R^{30}$—C(O)—N(R$^{71}$)—, $R^{30}$—S(O)$_2$—NH—, $R^{30}$—S(O)$_2$—N(R$^{71}$)—, $R^{30}$—C(O)—, HO—C(O)—, $R^{30}$—O—C(O)—, H$_2$N—C(O)—, $R^{30}$—NH—C(O)—, $R^{30}$—N(R$^{30}$)—C(O)—, H$_2$N—S(O)$_2$—, $R^{30}$—NH—S(O)$_2$—, $R^{30}$—N(R$^{30}$)—S(O)$_2$—, NC—, O$_2$N— and Het$^1$. In another embodiment, the group $R^{22}$ is a group of the formula II and the group $R^{21}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, H$_2$N—, $R^{30}$—NH—, $R^{30}$—N(R$^{30}$)—, $R^{30}$—C(O)—NH—, $R^{30}$—C(O)—N(R$^{71}$)—, $R^{30}$—S(O)$_2$—NH—, $R^{30}$—S(O)$_2$—N(R$^{71}$)—, $R^{30}$—C(O)—, HO—C(O)—, $R^{30}$—O—C(O)—, H$_2$N—C(O)—, $R^{30}$—NH—C(O)—, $R^{30}$—N(R$^{30}$)—C(O)—, H$_2$N—S(O)$_2$—, $R^{30}$—NH—S(O)$_2$—, $R^{30}$—N(R$^{30}$)—S(O)$_2$—, NC—, O$_2$N— and Het$^1$.

In one embodiment of the invention, the one of the groups $R^{21}$ and $R^{22}$ which is not a group of the formula II, is chosen from the series consisting of hydrogen, halogen, $R^{30}$, $R^{30}$—O—, $R^{30}$—C(O)—O—, $R^{30}$—S(O)$_m$—, H$_2$N—, $R^{30}$—NH—, $R^{30}$—N(R$^{30}$)—, $R^{30}$—C(O)—NH—, $R^{30}$—C(O)— and NC—, in another embodiment from the series consisting of hydrogen, halogen, $(C_1-C_4)$-alkyl, HO—$(C_1-C_4)$-alkyl-, $(C_1-C_4)$-alkyl-O—, $(C_1-C_4)$-alkyl-S(O)$_m$—, $(C_1-C_4)$-alkyl-NH—, di(($C_1-C_4$)-alkyl)N—, $(C_1-C_4)$-alkyl-C(O)— and NC—, in another embodiment from the series consisting of hydrogen, halogen, $(C_1-C_4)$-alkyl, HO—$(C_1-C_4)$-alkyl-, $(C_1-C_4)$-alkyl-O—, $(C_1-C_4)$-alkyl-S(O)$_m$—, $(C_1-C_4)$-alkyl-C(O)— and NC—, in another embodiment from the series consisting of halogen, $(C_1-C_4)$-alkyl, HO—$(C_1-C_4)$-alkyl-, $(C_1-C_4)$-alkyl-O—, $(C_1-C_4)$-alkyl-S(O)$_m$—, H$_2$N—, $(C_1-C_4)$-alkyl-NH—, di(($C_1-C_4$)-alkyl)N—, $(C_1-C_4)$-alkyl-C(O)— and NC—, in another embodiment from the series consisting of $(C_1-C_4)$-alkyl, HO—$(C_1-C_4)$-alkyl-, $(C_1-C_4)$-alkyl-O—, $(C_1-C_4)$-alkyl-S(O)$_m$—, H$_2$N—, $(C_1-C_4)$-alkyl-NH—, di(($C_1-C_4$)-alkyl)N—, $(C_1-C_4)$-alkyl-C(O)— and NC—, in another embodiment from the series consisting of $(C_1-C_4)$-alkyl, HO—$(C_1-C_4)$-alkyl-, $(C_1-C_4)$-alkyl-O—, $(C_1-C_4)$-alkyl-S(O)$_m$—, $(C_1-C_4)$-alkyl-NH—, di(($C_1-C_4$)-alkyl)N— and $(C_1-C_4)$-alkyl-C(O)—. In one embodiment of the invention, the one of the groups $R^{21}$ and $R^{22}$ which is not a group of the formula II, is chosen from the series consisting of $(C_1-C_4)$-alkyl, $(C_1-C_4)$-alkyl-O—, $(C_1-C_4)$-alkyl-S(O)$_m$—, $(C_1-C_4)$-alkyl-NH— and di(($C_1-C_4$)-alkyl)N—, in another embodiment from the series consisting of $(C_1-C_4)$-alkyl, $(C_1-C_4)$-alkyl-O— and $(C_1-C_4)$-alkyl-S(O)$_m$—, in another embodiment from the series consisting of $(C_1-C_4)$-alkyl-O— and $(C_1-C_4)$-alkyl-S(O)$_m$—. In another embodiment, the one of the groups $R^{21}$ and $R^{22}$ which is not a group of the formula II, is chosen from the series consisting of $(C_1-C_4)$-alkyl, HO—$(C_1-C_4)$-alkyl-, $(C_1-C_4)$-alkyl-O— and $(C_1-C_4)$-alkyl-C(O)—, in another embodiment from the series consisting of $(C_1-C_4)$-alkyl, HO—$(C_1-C_4)$-alkyl- and $(C_1-C_4)$-alkyl-O—, in another embodiment from the series consisting of $(C_1-C_4)$-alkyl and $(C_1-C_4)$-alkyl-O—. In another embodiment, the one of the groups $R^{21}$ and $R^{22}$ which is not a group of the formula II, is $(C_1-C_4)$-alkyl-O—, for example methoxy or ethoxy.

In one embodiment of the invention, in case the group $R^{21}$ is a group of the formula II, the group $R^{22}$ is chosen from the series consisting of $(C_1-C_4)$-alkyl and $(C_1-C_4)$-alkyl-O—, and in another embodiment it is $(C_1-C_4)$-alkyl-O—, and in case the group $R^{22}$ is a group of the formula II, the group $R^{21}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, H$_2$N—, $R^{30}$—NH—, $R^{30}$—N(R$^{30}$)—, $R^{30}$—C(O)—NH—, $R^{30}$—C(O)—N(R$^{71}$)—, $R^{30}$—S(O)$_2$—NH—, $R^{30}$—S(O)$_2$—N(R$^{71}$)—, $R^{30}$—C(O)—, HO—C(O)—, $R^{30}$—O—C(O)—, H$_2$N—C(O)—, $R^{30}$—NH—C(O)—, $R^{30}$—N(R$^{30}$)—C(O)—, H$_2$N—S(O)$_2$—, $R^{30}$—NH—S(O)$_2$—, $R^{30}$—N(R$^{30}$)—S(O)$_2$—, NC—, O$_2$N— and Het$^1$, or is defined as in any of the embodiments or other definitions of $R^{21}$ specified herein.

The number of chain members in a chain representing $R^{23}$ can be 1, 2, 3, 4 or 5. In one embodiment of the invention, the divalent group $R^{23}$ is a direct bond, i.e. the group $R^{24}$ is directly bonded to the ring comprising the groups Y and Z which is depicted in formula I. In another embodiment $R^{23}$ is a direct bond or a chain consisting of 1, 2, 3 or 4 chain members. In another embodiment $R^{23}$ is a direct bond or a chain consisting of 2, 3 or 4 chain members, in another embodiment a direct bond or a chain consisting of 2 or 3 chain members, in another embodiment a direct bond or a chain consisting of 3 chain members, wherein in these embodiments the chain members are defined as above or below. In another embodiment $R^{23}$ is a chain consisting of 1, 2, 3, 4 or 5 chain members, in another embodiment a chain consisting of 1, 2, 3 or 4 chain members, in another embodiment a chain consisting of 2, 3 or 4 chain members, in another embodiment a chain consisting of 2 or 3 chain members, in another embodiment a chain consisting of 3 chain members, wherein in these embodiments the chain members are defined as above or below. In one embodiment of the invention, zero or one of the chain members in a chain representing $R^{23}$ is a hetero chain member, and in another embodiment one of the chain members in a chain representing $R^{23}$ is a hetero chain member, wherein in these embodiments the hetero chain members are defined as above or below. In another embodiment of the invention, none of the chain members in a chain representing $R^{23}$ is a hetero chain member. In one embodiment of the invention, the hetero chain members in a chain representing $R^{23}$ are chosen from the series consisting of $N(R^{25})$, O, S and $S(O)_2$. In another embodiment of the invention, the hetero chain members in a chain representing $R^{23}$ are chosen from the series consisting of $N(R^{25})$, O and S, in another embodiment from the series consisting of $N(R^{25})$ and O, in another embodiment from the series consisting of O and S, in another embodiment from the series consisting of $N(R^{25})$, O and $S(O)_2$, in another embodiment from the series consisting of $N(R^{25})$ and $S(O)_2$, in another embodiment from the series consisting of O and $S(O)_2$. In another embodiment of the invention, the hetero chain members which can be present in a chain representing $R^{23}$, are O (oxygen), and in another embodiment the hetero chain members which can be present in a chain representing $R^{23}$, are $N(R^{25})$. In another embodiment of the invention, zero or one hetero chain member is present in a chain representing $R^{23}$ which is O (oxygen), and in another embodiment one hetero chain member is present which is O. In another embodiment of the invention, zero or one hetero chain member is present in a chain representing $R^{23}$ which is $N(R^{25})$, and in another embodiment one hetero chain member is present which is $N(R^{25})$.

Hetero chain members in a chain representing $R^{23}$ can be present in any positions of the chain provided that the resulting moiety complies with the prerequisites specified above with respect to $R^{23}$ and the compounds of the invention in general. In case two adjacent groups $C(R^{26})(R^{26})$ in a chain representing $R^{23}$ are connected to each other by a double bond or triple bond, in one embodiment of the invention hetero chain members are not present in positions adjacent to such a double bond or triple bond.

Hetero chain members can be present at any one end or at both ends of the chain, and can thus be directly bonded to the group $R^{24}$ and/or the ring comprising the groups Y and Z which is depicted in formula I, and/or inside the chain. In case one or two hetero chain members are present in a chain representing $R^{23}$, in one embodiment of the invention at least one of the terminal chain members is a hetero chain member, and in another embodiment the terminal chain member which is bonded to the group $R^{24}$ is a hetero chain member, and in another embodiment the terminal chain member which is bonded to the ring comprising the groups Y and Z is a hetero chain member. In one embodiment of the invention, one of the chain members in a chain representing $R^{23}$ is a hetero chain member and this hetero chain member is the terminal chain member bonded to the group $R^{24}$. In another embodiment, one of the chain members in a chain representing $R^{23}$ is a hetero chain member and this hetero chain member is the terminal chain member bonded to the ring comprising the groups Y and Z which is depicted in formula I.

If two adjacent groups $C(R^{26})(R^{26})$ within a chain representing $R^{23}$ are connected to each other by a double bond or a triple bond, the chain thus comprises an unsaturated divalent group of the formula $-C(R^{26})=C(R^{26})-$, wherein $R^{26}$ is defined as above and in one embodiment of the invention is chosen from the series consisting of hydrogen and $(C_1-C_4)$-alkyl, or an unsaturated group of the formula $-C\equiv C-$. Chain members which are not connected to each other by a double bond or triple bond, are connected to each other by a single bond. If a double bond is present between two adjacent groups $C(R^{26})(R^{26})$, one of the groups $R^{26}$ in each of the two adjacent groups $C(R^{26})(R^{26})$ can be regarded as being a free bond, the two free bonds together then forming a second bond between the respective carbon atoms. If a triple bond is present between two adjacent groups $C(R^{26})(R^{26})$, both groups $R^{26}$ in each of the two adjacent groups $C(R^{26})(R^{26})$ can be regarded as being a free bond, the two pairs of free bonds together then forming a second and a third bond between the respective carbon atoms. In one embodiment of the invention, the said unsaturated group is present not more than once in a chain representing $R^{23}$. The said unsaturated group can be present in any position of a chain representing $R^{23}$ and occur at any one end of the chain, and can thus be bonded directly to the group $R^{24}$ and/or the ring comprising the groups Y and Z which is depicted in formula I, or occur inside the chain. In one embodiment of the invention the said unsaturated group is not adjacent to a hetero chain member. In one embodiment of the invention, a chain representing $R^{23}$ does not contain a double bond or triple bond. In another embodiment it is possible for two adjacent groups $C(R^{26})(R^{26})$ to be connected to each other by a double bond. In another embodiment it is possible for two adjacent groups $C(R^{26})(R^{26})$ to be connected to each other by a triple bond. In another embodiment two adjacent groups $C(R^{26})(R^{26})$ are connected to each other by a triple bond, i.e., in this embodiment a chain representing $R^{23}$ comprises a triple bond. In a another embodiment the group $R^{23}$ is a group of the formula $-C\equiv C-$.

In one embodiment of the invention $R^{23}$ is chosen from a direct bond and from any one or more of the chains which are present in the following examples of groups of the formula II, which groups are bonded to the ring comprising the groups Y and Z which is depicted in formula I by the free bond represented by the terminal hyphen, and from which groups of the formula II the groups $R^{23}$ themselves are obtained by removing the group $R^{24}$:

$R^{24}-C(R^{26})(R^{26})-$,  $R^{24}-C(R^{26})(R^{26})-C(R^{26})(R^{26})-$,
$R^{24}-C\equiv C-$,  $R^{24}-C(R^{26})(R^{26})-O-$,
$R^{24}-C(R^{26})(R^{26})-S-$,  $R^{24}-C(R^{26})(R^{26})-N(R^{25})-$,
$R^{24}-S(O)_2-O-$,  $R^{24}-C(R^{26})(R^{26})-C(R^{26})(R^{26})-C(R^{26})(R^{26})-$,
$R^{24}-C(R^{26})=C(R^{26})-C(R^{26})(R^{26})-$,  $R^{24}-C(R^{26})(R^{26})-C(R^{26})(R^{26})-O-$,
$R^{24}-O-C(R^{26})(R^{26})-C(R^{26})(R^{26})-$,  $R^{24}-C(R^{26})(R^{26})-O-C(R^{26})(R^{26})-$,
$R^{24}-C(R^{26})(R^{26})-C(R^{26})(R^{26})-S-$,  $R^{24}-C(R^{26})(R^{26})-S-C(R^{26})(R^{26})-$,
$R^{24}-S-C(R^{26})(R^{26})-C(R^{26})(R^{26})-$,  $R^{24}-C(R^{26})(R^{26})-C(R^{26})(R^{26})-N(R^{25})-$, wherein in these groups of the formula II the groups $R^{24}$, $R^{25}$ and $R^{26}$ are defined as above or below.

In one embodiment of the invention, $R^{24}$ is chosen from the series consisting of $R^{31}$, $R^{31}-O-$, $R^{31}-S(O)_m-$, $H_2N-$, $R^{31}-NH-$, $R^{31}-N(R^{31})-$, $R^{31}-C(O)-NH-$, $R^{31}-C(O)-N(R^{71})-$, $HO-C(O)-$, $R^{31}-O-C(O)-$, $H_2N-C(O)-$, $R^{31}-NH-C(O)-$, $R^{31}-N(R^{31})-C(O)-$, $NC-$ and a 3-membered to 10-membered, monocyclic, bicyclic or tricyclic ring, in another embodiment from the series consisting of $R^{31}$, $R^{31}$—O—, $R^{31}$—S(O)$_m$—, NC— and a 3-membered to 10-membered, monocyclic, bicyclic or tricyclic ring, in another embodiment from the series consisting of $R^{31}$, $R^{31}$—O— and a 3-membered to 10-membered, monocyclic, bicyclic or tricyclic ring, in another embodiment from the series consisting of $(C_1-C_6)$-alkyl, $(C_1-C_6)$-alkyl-O— and a 3-membered to 10-membered, monocyclic, bicyclic or tricyclic ring, wherein in all these embodiments the 3-membered to 10-membered, monocyclic, bicyclic or tricyclic ring is defined as above or below and is saturated or unsaturated and contains 0, 1, 2 or 3 identical or different hetero ring members chosen from the series consisting of N, N($R^{32}$), O, S, S(O) and S(O)$_2$ and is optionally substituted on ring carbon atoms by one or more identical or different substituents chosen from the series consisting of halogen, $R^{33}$, HO—, $R^{33}$—O—, $R^{33}$—C(O)—O—, $R^{33}$—S(O)$_2$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, $R^{33}$—C(O)—, HO—C(O)—, $R^{33}$—O—C(O)—, H$_2$N—C(O)—, $R^{33}$—NH—C(O)—, $R^{33}$—N($R^{33}$)—C(O)—, H$_2$N—S(O)$_2$—, $R^{33}$—NH—S(O)$_2$—, $R^{33}$—N($R^{33}$)—S(O)$_2$—, NC—, O$_2$N—, oxo, phenyl and Het, or has any of its other meanings indicated herein. In another embodiment of the invention $R^{24}$ is a 3-membered to 10-membered, monocyclic, bicyclic or tricyclic ring which is defined as above or below and is saturated or unsaturated and contains 0, 1, 2 or 3 identical or different hetero ring members chosen from the series consisting of N, N($R^{32}$), O, S, S(O) and S(O)$_2$, which ring is optionally substituted on ring carbon atoms by one or more identical or different substituents chosen from the series consisting of halogen, $R^{33}$, HO—, $R^{33}$—O—, $R^{33}$—C(O)—O—, $R^{33}$—S(O)$_2$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, $R^{33}$—C(O)—, HO—C(O)—, $R^{33}$—O—C(O)—, H$_2$N—C(O)—, $R^{33}$—NH—C(O)—, $R^{33}$—N($R^{33}$)—C(O)—, H$_2$N—S(O)$_2$—, $R^{33}$—NH—S(O)$_2$—, $R^{33}$—N($R^{33}$)—S(O)$_2$—, NC—, O$_2$N—, oxo, phenyl and Het, or has any of its other meanings indicated herein.

In one embodiment of the invention, a 3-membered to 10-membered, monocyclic, bicyclic or tricyclic ring representing $R^{24}$ is a monocyclic or bicyclic ring, and in another embodiment it is a monocyclic ring, which rings are all optionally substituted as indicated above or below. In one embodiment of the invention, a monocyclic ring representing $R^{24}$ is 3-membered to 7-membered, in another embodiment 3-membered or 5-membered to 7-membered, in another embodiment 3-membered, 5-membered or 6-membered, in another embodiment 5-membered or 6-membered, in another embodiment 6-membered, which rings are all optionally substituted as indicated above or below. In one embodiment of the invention, a bicyclic or tricyclic ring representing $R^{24}$ is 7-membered to 10-membered, which rings are all optionally substituted as indicated above or below. In one embodiment of the invention, a ring representing $R^{24}$ is a saturated ring or an unsaturated ring including a partially unsaturated, i.e. non-aromatic, ring which contains zero, one, two or three, for example zero, one or two, double bonds within the ring, or an aromatic ring, which rings are all optionally substituted as indicated above or below. In another embodiment, a ring representing $R^{24}$ is a saturated ring or a partially unsaturated ring which contains zero, one, two or three, for example zero, one or two, double bonds within the ring, which rings are all optionally substituted as indicated above or below. In another embodiment of the invention, a ring representing $R^{24}$ is an aromatic ring, in another embodiment an aromatic ring chosen from benzene, aromatic 5-membered and 6-membered monocyclic heterocycles, naphthalene and aromatic 9-membered and 10-membered bicyclic heterocycles, in another embodiment an aromatic ring chosen from benzene and aromatic 5-membered and 6-membered monocyclic heterocycles, in another embodiment an aromatic ring chosen from benzene and thiophene, which rings are all optionally substituted as indicated above or below. In another embodiment, a ring representing $R^{24}$ is a benzene ring which is optionally substituted as indicated above or below, i.e. by the substituents specified above or below with respect to the 3-membered to 10-membered ring representing $R^{24}$. In terms of residues, in this latter embodiment $R^{24}$ is a phenyl group which is optionally substituted as indicated above or below, i.e. by the substituents specified above or below with respect to the 3-membered to 10-membered ring representing $R^{24}$.

In one embodiment of the invention, the number of hetero ring members which can be present in a 3-membered to 10-membered ring representing $R^{24}$ is 0, 1 or 2, in another embodiment of the invention the number of hetero ring members is 0 or 1, and in another embodiment of the invention the number of hetero ring members is 0 (zero), i.e., in this latter embodiment a 3-membered to 10-membered ring representing $R^{24}$ is a carbocyclic ring, which rings are all optionally substituted as indicated above or below. In one embodiment of the invention, the hetero ring members which can be present in a 3-membered to 10-membered ring representing $R^{24}$ are chosen from N, N($R^{32}$), O, S and S(O)$_2$, in another embodiment from N, N($R^{32}$), O and S, in another embodiment from N, O and S, in another embodiment from N($R^{32}$), O and S, in another embodiment from N and S.

In one embodiment of the invention, the number of substituents which are optionally present on ring carbon atoms in a 3-membered to 10-membered ring representing $R^{24}$ is 1, 2, 3, 4, or 5, in another embodiment the number of substituents which are optionally present on ring carbon atoms is 1, 2, 3 or 4, in another embodiment the number of substituents which are optionally present on ring carbon atoms is 1, 2 or 3, in another embodiment the number of substituents which are optionally present on ring carbon atoms is 1 or 2.

In one embodiment of the invention, the substituents which are optionally present on ring carbon atoms in a 3-membered to 10-membered ring representing $R^{24}$, including a benzene ring or a phenyl group, respectively, representing $R^{24}$, are chosen from the series consisting of halogen, $R^{33}$, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, HO—C(O)—, $R^{33}$—O—C(O)—, H$_2$N—C(O)—, $R^{33}$—NH—C(O)—, $R^{33}$—N($R^{33}$)—C(O)—, NC—, oxo, phenyl and Het, in another embodiment from the series consisting of halogen, $R^{33}$, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N ($R^{71}$)—, HO—C(O)—, $R^{33}$—O—C(O)—, $H_2N$—C(O)—, $R^{33}$—NH—C(O)—, $R^{33}$—N($R^{33}$)—C(O)— and NC—, in another embodiment from the series consisting of halogen, $R^{33}$, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—S(O)$_2$—NH—, $H_2N$—S(O)$_2$—NH—, $R^{33}$—NH—S(O)$_2$—NH—, $R^{33}$—N($R^{33}$)—S(O)$_2$—NH—, HO—C(O)—, $R^{33}$—O—C(O)—, $H_2N$—C(O)—, $R^{33}$—NH—C(O)—, $R^{33}$—N($R^{33}$)—C(O)— and NC—, in another embodiment from the series consisting of halogen, $R^{33}$, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—S(O)$_2$—NH—, $H_2N$—S(O)$_2$—NH—, $R^{33}$—NH—S(O)$_2$—NH—, $R^{33}$—N($R^{33}$)—S(O)$_2$—NH—, $H_2N$—C(O)—, $R^{33}$—NH—C(O)—, $R^{33}$—N($R^{33}$)—C(O)— and NC—, in another embodiment from the series consisting of halogen, $R^{33}$, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—S(O)$_2$—NH—, $H_2N$—C(O)—, $R^{33}$—NH—C(O)—, $R^{33}$—N($R^{33}$)—C(O)— and NC—, in another embodiment from the series consisting of halogen, $R^{33}$, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, $H_2N$—C(O)—, $R^{33}$—NH—C(O)—, $R^{33}$—N($R^{33}$)—C(O)— and NC—, in another embodiment from the series consisting of halogen, $R^{33}$, HO—, $R^{33}$—O—, $R^{33}$—S(O)$_m$—, $R^{33}$—C(O)—NH—, $R^{33}$—S(O)$_2$—NH—, $H_2N$—C(O)—, $R^{33}$—NH—C(O)—, $R^{33}$—N($R^{33}$)—C(O)— and NC—, in another embodiment from the series consisting of halogen, $R^{33}$, HO—, $R^{33}$—O—, $R^{33}$—C(O)—NH—, $R^{33}$—S(O)$_2$—NH—, $H_2N$—C(O)—, $R^{33}$—NH—C(O)—, $R^{33}$—N($R^{33}$)—C(O)— and NC—, in another embodiment from the series consisting of halogen, $R^{33}$, $R^{33}$—O—, $R^{33}$—C(O)—NH—, $R^{33}$—S(O)$_2$—NH—, $H_2N$—C(O)—, $R^{33}$—NH—C(O)—, $R^{33}$—N($R^{33}$)—C(O)— and NC—, in another embodiment from the series consisting of halogen, $R^{33}$, $R^{33}$—O— and NC—, in another embodiment from the series consisting of halogen, $R^{33}$ and $R^{33}$—O—, in another embodiment from the series consisting of halogen and $R^{33}$, wherein in all these embodiments $R^{33}$ and $R^{71}$ are defined as indicated above or below and $R^{33}$ is optionally substituted by one or more identical or different substituents $R^{70}$. In one embodiment of the invention, the groups $R^{33}$ in these substituents on a ring representing $R^{24}$ are independently of each other chosen from the series consisting of ($C_1$-$C_6$)-alkyl, ($C_3$-$C_7$)-cycloalkyl and ($C_3$-$C_7$)-cycloalkyl-($C_1$-$C_4$)-alkyl-, in another embodiment from the series consisting of ($C_1$-$C_6$)-alkyl, ($C_3$-$C_6$)-cycloalkyl and ($C_3$-$C_6$)-cycloalkyl-($C_1$-$C_2$)-alkyl-, in another embodiment from the series consisting of ($C_1$-$C_6$)-alkyl, ($C_3$-$C_6$)-cycloalkyl and ($C_3$-$C_6$)-cycloalkyl-$CH_2$—, in another embodiment from the series consisting of ($C_1$-$C_6$)-alkyl, cyclopropyl and cyclopropyl-$CH_2$—, for example from the series consisting of ($C_1$-$C_6$)-alkyl, in another embodiment from the series consisting of ($C_1$-$C_4$)-alkyl, cyclopropyl and cyclopropyl-$CH_2$—, for example from the series consisting of ($C_1$-$C_4$)-alkyl. In one embodiment of the invention, the number of substituents $R^{70}$, which are optionally present in these groups $R^{33}$ besides any fluorine substituents and, in the case of cycloalkyl groups, any ($C_1$-$C_4$)-alkyl substituents, is independently of each other 0, 1, 2 or 3, in another embodiment 0, 1 or 2, in another embodiment 0 or 1, in another embodiment 0. In one embodiment of the invention, the substituents $R^{70}$ in these groups $R^{33}$ are independently of each other chosen from the series consisting of HO—, $R^{71}$—O—, $R^{71}$—C(O)—O—, $H_2N$—, $R^{71}$—NH—, $R^{71}$—N($R^{71}$)—, $R^{71}$—C(O)—NH—, $R^{71}$—C(O)—N($R^{71}$)—, $R^{71}$—S(O)$_2$—NH— and $R^{71}$—S(O)$_2$—N($R^{71}$)—, in another embodiment from the series consisting of HO—, $R^{71}$—C(O)—O—, $H_2N$—, $R^{71}$—C(O)—NH— and $R^{71}$—S(O)$_2$—NH—, in another embodiment from the series consisting of HO—, $R^{71}$—C(O)—O— and $R^{71}$—C(O)—NH—, in another embodiment from the series consisting of HO— and $R^{71}$—C(O)—NH—, in another embodiment from the series consisting of HO— and $R^{71}$—O—, and in another embodiment of the invention substituents $R^{70}$ in these groups $R^{33}$ are HO—. In one embodiment of the invention, the groups $R^{71}$ present in these groups $R^{33}$ are independently of each other chosen from the series consisting of ($C_1$-$C_4$)-alkyl, cyclopropyl and cyclopropyl-, in another embodiment from the series consisting of ($C_1$-$C_4$)-alkyl and cyclopropyl, in another embodiment from the series consisting of ($C_1$-$C_4$)-alkyl. In one embodiment of the invention, $R^{24}$ is a benzene ring or a thiophene ring, for example a benzene ring, or, in terms of the respective residues, $R^{24}$ is a phenyl group or a thiophenyl (thienyl) group, for example a phenyl group, which are all optionally substituted as indicated afore.

Examples of specific residues of benzene and thiophene rings, i.e. of specific phenyl and thiophenyl groups, representing $R^{24}$, from any one or more of which examples the group $R^{24}$ is chosen in one embodiment of the invention, are phenyl, 2-fluoro-phenyl, 3-fluoro-phenyl, 2-chloro-phenyl, 3-chloro-phenyl, 4-chloro-phenyl, 3-bromo-phenyl, 2,3-dichloro-phenyl, 3,4-dichloro-phenyl, 2,5-difluoro-phenyl, 2,5-dichloro-phenyl, 2-chloro-6-fluoro-phenyl, 3,4,5-trifluoro-phenyl, 3-methyl-phenyl (m-tolyl), 3-ethyl-phenyl, 3-isopropyl-phenyl, 3-cyclopropyl-phenyl, 3-tert-butyl-5-methyl-phenyl, 3-trifluoromethyl-phenyl, 3-(2-hydroxyethyl)-phenyl, 3-(2-hydroxy-2-methyl-propyl)-phenyl, 3-(2-acetylaminoethyl)-phenyl, 2-fluoro-5-methyl-phenyl, 3-chloro-2-methyl-phenyl, 5-chloro-2-methyl-phenyl, 5-chloro-2-fluoro-3-methyl-phenyl, 2-fluoro-3-trifluoromethyl-phenyl, 2-fluoro-5-trifluoromethyl-phenyl, 4-fluoro-3-trifluoromethyl-phenyl, 5-fluoro-3-trifluoromethyl-phenyl, 3-chloro-4-trifluoromethyl-phenyl, 5-chloro-2-trifluoromethyl-phenyl, 5-chloro-3-trifluoromethyl-phenyl, 3-ethoxy-phenyl, 2-propoxy-phenyl, 3-isopropoxy-phenyl, 3-trifluoromethoxy-phenyl, 3-(2,2,2-trifluoroethoxy)-phenyl, 5-chloro-2-methoxy-phenyl, 3-chloro-4-methoxy-phenyl, 5-fluoro-3-isopropoxy-phenyl, 2-fluoro-3-trifluoromethoxy-phenyl, 4-methoxy-3,5-dimethyl-phenyl, 3-methoxy-5-trifluoromethyl-phenyl, 3-methylsulfanyl-phenyl, 3-ethylsulfanyl-phenyl, 3-trifluoromethylsulfanyl-phenyl, 3-ethanesulfonyl-phenyl, 3-acetylamino-phenyl, 3-methanesulfonylamino-phenyl, 3-dimethylaminosulfonylamino-phenyl, 3-cyano-phenyl, 2-thienyl, 3-thienyl, 4-methyl-2-thienyl, 5-methyl-3-thienyl.

In one embodiment of the invention, the total number of C, N, O and S atoms which is present in the two groups $R^{23}$ and $R^{24}$, i.e. in the substituent group $R^{24}$-$R^{23}$- on the ring comprising the groups Y and Z which is depicted in formula I, is at least 6, in another embodiment at least 7, in another embodiment at least 8, in another embodiment at least 9.

In one embodiment of the invention, $R^{25}$ is chosen from the series consisting of hydrogen and methyl, in another embodiment $R^{25}$ is hydrogen. In another embodiment of the invention $R^{25}$ is ($C_1$-$C_4$)-alkyl, for example methyl.

In one embodiment of the invention, $R^{26}$, independently of each other group $R^{26}$, is chosen from the series consisting of hydrogen, fluorine, methyl and HO—, in another embodiment from the series consisting of hydrogen, fluorine and ($C_1$-$C_4$)-alkyl, in another embodiment from the series consisting of hydrogen, fluorine and methyl, in another embodiment from the series consisting of hydrogen and fluorine, in another embodiment from the series consisting of hydrogen and methyl, and in another embodiment $R^{26}$ is hydrogen, or in all these embodiments two groups $R^{26}$ bonded to the same carbon atom together are oxo, or two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, $N(R^{34})$, O, S, S(O) and $S(O)_2$, which ring is optionally substituted on ring carbon atoms by one more identical or different substituents chosen from the series consisting of fluorine and $(C_1-C_4)$-alkyl. In another embodiment of the invention, $R^{26}$, independently of each other group $R^{26}$, is chosen from the series consisting of hydrogen, fluorine, methyl and HO—, in another embodiment from the series consisting of hydrogen, fluorine and $(C_1-C_4)$-alkyl, in another embodiment from the series consisting of hydrogen, fluorine and methyl, in another embodiment from the series consisting of hydrogen and fluorine, in another embodiment from the series consisting of hydrogen and methyl, and in another embodiment $R^{26}$ is hydrogen, or in all these embodiments two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, $N(R^{34})$, O, S, S(O) and $S(O)_2$, which ring is optionally substituted on ring carbon atoms by one more identical or different substituents chosen from the series consisting of fluorine and $(C_1-C_4)$-alkyl. In another embodiment of the invention, $R^{26}$, independently of each other group $R^{26}$, is chosen from the series consisting of hydrogen, fluorine, methyl and HO—, in another embodiment from the series consisting of hydrogen, fluorine and $(C_1-C_4)$-alkyl, in another embodiment from the series consisting of hydrogen, fluorine and methyl, in another embodiment from the series consisting of hydrogen and fluorine, in another embodiment from the series consisting of hydrogen and methyl, and in another embodiment all groups $R^{26}$ are hydrogen.

In one embodiment of the invention, the number of groups $R^{26}$ in a chain representing $R^{23}$ which are HO—, is zero, one or two, in another embodiment zero or one, in another embodiment zero, in another embodiment one. In one embodiment of the invention, a HO— group representing $R^{26}$ is not present on a carbon atom which is adjacent to a hetero chain member in a chain representing $R^{23}$. In another embodiment a HO— group representing $R^{26}$ is not bonded to a carbon atom which is connected to an adjacent group $C(R^{26})(R^{26})$ by a double bond. In one embodiment of the invention the number of groups $R^{26}$ in a chain representing $R^{23}$ which are $(C_1-C_4)$-alkyl such as methyl, is zero, one or two, in another embodiment zero or one, in another embodiment zero, in another embodiment one, in another embodiment two. In one embodiment of the invention the number of groups $R^{26}$ in a chain representing $R^{23}$ which are fluorine, is zero, one, two, three or four, in another embodiment zero, one, two or three, in another embodiment zero, one or two, in another embodiment zero or one, in another embodiment zero, in another embodiment one, in another embodiment two. In one embodiment of the invention, the number of oxo substituents in a chain representing $R^{23}$ which are formed by two groups $R^{26}$ bonded to the same carbon atom, is zero, one or two, in another embodiment zero or one, in another embodiment zero, in another embodiment one. In one embodiment of the invention, an oxo substituent in a chain representing $R^{23}$ is not present on a carbon atom which is adjacent to a hetero chain member chosen from the series consisting of S(O) and $S(O)_2$, in another embodiment from the series consisting of S, S(O) and $S(O)_2$, in another embodiment from the series consisting of O, S, S(O) and $S(O)_2$.

In one embodiment of the invention, the number of rings which are formed by two of the groups $R^{26}$ or one group $R^{25}$ and one group $R^{26}$, together with the comprised chain members, is zero, one or two, in another embodiment zero or one, in another embodiment one, in another embodiment zero. In one embodiment of the invention a ring formed by two of the groups $R^{26}$ or one group $R^{25}$ and one group $R^{26}$, together with the comprised chain members, is a 3-membered, 4-membered, 5-membered or 6-membered ring, in another embodiment a 3-membered, 5-membered or 6-membered ring, in another embodiment a 3-membered ring, in another embodiment a 5-membered or 6-membered ring. In one embodiment of the invention, it is possible for two of the groups $R^{26}$, together with the comprised chain members, to form a ring, but not for one group $R^{25}$ and one group $R^{26}$. In one embodiment of the invention the number of chain members which is comprised by a ring formed by two of the groups $R^{26}$ or one group $R^{25}$ and one group $R^{26}$, is one, two, three or four, in another embodiment it is one, two or three, in another embodiment it is one or two, in another embodiment it is one. In case such ring comprises only one chain member, the two of the groups $R^{26}$ forming the ring are bonded to the same carbon atom in the chain and the said one chain member is the carbon atom carrying the two groups $R^{26}$. Examples of rings, which are formed by two groups $R^{26}$ bonded to the same carbon atom and the one comprised chain member, are cycloalkane rings such as cyclopropane, cyclobutane, cyclopentane or cyclohexane, and heterocyclic rings such as tetrahydrothiophene, tetrahydrothiopyran, oxetane, tetrahydrofuran, tetrahydropyran, azetidine, pyrrolidine or piperidine, for example cyclopropane, which carry any adjacent chain members of a chain representing $R^{23}$ and/or the group $R^{24}$ and/or the ring comprising the groups Y and Z which is depicted in formula I, on the same ring carbon atom, and which rings can all be substituted as indicated. In case a ring formed by two of the groups $R^{26}$ or one group $R^{25}$ and one group $R^{26}$, together with the comprised chain members, comprises two chain members, the two groups $R^{26}$ forming the ring are bonded to two adjacent carbon atoms in the chain or the one group $R^{26}$ is bonded to a carbon atom which is adjacent to the group $N(R^{25})$, respectively. Examples of rings, which are formed in such case, are likewise cycloalkane rings such as cyclopropane, cyclobutane, cyclopentane or cyclohexane, and heterocyclic rings such as tetrahydrothiophene, tetrahydrothiopyran, oxetane, tetrahydrofuran, tetrahydropyran, azetidine, pyrrolidine or piperidine, for example cyclopropane, which carry any adjacent chain members of a chain representing $R^{23}$ and/or the group $R^{24}$ and/or the ring comprising the groups Y and Z which is depicted in formula I, on two adjacent ring carbon atoms or on the ring nitrogen atom and an adjacent ring carbon atom, and which rings can all be substituted as indicated.

In case a ring formed by two of the groups $R^{26}$ or one group $R^{25}$ and one group $R^{26}$, together with the comprised chain members, comprises more than one chain members, besides at least one group $C(R^{26})(R^{26})$ the comprised chain members can also be hetero chain members including the group $N(R^{25})$ which then are hetero ring members of the formed ring. In one embodiment of the invention, the total number of hetero ring members in such a ring is zero, one or two, in another embodiment zero or one, in another embodiment zero, in another embodiment one. In one embodiment of the invention, hetero ring members in such a ring are chosen from the series consisting of N, N($R^{34}$), O and S, in another embodiment form the series consisting of N, N($R^{34}$) and O, in another embodiment from the series consisting of N and N($R^{34}$), in another embodiment from the series consisting of N($R^{34}$) and O, in another embodiment from the series consisting of N($R^{34}$), and in another embodiment hetero ring members in such a ring are N, and in still another embodiment hetero ring members in such a ring are O, wherein a hetero ring member N in a ring formed by two of the groups $R^{26}$ or one group $R^{25}$ and one group $R^{26}$, together with the comprised chain members, is the nitrogen atom of a hetero chain member N($R^{25}$).

In one embodiment of the invention, the number of substituents which are optionally present in a ring formed by two of the groups $R^{26}$ or one group $R^{25}$ and one group $R^{26}$, together with the comprised chain members, is 0, 1, 2, 3 or 4, in another embodiment 0, 1, 2 or 3, in another embodiment 0, 1 or 2, in another embodiment 0 or 1, in another embodiment 0. In one embodiment of the invention, ($C_1$-$C_4$)-alkyl substituents which are present in a ring formed by two of the groups $R^{26}$ or one group $R^{25}$ and one group $R^{26}$, together with the comprised chain members, are methyl. In one embodiment of the invention substituents present in a ring formed by two of the groups $R^{26}$ or one group $R^{25}$ and one group $R^{26}$, together with the comprised chain members, are fluorine, in another embodiment they are identical or different ($C_1$-$C_4$)-alkyl groups, for example methyl.

Examples of specific groups $R^{23}$ including specific groups $R^{26}$ contained therein are given in the following examples of groups of the formula II, which groups are bonded to the ring comprising the groups Y and Z which is depicted in formula I by the free bond represented by the terminal hyphen or the terminal line in the structural formula, and from which groups of the formula II the groups $R^{23}$ themselves are obtained by removing the group $R^{24}$, wherein in these groups of the formula II the group $R^{24}$ is defined as above or below:

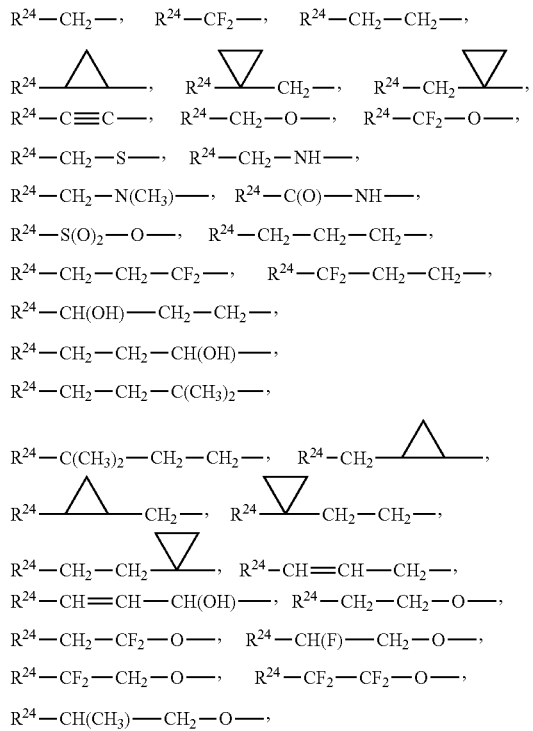

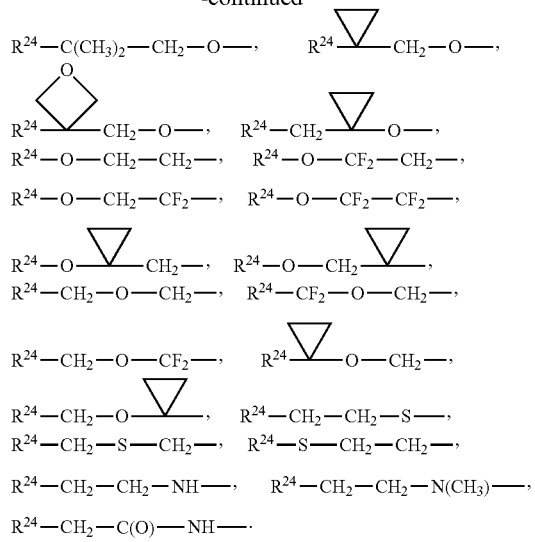

In one embodiment of the invention, $R^{23}$ is chosen from a direct bond and any one or more of the chains $R^{23}$ in the preceding examples of groups of the formula II and, likewise, the group of the formula II is chosen from the group $R^{24}$ and any one or more of the preceding examples of the groups of the formula II.

In one embodiment of the invention, the number of substituents $R^{70}$ which are optionally present in the group $R^{31}$, is zero, one, two or three, in another embodiment zero, one or two, in another embodiment zero or one, in another embodiment zero. In one embodiment of the invention, $R^{31}$ is chosen from the series consisting of ($C_1$-$C_6$)-alkyl, in another embodiment from the series consisting of ($C_1$-$C_4$)-alkyl, which are all optionally substituted by one or more identical or different substituents $R^{70}$.

In one embodiment of the invention, $R^{32}$ and $R^{34}$ are independently of each other chosen from the series consisting of hydrogen, $R^{35}$, $R^{35}$—C(O)—, $R^{35}$—O—C(O)—, phenyl and Het, in another embodiment from the series consisting of hydrogen, $R^{35}$, $R^{35}$—C(O)—, $R^{35}$—O—C(O)—, phenyl and $Het^2$, in another embodiment from the series consisting of hydrogen, $R^{35}$, $R^{35}$—C(O)—, $R^{35}$—O—C(O)— and phenyl, in another embodiment from the series consisting of hydrogen, $R^{35}$, $R^{35}$—C(O)— and $R^{35}$—O—C(O)—, in another embodiment from the series consisting of hydrogen, $R^{35}$ and $R^{35}$—C(O)—, in another embodiment from the series consisting of hydrogen, $R^{35}$, phenyl and Het, in another embodiment from the series consisting of hydrogen, $R^{35}$, phenyl and $Het^2$, in another embodiment from the series consisting of hydrogen, $R^{35}$ and phenyl, in another embodiment from the series consisting of hydrogen and $R^{35}$, wherein in these embodiments a group Het or $Het^2$ occurring in $R^{32}$ and $R^{34}$ in one embodiment of the invention is chosen from pyridinyl and thiophenyl. In one embodiment of the invention, the groups $R^{35}$ occurring in $R^{32}$ and $R^{34}$ are independently of each other chosen from ($C_1$-$C_6$)-alkyl, ($C_3$-$C_7$)-cycloalkyl and ($C_3$-$C_7$)-cycloalkyl-($C_1$-$C_4$)-alkyl-, in another embodiment from ($C_1$-$C_6$)-alkyl, ($C_3$-$C_7$)-cycloalkyl and ($C_3$-$C_7$)-cycloalkyl-($C_1$-$C_2$)-alkyl-, in another embodiment from ($C_1$-$C_6$)-alkyl, ($C_3$-$C_7$)-cycloalkyl and ($C_3$-$C_7$)-cycloalkyl-$CH_2$—, in another embodiment from ($C_1$-$C_6$)-alkyl and ($C_3$-$C_7$)-cycloalkyl, in another embodiment from ($C_1$-$C_6$)-alkyl, in another embodiment from ($C_1$-$C_4$)-alkyl, which are all optionally substituted by one or more identical or different substituents $R^{70}$ and wherein in these groups besides any substituents $R^{70}$ one or more fluorine substituents are optionally present and in cycloalkyl groups one or more $(C_1$-$C_4)$-alkyl substituents are optionally present as applies to alkyl and cycloalkyl groups in general.

In one embodiment of the invention, the number of substituents $R^{70}$ which are optionally present in a group $R^{35}$ occurring in $R^{32}$ and $R^{34}$ besides any fluorine substituents and, in the case of a cycloalkyl group, alkyl substituents, is, independently of each other group, 0, 1, 2, 3 or 4, in another embodiment 0, 1, 2 or 3, in another embodiment 0, 1 or 2, in another embodiment 0 or 1, in another embodiment 0. In one embodiment of the invention, substituents $R^{70}$ which are optionally present in a group $R^{35}$ occurring in $R^{32}$ and $R^{34}$ are, independently of each other group, chosen from the series consisting of HO—, $R^{71}$—O—, NC—, phenyl and Het$^2$, in another embodiment from the series consisting of phenyl and Het$^2$, in another from the series consisting of phenyl, wherein phenyl and Het$^2$ are defined and optionally substituted as indicated.

In one embodiment of the invention, $R^{50}$ is chosen from $R^{51}$—O— and $R^{52}$—NH—, in another embodiment from $R^{51}$—O— and H$_2$N—. In another embodiment $R^{50}$ is $R^{51}$—O—.

In one embodiment of the invention, $R^{51}$ is hydrogen. In another embodiment of the invention, $R^{51}$ is $R^{54}$.

In one embodiment of the invention, $R^{52}$ is chosen from the series consisting of hydrogen, $R^{55}$ and $R^{56}$—S(O)$_2$—, in another embodiment from the series consisting of hydrogen, $(C_1$-$C_4)$-alkyl which is optionally substituted by one or more identical or different substituents $R^{70}$, and $R^{56}$—S(O)$_2$—, in another embodiment from the series consisting of hydrogen, unsubstituted $(C_1$-$C_4)$-alkyl and $R^{56}$—S(O)$_2$—, in another embodiment from the series consisting of hydrogen, unsubstituted methyl and $R^{56}$—S(O)$_2$—, in another embodiment from the series consisting of hydrogen and $(C_1$-$C_4)$-alkyl which is optionally substituted by one or more identical or different substituents $R^{70}$, in another embodiment from the series consisting of hydrogen and unsubstituted $(C_1$-$C_4)$-alkyl, in another embodiment from the series consisting of hydrogen and unsubstituted methyl. In another embodiment of the invention, $R^{52}$ is hydrogen.

In one embodiment of the invention, $R^{53}$ is chosen from the series consisting of hydrogen and $(C_1$-$C_4)$-alkyl which is optionally substituted by one or more identical or different substituents $R^{70}$, in another embodiment from the series consisting of hydrogen and unsubstituted $(C_1$-$C_4)$-alkyl, in another embodiment from the series consisting of hydrogen and unsubstituted methyl. In another embodiment of the invention, $R^{53}$ is hydrogen.

In one embodiment of the invention, $R^{54}$ is chosen from $(C_1$-$C_6)$-alkyl, $(C_3$-$C_7)$-cycloalkyl and $(C_3$-$C_7)$-cycloalkyl-$(C_1$-$C_4)$-alkyl-, in another embodiment from $(C_1$-$C_6)$-alkyl, $(C_3$-$C_7)$-cycloalkyl and $(C_3$-$C_7)$-cycloalkyl-$(C_1$-$C_2)$-alkyl-, in another embodiment from $(C_1$-$C_6)$-alkyl, $(C_3$-$C_7)$-cycloalkyl and $(C_3$-$C_7)$-cycloalkyl-CH$_2$—, in another embodiment from $(C_1$-$C_6)$-alkyl and $(C_3$-$C_7)$-cycloalkyl, in another embodiment from $(C_1$-$C_6)$-alkyl, in another embodiment from $(C_1$-$C_4)$-alkyl, in another embodiment from $(C_1$-$C_3)$-alkyl, which are all optionally substituted by one or more identical or different substituents $R^{70}$ and wherein in these groups besides any substituents $R^{70}$ one or more fluorine substituents are optionally present and in cycloalkyl groups one or more $(C_1$-$C_4)$-alkyl substituents are optionally present as applies to alkyl and cycloalkyl groups in general. In one embodiment of the invention, the number of substituents $R^{70}$ which are optionally present in a group $R^{54}$ besides any fluorine substituents and, in the case of a cycloalkyl group, any alkyl substituents, is 0, 1 or 2, in another embodiment 0 or 1, in another embodiment 1, in another embodiment 0. In another embodiment of the invention, a group $R^{54}$ is neither substituted by $R^{70}$ nor by fluorine substituents nor, in the case of a cycloalkyl group, by alkyl substituents, and $R^{54}$ in this embodiment thus is chosen, for example, from the series consisting of $C_1$-$C_6$)-alkyl, $(C_2$-$C_6$)-alkenyl, $(C_2$-$C_6$)-alkynyl, $(C_3$-$C_7$)-cycloalkyl and $(C_3$-$C_7$)-cycloalkyl-$(C_1$-$C_4$)-alkyl-, or from the series consisting of $(C_1$-$C_6$)-alkyl, $(C_3$-$C_7$)-cycloalkyl and $(C_3$-$C_7$)-cycloalkyl-CH$_2$—, or from the series consisting of $(C_1$-$C_6$)-alkyl, or from the series consisting of $(C_1$-$C_4$)-alkyl, or from the series consisting of $(C_1$-$C_3$)-alkyl, which are all unsubstituted. In one embodiment of the invention, substituents $R^{70}$ which are optionally present in a group $R^{54}$, are independently of each other chosen from the series consisting of HO—, $R^{71}$—O—, $R^{71}$—C(O)—O—, HO—C(O)— and $R^{71}$—O—C(O)—, in another embodiment from the series consisting of HO—, $R^{71}$—O— and $R^{71}$—C(O)—O—, in another embodiment from the series consisting of HO— and $R^{71}$—C(O)—O—.

In one embodiment of the invention, $R^{56}$ is chosen from the series consisting of phenyl which is optionally substituted as indicated above or below, and unsubstituted $(C_1$-$C_4)$-alkyl, in another embodiment from the series consisting of phenyl which is optionally substituted as indicated above or below, and unsubstituted methyl, in another embodiment from unsubstituted $(C_1$-$C_4)$-alkyl, in another embodiment from unsubstituted $(C_1$-$C_3)$-alkyl. In another embodiment $R^{56}$ is unsubstituted methyl, in another embodiment phenyl which is optionally substituted as indicated.

In one embodiment of the invention, $R^{60}$ is chosen from the series consisting of hydrogen and methyl. In another embodiment $R^{60}$ is hydrogen. In another embodiment $R^{60}$ is $(C_1$-$C_4)$-alkyl, for example methyl.

In one embodiment of the invention, a group $R^{70}$ in any of its occurrences is, independently of groups $R^{70}$ in other occurrences and unless specified otherwise, chosen from the series consisting of HO—, $R^{71}$—O—, $R^{71}$—C(O)—O—, $R^{71}$—S(O)$_m$—, H$_2$N—, $R^{71}$—NH—, $R^{71}$—N(R$^{71}$)—, $R^{71}$—C(O)—NH—, $R^{71}$—C(O)—N(R$^{71}$)—, $R^{71}$—S(O)$_2$—NH—, $R^{71}$—S(O)$_2$—N(R$^{71}$)—, HO—C(O)—, $R^{71}$—O—C(O)—, H$_2$N—C(O)—, $R^{71}$—NH—C(O)—, $R^{71}$—N(R$^{17}$)—C(O)—, NC—, oxo, phenyl and Het$^2$, in another embodiment from the series consisting of HO—, $R^{71}$—O—, $R^{71}$—C(O)—O—, $R^{71}$—S(O)$_m$—, H$_2$N—, $R^{71}$—NH—, $R^{71}$—N(R$^{71}$)—, $R^{71}$—C(O)—NH—, $R^{71}$—S(O)$_2$—NH—, HO—C(O)—, $R^{71}$—O—C(O)—, H$_2$N—C(O)—, $R^{71}$—NH—C(O)—, $R^{71}$—N(R$^{17}$)—C(O)—, NC—, oxo, phenyl and Het$^2$, in another embodiment from the series consisting of HO—, $R^{71}$—O—, $R^{71}$—C(O)—O—, $R^{71}$—S(O)$_m$—, HO—C(O)—, $R^{71}$—O—C(O)—, H$_2$N—C(O)—, $R^{71}$—NH—C(O)—, $R^{71}$—N(R$^{17}$)—C(O)—, NC—, oxo, phenyl and Het$^2$, in another embodiment from the series consisting of HO—, $R^{71}$—O—, $R^{71}$—C(O)—O—, $R^{71}$—S(O)$_m$—, H$_2$N—, $R^{71}$—NH—, $R^{71}$—N(R$^{71}$)—, $R^{71}$—C(O)—NH—, $R^{71}$—S(O)$_2$—NH—, NC—, oxo, phenyl and Het$^2$, in another embodiment from the series consisting of HO—, $R^{71}$—O—, $R^{71}$—C(O)—O—, $R^{71}$—S(O)$_m$—, NC—, oxo, phenyl and Het$^2$, in another embodiment from the series consisting of HO—, $R^{71}$—O—, $R^{71}$—S(O)$_m$—, NC—, oxo, phenyl and Het$^2$, in another embodiment from the series consisting of HO—, $R^{71}$—O—, $R^{71}$—C(O)—O—, $R^{71}$—S(O)$_m$—, NC—, phenyl and Het$^2$, in another embodiment from the series consisting of HO—, $R^{71}$—O—, NC—, phenyl and Het$^2$, in another embodiment from the series consisting of HO—, $R^{71}$—O—, phenyl and Het$^2$, in another embodiment from the series consisting of HO—, $R^{71}$—O— and phenyl, in another embodiment from the series consisting of HO— and $R^{71}$—O—, in another embodiment from the series consisting of HO— and $R^{71}$—C(O)—O—, in another embodiment from the series consisting of phenyl and $Het^2$, in another embodiment from the series consisting of phenyl, in another embodiment from the series consisting of HO—C(O)—, $R^{71}$—O—C(O)—, $H_2N$—C(O)—, $R^{71}$—NH—C(O)—, $R^{71}$—N($R^{17}$)—C(O)—, in another embodiment from the series consisting of HO—C(O)—, and $R^{71}$—O—C(O)—, and in another embodiment $R^{70}$ is HO—, wherein $R^{71}$, phenyl and $Het^2$ are defined and optionally substituted as indicated above or below. In the latter embodiment, in which $R^{70}$ is HO—, a ($C_1$-$C_6$)-alkyl group, for example, which is optionally substituted by the said $R^{70}$, can among others be a group such as ($C_1$-$C_6$)-alkyl, HO—($C_1$-$C_6$)-alkyl-, i.e. hydroxy-($C_1$-$C_6$)-alkyl-, $(HO)_2$($C_2$-$C_6$)-alkyl-, i.e. dihydroxy-($C_2$-$C_6$)-alkyl-, and a ($C_1$-$C_4$)-alkyl group which is optionally substituted by $R^{70}$, can among others be a group such as ($C_1$-$C_4$)-alkyl, HO—($C_1$-$C_4$)-alkyl-, i.e. hydroxy-($C_1$-$C_4$)-alkyl-, $(HO)_2$($C_2$-$C_4$)-alkyl-, i.e. dihydroxy-($C_2$-$C_4$)-alkyl-, wherein the alkyl groups are optionally substituted by one or more fluorine substituents. In one embodiment of the invention, a carbon atom does not carry more than one HO— group.

In one embodiment of the invention, $R^{71}$ is chosen from ($C_1$-$C_4$)-alkyl, cyclopropyl and cyclopropyl-$CH_2$—, in another embodiment from ($C_1$-$C_4$)-alkyl and cyclopropyl, in another embodiment from ($C_1$-$C_4$)-alkyl, in another embodiment from ($C_1$-$C_3$)-alkyl, unless specified otherwise.

A subject of the invention are all compounds of the formula I wherein any one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratios, and their physiologically acceptable salts, and the physiologically acceptable solvates of any of them, are a subject of the present invention.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that all their stereoisomeric forms and mixtures of stereoisomeric forms in any ratio, and their physiologically acceptable salts, and the physiologically acceptable solvates of any of them are a subject of the present invention. A subject of the invention also are all specific compounds disclosed herein, irrespective thereof whether they are disclosed as a free compound and/or as a specific salt, both in the form of the free compound and in the form of all its physiologically acceptable salts, and if a specific salt is disclosed, additionally in the form of this specific salt, and the physiologically acceptable solvates of any of them. For example, in the case of the specific compound 2-{2-chloro-5-[2-(3-chloro-phenyl)-ethoxy]-4-methoxy-benzoylamino}-indane-2-carboxylic acid which is disclosed in the form of the free compound, a subject of the invention are 2-{2-chloro-5-[2-(3-chloro-phenyl)-ethoxy]-4-methoxy-benzoylamino}-indane-2-carboxylic acid and its physiologically acceptable salts and the physiologically acceptable solvates of any of them.

Thus, a subject of the invention also is a compound of the formula I which is chosen from any of the specific compounds of the formula I which are disclosed herein, or is any one of the specific compounds of the formula I which are disclosed herein, irrespective thereof whether they are disclosed as a free compound and/or as a specific salt, for example a compound of the formula I which is chosen from 2-[4-methylsulfanyl-3-(2-m-tolyl-ethoxy)-benzoylamino]-indane-2-carboxylic acid,
2-[4-acetyl-3-(2-m-tolyl-ethoxy)-benzoylamino]-indane-2-carboxylic acid,
2-[4-ethyl-3-(2-m-tolyl-ethoxy)-benzoylamino]-indane-2-carboxylic acid,
2-[4-ethoxy-3-(2-m-tolyl-ethoxy)-benzoylamino]-indane-2-carboxylic acid,
2-[4-methoxy-3-(2-m-tolyl-ethoxy)-benzoylamino]-indane-2-carboxylic acid,
2-{4-methoxy-3-[2-(3-trifluoromethylsulfanyl-phenyl)-ethoxy]-benzoylamino}-indane-2-carboxylic acid,
2-[4-methoxy-3-(1-m-tolyl-cyclopropylmethoxy)-benzoylamino]-indane-2-carboxylic acid,
2-{3-[2-(3-cyano-phenyl)-ethoxy]-4-methoxy-benzoylamino}-indane-2-carboxylic acid,
5-[4-methoxy-3-(2-m-tolyl-ethoxy)-benzoylamino]-5,6-dihydro-4H-cyclopenta[c]thiophene-5-carboxylic acid,
5-[4-methoxy-3-(2-m-tolyl-ethoxy)-benzoylamino]-5,6-dihydro-4H-cyclopenta[b]thiophene-5-carboxylic acid,
2-{[5-acetyl-4-(2-m-tolyl-ethoxy)-thiophene-2-carbonyl]-amino}-indane-2-carboxylic acid,
2-[3-fluoro-4-methoxy-5-(2-m-tolyl-ethoxy)-benzoylamino]-indane-2-carboxylic acid,
2-[4-methoxy-3-(2-m-tolyloxy-ethyl)-benzoylamino]-indane-2-carboxylic acid,
2-[4-methoxy-3-(3-m-tolyl-propyl)-benzoylamino]-indane-2-carboxylic acid,
5-fluoro-2-[4-methoxy-3-(2-m-tolyl-ethoxy)-benzoylamino]-indane-2-carboxylic acid,
2-[4-methoxy-3-(2-m-tolyl-ethoxy)-benzoylamino]-5,6-dimethyl-indane-2-carboxylic acid,
2-[4-cyano-3-(2-m-tolyl-ethoxy)-benzoylamino]-indane-2-carboxylic acid,
2-[4-methoxy-3-(2-m-tolyl-ethylamino)-benzoylamino]-indane-2-carboxylic acid,
2-{3-[2-(3-chloro-phenyl)-ethoxy]-4-methyl-benzoylamino}-indane-2-carboxylic acid,
2-[4-methoxy-3-(2-m-tolyl-ethylsulfanyl)-benzoylamino]-indane-2-carboxylic acid,
2-[3-(2-m-tolyl-ethoxy)-4-trifluoromethyl-benzoylamino]-indane-2-carboxylic acid,
2-{3-[2-(2-fluoro-5-methyl-phenyl)-ethoxy]-4-trifluoromethyl-benzoylamino}-indane-2-carboxylic acid,
2-(3-{2-[3-(2-hydroxy-ethyl)-phenyl]-ethoxy}-4-methoxy-benzoylamino)-indane-2-carboxylic acid,
2-{[6-methoxy-5-(2-m-tolyl-ethoxy)-pyridine-3-carbonyl]-amino}-indane-2-carboxylic acid,
2-[(3'-methanesulfonylamino-6-methoxy-biphenyl-3-carbonyl)-amino]-indane-2-carboxylic acid,
2-[(3'-dimethylaminosulfonylamino-6-methoxy-biphenyl-3-carbonyl)-amino]-indane-2-carboxylic acid,
2-[(6-methoxy-3'-trifluoromethoxy-biphenyl-3-carbonyl)-amino]-indane-2-carboxylic acid,
2-[(3'-cyanomethyl-6-methoxy-biphenyl-3-carbonyl)-amino]-indane-2-carboxylic acid,
2-[(3'-isopropyl-6-methoxy-biphenyl-3-carbonyl)-amino]-indane-2-carboxylic acid,
2-[(3'-chloro-6-methoxy-2'-methyl-biphenyl-3-carbonyl)-amino]-indane-2-carboxylic acid, 2-{[5-(3-chloro-phenyl)-6-methoxy-pyridine-3-carbonyl]-amino}-indane-2-carboxylic acid, and 2-[3-(2,2-difluoro-2-phenyl-ethoxy)-4-methoxy-benzoylamino]-indane-2-carboxylic acid, or which is any one of these compounds, or a physiologically acceptable salt thereof, or physiologically acceptable solvate of any of them, wherein the compound of the formula I is a subject of the invention in any of its stereoisomeric forms or a mixture of stereoisomeric forms in any ratio where applicable.

As an example of compounds of the invention which with respect to any structural elements are defined as in specified embodiments of the invention or definitions of such elements, compounds of the formula I may be mentioned wherein ring A is a cyclohexane ring, a benzene ring, a pyridine ring, a pyridazine ring or a thiophene ring, wherein the cyclohexane ring is optionally substituted by one or more identical or different substituents chosen from the series consisting of fluorine and ($C_1$-$C_4$)-alkyl, and the benzene ring, the pyridine ring, the pyridazine ring and the thiophene ring are optionally substituted by one or more identical or different substituents chosen from the series consisting of halogen, $R^1$, HO—, $R^1$—O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, H$_2$N—C(O)—, $R^1$—NH—C(O)—, $R^1$—N($R^1$)—C(O)—, H$_2$N—S(O)$_2$—, $R^1$—NH—S(O)$_2$—, $R^1$—N($R^1$)—S(O)$_2$—, NC— and O$_2$N—;

Y is chosen from the series consisting of S, $C(R^{12})$=$C(R^{13})$, and $C(R^{15})$=N;

Z is $C(R^{16})$;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example compounds of the formula I may be mentioned, wherein ring A is a benzene ring, a pyridine ring, a pyrazine or a thiophene ring which rings are all optionally substituted by one or two identical or different substituents chosen from the series consisting of halogen, ($C_1$-$C_4$)-alkyl and ($C_1$-$C_4$)-alkyl-O—;

Y is chosen from the series consisting of S, $C(R^{12})$=$C(R^{13})$ and $C(R^{15})$=N;

Z is $C(R^{16})$;

$R^3$ and $R^5$ are independently of each other chosen from the series consisting of hydrogen and ($C_1$-$C_4$)-alkyl;

$R^4$ and $R^6$ are hydrogen;

$R^{12}$, $R^{13}$, $R^{15}$ and $R^{16}$ are independently of each other chosen from the series consisting of hydrogen, halogen ($C_1$-$C_4$)-alkyl, ($C_1$-$C_4$)-alkyl-O— and NC—;

$R^{20}$ is hydrogen;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example compounds of the formula I may be mentioned, wherein $R^{21}$ is chosen from the series consisting of hydrogen, halogen, ($C_1$-$C_4$)-alkyl, HO—($C_1$-$C_4$)-alkyl-, ($C_1$-$C_4$)-alkyl-O—, ($C_1$-$C_4$)-alkyl-S(O)$_m$—, H$_2$N—, ($C_1$-$C_4$)-alkyl-NH—, di(($C_1$-$C_4$)-alkyl)N—, ($C_1$-$C_4$)-alkyl-C(O)— and NC—;

$R^{22}$ is a group of the formula II;

$$R^{24}\text{-}R^{23}\text{-} \qquad \qquad \text{II}$$

$R^{23}$ is a direct bond or a chain consisting of 2, 3 or 4 chain members of which 0 or 1 chain members are hetero chain members chosen from the series consisting of N($R^{25}$), O, S, S(O) and S(O)$_2$ and the other chain members are identical or different groups $C(R^{26})(R^{26})$, wherein two adjacent groups $C(R^{26})(R^{26})$ can be connected to each other by a double bond or a triple bond;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example compounds of the formula I may be mentioned, wherein $R^{24}$ is a 3-membered to 7-membered monocyclic ring or a 7-membered to 10-membered bicyclic ring, which rings are saturated or unsaturated and contain 0, 1 or 2 identical or different hetero ring members chosen from the series consisting of N, N($R^{32}$), O, S, S(O) and S(O)$_2$, and which rings are optionally substituted on ring carbon atoms by one or more identical or different substituents chosen from the series consisting of halogen, $R^{33}$, HO—, $R^{33}$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, HO—C(O)—, $R^{33}$—O—C(O)—, H$_2$N—C(O)—, $R^{33}$—NH—C(O)—, $R^{33}$—N($R^{33}$)—C(O)—, NC—, oxo, phenyl and Het;

$R^{32}$ is chosen from the series consisting of hydrogen, $R^{35}$, $R^{35}$—C(O)—, $R^{35}$—O—C(O)— and phenyl;

and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example compounds of the formula I may be mentioned, wherein ring A is a benzene ring, a pyridine ring, a pyrazine or a thiophene ring which rings are all optionally substituted by one or two identical or different substituents chosen from the series consisting of halogen, ($C_1$-$C_4$)-alkyl and ($C_1$-$C_4$)-alkyl-O—;

Y is chosen from the series consisting of S, $C(R^{12})$=$C(R^{13})$ and $C(R^{15})$=N;

Z is $C(R^{16})$;

$R^3$ and $R^5$ are independently of each other chosen from the series consisting of hydrogen and ($C_1$-$C_4$)-alkyl;

$R^4$ and $R^6$ are hydrogen;

$R^{12}$, $R^{13}$, $R^{15}$ and $R^{16}$ are independently of each other chosen from the series consisting of hydrogen, halogen ($C_1$-$C_4$)-alkyl, ($C_1$-$C_4$)-alkyl-O— and NC—;

$R^{20}$ is hydrogen;

$R^{21}$ is chosen from the series consisting of hydrogen, halogen, ($C_1$-$C_4$)-alkyl, HO—($C_1$-$C_4$)-alkyl-, ($C_1$-$C_4$)-alkyl-O—, ($C_1$-$C_4$)-alkyl-S(O)$_m$—, H$_2$N—, ($C_1$-$C_4$)-alkyl-NH—, di((C$_1$-C$_4$)-alkyl)N—, (C$_1$-C$_4$)-alkyl-C(O)— and NC—;
R$^{22}$ is a group of the formula II;

$$R^{24}\text{-}R^{23}\text{-} \qquad\qquad II$$

R$^{23}$ is a direct bond or a chain consisting of 2, 3 or 4 chain members of which 0 or 1 chain members are hetero chain members chosen from the series consisting of N(R$^{25}$), O, S, S(O) and S(O)$_2$, and the other chain members are identical or different groups C(R$^{26}$)(R$^{26}$), wherein two adjacent groups C(R$^{26}$)(R$^{26}$) can be connected to each other by a double bond or a triple bond;
R$^{24}$ is a 3-membered to 7-membered monocyclic ring or a 7-membered to 10-membered bicyclic ring, which rings are saturated or unsaturated and contains 0, 1 or 2 identical or different hetero ring members chosen from the series consisting of N, N(R$^{32}$), O, S, S(O) and S(O)$_2$, which ring is optionally substituted on ring carbon atoms by one or more identical or different substituents chosen from the series consisting of halogen, R$^{33}$, HO—, R$^{33}$—O—, R$^{33}$—S(O)$_m$—, H$_2$N—, R$^{33}$—NH—, R$^{33}$—N(R$^{33}$)—, R$^{33}$—C(O)—NH—, R$^{33}$—C(O)—N(R$^{71}$)—, R$^{33}$—S(O)$_2$—NH—, R$^{33}$—S(O)$_2$—N(R$^{71}$)—, HO—C(O)—, R$^{33}$—O—C(O)—, H$_2$N—C(O)—, R$^{33}$—NH—C(O)—, R$^{33}$—N(R$^{33}$)—C(O)—, NC—, oxo, phenyl and Het;
R$^{32}$ is chosen from the series consisting of hydrogen, R$^{35}$, R$^{35}$—C(O)—, R$^{35}$—O—C(O)— and phenyl;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example compounds of the formula I may be mentioned, wherein ring A is a benzene ring which is optionally substituted by one or two identical or different substituents chosen from the series consisting of halogen, (C$_1$-C$_4$)-alkyl and (C$_1$-C$_4$)-alkyl-O—;
Y is C(R$^{12}$)=C(R$^{13}$);
Z is C(R$^{16}$);
R$^3$, R$^4$, R$^5$ and R$^6$ are hydrogen;
R$^{12}$, R$^{13}$ and R$^{16}$ are independently of each other chosen from the series consisting of hydrogen, halogen, (C$_1$-C$_4$)-alkyl, (C$_1$-C$_4$)-alkyl-O— and NC—;
R$^{20}$ is hydrogen;
R$^{21}$ is chosen from the series consisting of hydrogen, halogen, (C$_1$-C$_4$)-alkyl, HO—(C$_1$-C$_4$)-alkyl-, (C$_1$-C$_4$)-alkyl-O—, (C$_1$-C$_4$)-alkyl-S(O)$_m$—, (C$_1$-C$_4$)-alkyl-C(O)— and NC—;
R$^{22}$ is a group of the formula II;

$$R^{24}\text{-}R^{23}\text{-} \qquad\qquad II$$

R$^{23}$ is a direct bond or a chain consisting of 2, 3 or 4 chain members of which 0 or 1 chain members are hetero chain members chosen from the series consisting of N(R$^{25}$), O, S, S(O) and S(O)$_2$, and the other chain members are identical or different groups C(R$^{26}$)(R$^{26}$);
R$^{24}$ is a benzene ring which is optionally substituted by one or more identical or different substituents chosen from the series consisting of halogen, R$^{33}$, HO—, R$^{33}$—O—, R$^{33}$—S(O)$_m$—, H$_2$N—, R$^{33}$—NH—, R$^{33}$—N(R$^{33}$)—, R$^{33}$—C(O)—NH—, R$^{33}$—S(O)$_2$—NH—, HO—C(O)—, R$^{33}$—O—C(O)—, H$_2$N—C(O)—, R$^{33}$—NH—C(O)—, R$^{33}$—N(R$^{33}$)—C(O)— and NC—;
provided that the total number of C, N, O and S atoms which is present in the two groups R$^{23}$ and R$^{24}$, is at least 5;
R$^{25}$ is chosen from the series consisting of hydrogen and (C$_1$-C$_4$)-alkyl;
R$^{26}$, independently of each other group R$^{26}$, is chosen from the series consisting of hydrogen, fluorine, (C$_1$-C$_4$)-alkyl and HO—, or two of the groups R$^{26}$ which are bonded to the same carbon atom in the chain, together with the carbon atom carrying them, form a cyclopropane ring;
R$^{33}$ is, independently of each other group R$^{33}$, chosen from the series consisting of (C$_1$-C$_4$)-alkyl, (C$_3$-C$_7$)-cycloalkyl and (C$_3$-C$_7$)-cycloalkyl-(C$_1$-C$_2$)-alkyl-, which are all optionally substituted by one or more identical or different substituents R$^{70}$;
R$^{50}$ is chosen from the series consisting of R$^{51}$—O— and R$^{52}$—N(R$^{53}$)—;
R$^{51}$ is chosen from the series consisting of hydrogen and (C$_1$-C$_4$)-alkyl;
R$^{52}$ is chosen from the series consisting of hydrogen and (C$_1$-C$_4$)-alkyl;
R$^{53}$ is chosen from the series consisting of hydrogen and (C$_1$-C$_4$)-alkyl;
R$^{70}$ is chosen from the series consisting of HO— and R$^{71}$—O—;
R$^{71}$ is (C$_1$-C$_4$)-alkyl;
m, independently of each other number m, is an integer chosen from the series consisting of 0 and 2;
cycloalkyl, independently of each other group cycloalkyl, and independently of any other substituents on cycloalkyl, is optionally substituted by one or more identical or different substituents chosen from fluorine and (C$_1$-C$_4$)-alkyl;
alkyl, independently of each other group alkyl, and independently of any other substituents on alkyl, is optionally substituted by one or more fluorine substituents; in any of their stereoisomeric forms or a mixture of stereoisomeric forms in any ratio, and their physiologically acceptable salts, and the physiologically acceptable solvates of any of them.

Another subject of the present invention are processes for the preparation of the compounds of the formula I which are outlined below and by which the compounds are obtainable. For example, the preparation of the compounds of the formula I can be carried out by reacting a compound of the formula III with a compound of the formula IV with formation of an amide bond.

The ring A and the groups Y, Z, R$^3$ to R$^6$, R$^{20}$ to R$^{22}$ and R$^{50}$ in the compounds of the formulae III and IV are defined as in the compounds of the formula I and additionally functional groups can be present in protected form or in the form of a precursor group which is later converted into the final group. The group G in the compounds of the formula IV can be HO— (hydroxy), i.e. the compound of the formula IV can thus be a carboxylic acid, or another group which can be replaced by the group $N(R^{20})$ in the compound of the formula III in a substitution reaction, for example an aryloxy group such as optionally substituted phenoxy or an alkyloxy group such as a $(C_1-C_4)$-alkyl-O— group, for example a $(C_1-C_3)$-alkyl-O— group like methoxy or ethoxy, or halogen, for example chlorine or bromine, and the compound of the formula IV can thus be a reactive ester like an aryl ester or alkyl ester, for example a methyl ester or ethyl ester, or an acid halide, for example an acid chloride or acid bromide, of the respective carboxylic acid. The compound of the formula III and/or the compound of the formula IV can also be employed, and the compounds of the formula I obtained, in the form of a salt, for example an acid addition salt such as an hydrohalide, for example a hydrochloride, of the compound of the formula III and/or an alkaline metal salt, for example a sodium salt, of a compound of the formula IV in which G is HO—. Likewise, in all other reactions in the preparation of the compounds of the formula I, including the preparation of starting compounds, compounds can also be employed and/or products obtained in the form a salt.

In case a compound of the formula IV is employed in which G is HO—, the carboxylic acid group HO—C(O)— is generally activated in situ by means of a customary amide coupling reagent or converted into a reactive carboxylic acid derivative which can be prepared in situ or isolated. For example, the compound of the formula IV in which G is HO— can be converted into an acid halide, e.g. the compound of the formula IV in which G is Cl or Br, by treatment with thionyl chloride, phosphorus pentachloride, phosphorus tribromide or oxalyl chloride, or treated with an alkyl chloroformate like ethyl chloroformate or isobutyl chloroformate to give a mixed anhydride. Customary coupling reagents which can be employed, are propanephosphonic anhydride, N,N'-carbonyldiazoles like N,N'-carbonyldiimidazole (CD), carbodiimides like 1,3-diisopropylcarbodiimide (DIC), 1,3-dicyclohexylcarbodiimide (DCC) or 1-(3-dimethylaminopropyl)-3-ethylcarbodiimide hydrochloride (EDC), carbodiimides together with additives like 1-hydroxy-benzotriazole (HOBT) or 1-hydroxy-7-azabenzotriazole (HOAT), uronium-based coupling reagents like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), and phosphonium-based coupling reagents like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP).

The reaction conditions for the preparation of the compounds of the formula I from compounds of the formulae III and IV depend on the particulars of the specific case, for example the meaning of the group G or the employed coupling reagent, and are well known to a skilled person in view of the general knowledge in the art. For example, in case a compound of the formula IV in which G is alkyl-O—, like methoxy or ethoxy, is reacted with a compound of the formula III, generally the reaction is carried out in an inert solvent, for example a hydrocarbon or chlorinated hydrocarbon like benzene, toluene, xylene, chlorobenzene, dichloromethane, chloroform or dichloroethane, an ether like tetrahydrofuran (THF), dioxane, dibutyl ether, diisopropyl ether or dimethoxyethane (DME), or a mixture of solvents, at elevated temperatures, for example at temperatures from about 40° C. to about 140° C., in particular at temperatures from about 50° C. to about 120° C., for example at about the boiling temperature of the solvent. In case a compound of the formula IV in which G is halogen, like chlorine or bromine, is reacted with a compound of the formula III, generally the reaction is likewise carried out in an inert solvent, for example a hydrocarbon or chlorinated hydrocarbon or ether like the aforementioned ones, an ester like ethyl acetate or butyl acetate, a nitrile like acetonitrile, or water, or a mixture of solvents including a mixture of water and an organic solvent which is miscible or immiscible with water, at temperatures from about −10° C. to about 100° C., in particular at temperatures from about 0° C. to about 80° C., for example at about room temperature. Favorably, the reaction of a compound of the formula IV in which G is halogen with a compound of the formula III is carried out in the presence of a base such as a tertiary amine, like triethylamine, ethyldiisopropylamine, N-methylmorpholine or pyridine, or an inorganic base such as an alkaline metal hydroxide, carbonate or hydrogencarbonate, like sodium hydroxide, potassium hydroxide, sodium carbonate or sodium hydrogencarbonate.

In case a compound of the formula IV in which G is HO— is reacted with a compound of the formula III and the carboxylic acid group is activated by means of an amide coupling reagent such as, for example, a carbodiimide or TOTU, the reaction is generally carried out under anhydrous conditions in an inert aprotic solvent, for example an ether like THF, dioxane or DME, an amide like N,N-dimethylformamide (DMF) or N-methylpyrrolidone (NMP), at temperatures from about −10° C. to about 40° C., in particular at temperatures from about 0° C. to about 30° C. in the presence of a base such as a tertiary amine, like triethylamine, ethyldiisopropylamine or N-methylmorpholine. In case the compound of the formula III is employed in the form of an acid addition salt in the reaction with the compound of the formula IV, usually a sufficient amount of a base is added in order to liberate the free compound of the formula III.

As indicated above, during the formation of the amide bond between the compounds of the formulae III and IV functional groups in the compounds of the formulae III and IV can be present in protected form or in the form of a precursor group. Depending on the particulars of the specific case, it may be necessary or advisable for avoiding an undesired course of the reaction or side reactions to temporarily block any functional groups by protective groups and remove them later, or to let functional groups be present in the form of a precursor group which is later converted into the desired final group. This applies correspondingly to all reactions in the course of the synthesis of the compounds of the formula I including the synthesis of intermediates outlined below and the synthesis of starting compounds and building blocks. Respective synthetic strategies are commonly used in the art. Details about protective groups and their introduction and removal are found in P. G. M. Wuts and T. W. Greene, Greene's Protective Groups in Organic Synthesis, 4. ed. (2007), John Wiley & Sons, for example. Examples of protective groups which may be mentioned, are benzyl protective groups which may occur in the form of benzyl ethers of hydroxy groups and benzyl esters of carboxylic acid groups from which the benzyl group can be removed by catalytic hydrogenation in the presence of a palladium catalyst, tert-butyl protective groups which may occur in the form of tert-butyl esters of carboxylic acid groups from which the tert-butyl group can be removed by treatment with trifluoroacetic acid, acyl protective groups which may be used to protect hydroxy groups and amino groups in the form of esters and amides and which can be cleaved by acidic or basic hydrolysis, and alkyloxycarbonyl protective groups which may occur in the form of tert-butoxycarbonyl derivatives of amino groups which can be cleaved by treatment with trifluoroacetic acid. Undesired reactions of carboxylic acid groups, for example the carboxylic acid group present in the compound of the formula III in case $R^{50}$ is HO—, can also be avoided by employing them in the reaction of the compounds of the formulae III and IV in the form of other esters, for example in the form of alkyl esters like the methyl or ethyl ester which can be cleaved by hydrolysis, for example by means of an alkaline metal hydroxide like sodium hydroxide or lithium hydroxide. Examples of precursor groups which may be mentioned, are nitro groups which can be converted into amino groups by catalytic hydrogenation or by reduction with sodium dithionite, for example, and cyano groups (NC—, N≡C—) which can be converted to carboxamide groups and carboxylic acid groups by hydrolysis. Another example of a precursor group is an oxo group which represents the groups $R^3$ and $R^4$ together or the two groups $R^5$ and $R^6$ together, and which may initially be present in the course of the synthesis of compounds of the formula I in which $R^3$ or $R^5$ is hydroxy. In an approach for the synthesis of such compounds of the formula I, a compound of the formula III in which the groups $R^3$ and $R^4$ together are oxo or the groups $R^5$ and $R^6$ together are oxo, may be obtained from the respective compound which contains a bromine atom instead of the group $R^{20}$—NH— by reaction with sodium azide and subsequently with tributyl tin hydride as described in L. Benati et al., J. Org. Chem. 64 (1999), 7836-7841, the obtained amino compound reacted with a compound of the formula IV, the oxo group reduced, for example with a complex hydride such as sodium borohydride, or reacted with an organometallic compound, for example a Grignard compound, and finally any protective groups removed. If any protective groups or precursor groups are present in the compounds of the formulae III and IV and the direct product of the reaction of the compounds of the formulae III and IV is not yet the desired final compound, the removal of the protective group or conversion into the desired compound can in general also be carried out in situ.

The compounds of the formula III are commercially available or can be obtained according to, or analogously to, procedures described in the literature, for example by di-alkylation of an aminoacetic acid derivative of the formula VI with a compound of the formula V analogously as described in Kotha et al., J. Org. Chem. 65 (2000), 1359-1365, for example.

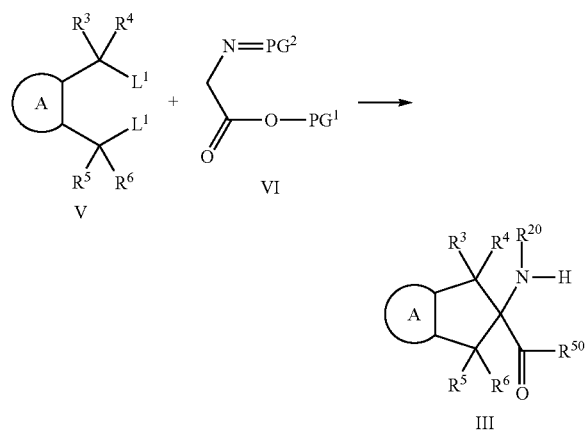

The ring A and the groups $R^3$ to $R^6$ in the compound of the formula V are defined as in the compounds of the formula I and additionally functional groups can be present in protected form or in the form of a precursor group which is later converted into the final group. The groups $L^1$ in the alkylating compound of the formula V are leaving groups such as halogen, for example chlorine or bromine, or sulfonyloxy groups, for example methanesulfonyloxy or trifluoromethanesulfonyloxy. The group $PG^1$ in the compound of the formula VI is a protective group of the carboxylic acid group of aminoacetic acid and can be a group such as ($C_1$-$C_4$)-alkyl, for example methyl, ethyl or tert-butyl, or benzyl. The group $PG^2$ in the compound of the formula VI is a divalent protective group of the amino group of aminoacetic acid and can be a carbon atom, and the group —N=$PG^2$ thus be the isocyano group —N≡C, or a carbon atom carrying two phenyl groups, and the group —N=$PG^2$ thus be the benzhydrylideneamino group —N=C(phenyl)$_2$, for example. The alkylation reaction of the compound of the formula VI with the compound of the formula V is carried out in the presence of base, for example an alkaline metal alkoxide such as potassium tert-butoxide, or an alkaline metal hydride such as sodium hydride, or an alkaline metal carbonate such as potassium carbonate with addition of a phase transfer catalyst such as tetrabutylammonium hydrogensulfate under solid-liquid phase transfer conditions, in an inert solvent such as an amide like DMF or NMP or a nitrile like acetonitrile at temperatures from about −40° C. to about 80° C., depending on the particulars of the specific case. Subsequent to the alkylation, the protective group $PG^2$ is cleaved, for example by treatment with hydrochloric acid in ethanol in the case of a isocyano group or with aqueous hydrochloric acid in the case of a benzhydrylideneamino group, optionally with concomitant cleavage of the protective group $PG^1$, to give a compound of the formula III in which $R^{50}$ is ($C_1$-$C_4$)-alkyl-O—, for example methoxy, ethoxy or tert-butoxy, or benzyloxy, or HO—, and $R^{20}$ is hydrogen. Compounds of the formula III in which $R^{20}$ is different from hydrogen, can be obtained from the compounds in which $R^{20}$ is hydrogen by alkylation or by acylation and subsequent reduction of the obtained amide to the amine. If desired, compounds of the formula III in which $R^{50}$ is HO— can be obtained by acidic or basic hydrolysis from compounds in which $R^{50}$ is ($C_1$-$C_4$)-alkyl-O— or by hydrogenation from compounds in which $R^{50}$ is benzyloxy, for example.

The starting compounds of the formula V can be obtained from the respective dihydroxy compounds, which contain hydroxy groups instead of the groups $L^1$, by treatment with an halogenating agent, for example thionyl chloride or phosphorus tribromide, or a sulfonylating agent such as methanesulfonyl chloride or trifluoromethanesulfonic anhydride, or from the respective hydrocarbons which contain hydrogen atoms instead of the groups $L^1$, by benzylic bromination, for example with N-bromosuccinimide. The said dihydroxy compounds can be obtained from the respective dicarboxylic acids, which contain carboxylic acid groups HO—C(O) instead of the groups $L^1$-C($R^3$)($R^4$)— and $L^1$-C($R^5$)($R^6$)—, or esterified carboxylic acid groups, by reduction, for example with lithium aluminium hydride, in case all groups $R^3$ to $R^6$ are hydrogen, or by reaction with an organometallic compound such as a Grignard compound or an organolithium compound, for example methyl lithium, and optionally by reduction, in case groups $R^3$ to $R^6$ are different from hydrogen. Compounds of the formula III in which A is a cycloalkane ring, can additionally be obtained by hydrogenation in the presence of a transition metal hydrogenation catalyst such as a platinum catalyst, for example, from the respective compounds in which ring A is an unsaturated ring, in particular in the case of compounds of the formula III in which A is a cyclohexane ring which can be obtained from the respective compounds in which A is a benzene ring. In another approach, compounds of the formula III can be obtained from the respective ketones, i.e. the compounds of the formula III in which the two groups $R^{20}$—NH— and $R^{50}$—C(O)— are replaced with an oxo group, according to the classical routes for the synthesis of amino acids like the Strecker synthesis or the Bucherer-Bergs synthesis. All said reactions are standard reactions which are well known to a person skilled in the art.

The compounds of the formula IV likewise are commercially available or can be obtained according to, or analogously to, procedures described in the literature. Customarily, in synthetic procedures for the preparation of compounds of the formula IV compounds are prepared in which the group G in the compounds of the formula IV is a group like $(C_1-C_4)$-alkyl-O— and the group G-C(O)— thus is a $(C_1-C_4)$-alkyl ester group, or the group G-C(O)— is any other ester group such as a benzyl ester phenyl-$CH_2$—O—C(O)— and the group G thus is a benzyloxy group. Compounds of the formula IV in which G is HO—, can be obtained from such compounds of the formula IV by acidic or basic hydrolysis of alkyl esters or by hydrogenation of benzyl esters under standard conditions. Compounds of the formula IV in which G is HO— can then be converted into compounds of the formula IV in which G is halogen as already explained above, which latter compounds can be converted into compounds in which G is aryloxy, for example by reaction with a hydroxyarene such as phenol. In the following, various synthetic procedures for the preparation of compounds of the formula IV in which the group $R^{23}$ in the group $R^{24}$-$R^{23}$-, i.e. in the group of the formula II which represents one of the groups $R^{21}$ and $R^{22}$, has different meanings, are exemplarily outlined.

In a procedure for the preparation of compounds of the formula IV in which the group $R^{23}$ is a chain wherein the terminal chain member which is bonded to the ring comprising the groups Y and Z, is a hetero chain member, a compound of the formula VII is reacted with a compound of the formula VIII to give a compound of the formula IVa.

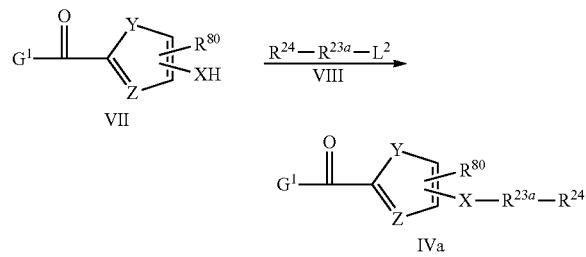

In the compounds of the formulae IVa, VII and VIII the groups Y, Z and $R^{24}$ are defined as in the compounds of the formula I. The group $R^{80}$ is chosen from the series consisting of hydrogen, halogen, $R^{30}$, HO—, $R^{30}$—O—, $R^{30}$—C(O)—O—, $R^{30}$—S(O)$_2$—O—, $R^{30}$—S(O)$_m$—, $H_2N$—, $R^{30}$—NH—, $R^{30}$—N($R^{30}$)—, $R^{30}$—C(O)—NH—, $R^{30}$—C(O)—N($R^{71}$)—, $R^{30}$—S(O)$_2$—NH—, $R^{30}$—S(O)$_2$—N($R^{71}$)—, $R^{30}$—C(O)—, HO—C(O)—, $R^{30}$—O—C(O)—, $H_2N$—C(O)—, $R^{30}$—NH—C(O)—, $R^{30}$—N($R^{30}$)—C(O)—, $H_2N$—S(O)$_2$—, $R^{30}$—NH—S(O)$_2$—, $R^{30}$—N($R^{30}$)—S(O)$_2$—, NC—, $O_2N$— and $Het^1$; i.e. it has the meaning of the one of the groups $R^{21}$ and $R^{22}$ in the compounds of the formula I which is not a group of the formula II. Additionally, functional groups in the compounds of the formulae IVa, VII and VIII can be present in protected form or in the form of a precursor group which is later converted into the final group.

The group $G^1$-C(O)— is an ester group and the group $G^1$ a group such as $(C_1-C_4)$-alkyl-O— or benzyloxy. The group X is a hetero chain member as specified in the definition of $R^{23}$, i.e. a group chosen from the series consisting of N($R^{25}$), O, S, S(O) and S(O)$_2$, in particular from the series consisting of N($R^{25}$), O and S. The groups $R^{23a}$ and X together represent the group $R^{23}$ as specified above wherein a terminal chain member which is a hetero chain member, is bonded to the ring comprising the groups Y and Z. $R^{23a}$ thus is a direct bond or a chain consisting of 1 to 4 chain members of which 0 or 1 chain member is a hetero chain member chosen from the series consisting of N($R^{25}$), O, S, S(O) and S(O)$_2$, provided that the terminal chain member adjacent to the group $L^2$ can only be a hetero chain member which leads to the formation of compound of the formula IVa in which one of the group X and the said terminal chain member is chosen from the series consisting of S(O) and S(O)$_2$ and the other is chosen from the series consisting of N($R^{25}$), O and S, and the other chain members are identical or different groups C($R^{26}$)($R^{26}$), wherein two adjacent groups C($R^{26}$)($R^{26}$) can be connected to each other by a double bond or a triple bond. As is symbolized by the bonds connecting the groups $R^{80}$ and XH in the compounds of the formula VII, as well as the groups $R^{80}$ and X—$R^{23a}$—$R^{24}$ in the compounds of the formula IVa, which bonds are not directed to a specific ring carbon atom, each of the said two groups can be located in each of the two positions of the moiety C=C in the ring comprising the groups Y and Z which is depicted in the formulae. I.e., $R^{80}$ can be located on the ring carbon which is adjacent to the group Y and the other of the two groups on the ring carbon atom which is adjacent to the group Z, as well as $R^{80}$ can be located on the ring carbon which is adjacent to the group Z and the other of the two groups on the ring carbon atom which is adjacent to the group Y. This applies to all compounds defined below containing a group $R^{80}$ and a second group in which the bonds connecting the group to the ring comprising the groups Y and Z are not directed to a specific ring carbon atoms. The group $L^2$ in the compounds of the formula VIII is a leaving group which can be replaced with the group X, such as halogen, fore example chlorine or bromine, a sulfonyloxy group, for example methanesulfonyloxy, trifluoromethanesulfonyloxy or toluene-4-sulfonyloxy, or hydroxy, for example.

The reaction of a compound of the formula VII with a compound of the formula VIII is a nucleophilic substitution reaction which can be carried out under standard conditions for such reactions which are well known to a person skilled in the art. Generally, the reaction is performed in an inert solvent, for example a hydrocarbon or chlorinated hydrocarbon like benzene, toluene, xylene, chlorobenzene, dichloromethane, chloroform or dichloroethane, an ether like THF, dioxane, dibutyl ether, diisopropyl ether or DME, an alcohol like methanol, ethanol or isopropanol, a ketone like acetone or butan-2-one, an ester like ethyl acetate or butyl acetate, a nitrile like acetonitrile, an amide like DMF or NMP, a sulfoxide like DMSO or a sulfone like sulfolane, or a mixture of solvents, at temperatures from about −10° C. to about 120° C., in particular at temperatures from about 0° C. to about 100° C., depending on the particulars of the specific case. In many cases it is favorable for enhancing the nucleophilicity of the compound of the formula VII and/or binding an acid which is liberated during the reaction, to add a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula VII can also be treated with a base and converted into a salt in a separate step. Compounds of the formula VIII in which the group $L^2$ is hydroxy can favorably be reacted with compounds of the formula VII under the conditions of the Mitsunobu reaction in the presence of an azodicarboxylate like diethyl azodicarboxylate or diisopropyl azodicarboxylate and a phosphine like triphenylphosphine or tributylphosphine in an inert aprotic solvent such as an ether like THF or dioxane (cf. O. Mitsunobu, Synthesis (1981), 1-28).

In another procedure, compounds of the formula IVa can be obtained by reacting a compound of the formula IX with a compound of the formula X.

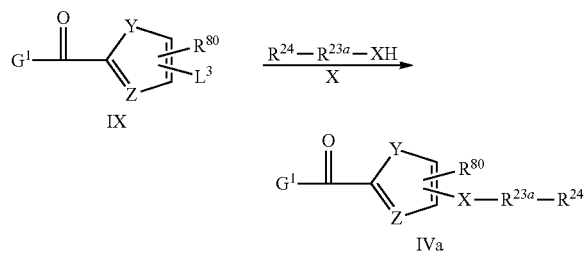

In the compounds of the formulae IX and X the groups Y, Z and $R^{24}$ are defined as in the compounds of the formula I. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IX and X can be present in protected form or in the form of a precursor group which is later converted into the final group. The group $G^1$-C(O)— is an ester group and the group $G^1$ a group such as ($C_1$-$C_4$)-alkyl-O— or benzyloxy. The group X is a hetero chain member as specified in the definition of $R^{23}$, i.e. a group chosen from the series consisting of $N(R^{25})$, O, S, S(O) and $S(O)_2$, in particular from the series consisting of $N(R^{25})$, O and S. In the compound of the formula X the groups $R^{23a}$ and X together represent the group $R^{23}$ as specified above wherein a terminal chain member which is a hetero chain member, is bonded to the ring comprising the groups Y and Z in the obtained compounds of the formula IVa. $R^{23a}$ thus is a direct bond or a chain consisting of 1 to 4 chain members of which 0 or 1 chain member is a hetero chain member chosen from the series consisting of $N(R^{25})$, O, S, S(O) and $S(O)_2$, provided that the terminal chain member adjacent to the group X can only be a hetero chain member if one of the group X and the said terminal chain member is chosen from the series consisting of S(O) and $S(O)_2$ and the other is chosen from the series consisting of $N(R^{25})$, O and S, and the other chain members are identical or different groups $C(R^{26})(R^{26})$, wherein two adjacent groups $C(R^{26})(R^{26})$ can be connected to each other by a double bond or a triple bond. The group $L^3$ in the compounds of the formulae IX is a leaving group which can be replaced with the group X, such as halogen like fluorine, chlorine, bromine or iodine, or a sulfonyloxy group like methanesulfonyloxy or trifluoromethanesulfonyloxy, for example. The reaction of a compound of the formula IX with a compound of the formula X formally is a nucleophilic substitution reaction at the ring comprising the groups Y and Z which can in particular be performed in case of compounds of the formulae IX which are susceptible to such a reaction because of the presence of electron-withdrawing substituents or ring hetero atoms. The reaction can be carried out under standard conditions for such reactions which are well known to a person skilled in the art. The explanations on the reaction conditions such as solvents or bases which are favorably added, which are given above with respect to the reaction of a compound of the formula VII with a compound of the formula VIII apply correspondingly to the reaction of a compound of the formula IX with a compound of the formula X.

The explanations on the reaction of a compound of the formula VII with a compound of the formula VIII also apply correspondingly to reactions for the preparation of compounds of the formula I in which a hetero chain member in the group $R^{23}$ is not present in the terminal position of the chain which is adjacent to the ring comprising the groups Y and Z, but is separated from the said ring by one or more groups $C(R^{26})(R^{26})$, which reactions are of the same type as the reactions outlined above. As an example, the preparation of a compound of the formula IVb from a compound of the formula XI and a compound of the formula XII may be illustrated.

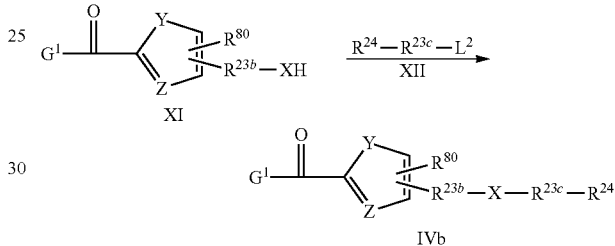

In the compounds of the formulae IVb, XI and XII the groups Y, Z and $R^{24}$ are defined as in the compounds of the formula I. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IX and X can be present in protected form or in the form of a precursor group which is later converted into the final group. Additionally, functional groups in the compounds of the formulae IVb, XI and XII can be present in protected form or in the form of a precursor group which is later converted into the final group. The group $G^1$-C(O)— is an ester group and the group $G^1$ a group such as ($C_1$-$C_4$)-alkyl-O— or benzyloxy. The group X is a hetero chain member as specified in the definition of $R^{23}$, i.e. a group chosen from the series consisting of $N(R^{25})$, O, S, S(O) and $S(O)_2$, in particular from the series consisting of $N(R^{25})$, O and S. The groups $R^{23b}$, $R^{23c}$ and X in the compounds of the formulae IVb together represent the group $R^{23}$ as specified above wherein X is a said hetero chain member. In case $R^{23}$ comprises only one hetero chain member, the group $R^{23b}$ in the compounds of the formulae IVb and XI is a chain consisting of 1 to 4 identical or different groups $C(R^{26})(R^{26})$ and the group $R^{23c}$ in the compounds of the formulae IVb and XII is a direct bond or a chain consisting of 1 to 3 identical or different groups $C(R^{26})(R^{26})$, provided that the total number of groups $C(R^{26})(R^{26})$ is not greater than 4, wherein two adjacent groups $C(R^{26})(R^{26})$ can be connected to each other by a double bond or a triple bond. In the group $R^{23c}$ in the compounds of the formulae IVb and XII a further hetero chain member chosen from the series consisting of $N(R^{25})$, O, S, S(O) and $S(O)_2$ can be present instead of one of the groups $C(R^{26})(R^{26})$, provided that such further hetero chain member can only be present in the terminal position adjacent to the group $L^2$ if one of the group X and the said chain member in the terminal position is chosen from the series consisting of S(O) and $S(O)_2$ and the other is chosen from the series consisting of $N(R^{25})$, O and S. The leaving group $L^2$ in the compounds of the formula XII is defined as in the compounds of the formula VIII. Correspondingly as outlined above with respect to the synthesis of the compounds of the formula IVa, which can be prepared by reacting a compound of the formula VII with a compound of the formula VIII as well as by reacting a compound of the formula IX with a compound of the formula X, compounds of the formula IVb can also be prepared by reacting a compound which is defined as the compound of the formula XI but contains a group $L^2$ instead of the group XH, with a compound which is defined as the compound of the formula XII but contains a group XH instead of the group $L^2$.

In a procedure for the preparation of compounds of the formula IV in which the group $R^{23}$ is a chain which does not comprise any hetero chain member, a carbonyl compound of the formula XIII is condensed with a compound of the formula XIV to give an olefin of the formula IVc which can subsequently be hydrogenated to give a compound of the formula IVd, respectively, or reacted with an organometallic compound of the formula XV to give an alcohol of the formula IVe which likewise can subsequently be hydrogenated to give a compound of the formula IVf.

verted into the final group. The group $G^1$-C(O)— is an ester group and the group $G^1$ a group such as $(C_1-C_4)$-alkyl-O— or benzyloxy. The groups $R^a$ and $R^b$ are independently of each other chosen from hydrogen and $(C_1-C_4)$-alkyl. The group $R^{23d}$ is a direct bond or a chain consisting of 1 to 3 identical or different groups $C(R^{26})(R^{26})$, the group $R^{23e}$ a direct bond or a chain consisting of 1 to 4 identical or different groups $C(R^{26})(R^{26})$. The group $L^4$ in the compounds of the formula XIV is group which allows for the formation of a double bond between the carbon atom carrying the group $L^4$ and the carbon atom of the aldehyde group or ketone group carrying the group $R^a$ in the compound of the formula XIII in a condensation reaction. Examples of suitable condensation reactions are the Wittig reaction and the Wittig-Horner reaction, and examples of suitable groups $L^4$ thus are trisubstituted phosphonio groups, such as the triphenylphosphonio group, having an anion, such as a halide anion, as counterion, and $di((C_1-C_4)$-alkyl)phosphonyl groups, such as the diethylphosphonyl group. The group $L^5$ in the compounds of the formula XV is a metal such as lithium or a magnesium halide group like MgCl, MgBr or MgI, and the compound of the formula XV thus an organolithium compound or a Grignard compound. The Wittig reaction and Wittig-Horner reaction and the addition of the organometallic compound of the formula XV to the compound of the formula XIII can be performed under standard conditions in an inert solvent such as a hydrocarbon like benzene or toluene or an ether like diethyl

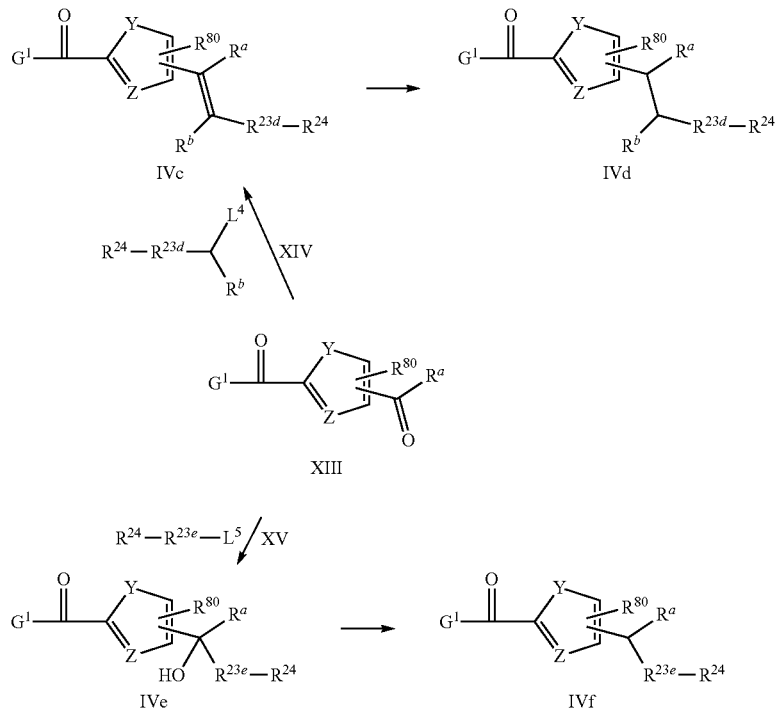

In the compounds of the formulae IVc to IVf, XIII, XIV and XV the groups Y, Z and $R^{24}$ are defined as in the compounds of the formula I. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IVc to IVf, XIII, XIV and XV can be present in protected form or in the form of a precursor group which is later conether, THF, dioxane or DME. The Wittig reaction and the Wittig-Horner reaction are performed in the presence of a base such as a hydride like sodium hydride, an amide like sodium amide or lithium diisopropylamide, or an alkoxide like potassium tert-butoxide. Depending on the particular case, instead of employing a phosphonium salt and deprotonating it, also stable phosphorus ylides can directly be employed in the reaction. The hydrogenation of the double bond in the compounds of the formula IVc to give the compounds of the formulae IVd, or of the benzylic hydroxy group in the compounds of the formulae IVe to give the compounds of the formulae IVf, can be performed in the presence of a hydrogenation catalyst such as palladium on charcoal.

Depending on the particulars of the specific case, various other reactions can be used for preparing compounds of the formula IV. As an example of the preparation of compounds in which the group $R^{23}$ is a chain comprising three groups $C(R^{26})(R^{26})$ and no hetero chain members, an aldol-type reaction of a compound of the formula XIIIa, which is a compound of the formula XIII in which the group $R^a$ is methyl, with an aldehyde of the formula XVI may be mentioned which leads to a compound of the formula IVg or the formula IVm which can be reduced to a compound of the formula IVh, IVk or IVn, for example.

uct of the formula IVm or a condensation product of the formula IVg can be carried under standard conditions for the aldol reaction in the presence of a base, such as an alkaline metal hydroxide like sodium hydroxide or potassium hydroxide, an alkoxide like sodium methoxide or sodium ethoxide or an amide like lithium diisopropylamide, in a solvent such as an alcohol like methanol or ethanol or an ether like diethyl ether, THF or dioxane. At lower temperatures, for example at temperatures from about −80° C. to about −30° C., the compound of the formula IVm can be obtained, at higher temperatures, for example at temperatures from about 10° C. to about 60° C., or by treatment of the compound of the formula IVm with an acid, the compound of the formula IVg can be obtained. The ketone function in the compounds of the formulae IVg and IVm can be reduced to an alcohol function, for

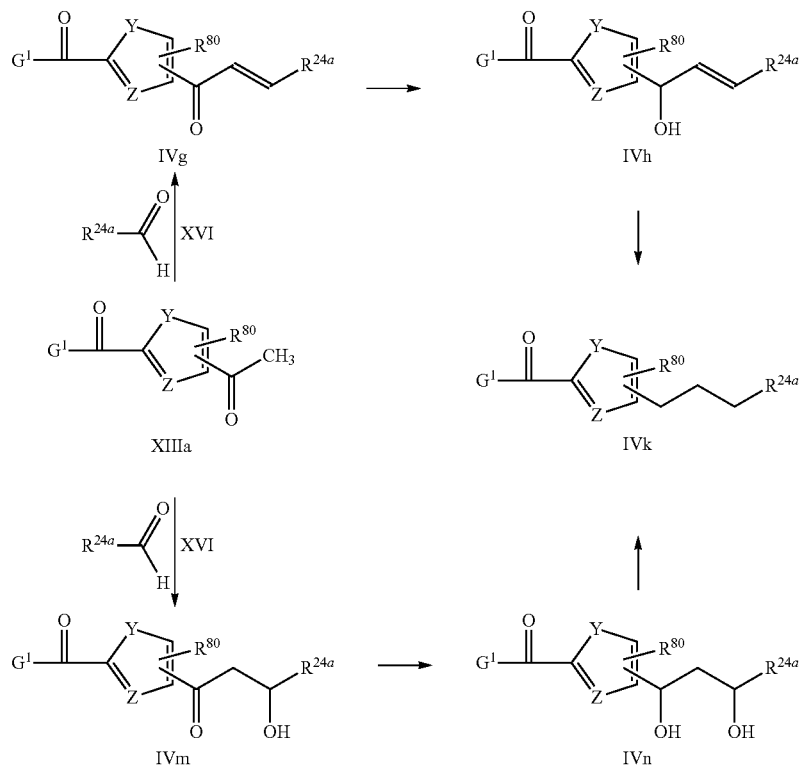

In the compounds of the formulae IVg to IVn and XIIIa the groups Y and Z are defined as in the compounds of the formula I. The group $R^{24a}$ in the compounds of the formulae IVg to IVn and XVI is a group $R^{31}$ or a 3-membered to 10-membered ring as it can represent the group $R^{24}$ in the compounds of the formula I which is bonded via a ring carbon atom, in particular an aromatic ring such as an optionally substituted phenyl, naphthyl or heteroaryl group. The group $R^{80}$ is defined as in the compounds of the formulae IVa and VII, i.e. it has the meaning of the one of the groups $R^{21}$ and $R^{22}$ in the compounds of the formula I which is not a group of the formula II. Additionally, functional groups in the compounds of the formulae IVg to IVn, XIIIa and XVI can be present in protected form or in the form of a precursor group which is later converted into the final group. The group $G^1$-C (O)— is an ester group and the group $G^1$ a group such as $(C_1-C_4)$-alkyl-O— or benzyloxy.

The reaction of a compound of the formula XIIIa with a compound of the formula XIV to give an aldol addition prodexample with a complex hydride such as a borohydride like lithium borohydride or sodium borohydride, to give a compound of the formula IVh or IVn, respectively, which can be converted into a compound of the formula IVk by dehydration in the presence of an acid and/or hydrogenation in the presence of a catalyst such as palladium on charcoal, for example.

As a further example of reactions which can be used for preparing compounds of the formula IV, transition metal-catalyzed C—C coupling reactions may be mentioned by which compounds can be obtained wherein the group $R^{23}$ is a direct bond or comprises a chain of two groups $C(R^{26})(R^{26})$, which are connected to each other by a triple bond, i.e. a group of the formula —C≡C—, in a position adjacent to the ring comprising the groups Y and Z. Such compounds can be obtained from a compound of the formula IX and a boronic acid, for example an optionally substituted phenylboronic acid, cycloalkylboronic acid or heteroarylboronic acid, or an ethyne, for example an optionally substituted phenylethyne.

As catalyst in such reactions, a palladium compound such as bis(triphenylphosphine)palladium(II) chloride or tetrakis(triphenylphosphine)palladium(0) and a copper compound such as copper(I) iodide can be used. Further details on such reactions are found in N. Miyaura et al., Chem. Rev. 95 (1995), 2457-2483; and R. Chinchilla et al., Chem. Rev. 107 (2007), 874-922, for example.

The order in which groups are introduced in the course of the synthesis of a compound of the formula I, can also be different from the ones outlined above. For example, instead of first preparing a compound of the formula IVa from a compound of the formula VII and a compound of the formula VIII, or from a compound of the formula IX and a compound of the formula X, and then reacting the compound of the formula IVa with a compound of the formula III to give a compound of the formula I, a compound of the formula III can also be reacted with a compound of the formula VII or a compound of the formula IX and the obtained compound of the formula XVII or XVIII reacted with a compound of the formula VIII or X, respectively, to give a compound of the formula Ik.

fied above wherein a terminal chain member which is a hetero chain member, is bonded to the ring comprising the groups Y and Z. $R^{23a}$ thus is a direct bond or a chain consisting of 1 to 4 chain members of which 0 or 1 chain member is a hetero chain member chosen from the series consisting of $N(R^{25})$, O, S, S(O) and S(O)$_2$, provided that the terminal chain member adjacent to the group X can only be a hetero chain member if one of the group X and the said terminal chain member is chosen from the series consisting of S(O) and S(O)$_2$ and the other is chosen from the series consisting of $N(R^{25})$, O and S, and the other chain members are identical or different groups $C(R^{26})(R^{26})$, wherein two adjacent groups $C(R^{26})(R^{26})$ can be connected to each other by a double bond or a triple bond. Additionally, functional groups in the compounds of the formulae Ik, XVII and XVIII can be present in protected form or in the form of a precursor group which is later converted into the final group. As indicated above and as applies to all compounds which contain a group $R^{80}$ and another group which are connected to the ring comprising the groups Y and Z by bonds which are not directed to a specific ring carbon atom, the groups $R^{80}$ and X in the compounds of the formula

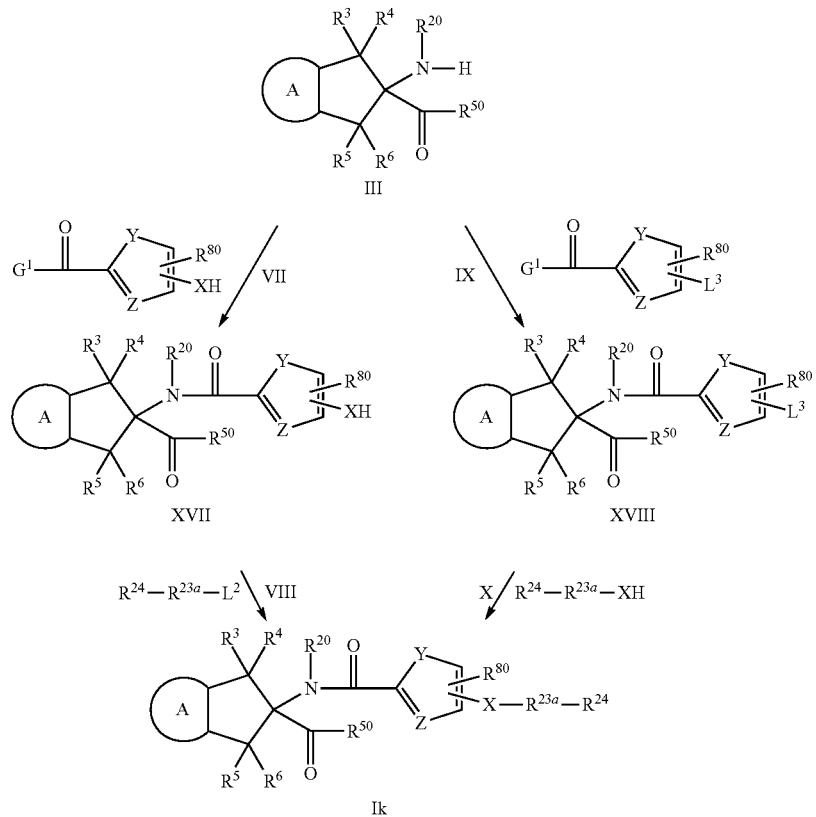

In the compounds of the formulae Ik, XVII and XVIII the ring A and the groups Y, Z, $R^3$ to $R^6$, $R^{20}$, $R^{24}$ and $R^{50}$ are defined as in the compounds of the formula I. The groups X, $R^{23a}$ and $R^{80}$ are defined as in the compounds of the formula IVa. Thus, $R^{80}$ has the meaning of the one of the groups $R^{21}$ and $R^{22}$ in the compounds of the formula I which is not a group of the formula II. The group X is a hetero chain member as specified in the definition of $R^{23}$, i.e. a group chosen from the series consisting of $N(R^{25})$, O, S, S(O) and S(O)$_2$, in particular from the series consisting of $N(R^{25})$, O and S. The groups $R^{23a}$ and X together represent the group $R^{23}$ as speci- XVII, the groups $R^{80}$ and $L^3$ in the compounds of the formula XVIII, and the groups $R^{80}$ and X—$R^{23a}$—$R^{24}$ in the compounds of the formula Ik can be located in each of the two positions of the moiety C=C in the ring comprising the groups Y and Z. The explanations given above with respect to the reaction of a compound of the formula III with a compound of the formula IV, the reaction of a compound of the formula VII with a compound of the formula VIII, and the reaction of a compound of the formula IX with a compound of the formula X apply correspondingly to the reaction of a compound of the formula III with a compound of the formula VII or a compound of the formula IX, the reaction of a compound of the formula XVII with a compound of the formula VIII, and the reaction of a compound of the formula XVIII with a compound of the formula X. The order in which groups are introduced in the course of the synthesis of a compound of the formula I, can also be varied with respect to other reactions. For example, a compound of the formula XVIII can be employed in a transition-metal catalyzed C—C coupling reaction as referred to above, or a compound of the formula XIIIa can be reacted with a compound of the formula III and the obtained compound modified at the CH$_3$—C(O)— group to give a compound of the formula I.

The starting compounds and building blocks for the synthesis of the compounds of the formula I are commercially available or can be prepared according to procedures described in the literature or analogously to such procedures. Exemplarily the preparation of compounds of the formula VIII in which R$^{24}$ is an optionally substituted phenyl or naphthyl group, R$^{23a}$ is an optionally alkyl-substituted CH$_2$CH$_2$ group and L$^2$ is a hydroxy group, may be mentioned in which use can be made of the procedure for the coupling of aryl halides with ester enolates described by M. Jorgensen et al., J. Am. Chem. Soc. 124 (2002), 12557-12565. In the said procedure an optionally alkyl-substituted acetic acid ester, for example acetic acid tert-butyl ester or isobutyric acid methyl ester, is deprotonated with a base such as lithium dicyclohexylamide and reacted with an optionally substituted aryl bromide in the presence of a palladium compound such as bis(dibenzylideneacetone)palladium or tris(dibenzylideneactone)dipalladium and tri(tert-butyl)phosphine to give a 2-(optionally substituted aryl)acetic acid ester which is optionally alkyl-substituted in the 2-position of the acetic acid moiety. Reduction of the ester function under standard conditions, for example with lithium aluminium hydride, then affords the 2-(optionally substituted aryl)ethanol which is optionally alkyl-substituted in the 2-position.

For obtaining further compounds of the formula I, various transformations of functional groups can be carried out under standard conditions in compounds of the formula I or intermediates or starting compounds in the synthesis of the compounds of the formula I. For example, a hydroxy group can be esterified to give a carboxylic acid ester or a sulfonic acid ester, or etherified. Etherifications of hydroxy groups can favorably be performed by alkylation with the respective halogen compound, for example a bromide or iodide, in the presence of a base such an alkali metal carbonate like potassium carbonate or cesium carbonate in an inert solvent such as an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with an activated carboxylic acid or a carboxylic acid derivate like an acid chloride or anhydride or a sulfonic acid chloride. A carboxylic ester group can be hydrolyzed under acidic or basic conditions to give a carboxylic acid. A carboxylic acid group can be activated or converted into a reactive derivative as outlined above with respect to the compounds of the formula IX and reacted with an alcohol or an amine or ammonia to give an ester or amide. A primary amide can be dehydrated to give a nitrile. A sulfur atom in an alkyl-S— group or in a heterocyclic ring or a sulfur atom occurring in a chain representing the group R$^{23}$ can be oxidized with a peroxide like hydrogen peroxide or a peracid to give a sulfoxide moiety S(O) or a sulfone moiety S(O)$_2$. A carboxylic acid group, carboxylic acid ester group and a ketone group can be reduced to an alcohol, for example with a complex hydride such al lithium aluminium hydride, lithium borohydride or sodium borohydride. All reactions in the preparation of the compounds of the formula I are known per se and can be carried out in a manner familiar to a person skilled in the art according to, or analogously, to procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein. Furthermore, besides by techniques of solution chemistry, the compounds of the formula I can also be obtained by solid phase chemistry.

Another subject of the present invention are the novel starting compounds and intermediates occurring in the synthesis of the compounds of the formula I, including the compounds of the formulae III, IV, IV, IVb, IVc, IVd, IVe, IVf, IVg, IVh, IVk, IVm, IVn, V, VI, VII, VIII, IX, X, XI, XII, XIII, XIV, XV, XVI, XVII and XVIII, wherein the ring A and the groups G, G$^1$, L$^1$, L$^2$, L$^3$, PG$^1$, PG$^2$, X, Y, Z, R$^3$ to R$^6$, R$^{20}$ to R$^{23}$, R$^{23a}$, R$^{23b}$, R$^{23c}$, R$^{24}$, R$^{24a}$, R$^{50}$, R$^{80}$, R$^a$ and R$^b$ are defined as above, in any of their stereoisomeric forms or a mixture of stereoisomeric forms in any ratio, and their salts, and solvates of any of them, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit the Edg-2 receptor (LPA$_1$ receptor) as can be demonstrated in the pharmacological test described below and in other tests which are known to a person skilled in the art. The compounds of the formula I and their physiologically acceptable salts and solvates therefore are valuable pharmaceutical active compounds. The compounds of the formula I and their physiologically acceptable salts and solvates can be used for the treatment of cardiovascular diseases such as heart failure including systolic heart failure, diastolic heart failure, diabetic heart failure and heart failure with preserved ejection fraction, cardiomyopathy, myocardial infarction, myocardial remodeling including myocardial remodeling after infarction or after cardiac surgery, vascular remodeling including vascular stiffness, hypertension including pulmonary hypertension, portal hypertension and systolic hypertension, atherosclerosis, peripheral arterial occlusive disease (PAOD), restenosis, thrombosis or vascular permeability disorders, for cardioprotection such as cardioprotection after myocardial infarction or after cardiac surgery, for renoprotection, or for the treatment of inflammation or inflammatory diseases such as rheumatoid arthritis, osteoarthritis, renal diseases such as renal papillary necrosis or renal failure including renal failure after ischemia/reperfusion, pulmonary diseases such as chronic obstructive pulmonary disease (COPD), asthma or acute respiratory dystress syndrome (ARDS), immunological diseases, allergic diseases, tumor growth, metastasis, metabolic diseases, fibrotic diseases such as pulmonary fibrosis including idiopathic lung fibrosis, cardiac fibrosis, vascular fibrosis, perivascular fibrosis, renal fibrosis including renal tubulointerstitial fibrosis, liver fibrosis, fibrosing skin conditions including keloid formation, collagenosis, scleroderma, progressive systemic sclerosis and nephrogenic fibrosing dermopathy, or other types of fibrosis including Dupuytren's contracture, psoriasis, pain such as neuropathic pain, diabetic pain or inflammatory pain, pruritus, retinal ischemia/reperfusion damage, macular degeneration, psychiatric disorders, neurodegenerative diseases, cerebral nerve disorders, peripheral nerve disorders, endocrinic disorders such as hyperthyroidism, scarring disorders or wound healing disorders, for example. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarction can be prevented or its extent and sequelae decreased, or in patients who are susceptible to disturbed wound healing, by means of the prophylactic or preventive medicinal treatment wound healing after surgery can favorably be influenced. The treatment of diseases can occur both in acute cases and in chronic cases. The efficacy of the compounds of the formula I can be demonstrated in the pharmacological tests described below and in other tests which are known to a person skilled in the art The compounds of the formula I and their physiologically acceptable salts and solvates can therefore be used in animals, in particular in mammals and specifically in humans, as a pharmaceutical or medicament on their own, in mixtures with one another or in the form of pharmaceutical compositions. A subject of the present invention also are the compounds of the formula I and their physiologically acceptable salts and solvates for use as a pharmaceutical, as well as pharmaceutical compositions and medicaments which comprise an efficacious dose of at least one compound of the formula I and/or a physiologically acceptable salt thereof and/or solvate thereof as an active ingredient and a pharmaceutically acceptable carrier, i.e. one or more pharmaceutically innocuous, or non-hazardous, vehicles and/or excipients, and optionally one or more other pharmaceutical active compounds. A subject of the present invention furthermore are the compounds of the formula I and their physiologically acceptable salts and solvates for use in the treatment of the diseases mentioned above or below, including the treatment of any one of the mentioned diseases, for example heart failure or fibrotic diseases such as pulmonary fibrosis, cardiac fibrosis, vascular fibrosis, perivascular fibrosis, renal fibrosis, liver fibrosis or fibrosing skin conditions, the use of the compounds of the formula I and their physiologically acceptable salts and solvates for the manufacture of a medicament for the treatment of the diseases mentioned above or below, including the treatment of any one of the mentioned diseases, for example heart failure or fibrotic diseases such as pulmonary fibrosis, cardiac fibrosis, vascular fibrosis, perivascular fibrosis, renal fibrosis, liver fibrosis or fibrosing skin conditions, wherein the treatment of diseases comprises their therapy and prophylaxis as mentioned above, as well as their use for the manufacture of a medicament for the inhibition of the Edg-2 receptor (LPA$_1$ receptor). A subject of the invention also are methods for the treatment of the diseases mentioned above or below, including the treatment of any one of the mentioned diseases, for example heart failure or fibrotic diseases such as pulmonary fibrosis, cardiac fibrosis, vascular fibrosis, perivascular fibrosis, renal fibrosis, liver fibrosis or fibrosing skin conditions, which comprise administering an efficacious amount of at least one compound of the formula I and/or a physiologically acceptable salt thereof and/or solvate thereof to a human or an animal which is in need thereof. The compounds of the formula I and pharmaceutical compositions and medicaments comprising them can be administered enterally, for example by oral, sublingual or rectal administration, parenterally, for example by intravenous, intramuscular, subcutaneous or intraperitoneal injection or infusion, or by another type of administration such as topical, percutaneous, transdermal, intra-articular, intranasal or intraocular administration.

The compounds of the formula I and their physiologically acceptable salts and solvates can also be used in combination with other pharmaceutical active compounds, wherein in such a combination use the compounds of the formula I and/or their physiologically acceptable salts and/or solvates and one or more other pharmaceutical active compounds can be present in one and the same pharmaceutical composition or in two or more pharmaceutical compositions for separate, simultaneous or sequential administration. Examples of such other pharmaceutical active compounds are angiotensin converting enzyme (ACE) inhibitors, ramipril, angiotensin II receptor subtype 1 (AT1) antagonists, irbesartan, antiarrhythmics, dronedarone, peroxisome proliferator-activated receptor-alpha (PPAR-α) activators, peroxisome proliferator-activated receptor-gamma (PPAR-γ) activators, pioglitazone, rosiglitazone, prostanoids, endothelin receptor antagonists, bosentan, elastase inhibitors, calcium antagonists, beta blockers, diuretics, aldosterone receptor antagonists, eplerenone, renin inhibitors, rho kinase inhibitors, soluble guanylate cyclase (sGC) activators, sGC sensitizers, phosphodiesterase (PDE) inhibitors, phosphodiesterase type 5 (PDE5) inhibitors, NO donors, digitalis drugs, angiotensin converting enzyme/neutral endopeptidase (ACE/NEP) inhibitors, statins, bile acid reuptake inhibitors, platelet derived growth factor (PDGF) receptor antagonists, vasopressin antagonists, aquaretics, sodium hydrogen exchanger subtype 1 (NHE1) inhibitors, factor II/factor IIa antagonists, factor IX/factor IXa antagonists, factor X/factor Xa antagonists, factor XIII/factor XIIIa antagonists, anticoagulants, antithrombotics, platelet inhibitors, profibrinolytics, thrombin-activatable fibrinolysis inhibitors (TAFI), plasminogen activator inhibitor-1 (PAI 1), coumarins, heparins, thromboxane antagonists, serotonin antagonists, cyclooxygenase inhibitors, acetylsalicylic acid, therapeutic antibodies, glycoprotein IIb/IIIa (GPIIb/IIIa) antagonists including abciximab, chymase inhibitors, cytostatics, taxanes, paclitaxel, docetaxel, aromatase inhibitors, estrogen receptor antagonists, selective estrogen receptor modulators (SERM), tyrosine kinase inhibitors, imatinib, receptor tyrosine kinase inhibitors, RAF kinase inhibitors, p38 mitogen-activated protein kinase (p38 MAPK) inhibitors, pirfenidone, multi-kinase inhibitors, and sorafenib. A subject of the present invention also is the said combination use of any one or more of the compounds of the formula I disclosed herein and their physiologically acceptable salts and solvates, with any one or more, for example one or two, of the mentioned other pharmaceutical active compounds.

The pharmaceutical compositions and medicaments according to the invention normally contain from about 0.5 to about 90 percent by weight of compounds of the formula I and/or physiologically acceptable salts and/or solvates thereof, and an amount of active ingredient of the formula I and/or its physiologically acceptable salt and/or solvate which in general is from about 0.2 mg to about 1000 mg, in particular from about 0.2 mg to about 500 mg, for example from about 1 mg to about 300 mg, per unit dose. Depending on the kind of the pharmaceutical composition and other particulars of the specific case, the amount may deviate from the indicated ones. The production of the pharmaceutical compositions and medicaments can be carried out in a manner known per se. For this, the compounds of the formula I and/or their physiologically acceptable salts and/or solvates are mixed together with one or more solid or liquid vehicles and/or excipients, if desired also in combination with one or more other pharmaceutical active compounds such as those mentioned above, and brought into a suitable form for dosage and administration, which can then be used in human medicine or veterinary medicine.

As vehicles, which may also be looked upon as diluents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of vehicles and excipients are water, vegetable oils, waxes, alcohols such as ethanol, isopropanol, 1,2-propanediol, benzyl alcohols, glycerol, polyols, polyethylene glycols or polypropylene glycols, glycerol triacetate, polyvinylpyrrolidone, gelatin, cellulose, carbohydrates such as lactose or starch like corn starch, sodium chloride, stearic acid and its salts such as magnesium stearate, talc, lanolin, petroleum jelly, or mixtures thereof, for example saline or mixtures of water with one or more organic solvents such as mixtures of water with alcohols. For oral and rectal use, pharmaceutical forms such as, for example, tablets, film-coated tablets, sugar-coated tablets, granules, hard and soft gelatin capsules, suppositories, solutions, including oily, alcoholic or aqueous solutions, syrups, juices or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Further suitable pharmaceutical forms are, for example, implants and patches and forms adapted to inhalation. The compounds of the formula I and their physiologically acceptable salts can also be lyophilized and the obtained lyophilizates used, for example, for the production of injectable compositions. In particular for topical application, also liposomal compositions are suitable. The pharmaceutical compositions and medicaments can also contain one or more other active ingredients and/or, for example, one or more vitamins.

As usual, the dosage of the compounds of the formula I depends on the circumstances of the specific case and is adjusted by the physician according to the customary rules and procedures. It depends, for example, on the compound of the formula I administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 10 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in-vitro diagnoses of biological samples, if an inhibition of the Edg-2 receptor is intended. The compounds of the formula I and their salts can also be used as intermediates for the preparation of further pharmaceutical active substances.

The following examples illustrate the invention.

ABBREVIATIONS

ACN acetonitrile
DCM dichloromethane
DIAD diisopropyl azodicarboxylate
DIC 1,3-diisopropylcarbodiimide
DMF dimethylformamide
DMSO dimethyl sulfoxide
EA ethyl acetate
EDIA N-ethyldiisopropylamine
EDC 1-(3-dimethylaminopropyl)-3-ethylcarbodiimide hydrochloride
FMOC fluoren-9-ylmethoxycarbonyl
HEP heptane
HOBT 1-hydroxy-benzotriazole
NMM N-methyl-morpholine
TFA trifluoroacetic acid
THF tetrahydrofuran In general, reactions were carried out under argon. When example compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the workup such as evaporation or lyophilization conditions. In the names of the example compounds and the structural formulae such contained trifluoroacetic acid is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. Unless specified otherwise, $^1$H-NMR spectra were recorded at 500 MHz in $D_6$-DMSO as solvent at 298 K. In the NMR characterization, the chemical shift δ (in ppm), the number of hydrogen atoms (H) and the multiplicity (s: singlet, d: doublet, dd: double doublet, t: triplet, dt: double triplet, q: quartet, m: multiplet; br: broad) of the peaks as determined on printouts are given. In the MS characterization, in general the mass number (m/z) of the peak of the molecular ion [M], e.g. [M$^+$], or of a related ion such as the ion [M+1], e.g. [(M+1)$^+$], i.e. the protonated molecular ion [(M+H)$^+$] abbreviated as [MH$^+$], or the ion [M−1], e.g. [(M−1)$^-$], i.e. the deprotonated molecular ion [(M−H)$^-$], which was formed depending on the ionization method used, is given. Generally, the ionization method was electrospray ionization (ESI) or atmospheric pressure chemical ionization (APCI). The particulars of the LC/MS methods used are as follows.

Method LC1
Column: YMC J'sphere H80, 20×2.1 mm, 4 μm; 30° C.; flow: 1.0 ml/min; eluent A: ACN; eluent B: water+0.05% TFA; gradient: from 4% A+96% B to 95% A+5% B within 2.4 min, then to 4% A+96% B within 0.05 min, then 4% A+96% B for 0.05 min; MS ionization method: ESI$^+$ Method LC2
Column: YMC J'sphere H80, 20×2.1 mm, 4 μm; 30° C.; flow: 1.0 ml/min; eluent A: ACN; eluent B: water+0.05% TFA; gradient: from 4% A+96% B to 95% A+5% B within 2.4 min, then to 4% A+96% B within 0.05 min, then 4% A+96% B for 0.05 min; MS ionization method: ESI$^+$ Method LC3
Column: YMC J'sphere H80, 33×2.1 mm, 4 μm; flow: 1.3 ml/min; eluent A: ACN+0.05% TFA; eluent B: water+0.05% TFA; gradient: from 5% A+95% B to 95% A+5% B within 2.5 min, then 95% A+5% B for 0.5 min; then to 5% A+95% B within 0.2 min; MS ionization method: ESI$^+$ Method LC4
Column: YMC J'sphere H80, 33×2.1 mm, 4 μm; flow: 1.0 ml/min; eluent A: ACN+0.05% TFA; eluent B: water+0.05% TFA; gradient: from 5% A+95% B to 95% A+5% B within 3.4 min, then 95% A+5% B for 1.0 min, then to 5% A+95% B within 0.2 min, then 5% A+95% B for 0.5 min; MS ionization method: ESI$^+$ Method LC5
Column: YMC J'sphere H80, 33×2.1 mm, 4 μm; flow: 1.3 ml/min; eluent A: ACN+0.08% formic acid; eluent B: water+0.1% formic acid; gradient: from 5% A+95% B to 95% A+5% B within 2.5 min, then 95% A+5% B for 0.5 min; MS ionization method: ESI$^+$ Method LC6
Column: YMC J'sphere H80, 33×2.1 mm, 4 μm; flow: 1.3 ml/min; eluent A: ACN+0.05% TFA; eluent B: water+0.05% TFA; gradient: from 5% A+95% B to 95% A+5% B within 2.5 min, then to 5% A+95% B within 0.5 min; MS ionization method: ESI$^+$ Method LC7
Column: Thermo Javelin C18, 40×2.1 mm, 5 μm; flow: 1.0 ml/min; eluent A: ACN+0.1% TFA; eluent B: water+0.1% TFA; gradient: from 2% A+98% B to 80% A+20% B within 7.0 min, then to 100% A+0% B within 0.2 min, then 100% A+0% B for 1.0 min, then to 2% A+98% B within 0.3 min, then 2% A+98% B for 0.5 min; MS ionization method: ESI$^+$ Method LC8
Column: Thermo Javelin C18, 40×2.1 mm, 5 μm; flow: 1.0 ml/min; eluent A: ACN+0.1% TFA; eluent B: water+0.1% TFA; gradient: from 2% A+98% B to 80% A+20% B within 5.0 min, then to 100% A+0% B within 0.2 min, then 100% A+0% B for 1.0 min, then to 2% A+98% B within 0.3 min, then 2% A+98% B for 0.5 min; MS ionization method: ESI$^+$ Method LC9
Column: HP Waters Atlantis dC18, 50×2.1 mm, 5 μm; flow: 0.6 ml/min; eluent A: ACN+0.1% TFA; eluent B: water+0.1% TFA; gradient: from 2% A+98% B to 80% A+20% B within 5.0 min, then to 100% A+0% B within 0.2 min, then 100% A+0% B for 1.0 min, then to 2% A+98% B within 0.3 min, then 2% A+98% B for 0.5 min; MS ionization method: ESI$^+$ Method LC10
Column: YMC J'sphere H80, 33×2.1 mm, 4 μm; flow: 1.3 ml/min; eluent A: ACN+0.05% TFA; eluent B: water+0.05% TFA; gradient: 5% A+95% B for 0.5 min, then to 95% A+5% B within 3.0 min, then to 5% A+95% B within 0.5 min; MS ionization method: ESI$^+$ Method LC11
Column: YMC J'sphere H80, 33×2.1 mm, 4 μm; flow: 1.3 ml/min; eluent A: ACN+0.05% TFA; eluent B: water+0.05% TFA; gradient: from 5% A+95% B to 95% A+5% B within 2.5 min, then 95% A+5% B for 0.5 min; MS ionization method: ESI$^+$ Method LC12
Column: YMC J'sphere H80, 33×2.1 mm, 4 μm; flow: 1 ml/min; eluent A: ACN+0.05% TFA; eluent B: water+0.05% TFA; gradient: 2% A+98% B for 1 min, then to 95% A+5% B within 4 min, then 95% A+5% B for 1.25 min; MS ionization method: ESI$^+$ Method LC13
Column: YMC J'sphere H80, 33×2.1 mm, 4 μm; flow: 1.3 ml/min; eluent A: ACN+0.05% TFA; eluent B: water+0.05% TFA; gradient: 5% A+95% B for 0.5 min, then to 95% A+5% B within 3 min, then 95% A+5% B for 0.5 min; MS ionization method: ESI$^+$ Method LC14
Column: Waters XBridge C18, 50×4.6 mm, 2.5 μm; flow: 1.3 ml/min, 50° C.; eluent A: ACN+0.05% TFA; eluent B: water+0.05% TFA; gradient: 5% A+95% B for 0.3 min, then to 95% A+5% B within 3.2 min, then 95% A+5% B for 0.5 min; MS ionization method: ESI$^+$ Method LC15
Column: Waters XBridge C18, 50×4.6 mm, 2.5 μm; flow: 1.3 ml/min, 50° C.; eluent A: ACN+0.1% formic acid; eluent B: water+0.1% formic acid; gradient: from 3% A+97% B to 60% A+40% B within 3.5 min, then to 98% A+2% B within 0.5 min, then 98% A+2% B for 1 min, then to 3% A+97% B within 0.2 min, then 3% A+97% B for 1.3 min; MS ionization method: APCI$^+$ Method LC16
Column: Waters XBridge C18, 50×4.6 mm, 2.5 μm; flow: 1.3 ml/min, eluent A: ACN+0.08% formic acid; eluent B: water+0.1% formic acid; gradient: from 3% A+97% B to 60% A+40% B within 3.5 min, then to 98% A+2% B within 0.5 min, then 98% A+2% B for 1 min, then to 3% A+97% B within 0.2 min, then 3% A+97% B for 1.3 min; MS ionization method: ESI$^-$ Method LC17
Column: Waters XBridge C18, 50×4.6 mm, 2.5 μm; flow: 1.3 ml/min, eluent A: ACN+0.08% formic acid; eluent B: water+0.1% formic acid; gradient: from 3% A+97% B to 60% A+40% B within 3.5 min, then to 98% A+2% B within 0.5 min, then 98% A+2% B for 1 min, then to 3% A+97% B within 0.2 min, then 3% A+97% B for 1.3 min; MS ionization method: ESI$^+$ Method LC18
Column: Waters XBridge C18, 50×4.6 mm, 2.5 μm; flow: 1.7 ml/min, 50° C., eluent A: ACN+0.05% TFA; eluent B: water+0.05% TFA; gradient: 5% A+95% B for 0.2 min, then to 95% A+5% B within 2.2 min, then 95% A+5% B for 1.1 min, then to 5% A+95% B within 0.1 min, then 5% A+95% B for 0.9 min; MS ionization method: ESI$^+$ Method LC19
Column: Waters XBridge C18, 50×4.6 mm, 2.5 μm; flow: 1.3 ml/min, 50° C., eluent A: ACN+0.1% formic acid; eluent B: water+0.1% formic acid; gradient: from 3% A+97% B to 60% A+40% B within 3.5 min, then to 98% A+2% B within 0.5 min, then 98% A+2% B for 1 min, then to 3% A+97% B within 0.2 min, then 3% A+97% B for 1.3 min; MS ionization method: ESI$^+$ Method LC20

Column: Waters XBridge C18, 50×4.6 mm, 2.5 µm; flow: 1.3 ml/min, eluent A: ACN+0.08% formic acid; eluent B: water+0.1% formic acid; gradient: from 3% A+97% B to 98% A+2% B within 18 min, then 98% A+2% B for 1 min, then to 3% A+97% B within 0.5 min, then 3% A+97% B for 0.5 min; MS ionization method: ESI+

Method LC21

Column: Waters XBridge C18, 50×4.6 mm, 2.5 µm; flow: 1.3 ml/min, 50° C., eluent A: ACN+0.1% formic acid; eluent B: water+0.1% formic acid; gradient: from 3% A+97% B to 60% A+40% B within 3.5 min, then to 98% A+2% B within 0.5 min, then 98% A+2% B for 1 min, then to 3% A+97% B within 0.2 min, then 3% A+97% B for 1.3 min; MS ionization method: ESI−

Method LC22

Column: YMC J'sphere H80, 33×2.1 mm, 4 µm; flow: 1 ml/min; eluent A: ACN+0.05% TFA; eluent B: water+0.05% TFA; gradient: from 5% A+95% B to 95% A+5% B within 3.7 min; MS ionization method: ESI+

EXAMPLE 1

2-[4-Bromo-3-(2-m-tolyl-ethoxy)-benzoylamino]-indane-2-carboxylic acid methyl ester

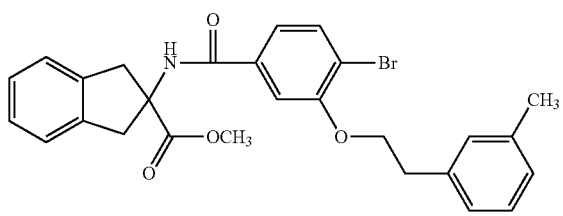

Step 1

4-Bromo-3-(2-m-tolyl-ethoxy)-benzoic acid methyl ester

4-Bromo-3-hydroxy-benzoic acid methyl ester (1.00 g, 4.32 mmol) and triphenylphosphine (1.36 g, 5.19 mmol) were dissolved in THF. 2-(3-Methylphenyl)-ethanol (2-m-tolyl-ethanol) (0.707 g, 5.19 mmol) was added, the mixture was cooled in an ice bath, and DIAD (1.05 g, 5.19 mmol) was added slowly with stirring. The ice bath was removed and stirring continued overnight at room temperature. The volatiles were evaporated in vacuo, and the residue was purified by silica gel chromatography (HEP/EA gradient) to give 1.55 g of the title compound.

Step 2

4-Bromo-3-(2-m-tolyl-ethoxy)-benzoic acid

The compound of step 1 (0.50 g, 1.43 mmol) was dissolved in dioxane (5 ml), lithium hydroxide (7.1 ml of an aqueous 1 M (i.e. 1 mol per liter) solution) was added, and the mixture was reacted overnight. The mixture was partitioned between 2 N hydrochloric acid and EA, the aqueous phase extracted with EA, and the organic extracts were dried over sodium sulfate, filtered and evaporated to dryness in vacuo to give 0.414 g of the title compound.

$^1$H-NMR: δ=13.2 (br s, 1H); 7.7 (d, 1H); 7.52 (d, 1H); 7.42 (dd, 1H); 7.22-7.11 (m, 3H); 7.02 (d, 1H); 4.30 (t, 2H); 3.03 (t, 2H); 2.29 (s, 3H)

Step 3

2-[4-Bromo-3-(2-m-tolyl-ethoxy)-benzoylamino]-indane-2-carboxylic acid methyl ester The compound of step 2 (0.410 g, 1.22 mmol) was dissolved in DMF (5 ml), EDIA (0.790 g, 6.12 mmol), HOBT (33 mg, 0.244 mmol), and 2-amino-indane-2-carboxylic acid methyl ester hydrochloride (0.246 g, 1.47 mmol) were added, the mixture was cooled in an ice bath and EDC (352 mg, 1.84 mmol) was added. The mixture was stirred overnight. The volatiles were evaporated in vacuo, the mixture was partitioned between 2 N hydrochloric acid and EA, the organic phase was dried over magnesium sulfate and evaporated to dryness. The residue was purified by silica gel chromatography (HEP/EA gradient) to give 0.56 g of the title compound.

LC/MS (Method LC1): Rt=1.98 min; m/z=508.1/510.1 [MH+]

EXAMPLE 2

2-[4-Bromo-3-(2-m-tolyl-ethoxy)-benzoylamino]-indane-2-carboxylic acid

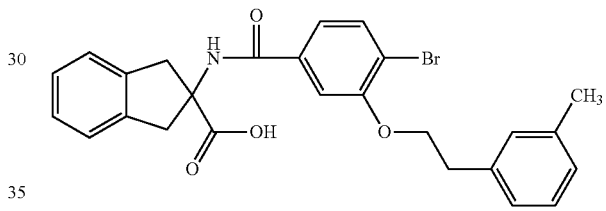

The compound of example 1 (60 mg, 0.118 mmol) was dissolved in dioxane (1.5 ml), lithium hydroxide (0.59 ml of an aqueous 1 M solution) was added and the mixture was reacted for 20 min at 60° C. The mixture was partitioned between 2 N hydrochloric acid and EA, the aqueous phase extracted with EA, and the organic extracts were dried over sodium sulfate, filtered and evaporated to dryness in vacuo. The residue was stirred overnight with a mixture of diethyl ether and HEP, filtered, and the solid was dried in vacuo to give 43 mg of the title compound.

$^1$H-NMR: δ=12.45 (br s, 1H); 8.87 (s, 1H); 7.64 (d, 1H); 7.46 (d, 1H); 7.37 (dd, 1H); 7.25-7.11 (m, 7H); 7.02 (d, 1H); 4.27 (t, 2H); 3.60 (d, 2H); 3.37 (d, 2H); 3.02 (t, 2H); 2.28 (s, 3H)

EXAMPLE 3

2-[4-Methylsulfanyl-3-(2-m-tolyl-ethoxy)-benzoylamino]-indane-2-carboxylic acid methyl ester

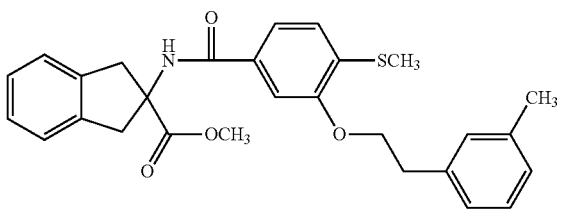

Step 1

4-Nitro-3-(2-m-tolyl-ethoxy)-benzoic acid methyl ester

3-Hydroxy-4-nitro-benzoic acid methyl ester (1.00 g, 5.07 mmol) and 2-(3-methylphenyl)-ethanol (0.829 g, 6.09 mmol) were reacted in analogy to step 1 of example 1 to give 1.39 g of the title compound.

$^1$H-NMR: δ=7.96 (d, 1H); 7.75 (s, 1H); 7.63 (d, 1H); 7.18 (t, 1H); 7.11 (s, 1H); 7.08 (d, 1H); 7.03 (d, 1H); 4.41 (t, 2H); 3.89 (s, 3H); 3.01 (t, 2H); 2.28 (s, 3H)

Step 2

4-Methylsulfanyl-3-(2-m-tolyl-ethoxy)-benzoic acid methyl ester

The compound of step 1 (900 mg, 2.85 mmol) was dissolved in 1,3-dimethyl-2-imidazolidinone (6 ml), and sodium methanethiolate (0.23 g, 3.29 mmol) was added. The mixture was reacted at room temperature for 60 h, then partitioned between a saturated sodium chloride solution and EA, and the aqueous phase extracted with EA. The organic extracts were dried over sodium sulfate, filtered and evaporated to dryness. The residue was purified by silica gel chromatography (HEP/EA gradient) to give 600 mg of the title compound.

$^1$H-NMR: δ=7.56 (d, 1H); 7.39 (s, 1H); 7.23 (d, 1H); 7.21-7.12 (m, 3H); 7.02 (d, 1H); 4.25 (t, 2H); 3.82 (s, 3H); 3.01 (t, 2H); 2.41 (s, 3H); 2.29 (s, 3H)

Step 3

4-Methylsulfanyl-3-(2-m-tolyl-ethoxy)-benzoic acid

The compound of step 2 (450 mg, 1.42 mmol) was hydrolyzed in analogy to example 2 to give 395 mg of the title compound.

$^1$H-NMR: δ=12.8 (br s, 1H); 7.55 (d, 1H); 7.38 (s, 1H); 7.23-7.10 (m, 4H); 7.02 (d, 1H); 4.25 (t, 2H); 3.82 (s, 3H); 3.00 (t, 2H); 2.41 (s, 3H); 2.29 (s, 3H)

Step 4

2-[4-Methylsulfanyl-3-(2-m-tolyl-ethoxy)-benzoylamino]-indane-2-carboxylic acid methyl ester The compound of step 3 (395 mg, 1.31 mmol) was dissolved in DCM (5 ml). DMF (29 mg, 0.39 mmol) and oxalyl chloride (3.9 ml of a 2 M solution in DCM) were added at room temperature. The mixture was stirred for 60 min, evaporated to dryness in vacuo, dissolved in dioxane and evaporated again. The residue was dissolved in DCM (2 ml) and the solution was slowly added with stirring to an ice-cooled mixture of 2-amino-indane-2-carboxylic acid methyl ester hydrochloride (5.42 g, 23.8 mmol), EA and an excess of saturated aqueous sodium hydrogencarbonate solution. After 2 h, the organic layer was separated, washed with a saturated sodium chloride solution, dried over sodium sulfate, filtered and evaporated to dryness. 582 mg of the title compound were obtained.

$^1$H-NMR: δ=8.86 (s, 1H); 7.5 (dd, 1H); 7.36 (d, 1H); 7.25-7.11 (m, 8H); 7.02 (d, 1H); 4.23 (t, 2H); 3.61 (d, 2H); 3.60 (s, 3H); 3.37 (d, 2H); 3.01 (t, 2H); 2.39 (s, 3H); 2.28 (s, 3H)

EXAMPLE 4

2-[4-Methylsulfanyl-3-(2-m-tolyl-ethoxy)-benzoylamino]-indane-2-carboxylic acid

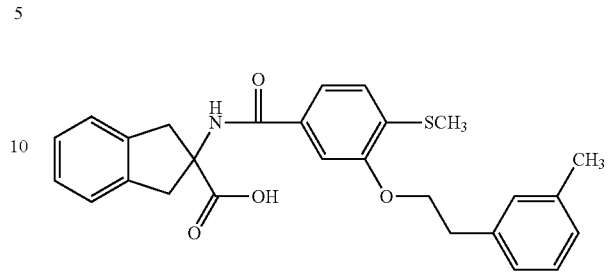

The compound of example 3 (580 mg, 1.22 mmol) was hydrolyzed in analogy to example 2 to give 480 mg of the title compound.

$^1$H-NMR: δ=12.4 (br s, 1H); 8.73 (s, 1H); 7.50 (dd, 1H); 7.35 (d, 1H); 7.24-7.11 (m, 8H); 7.02 (d, 1H); 4.24 (t, 2H); 3.59 (d, 2H); 3.37 (d, 2H); 3.01 (t, 2H); 2.39 (s, 3H); 2.28 (s, 3H)

EXAMPLE 5

2-[4-Methanesulfinyl-3-(2-m-tolyl-ethoxy)-benzoylamino]-indane-2-carboxylic acid

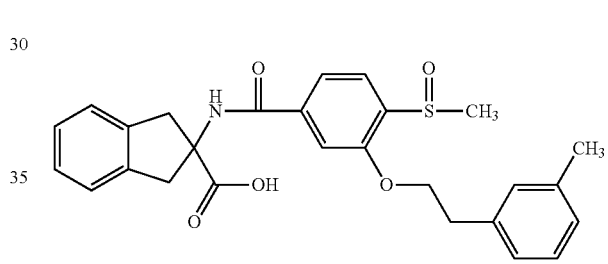

The compound of example 4 (100 mg, 0.216 mmol) was dissolved in acetic acid (7.5 ml), hydrogen peroxide (74 mg of a 30% solution in water, 0.65 mmol) was added, and the mixture was reacted at room temperature for 9 h. The mixture was partitioned between EA and a 1% aqueous sodium sulfite solution, the aqueous phase extracted with EA, and the organic extracts were dried over sodium sulfate, filtered and evaporated to dryness. The residue was stirred with diethyl ether, filtered, and dried in vacuo to give 79 mg of the title compound.

LC/MS (Method LC1): Rt=1.48 min; m/z=478.2 [MH$^+$]

EXAMPLE 6

2-[4-Methanesulfonyl-3-(2-m-tolyl-ethoxy)-benzoylamino]-indane-2-carboxylic acid

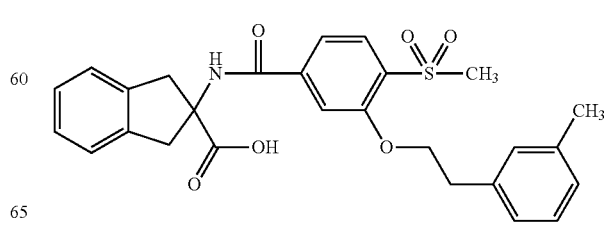

The compound of example 4 (140 mg, 0.30 mmol) was dissolved in acetic acid (7.5 ml), hydrogen peroxide (103 mg of a 30% solution in water, 0.91 mmol) was added and the mixture was reacted at 70° C. for 8 h. The mixture was partitioned between EA and 1% aqueous sodium sulfite solution, the aqueous phase extracted with EA, and the organic extracts were dried over sodium sulfate, filtered and evaporated to dryness. The residue was stirred with diethyl ether, filtered, and dried in vacuo to give 143 mg of the title compound.

LC/MS (Method LC1): Rt=1.55 min; m/z=494.0 [MH$^+$]

EXAMPLE 7

2-[4-Acetyl-3-(2-m-tolyl-ethoxy)-benzoylamino]-indane-2-carboxylic acid methyl ester

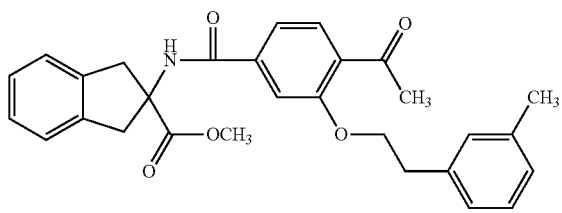 [SMILES: COC(=O)C1(NC(=O)c2ccc(C(C)=O)c(OCCc3cccc(C)c3)c2)Cc2ccccc2C1]

4-Acetyl-3-hydroxy-benzoic acid (M. E. Zwaagstra et. al., J. Med. Chem. 40 (1997), 1075-1089) was reacted with 2-amino-indane-2-carboxylic acid methyl ester hydrochloride in analogy to step 3 of example 1. From the obtained 2-[4-acetyl-3-hydroxy-benzoylamino]-indane-2-carboxylic acid methyl ester, the title compound was obtained by reaction with 2-(3-methylphenyl)-ethanol in analogy to step 1 of example 1.

LC/MS (Method LC1): Rt=1.83 min; m/z=472.2 [MH$^+$]

EXAMPLE 8

2-[4-Acetyl-3-(2-m-tolyl-ethoxy)-benzoylamino]-indane-2-carboxylic acid

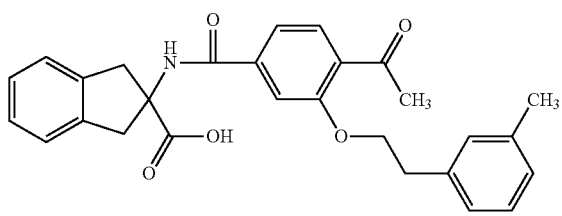

From the compound of example 7, the title compound was obtained by hydrolysis with lithium hydroxide in analogy to example 2.

LC/MS (Method LC1): Rt=1.67 min; m/z=458.0 [MH$^+$]

EXAMPLE 9

2-[4-(1-Hydroxy-ethyl)-3-(2-m-tolyl-ethoxy)-benzoylamino]-indane-2-carboxylic acid

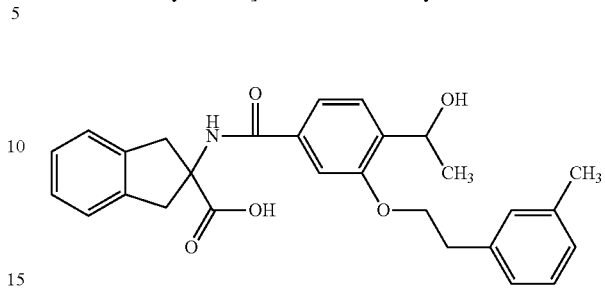

The compound of example 7 (300 mg, 0.636 mmol) was dissolved in 3 ml of ethanol, the mixture was cooled in an ice bath and sodium borohydride (24.1 mg, 0.636 mmol) was added. The reaction mixture was allowed to warm to room temperature and stirring was continued for 4 h. The mixture was partitioned between EA and a saturated aqueous sodium hydrogencarbonate solution, the aqueous phase extracted with EA, and the organic extracts were dried over sodium sulfate, filtered and evaporated to dryness. The residue was purified by preparative RP HPLC (water/ACN gradient) to give a mixture of 2-[4-(1-hydroxy-ethyl)-3-(2-m-tolyl-ethoxy)-benzoylamino]-indane-2-carboxylic acid methyl ester and 2-[4-(1-hydroxy-ethyl)-3-(2-m-tolyl-ethoxy)-benzoylamino]-indane-2-carboxylic acid ethyl ester.

LC/MS (Method LC1): Rt=1.70 min; m/z=474.2 [MH$^+$] (2-[4-(1-hydroxy-ethyl)-3-(2-m-tolyl-ethoxy)-benzoylamino]-indane-2-carboxylic acid methyl ester)

LC/MS (Method LC1): Rt=1.76 min; m/z=488.2 [MH$^+$] (2-[4-(1-hydroxy-ethyl)-3-(2-m-tolyl-ethoxy)-benzoylamino]-indane-2-carboxylic acid ethyl ester)

From the mixture of the methyl ester and the ethyl ester, the title compound was obtained by hydrolysis with lithium hydroxide in analogy to example 2.

LC/MS (Method LC1): Rt=1.54 min; m/z=460.2 [MH$^+$]

EXAMPLE 10

2-[4-Ethyl-3-(2-m-tolyl-ethoxy)-benzoylamino]-indane-2-carboxylic acid

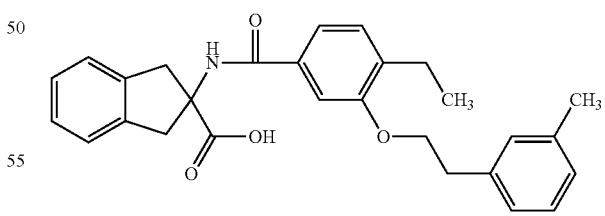

The compound of example 9 (80 mg, 0.174 mmol) was dissolved in methanol and hydrogenated in an H-cube™ hydrogenation reactor (ThalesNano, Budapest, Hungary) at a hydrogen pressure of 100 bar over a 10% palladium on charcoal cartridge. The reaction mixture was evaporated to dryness and the residue purified by preparative RP HPLC (water/ACN gradient).

$^1$H-NMR: δ=12.3 (br s, 1H); 8.72 (s, 1H); 7.40-7.33 (m, 2H); 7.25-7.12 (m, 7H); 7.10 (d, 1H); 7.02 (d, 1H); 4.20 (t,

2H); 3.59 (d, 2H); 3.37 (d, 2H); 3.02 (t, 2H); 2.56-2.51 (m, 2H); 2.27 (s, 3H); 1.02 (t, 3H)

EXAMPLE 11

2-[4-(1-Fluoro-ethyl)-3-(2-m-tolyl-ethoxy)-benzoylamino]-indane-2-carboxylic acid

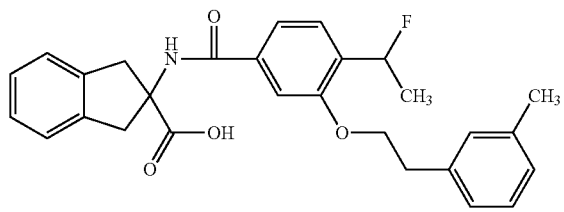 [SMILES: Cc1cccc(CCOc2cc(C(=O)NC3(C(=O)O)Cc4ccccc4C3)ccc2C(C)F)c1]

The mixture of 2-[4-(1-hydroxy-ethyl)-3-(2-m-tolyl-ethoxy)-benzoylamino]-indane-2-carboxylic acid methyl ester and 2-[4-(1-hydroxy-ethyl)-3-(2-m-tolyl-ethoxy)-benzoylamino]-indane-2-carboxylic acid ethyl ester obtained in example 9 (50 mg) was dissolved in DCM, and diethylaminosulfur trifluoride (33 mg, 0.204 mmol) was added in two portions (second portion after 3.5 h). After complete conversion as detected by HPLC, the mixture was partitioned between EA and a saturated aqueous sodium hydrogencarbonate solution and the aqueous phase extracted with EA. The combined organic extracts were dried over sodium sulfate, filtered and evaporated to dryness. The residue was stirred with a HEP/diethyl ether mixture, filtered, and dried in vacuo. The obtained ester was hydrolyzed in analogy to example 2 to give 12 mg of the title compound.

$^1$H-NMR: δ=12.4 (br s, 1H); 8.82 (s, 1H); 7.49 (d, 1H); 7.41 (s, 1H); 7.37 (d, 1H); 7.25-7.12 (m, 6H); 7.10 (d, 1H); 7.03 (d, 1H); 5.83/5.74 (dq, 1H); 4.26 (t, 2H); 3.58 (d, 2H); 3.39 (d, 2H); 3.02 (d, 2H); 2.27 (s, 3H); 1.40/1.35 (dd, 3H)

EXAMPLE 12

2-[4-Ethoxy-3-(2-m-tolyl-ethoxy)-benzoylamino]-indane-2-carboxylic acid

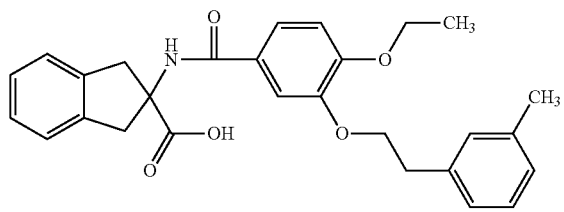 [SMILES: CCOc1ccc(C(=O)NC2(C(=O)O)Cc3ccccc3C2)cc1OCCc1cccc(C)c1]

Step 1

4-Ethoxy-3-hydroxy-benzoic acid ethyl ester 3,4-Dihydroxybenzoic acid ethyl ester (3.00 g, 16.0 mmol) was suspended in DMF (10 ml), potassium carbonate (2.21 g, 16.0 mmol) was added, the mixture was stirred for 5 min at room temperature, and then iodoethane (2.49 g, 16.0 mmol) was added. The mixture was stirred overnight, the addition of potassium carbonate and of iodoethane was repeated, and the mixture was stirred overnight again. The mixture was partitioned between 2 N hydrochloric acid and EA, the aqueous phase extracted with EA, and the combined organic extracts were washed with a saturated sodium hydrogencarbonate solution and a saturated sodium chloride solution, dried over sodium sulfate, filtered, and evaporated to dryness. The residue was purified by silica gel chromatography (HEP/EA gradient).

LC/MS (Method LC1): Rt=1.28 min; m/z=211.1 [MH$^+$]

Step 2

2-[4-Ethoxy-3-(2-m-tolyl-ethoxy)-benzoylamino]-indane-2-carboxylic acid

From the compound of step 1, the title compound was obtained by reaction with 2-(3-methylphenyl)-ethanol in analogy to step 1 of example 1, hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.

$^1$H-NMR: δ=12.4 (br s, 1H); 8.64 (s, 1H); 7.46 (d, 1H); 7.41 (s, 1H); 7.22-7.10 (m, 7H); 7.02 (d, 1H); 6.99 (d, 1H); 4.16 (t, 2H); 4.04 (q, 2H); 3.53 (d, 2H); 3.3-3.4 (2H); 2.98 (t, 2H); 2.28 (s, 3H); 1.32 (t, 3H)

EXAMPLE 13

2-[4-Methoxy-3-(2-m-tolyl-ethoxy)-benzoylamino]-indane-2-carboxylic acid methyl ester

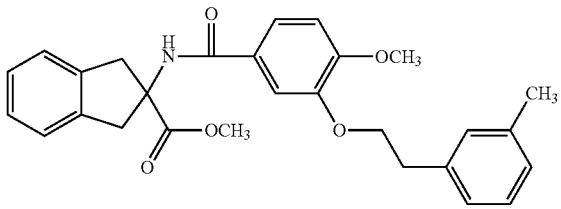

Step 1

4-Methoxy-3-(2-m-tolyl-ethoxy)-benzoic acid

From 3-hydroxy-4-methoxy-benzoic acid methyl ester, the title compound was obtained by reaction with 2-(3-methylphenyl)-ethanol in analogy to step 1 of example 1 and hydrolysis of the ester group in analogy to example 2.

$^1$H-NMR: δ=12.65 (br s, 1H); 7.56 (dd, 1H); 7.44 (d, 1H); 7.19 (t, 1H); 7.17-7.15 (m, 1H); 7.12 (d, 1H); 7.06-7.02 (m, 2H); 4.19 (t, 2H); 3.83 (s, 3H); 3.01 (t, 2H); 2.29 (s, 3H)

Step 2

2-[4-Methoxy-3-(2-m-tolyl-ethoxy)-benzoylamino]-indane-2-carboxylic acid methyl ester The compound of step 1 (1.98 g, 6.91 mmol) was dissolved in thionyl chloride (10 ml) and stirred for 20 min at 60° C. The solution was evaporated to dryness in vacuo and the residue was evaporated twice with dioxane in vacuo. The residue was dissolved in a little DCM and added to a well-stirred mixture of 2-amino-indane-2-carboxylic acid methyl ester hydrochloride (1.50 g, 6.58 mmol) in EA and an excess of a saturated aqueous sodium hydrogencarbonate solution. The mixture was stirred for 30 min at room temperature. The layers were separated, the aqueous phase was extracted with EA, the combined organic phases were washed with brine, dried over sodium sulfate, filtered and evaporated to dryness. This residue was stirred with diethyl ether overnight, filtered and dried in vacuo to give 1.92 g of the title compound.

$^1$H-NMR: δ=8.78 (s, 1H); 7.50 (dd, 1H); 7.43 (d, 1H); 7.24-7.14 (m, 6H); 7.11 (d, 1H); 7.03 (d, 1H); 7.01 (d, 1H); 4.17 (t, 2H); 3.80 (s, 3H); 3.59 (d, 2H); 3.59 (s, 3H); 3.36 (d, 2H); 3.00 (t, 2H); 2.28 (s, 3H)

EXAMPLE 14

2-[4-Methoxy-3-(2-m-tolyl-ethoxy)-benzoylamino]-indane-2-carboxylic acid

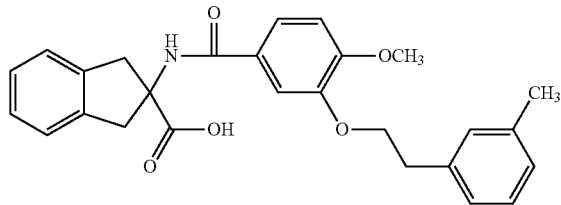

The compound of example 13 (1.92 g, 4.18 mmol) was dissolved in dioxane (40 ml), lithium hydroxide (10 ml, 1 M solution in water) was added and the mixture was stirred for 30 min at 60° C. The mixture was partitioned between 2 N hydrochloric acid and EA, the aqueous phase extracted with EA, and the combined organic extracts were washed with brine, dried over sodium sulfate, filtered and evaporated to dryness. The residue was stirred overnight in EA, filtered, and the crystals were dried in vacuo to give 1.35 g of the title compound.

$^1$H-NMR: δ=12.36 (br s, 1H); 8.63 (s, 1H); 7.50 (dd, 1H); 7.43 (d, 1H); 7.23-7.13 (m, 6H); 7.11 (d, 1H); 7.03 (d, 1H); 7.00 (d, 1H); 4.17 (t, 2H); 3.79 (s, 3H); 3.58 (d, 2H); 3.37 (d, 2H); 3.00 (t, 2H); 2.28 (s, 3H)

EXAMPLE 15

2-{4-Methoxy-3-[2-(3-methylsulfanyl-phenyl)-ethoxy]-benzoylamino}-indane-2-carboxylic acid methyl ester

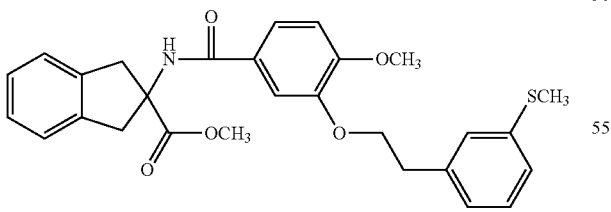

Step 1

2-(3-Acetoxy-4-methoxy-benzoylamino)-indane-2-carboxylic acid methyl ester

3-Acetoxy-4-methoxy-benzoic acid (5.00 g, 23.8 mmol) was dissolved in DCM (50 ml). DMF (167 mg, 2.38 mmol) and oxalyl chloride (35.6 ml of a 2 M solution in DCM) were added at room temperature. The mixture was stirred for 20 min, evaporated to dryness in vacuo, the residue redissolved in DCM and evaporated again. The residue was dissolved in DCM and slowly added to a stirred mixture of 2-amino-indane-2-carboxylic acid methyl ester hydrochloride (5.42 g, 23.8 mmol), EA and an excess of a saturated aqueous sodium hydrogencarbonate solution. After 90 min the organic layer was separated and washed with a saturated sodium hydrogencarbonate solution, 2 M hydrochloric acid and a saturated sodium chloride solution, dried over sodium sulfate, filtered and evaporated to dryness to give 8.95 g of the title compound.

$^1$H-NMR: δ=8.88 (s, 1H); 7.80 (dd, 1H); 7.62 (d, 1H); 7.28-7.13 (m, 5H); 3.81 (s, 3H); 3.60 (s, 3H); 3.58 (d, 2H); 3.37 (d, 2H); 2.27 (s, 3H)

Step 2

2-(3-Hydroxy-4-methoxy-benzoylamino)-indane-2-carboxylic acid methyl ester

The compound of step 1 (3.44 g, 8.97 mmol) was dissolved in methanol (50 ml), potassium carbonate (248 mg, 1.79 mmol) was added and the mixture was stirred for 2 h at room temperature. The mixture was evaporated to dryness, the residue partitioned between EA and 1 N hydrochloric acid and the aqueous phase extracted with EA. The combined organic extracts were dried over magnesium sulfate, filtered and evaporated to dryness to give 2.80 g of the title compound.

$^1$H-NMR: δ=9.14 (s, 1H); 8.71 (s, 1H); 7.32 (dd, 1H); 7.29 (d, 1H); 7.24-7.20 (m, 2H); 7.19-7.13 (m, 2H); 6.93 (d, 2H); 3.80 (s, 3H); 3.60 (s, 3H); 3.56 (d, 2H); 3.38 (d, 2H)

Step 3

2-{4-Methoxy-3-[2-(3-methylsulfanyl-phenyl)-ethoxy]-benzoylamino}-indane-2-carboxylic acid methyl ester The compound of step 2 (0.380 g, 1.11 mmol) and triphenylphosphine (0.461 g, 1.67 mmol) were dissolved in THF. 2-(3-Methylsulfanyl-phenyl)-ethanol (0.281 g, 1.67 mmol) and DIAD (0.359 g, 1.67 mmol) were added and the reaction mixture was stirred at room temperature for 2 h. The volatiles were evaporated in vacuo and the residue was purified by preparative RP HPLC (water/ACN gradient) to give 0.217 g of the title compound.

$^1$H-NMR: δ=8.78 (s, 1H); 7.50 (d, 1H); 7.41 (s, 1H); 7.28-7.20 (m, 4H); 7.20-7.13 (m, 2H); 7.13-7.08 (m, 2H); 7.00 (d, 1H); 4.18 (t, 2H); 3.79 (s, 3H); 3.62-3.55 (m, 5H); 3.38 (d, 2H); 3.01 (t, 2H); 2.45 (s, 3H)

EXAMPLE 16

2-{4-Methoxy-3-[2-(3-methylsulfanyl-phenyl)-ethoxy]-benzoylamino}-indane-2-carboxylic acid

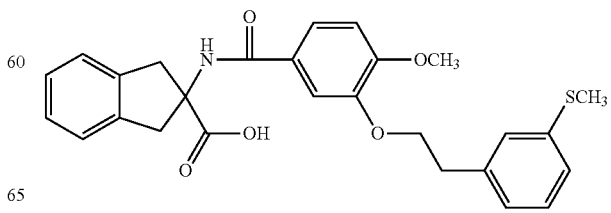

The compound of example 15 (195 mg, 0.397 mmol) was dissolved in dioxane (2 ml), lithium hydroxide (1.99 ml of an aqueous 1 M solution, 1.99 mmol) was added, and the mixture was stirred at 60° C. for 1 h. The mixture was partitioned between 2 N hydrochloric acid and EA, the aqueous phase extracted with EA, and the combined organic extracts were dried over sodium sulfate, filtered and evaporated to dryness to give 180 mg of the title compound.

$^1$H-NMR: δ=12.37 (br s, 1H); 8.65 (s, 1H); 7.47 (d, 1H); 7.41 (s, 1H); 7.29-7.18 (m, 4H); 7.18-7.08 (m, 4H); 7.01 (d, 1H); 4.17 (t, 2H); 3.79 (s, 3H); 3.54 (d, 2H); 3.37 (d, 2H); 3.01 (t, 2H); 2.45 (s, 3H)

EXAMPLE 17

2-{3-[2-(3-Methanesulfinyl-phenyl)-ethoxy]-4-methoxy-benzoylamino}-indane-2-carboxylic acid

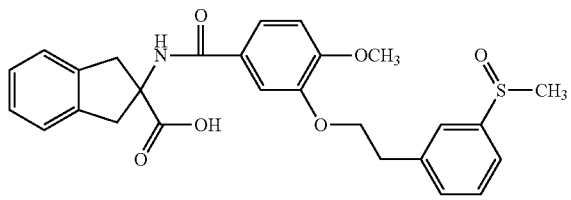 [SMILES: COc1ccc(C(=O)NC2(C(=O)O)Cc3ccccc3C2)cc1OCCc1cccc(S(C)=O)c1]

The compound of example 16 (35 mg, 0.078 mmol) was dissolved in acetic acid (2.5 ml), hydrogen peroxide (43 mg of a 30% solution in water, 0.38 mmol) was added and the mixture was stirred at room temperature for 2 h. The mixture was partitioned between EA and a 1% aqueous sodium sulfite solution, the aqueous phase extracted with EA, and the combined organic extracts were dried over sodium sulfate, filtered and evaporated to dryness to give 36 mg of the title compound.

$^1$H-NMR: δ=12.3 (br s, 1H); 8.62 (s, 1H); 7.65 (s, 1H); 7.56-7.47 (m, 4H); 7.43 (d, 1H); 7.23-7.19 (m, 2H); 7.17-7.12 (m, 2H); 7.00 (d, 1H); 4.24 (t, 2H); 3.80 (s, 3H); 3.57 (d, 2H); 3.38 (d, 2H); 3.14 (t, 2H); 2.72 (s, 3H)

EXAMPLE 18

2-{3-[2-(3-Methanesulfonyl-phenyl)-ethoxy]-4-methoxy-benzoylamino}-indane-2-carboxylic acid

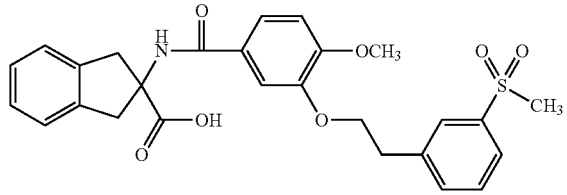 [SMILES: COc1ccc(C(=O)NC2(C(=O)O)Cc3ccccc3C2)cc1OCCc1cccc(S(C)(=O)=O)c1]

The title compound was synthesized in analogy to example 17 except that the reaction temperature was 70° C. Yield: 36 mg.

$^1$H-NMR: δ=12.35 (br s, 1H); 8.64 (s, 1H); 7.92 (s, 1H); 7.78 (d, 1H); 7.70 (d, 1H); 7.58 (dd, 1H); 7.49 (dd, 1H); 7.42 (d, 1H); 7.22-7.19 (m, 2H); 7.18-7.12 (m, 2H); 7.00 (d, 1H); 4.24 (t, 2H); 3.79 (s, 3H); 3.56 (d, 2H); 3.37 (d, 2H); 3.19 (s, 3H); 3.18 (t, 2H)

In analogy to the above examples, the example compounds of the formula Im listed in table 1 were prepared. In the formulae of the groups $R^{90}$ in table 1 the line crossed with the symbol ∼∼∼ represents the free bond via which the group $R^{90}$ is bonded to the oxygen atom which is attached to the 3-position of the benzoyl group depicted in formula Im. I.e., in the formula of the complete molecule the terminal endpoint of the line crossed with the said symbol ends at the oxygen atom attached to the 3-position of the benzoyl group. The compounds can be named as 2-[3-($R^{90}$-oxy)-4-methoxy-benzoylamino]-indane-2-carboxylic acid, for example as 2-{3-[2-(3-cyclopropyl-phenyl)-ethoxy]-4-methoxy-benzoylamino}-indane-2-carboxylic acid in the case of example 21.

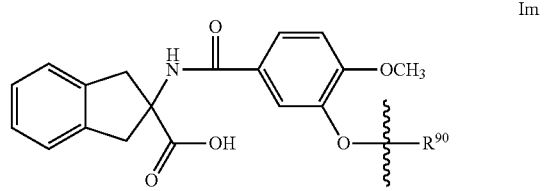

Im

TABLE 1

Example compounds of the formula Im

| Example | $R^{90}$ | LC/MS Method | m/z [MH$^+$] | Retention time [min] |
|---|---|---|---|---|
| 19 | ![CF3S-phenyl-ethyl] | LC3 | 532.09 | 2.04 |
| 20 | ![H3C-phenyl(F)-ethyl] | LC1 | 464.20 | 1.62 |

TABLE 1-continued
Example compounds of the formula Im
| Example | R⁹⁰ | LC/MS Method | m/z [MH⁺] | Retention time [min] |
|---|---|---|---|---|
| 21 | 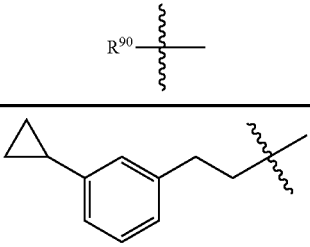 | LC1 | 472.2 | 1.68 |
| 22 | 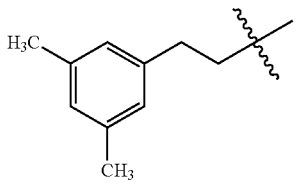 [SMILES: *CCc1cc(C)cc(C)c1] | LC1 | 460.2 | 1.70 |
| 23 | 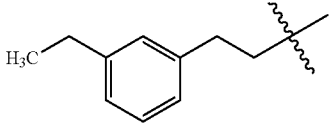 [SMILES: *CCc1cccc(CC)c1] | LC1 | 460.2 | 1.65 |
| 24 | 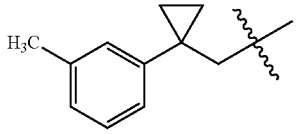 [SMILES: *CC1(c2cccc(C)c2)CC1] | LC1 | 472.2 | 1.70 |
| 25 | 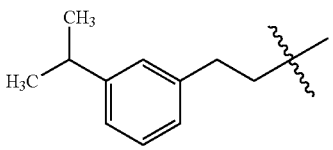 [SMILES: *CCc1cccc(C(C)C)c1] | LC1 | 474.2 | 1.75 |
| 26 | 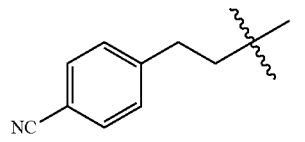 [SMILES: *CCc1ccc(C#N)cc1] | LC2 | 457.1 | 1.48 |
| 27 | 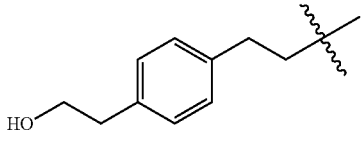 [SMILES: *CCc1ccc(CCO)cc1] | LC1 | 476.2 | 1.35 |
| 28 | 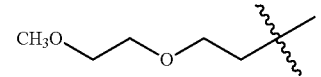 | LC3 | 430.3 | 1.41 |
| 29 | 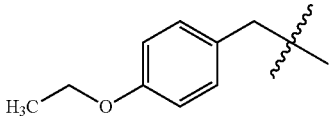 | LC3 | 462.35 | 1.82 |
| 30 | 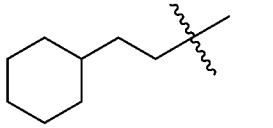 [SMILES: *CCC1CCCCC1] | LC3 | 438.36 | 2.04 |

TABLE 1-continued
Example compounds of the formula Im
| Example | R⁹⁰ | LC/MS Method | m/z [MH⁺] | Retention time [min] |
|---|---|---|---|---|
| 31 | 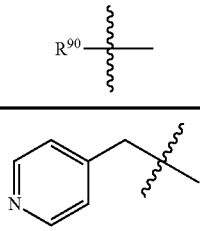 | LC3 | 419.28 | 1.15 |
| 32 | 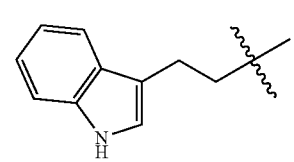 [SMILES: *CCc1c[nH]c2ccccc12] | LC4 | 471.27 | 2.14 |
| 33 | 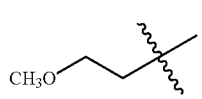 | LC3 | 386.28 | 1.41 |
| 34 | 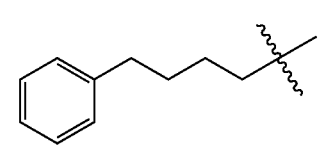 [SMILES: *CCCCc1ccccc1] | LC3 | 460.38 | 1.96 |
| 35 | 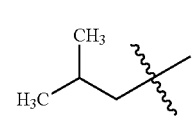 | LC3 | 384.31 | 1.73 |
| 36 | 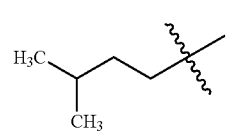 | LC3 | 398.36 | 1.81 |
| 37 | 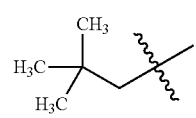 | LC4 | 398.25 | 2.29 |
| 38 | 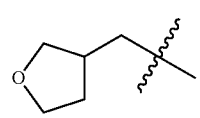 [SMILES: *CC1CCOC1] | LC3 | 412.31 | 1.45 |
| 39 | 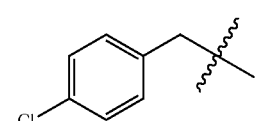 | LC3 | 452.30 | 1.86 |
| 40 | 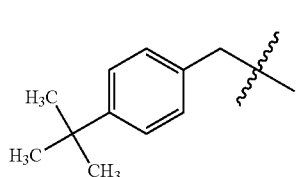 | LC3 | 474.39 | 2.06 |
| 41 | 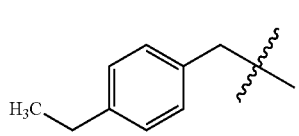 [SMILES: *Cc1ccc(CC)cc1] | LC3 | 446.34 | 1.93 |

TABLE 1-continued
Example compounds of the formula Im
| Example | R⁹⁰— | LC/MS Method | m/z [MH⁺] | Retention time [min] |
|---|---|---|---|---|
| 42 | 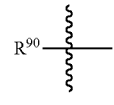 | LC3 | 410.34 | 1.85 |
| 43 | 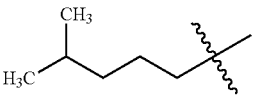 [SMILES: *CCCC(C)C] | LC3 | 412.33 | 1.92 |
| 44 | 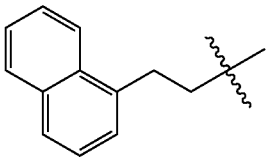 [SMILES: *CCc1cccc2ccccc12] | LC3 | 482.36 | 1.97 |
| 45 | 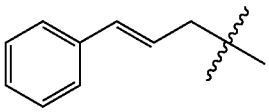 [SMILES: *C/C=C/c1ccccc1] | LC3 | 444.33 | 1.86 |
| 46 | 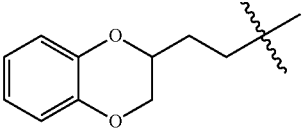 [SMILES: *CCC1COc2ccccc2O1] | LC3 | 476.33 | 1.80 |
| 47 | 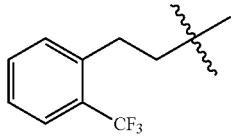 | LC3 | 500.31 | 1.94 |
| 48 | 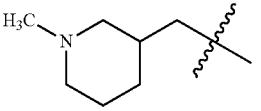 [SMILES: *CC1CCCN(C)C1] | LC4 | 439.29 | 1.22 |
| 49 | 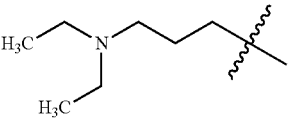 | LC3 | 441.35 | 1.18 |
| 50 | 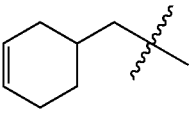 [SMILES: *CC1CC=CCC1] | LC3 | 422.33 | 1.87 |
| 51 | 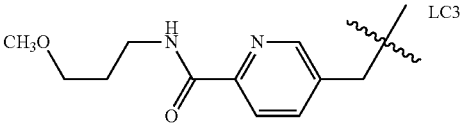 | LC3 | 520.35 | 1.48 |

TABLE 1-continued
Example compounds of the formula Im
| Example | R⁹⁰ | LC/MS Method | m/z [MH⁺] | Retention time [min] |
|---|---|---|---|---|
| 52 | 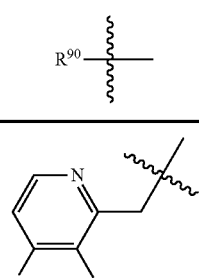 | LC3 | 483.26 | 1.60 |
| 53 | 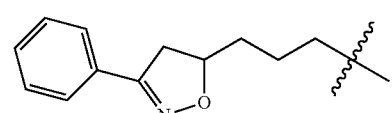 | LC3 | 515.37 | 1.81 |
| 54 | 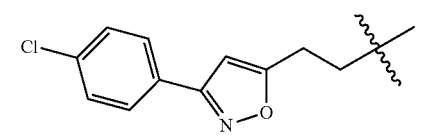 [SMILES: *CCc1cc(-c2ccc(Cl)cc2)no1] | LC4 | 533.25 | 2.37 |
| 55 | 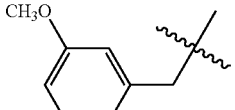 | LC4 | 449.26 | 1.24 |
| 56 | 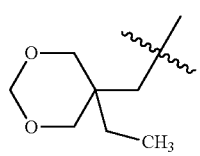 [SMILES: *CC1(CC)COCOC1] | LC4 | 456.27 | 2.09 |
| 57 | 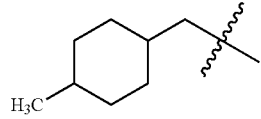 | LC3 | 438.36 | 2.06 |
| 58 | 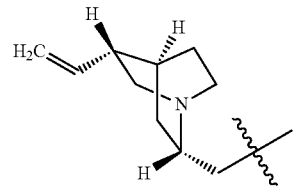 [SMILES: *C[C@@H]1C[C@@H]2CCN1C[C@@H]2C=C] | LC3 | 477.26 | 1.28 |
| 59 | 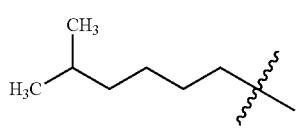 [SMILES: *CCCCC(C)C] | LC3 | 426.35 | 2.03 |
| 60 | 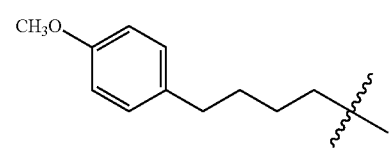 | LC3 | 490.37 | 1.94 |

TABLE 1-continued
Example compounds of the formula Im
R⁹⁰—⧸⧹
| Example | | LC/MS Method | m/z [MH⁺] | Retention time [min] |
|---|---|---|---|---|
| 61 | 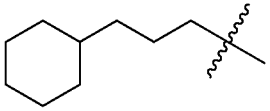 [SMILES: *CCCC1CCCCC1] | LC3 | 452.38 | 2.16 |
| 62 | 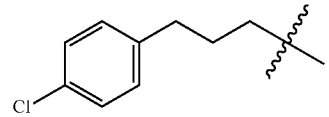 [SMILES: *CCCc1ccc(Cl)cc1] | LC3 | 480.31 | 2.00 |
| 63 | 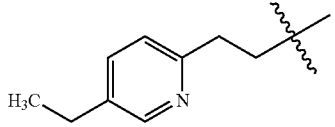 [SMILES: *CCc1ccc(CC)cn1] | LC3 | 461.32 | 1.25 |
| 64 | 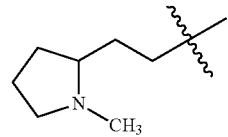 [SMILES: *CCC1CCCN1C] | LC3 | 439.33 | 1.16 |
| 65 | 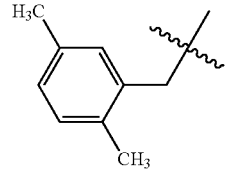 | LC3 | 446.33 | 1.91 |
| 66 | 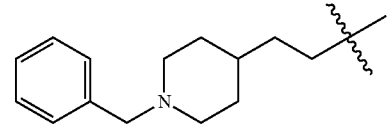 [SMILES: *CCC1CCN(Cc2ccccc2)CC1] | LC4 | 529.34 | 1.49 |
| 67 | 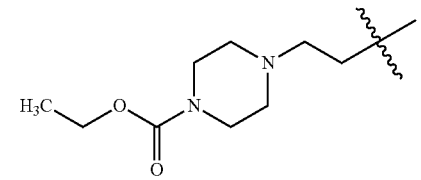 [SMILES: *CCN1CCN(C(=O)OCC)CC1] | LC3 | 512.38 | 1.23 |
| 68 | 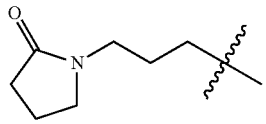 [SMILES: *CCCN1CCCC1=O] | LC3 | 453.34 | 1.38 |
| 69 | 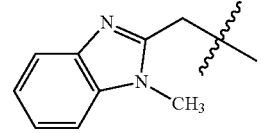 [SMILES: *Cc1nc2ccccc2n1C] | LC3 | 472.22 | 1.27 |

TABLE 1-continued
Example compounds of the formula Im
| Example | R⁹⁰— | LC/MS Method | m/z [MH⁺] | Retention time [min] |
|---|---|---|---|---|
| 70 | 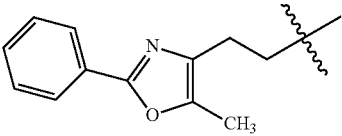 [SMILES: *CCc1nc(-c2ccccc2)oc1C] | LC3 | 513.35 | 1.85 |
| 71 | 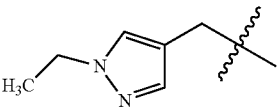 [SMILES: *Cc1cnn(CC)c1] | LC4 | 436.26 | 1.42 |
| 72 | 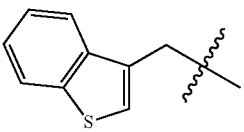 [SMILES: *Cc1csc2ccccc12] | LC3 | 474.30 | 1.89 |
| 73 | 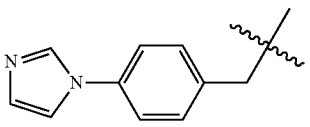 [SMILES: *Cc1ccc(-n2ccnc2)cc1] | LC3 | 484.33 | 1.24 |
| 74 | 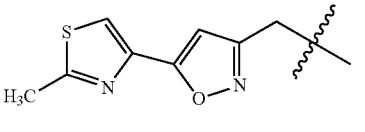 | LC3 | 506.28 | 1.64 |
| 75 | 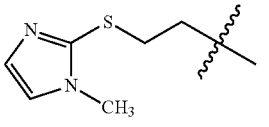 | LC4 | 468.24 | 1.32 |
| 76 | 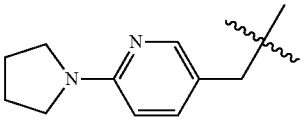 [SMILES: *Cc1ccc(N2CCCC2)nc1] | LC3 | 488.23 | 1.25 |
| 77 | 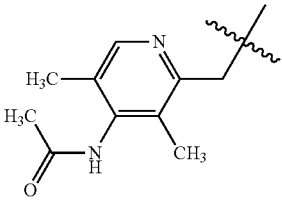 [SMILES: *Cc1ncc(C)c(NC(C)=O)c1C] | LC3 | 504.23 | 1.22 |
| 78 | 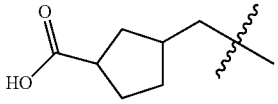 [SMILES: *CC1CCC(C(=O)O)C1] | LC3 | 454.22 | 1.49 |
| 79 | 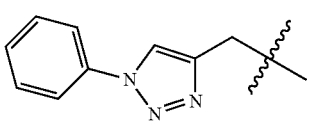 [SMILES: *Cc1cn(-c2ccccc2)nn1] | LC3 | 485.19 | 1.64 |

TABLE 1-continued
Example compounds of the formula Im
| Example | R⁹⁰— | LC/MS Method | m/z [MH⁺] | Retention time [min] |
|---|---|---|---|---|
| 80 | 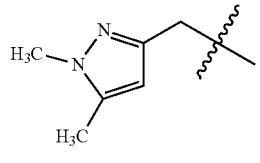 [SMILES: *Cc1cc(C)n(C)n1] | LC3 | 436.23 | 1.44 |
| 81 | 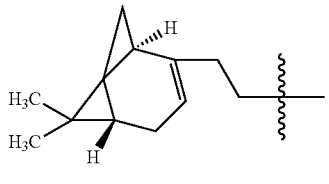 [SMILES: *CCC1=CC[C@@H]2C(C)(C)C23C[C@@H]13] | LC3 | 476.26 | 2.19 |
| 82 | 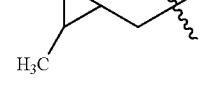 | LC3 | 396.20 | 1.72 |
| 83 | 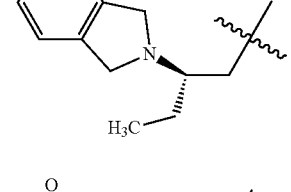 | LC3 | 501.24 | 1.33 |
| 84 | 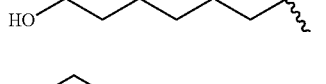 | LC3 | 442.21 | 1.49 |
| 85 | 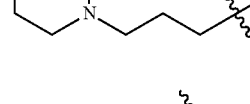 | LC3 | 453.23 | 1.19 |
| 86 |  | LC3 | 396.20 | 1.75 |
| 87 | 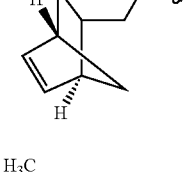 | LC3 | 434.22 | 1.89 |
| 88 | 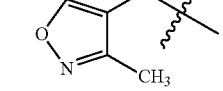 | LC3 | 437.2 | 1.55 |

TABLE 1-continued

Example compounds of the formula Im

| Example | R⁹⁰ | LC/MS Method | m/z [MH⁺] | Retention time [min] |
|---|---|---|---|---|
| 89 | (4-phenyl-1,2,3-thiadiazol-5-yl)methyl group | LC3 | 502.18 | 1.82 |
| 90 | (3-(pyridin-2-yl)-4,5-dihydroisoxazol-5-yl)methyl group | LC3 | 488.21 | 1.46 |
| 91 | (4-(pyridin-2-ylmethyl)cyclohexyl)methyl group | LC3 | 516.31 | 1.26 |

EXAMPLE 92

Starting Compound (1-m-Tolyl-cyclopropyl)-methanol

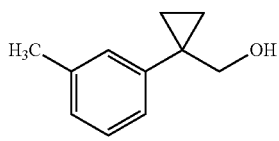

m-Tolylacetonitrile (1.00 g, 7.62 mmol) and 1,2-dibromoethane (1.86 g, 9.91 mmol) were dissolved in DMF (5 ml). The mixture was cooled in an ice bath and potassium tert-butoxide (855 mg, 19.1 mmol) was added slowly with stirring. After stirring for 30 min, the mixture was partitioned between EA and water. The organic layer was washed with water, dried over sodium chloride, decanted and evaporated to dryness.

After silica gel chromatography of the residue (HEP/EA gradient), an approximately 1:1 mixture of 1-m-tolyl-cyclopropanecarbonitrile and the starting compound m-tolylacetonitrile was obtained.

The obtained mixture of nitriles (500 mg) was dissolved in ethanol (2 ml) and 50 aqueous potassium hydroxide (2 ml). The mixture was reacted with microwave-heating at 140° C. for 4 h in a tightly closed vial. Then the mixture was partitioned between EA and 2 N hydrochloric acid, the aqueous phase extracted with EA, and the combined organic extracts dried over sodium chloride, decanted and evaporated to dryness to give a mixture of 1-m-tolyl-cyclopropanecarboxylic acid amide and m-tolyl-acetamide.

The obtained mixture of amides (600 mg) was dissolved in acetic acid (8.5 ml) and acetic anhydride (14.5 ml), the mixture was cooled in an ice bath, sodium nitrite (1.97 g, 28.5 mmol) was added, and the mixture was stirred for 2 h at room temperature. Water (15 ml) was added and the mixture was heated to 60° C. for 30 min. After evaporation to dryness in vacuo, the residue was partitioned between EA and 2 N hydrochloric acid, the aqueous phase extracted with EA, and the combined organic extracts were dried over sodium sulfate, decanted and evaporated to dryness to yield an approximately 1:1 mixture of 1-m-tolyl-cyclopropanecarboxylic acid and m-tolyl-acetic acid.

The obtained mixture of acids (430 mg) was dissolved in dimethoxyethane (8 ml), NMM (272 mg, 2.68 mmol) and isobutyl chloroformate (367 mg, 2.68 mmol) were added with stirring. After a few minutes, the mixture was filtered and sodium borohydride (369 mg, 9.76 mmol) was added to the clear filtrate. After cautious addition of water (4 ml; violent formation of hydrogen) stirring was continued for a few minutes until the reaction ceased, the mixture was partitioned between EA and 2 N hydrochloric acid, the aqueous phase extracted with EA, and the combined organic extracts were dried over sodium sulfate, decanted and evaporated to dryness. This residue was purified by preparative RP HPLC (water/ACN gradient) to give 133 mg of the title compound.

¹H-NMR: δ=7.18-7.06 (m, 3H); 6.98 (d, 1H); 4.59 (t, 1H); 3.51 (d, 2H); 0.83-0.78 (m, 2H); 0.70-0.67 (m, 2H)

EXAMPLE 93

Starting Compound 2-(2-Fluoro-5-methyl-phenyl)-ethanol

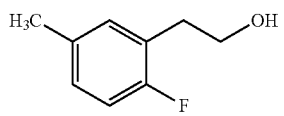

In analogy to the procedure described in M. Jorgensen et al., J. Am. Chem. Soc. 124 (2002), 12557-12565, in a first flask, dicyclohexylamine (3.06 g, 16.9 mmol) was dissolved in toluene and cooled in an ice bath. n-Butyllithium (6.14 ml, 2.5 M solution in hexane) was added. After 5 min, tert-butyl acetate (1.78 g, 15.3 mmol) was added slowly. A second flask was charged with tri-(tert-butyl)phosphonium tetrafluoroborate (83 mg, 0.30 mmol) and tris(dibenzylideneacetone)dipalladium(0) (146 mg, 0.153 mmol) and thoroughly flushed with argon. Toluene (100 ml) was added, followed by 3-bromo-4-fluoro-toluene (2.90 g, 15.3 mmol) and by the contents of the first flask. After stirring overnight, the formed suspension was filtered over a small plug of silica gel which was washed repeatedly with diethyl ether. The filtrates were evaporated in vacuo and the residue was purified by silica gel chromatography (HEP/EA gradient) to give 2.81 g of (2-fluoro-5-methyl-phenyl)-acetic acid tert-butyl ester.

$^1$H-NMR: δ=7.12-7.07 (m, 2H); 7.03 (t, 1H); 3.54 (s, 2H); 2.25 (s, 3H); 1.39 (s, 9H)

A flask was charged with lithium aluminium hydride (0.846 g, 22.3 mmol) and flushed with argon. THF (8 ml) was added, and the obtained (2-fluoro-5-methyl-phenyl)-acetic acid tert-butyl ester was slowly added with stirring. The reaction took place immediately. After 2 min, diethyl ether (30 ml) and EA (2.5 ml) were added. Then water was added cautiously and slowly with stirring until a greyish precipitate formed.

The solution was decanted and the precipitate was washed with EA. The combined solutions were dried over sodium sulfate, filtered and evaporated to dryness. The residue was purified by silica gel chromatography (HEP/EA gradient) to give 0.55 g of the title compound.

$^1$H-NMR: δ=7.10 (d, 1H); 7.05-6.96 (m, 2H); 4.70 (t, 1H); 3.56 (dt, 2H); 2.71 (t, 2H); 2.25 (s, 3H)

EXAMPLE 94

2-{3-[2-(3-Cyano-phenyl)-ethoxy]-4-methoxy-benzoylamino}-indane-2-carboxylic acid

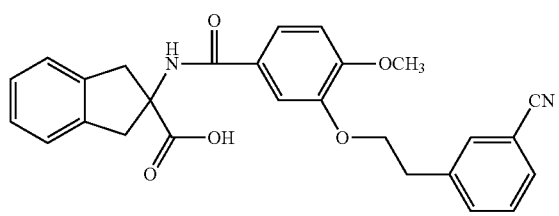 [SMILES: COc1ccc(C(=O)NC2(C(=O)O)Cc3ccccc3C2)cc1OCCc1cccc(C#N)c1]

Step 1

3-[2-(3-Bromo-phenyl)-ethoxy]-4-methoxy-benzoic acid methyl ester

Methyl 3-hydroxy-4-methoxybenzoate (500 mg, 2.75 mmol) and triphenylphosphine (1.08 g, 4.12 mmol) were dissolved in THF (13 ml), the solution was cooled in an ice bath and 2-(3-bromophenyl)-ethanol (662 mg, 3.29 mmol) and DIAD (886 mg, 4.12 mmol) were added sequentially. Stirring was continued for 3 h at room temperature. The reaction mixture was evaporated to dryness and the residue purified by preparative RP HPLC (water/ACN gradient) to give 900 mg of the title compound.

$^1$H-NMR: δ=7.62-7.58 (m, 2H); 7.45 (d, 1H); 7.41 (d, 1H); 7.35 (d, 1H); 7.28 (dd, 1H); 7.08 (d, 1H); 4.22 (t, 2H); 3.83 (s, 3H); 3.80 (s, 3H); 3.01 (t, 2H)

Step 2

3-[2-(3-Cyano-phenyl)-ethoxy]-4-methoxy-benzoic acid methyl ester

A flask was charged with zinc cyanide (129 mg, 1.10 mmol) and tetrakis(triphenylphosphine)palladium(0) (63 mg, 0.0547 mmol). Under an atmosphere of argon, a solution of the compound of step 1 (400 mg, 1.10 mmol) in DMF (1.9 ml) was added to the mixture. After stirring at 150° C. for 1 h and cooling, the mixture was diluted with methyl tert-butyl ether and filtered over celite. The filtrate was washed with water, dried over magnesium sulfate, filtered and evaporated to dryness to give 275 mg of the title compound.

$^1$H-NMR: δ=7.85 (s, 1H); 7.70 (dd, 1H); 7.58 (dd, 1H); 7.51 (dd, 1H); 7.44 (d, 1H); 7.07 (d, 1H); 4.26 (t, 2H); 3.82 (s, 3H); 3.80 (s, 3H); 3.11 (t, 2H)

Step 3

3-[2-(3-Cyano-phenyl)-ethoxy]-4-methoxy-benzoic acid

The compound of step 2 (274 mg, 0.883 mmol) was dissolved in dioxane (4.5 ml), lithium hydroxide (4.42 ml of a 1 M aqueous solution, 4.42 mmol) was added, and the mixture was stirred at 60° C. for 30 min. The mixture was partitioned between 2 N hydrochloric acid and EA, the aqueous phase extracted with EA, and the combined organic extracts were dried over sodium sulfate, filtered and evaporated to dryness. The residue was purified by preparative RP HPLC (water/ACN gradient) to give 160 mg of the title compound.

$^1$H-NMR: δ=12.65 (br s, 1H); 7.83 (s, 1H); 7.73-7.68 (m, 2H); 7.60-7.50 (m, 2H); 7.45 (d, 1H); 7.04 (d, 1H); 4.25 (t, 2H); 3.81 (s, 3H); 3.11 (t, 2H)

Step 4

2-{3-[2-(3-Cyano-phenyl)-ethoxy]-4-methoxy-benzoylamino}-indane-2-carboxylic acid methyl ester From the compound of step 3 and 2-amino-indane-2-carboxylic acid methyl ester hydrochloride, the title compound was obtained in a yield of 79% in analogy to step 1 of example 15.

LC/MS (Method LC2): Rt=1.63 min; m/z=471.1 [MH$^+$]

Step 5

2-{3-[2-(3-Cyano-phenyl)-ethoxy]-4-methoxy-benzoylamino}-indane-2-carboxylic acid From the compound of step 4, the title compound was obtained in a yield of 37% by hydrolysis with lithium hydroxide in analogy to step 3 except that the reaction was performed at room temperature.

$^1$H-NMR: δ=12.35 (br s, 1H); 8.61 (s, 1H); 7.84 (s, 1H); 7.72-7.68 (2d, 2H); 7.54-7.49 (m, 2H); 7.43 (d, 1H); 7.24-7.20 (m, 2H); 7.18-7.13 (m, 2H); 7.00 (d, 1H); 4.22 (t, 2H); 3.79 (s, 3H); 3.58 (d, 2H); 3.37 (d, 2H); 3.11 (t, 2H)

EXAMPLE 95

2-{3-[2-(3-Carbamoyl-phenyl)-ethoxy]-4-methoxy-benzoylamino}-indane-2-carboxylic acid

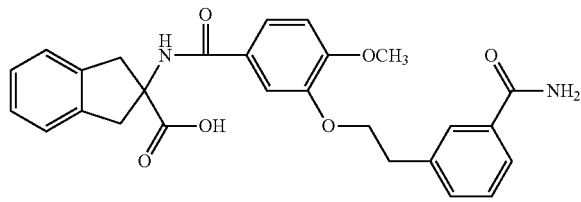 [SMILES: COc1ccc(C(=O)NC2(C(=O)O)Cc3ccccc3C2)cc1OCCc1cccc(C(N)=O)c1]

The compound of example 94 was reacted with lithium hydroxide at 60° C. for 50 min in analogy to step 3 of example 94. The obtained mixture of the title compound and 2-{3-[2-(3-carboxy-phenyl)-ethoxy]-4-methoxy-benzoylamino}-indane-2-carboxylic acid (example 96) was separated by preparative RP HPLC (water/ACN gradient).

$^1$H-NMR: δ=12.3 (s, 1H); 8.61 (s, 1H); 7.91 (s, 1H); 7.83 (s, 1H); 7.72 (d, 1H); 7.53-7.47 (m, 2H); 7.45 (d, 1H); 7.37 (t, 1H); 7.31 (s, 1H); 7.23-7.19 (m, 2H); 7.17-7.12 (m, 2H); 7.00 (d, 1H); 4.22 (t, 2H); 3.78 (s, 3H); 3.59 (d, 2H); 3.38 (d, 2H); 3.10 (t, 2H)

EXAMPLE 96

2-{3-[2-(3-Carboxy-phenyl)-ethoxy]-4-methoxy-benzoylamino}-indane-2-carboxylic acid

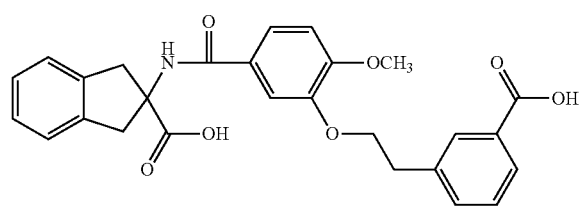 [SMILES: COc1ccc(C(=O)NC2(C(=O)O)Cc3ccccc3C2)cc1OCCc1cccc(C(=O)O)c1]

The title compound was prepared as described in Example 95.

$^1$H-NMR: δ=13.0-12.2 (br, 2H); 8.62 (s, 1H); 7.94 (s, 1H); 7.80 (d, 1H); 7.58 (d, 1H); 7.50 (dd, 1H); 7.47-7.42 (m, 2H); 7.22-7.19 (m, 2H); 7.17-7.12 (m, 2H); 7.00 (d, 1H); 4.22 (t, 2H); 3.78 (s, 3H); 3.59 (d, 2H); 3.37 (d, 2H); 3.12 (t, 2H)

EXAMPLE 97

5-[4-Methoxy-3-(2-m-tolyl-ethoxy)-benzoylamino]-5,6-dihydro-4H-cyclopenta[c]thiophene-5-carboxylic acid ethyl ester

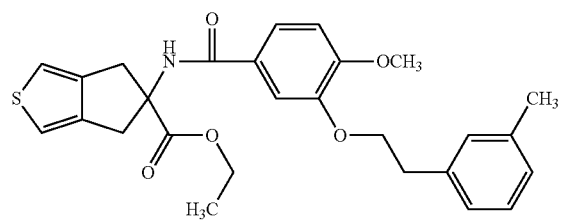 [SMILES: CCOC(=O)C1(NC(=O)c2ccc(OC)c(OCCc3cccc(C)c3)c2)Cc2cscc2C1]

(Benzhydrylidene-amino)-acetic acid ethyl ester (0.113 g, 0.414 mmol) was dissolved in DMF (3 ml) and cooled in an ice bath. Potassium tert-butoxide (94.8 mg, 0.828 mmol) was added, and the mixture was stirred for 10 min. The mixture was cooled to −30° C., and 3,4-bis-chloromethyl-thiophene (50 mg, 0.276 mmol) was added in one portion. The mixture was then placed into an ice bath again, and the reaction allowed to proceed for 20 min. The mixture was acidified with 2 N hydrochloric acid, stirred for 10 min and partitioned between water and diethyl ether. The aqueous phase was neutralized with a saturated sodium hydrogencarbonate solution and extracted with EA. The combined EA extracts were washed with a saturated sodium chloride solution, dried over sodium sulfate, filtered and evaporated to dryness. The residue was dissolved in diethyl ether, filtered, evaporated to dryness, acidified with hydrogen chloride in methanol and evaporated to dryness. The residue was stirred with an diethyl ether/HEP mixture, and the solid was filtered and dried in vacuo to give crude 5-amino-5,6-dihydro-4H-cyclopenta[c]thiophene-5-carboxylic acid ethyl ester hydrochloride. A part of the crude compound (27 mg, 0.109 mmol) was reacted without further purification with 4-methoxy-3-(2-m-tolyl-ethoxy)-benzoic acid in analogy to step 1 of example 15. After purification by preparative RP HPLC (water/ACN gradient), 23 mg of the title compound were obtained.

$^1$H-NMR: δ=8.78 (s, 1H); 7.50 (dd, 1H); 7.41 (d, 1H); 7.22-7.14 (m, 2H); 7.11 (d, 1H); 7.08-6.99 (m, 4H); 4.18 (t, 2H); 4.05 (q, 2H); 3.80 (s, 3H); 3.33 (d, 2H); 3.13 (d, 2H); 3.00 (t, 2H); 2.28 (s, 3H); 1.09 (t, 3H)

EXAMPLE 98

5-[4-Methoxy-3-(2-m-tolyl-ethoxy)-benzoylamino]-5,6-dihydro-4H-cyclopenta[c]thiophene-5-carboxylic acid

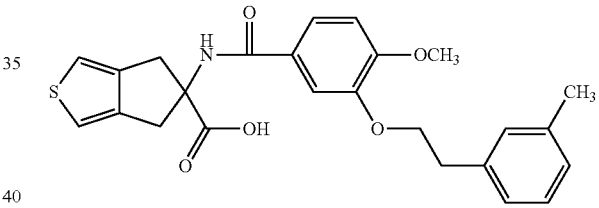

The compound of example 97 (21 mg, 0.0438 mmol) was hydrolyzed in analogy to step 3 of example 94. After evaporation to dryness, the residue was stirred with diethyl ether, filtered and dried in vacuo to give 16 mg of the title compound.

$^1$H-NMR: δ=8.69 (s, 1H); 7.48 (d, 1H); 7.41 (s, 1H); 7.21-7.09 (m, 3H); 7.05-6.98 (m, 4H); 4.19 (t, 2H); 3.80 (s, 3H); 3.30 (d, 2H); 3.11 (d, 2H); 3.00 (t, 2H); 2.29 (s, 3H)

EXAMPLE 99

5-[4-Methoxy-3-(2-m-tolyl-ethoxy)-benzoylamino]-5,6-dihydro-4H-cyclopenta[b]thiophene-5-carboxylic acid

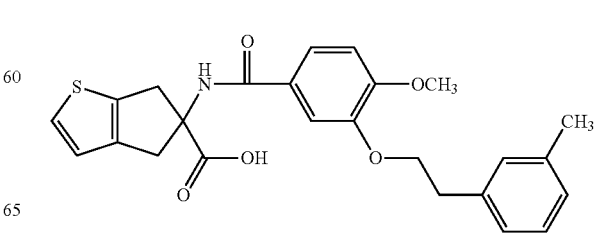

Starting from 2,3-bis-chloromethyl-thiophene, the title compound was obtained in analogy to examples 97 and 98.
LC/MS (Method LC1): Rt=1.60 min; m/z=452.0 [MH$^+$]

EXAMPLE 100

2-Chloro-5-[4-methoxy-3-(2-m-tolyl-ethoxy)-benzoylamino]-5,6-dihydro-4H-cyclopenta[b]thiophene-5-carboxylic acid

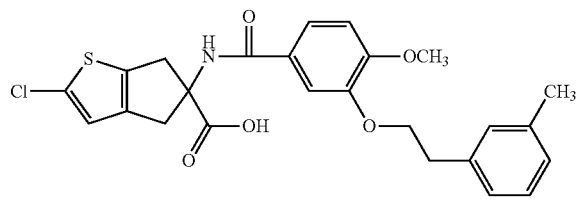 [SMILES: COc1ccc(C(=O)NC2(C(=O)O)Cc3cc(Cl)sc3C2)cc1OCCc1cccc(C)c1]

Step 1

5-Chloro-2,3-bis-chloromethyl-thiophene 2,3-Bis-chloromethyl-thiophene (500 mg, 2.76 mmol) was dissolved in acetic acid (10 ml). Sulfuryl chloride (372 mg, 2.76 mmol) was added and the mixture was stirred for 1 h at room temperature. The mixture was partitioned between EA, water and an excess of solid sodium hydrogencarbonate and the aqueous phase extracted with EA. The combined organic extracts were dried over magnesium sulfate, filtered and evaporated to dryness to give 240 mg of the title compound.
$^1$H-NMR: δ=7.13 (s, 1H); 5.16 (s, 2H); 4.76 (s, 2H)

Step 2

2-Chloro-5-[4-methoxy-3-(2-m-tolyl-ethoxy)-benzoylamino]-5,6-dihydro-4H-cyclopenta[b]thiophene-5-carboxylic acid From the compound of step 1, the title compound was obtained by reaction with (benzhydrylidene-amino)-acetic acid ethyl ester in analogy to example 97, step 1, reaction with 4-methoxy-3-(2-m-tolyl-ethoxy)-benzoic acid in analogy to step 3 of example 1, and ester hydrolysis in analogy to example 2.
LC/MS (Method LC1): Rt=1.74 min; m/z=486.0/488.0 [MH$^+$]

EXAMPLE 101

6-[4-Methoxy-3-(2-m-tolyl-ethoxy)-benzoylamino]-6,7-dihydro-5H-[1]pyrindine-6-carboxylic acid

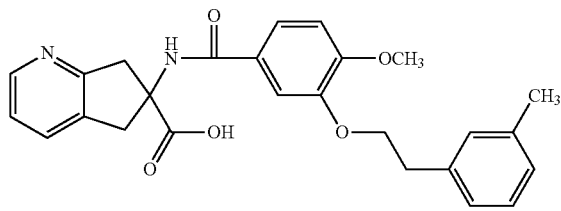 [SMILES: COc1ccc(C(=O)NC2(C(=O)O)Cc3cccnc3C2)cc1OCCc1cccc(C)c1]

Step 1

6-[4-Methoxy-3-(2-m-tolyl-ethoxy)-benzoylamino]-6,7-dihydro-5H-[1]pyrindine-6-carboxylic acid ethyl ester Isocyano-acetic acid methyl ester (112 mg, 1.13 mmol) and 2,3-bis-chloromethyl-pyridine (200 mg, 1.14 mmol) were dissolved in DMF. Potassium tert-butoxide (0.255 g, 2.27 mmol) was added and the reaction mixture was stirred for 1 h at room temperature. The mixture was partitioned between EA and a saturated aqueous sodium hydrogencarbonate solution, the aqueous phase extracted with EA, and the organic extracts were dried over sodium sulfate, filtered and evaporated to dryness. The residue was purified by silica gel chromatography (HEP/EA gradient) to give 6-isocyano-6,7-dihydro-5H-[1]pyrindine-6-carboxylic acid methyl ester. This compound was added to a solution of thionyl chloride (147 mg, 1.23 mmol) in ethanol (1 ml) and refluxed overnight. The mixture was evaporated to dryness, and the residue was stirred with HEP, filtered and dried in vacuo. The obtained product was reacted with 4-methoxy-3-(2-m-tolyl-ethoxy)-benzoic acid in analogy to step 1 of example 15 and the title compound purified by preparative RP HPLC (water/ACN gradient).
LC/MS (Method LC1): Rt=1.22 min; m/z=475.2 [MH$^+$]

Step 2

6-[4-Methoxy-3-(2-m-tolyl-ethoxy)-benzoylamino]-6,7-dihydro-5H-[1]pyrindine-6-carboxylic acid The compound of step 1 was hydrolyzed with lithium hydroxide in analogy to step 3 of example 94 to give 5 mg of the title compound.
LC/MS (Method LC1): Rt=1.11 min; m/z=447.1 [MH$^+$]

EXAMPLE 102

2-{[5-Acetyl-4-(2-m-tolyl-ethoxy)-thiophene-2-carbonyl]-amino}-indane-2-carboxylic acid

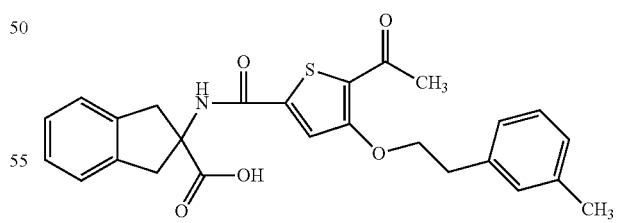

The title compound was synthesized by reaction of 5-acetyl-4-hydroxy-thiophene-2-carboxylic acid methyl ester with 2-(3-methylphenyl)-ethanol in analogy to step 1 of example 1, subsequent ester hydrolysis in analogy to example 2, reaction with 2-amino-indane-2-carboxylic acid methyl ester hydrochloride in analogy to step 1 of example 15, and ester hydrolysis in analogy to example 2.
LC/MS (Method LC1): Rt=1.66 min; m/z=464.0 [MH$^+$]

EXAMPLE 103

2-{5-[2-(3-Chloro-phenyl)-ethoxy]-4-methoxy-2-nitro-benzoylamino}-indane-2-carboxylic acid

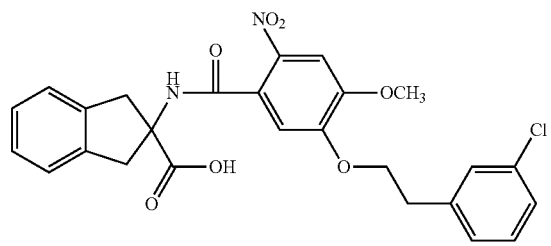 [SMILES: COc1cc([N+](=O)[O-])c(C(=O)NC2(C(=O)O)Cc3ccccc3C2)cc1OCCc1cccc(Cl)c1]

Step 1

5-[2-(3-Chloro-phenyl)-ethoxy]-4-methoxy-2-nitro-benzoic acid methyl ester

Methyl 3-hydroxy-4-methoxybenzoate and 2-(3-chlorophenyl)-ethanol were reacted in analogy to step 1 of example 1. The obtained 3-[2-(3-chloro-phenyl)-ethoxy]-4-methoxy-benzoic acid methyl ester (0.750 g, 2.34 mmol) was added slowly to ice-cooled 100% nitric acid (10 ml). The ice bath was removed and stirring was continued overnight. The mixture was cautiously transferred into a stirred mixture of EA, water and an excess of sodium hydrogencarbonate and extracted with EA. The combined organic extracts were washed with a saturated sodium chloride solution, dried over sodium sulfate, filtered and evaporated to dryness. The solid residue was extracted with diethyl ether, and the ethereal solution was evaporated. The residue was stirred with HEP, and the solid was filtered and dried in vacuo to give 0.680 g of the title compound.

$^1$H-NMR: δ=7.63 (s, 1H); 7.45 (s, 1H); 7.37 (s, 1H); 7.37-7.27 (m, 3H); 4.36 (t, 2H); 3.90 (s, 3H); 3.81 (s, 3H); 3.10 (t, 2H)

Step 2

2-{5-[2-(3-Chloro-phenyl)-ethoxy]-4-methoxy-2-nitro-benzoylamino}-indane-2-carboxylic acid From the compound of step 1, the title compound was obtained by hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.

$^1$H-NMR: δ=12.5 (s, 1H); 9.08 (s, 1H); 7.59 (s, 1H); 7.45 (s, 1H); 7.38-7.28 (m, 3H); 7.25-7.20 (m, 2H); 7.18-7.12 (m, 2H); 6.97 (s, 1H); 4.31 (t, 2H); 3.87 (s, 3H); 3.56 (d, 2H); 3.3 (d, 2H); 3.10 (t, 2H)

EXAMPLE 104

2-{2-Bromo-5-[2-(3-chloro-phenyl)-ethoxy]-4-methoxy-benzoylamino}-indane-2-carboxylic acid

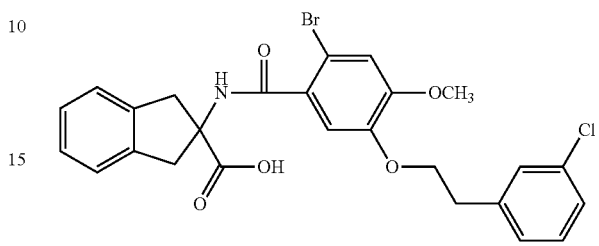

Step 1

2-Bromo-5-[2-(3-chloro-phenyl)-ethoxy]-4-methoxy-benzoic acid methyl ester

Methyl 3-hydroxy-4-methoxybenzoate and 2-(3-chlorophenyl)-ethanol were reacted in analogy to step 1 of example 1. The obtained 3-[2-(3-chloro-phenyl)-ethoxy]-4-methoxy-benzoic acid methyl ester (300 mg, 0.935 mmol) and sodium acetate (230 mg, 2.81 mmol) were dissolved in acetic acid (10 ml), bromine (224 mg, 1.40 mmol) was added, and the mixture was stirred at 95° C. with reaction control every hour. When the reaction did no more proceed, further bromine was added. After 5 h the reaction was completed. The volatiles were evaporated in vacuo, the residue was partitioned between EA and a saturated aqueous sodium hydrogencarbonate solution, and the aqueous phase extracted with EA. The combined organic extracts were washed with a saturated sodium chloride solution, dried over sodium sulfate, filtered and evaporated to dryness. This residue was purified by silica chromatography (HEP/EA gradient) to give 180 mg of the title compound.

$^1$H-NMR: δ=7.45-7.42 (m, 1H); 7.38 (s, 1H); 7.36-7.26 (m, 3H); 7.25 (s, 1H); 4.21 (t, 2H); 3.85 (s, 3H); 3.80 (s, 3H); 3.04 (t, 2H)

Step 2

2-{2-Bromo-5-[2-(3-chloro-phenyl)-ethoxy]-4-methoxy-benzoylamino}-indane-2-carboxylic acid From the compound of step 1, the title compound was obtained by hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.

LC/MS (Method LC1): Rt=1.64 min; m/z=544.0/546.0 [MH$^+$]

EXAMPLE 105

2-{2-Chloro-5-[2-(3-chloro-phenyl)-ethoxy]-4-methoxy-benzoylamino}-indane-2-carboxylic acid

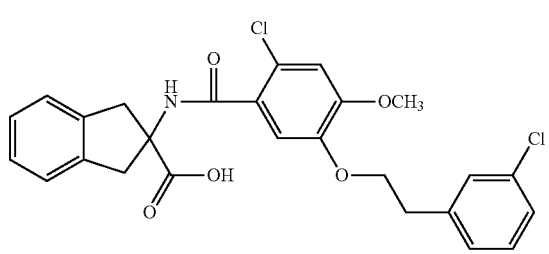 [SMILES: COc1cc(Br)c(C(=O)NC2(C(=O)O)Cc3ccccc3C2)cc1OCCc1cccc(Cl)c1]

Step 1

2-Chloro-5-[2-(3-chloro-phenyl)-ethoxy]-4-methoxy-benzoic acid methyl ester

Methyl 3-hydroxy-4-methoxybenzoate and 2-(3-chlorophenyl)-ethanol were reacted in analogy to step 1 of example 1. The obtained 3-[2-(3-chloro-phenyl)-ethoxy]-4-methoxy-benzoic acid methyl ester (300 mg, 0.935 mmol), N-chloro-succinimide (381 mg, 2.81 mmol), and zirconium tetrachloride (129 mg, 0.57 mmol) were suspended in DCM (4 ml) and the mixture was stirred under reflux for 5 h until the starting material was used up. The mixture was partitioned between EA and a saturated aqueous sodium hydrogencarbonate solution, the aqueous phase extracted with EA, and the combined organic extracts were dried over sodium sulfate, filtered and evaporated to dryness. The residue was purified by silica chromatography (HEP/EA gradient) to give 118 mg of the title compound.

LC/MS (Method LC1): Rt=1.82 min; m/z=355.0/357.0 [MH$^+$]

Step 2

2-{2-Chloro-5-[2-(3-chloro-phenyl)-ethoxy]-4-methoxy-benzoylamino}-indane-2-carboxylic acid From the compound of step 1, the title compound was obtained by hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.

LC/MS (Method LC1): Rt=1.64 min; m/z=500.1/502.1 [MH$^+$]

EXAMPLE 106

2-[3-Fluoro-4-methoxy-5-(2-m-tolyl-ethoxy)-benzoylamino]-indane-2-carboxylic acid

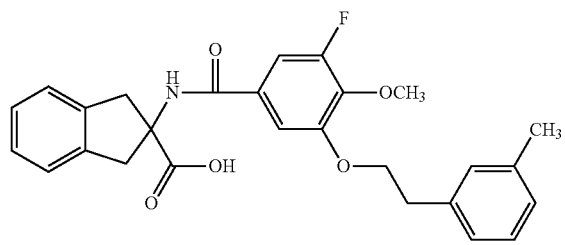 [SMILES: COc1c(F)cc(C(=O)NC2(C(=O)O)Cc3ccccc3C2)cc1OCCc1cccc(C)c1]

Step 1

3-Acetoxy-5-amino-4-methoxy-benzoic acid

3-Acetoxy-4-methoxy-5-nitro-benzoic acid (4.50 g, 17.6 mmol) (R. T. Borchardt et al., J. Med. Chem. 25 (1982), 312-323; F. Tiemann et al., Ber. dt. Chem. Ges. 9 (1876), 937) was dissolved in ethanol (180 ml) and 0.5 M hydrogen chloride in methanol (4 ml) and hydrogenated in an H-Cube™ hydrogenation reactor with 100 bar hydrogen at 40° C. over a 10% palladium on charcoal cartridge. The mixture was evaporated to dryness to give 4.1 g of the title compound.

LC/MS (Method LC1): Rt=0.75 min; m/z=226.0 [MH$^+$]

Step 2

3-Fluoro-5-hydroxy-4-methoxy-benzoic acid

The compound of step 1 (2.0 g, 8.88 mmol) was dissolved in aqueous tetrafluoroboric acid (48%, 4.5 ml), sodium nitrite (612 mg, 8.88 mmol) was added at 0° C., and the mixture was stirred at room temperature for 60 min. The volatiles were evaporated, toluene was added to the oily residue and the mixture was heated at 100° C. for 4 h. The mixture was partitioned between EA and 2 N hydrochloric acid, the aqueous phase extracted with EA, and the combined organic extracts were dried over sodium chloride, decanted and evaporated to dryness. The residue was purified by preparative RP HPLC (water/ACN gradient) to give 170 mg of the title compound.

$^1$H-NMR: δ=12.9 (br s, 1H); 10.1 (s, 1H); 7.29 (d, 1H); 7.18 (dd, 1H); 3.85 (s, 3H)

Step 3

3-Acetoxy-5-fluoro-4-methoxy-benzoic acid

The compound of step 2 (169 mg, 913 mmol) was suspended in acetic anhydride (1.75 ml) and heated at 100° C. for 3 h. The solution was cooled, water (2 ml) was added, and the mixture was stirred at 60° C. for 1 h. Upon cooling, crystals formed which were filtered off and dried in vacuo to give 120 mg of the title compound.

$^1$H-NMR: δ=13 (br s, 1H); 7.67 (dd, 1H); 7.55 (d, 1H); 3.92 (s, 3H); 2.32 (s, 3H)

Step 4

2-(3-Fluoro-5-hydroxy-4-methoxy-benzoylamino)-indane-2-carboxylic acid methyl ester The compound of step 3 (120 mg, 0.526 mmol) was reacted with 2-amino-indane-2-carboxylic acid methyl ester hydrochloride in analogy to step 1 of example 15. The obtained product was dissolved in methanol (0.77 ml), potassium carbonate (2 mg) was added, and the mixture was stirred at room temperature for 30 min. The solvent was evaporated, the residue was partitioned between EA and a saturated sodium chloride solution, and the aqueous phase extracted with EA. The combined organic extracts were dried over sodium sulfate, filtered and evaporated to dryness to give 60 mg of the title compound.

LC/MS (Method LC1): Rt=1.35 min; m/z=360.0 [MH$^+$]

Step 5

2-[3-Fluoro-4-methoxy-5-(2-m-tolyl-ethoxy)-benzoylamino]-indane-2-carboxylic acid From the compound of step 4, the title compound was obtained by reaction with 2-(3-methylphenyl)-ethanol in analogy to step 1 of example 1 and hydrolysis in analogy to example 2.

$^1$H-NMR: δ=12.4 (br s, 1H); 8.76 (s, 1H); 7.92-7.84 (m, 2H); 7.25-7.09 (m, 7H); 7.03 (d, 1H); 4.27 (t, 2H); 3.73 (s, 3H); 3.60 (d, 2H); 3.37 (d, 2H); 3.05 (t, 2H); 2.28 (s, 3H)

EXAMPLE 107

2-[4-Methoxy-3-nitro-5-(2-m-tolyl-ethoxy)-benzoylamino]-indane-2-carboxylic acid

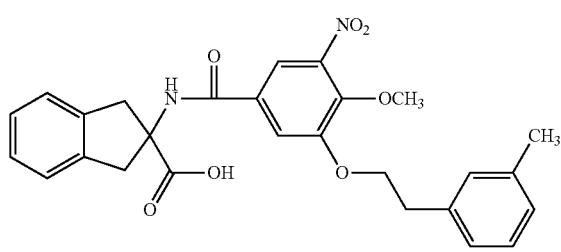 [SMILES: COc1c(OCCc2cccc(C)c2)cc(C(=O)NC2(C(=O)O)Cc3ccccc3C2)cc1[N+](=O)[O-]]

The title compound was obtained from 3-acetoxy-4-methoxy-5-nitro-benzoic acid by reaction with 2-amino-indane-2-carboxylic acid methyl ester hydrochloride, hydrolysis of the acetoxy group in analogy to step 4 of example 106, and reaction of the obtained product with 2-(3-methylphenyl)-ethanol and subsequent ester hydrolysis in analogy to step 5 of example 106.

LC/MS (Method LC1): Rt=1.77 min; m/z=491.0 [MH$^+$]

EXAMPLE 108

2-{[4-Methoxy-3-(2-m-tolyl-ethoxy)-benzoyl]-methyl-amino}-indane-2-carboxylic acid

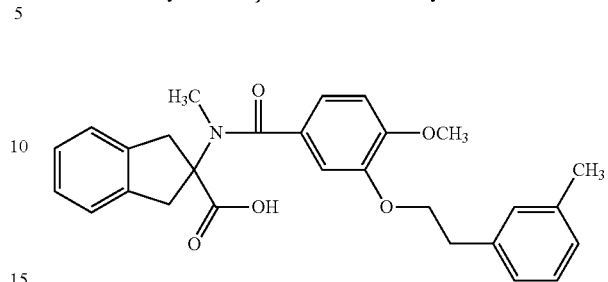

Step 1

1,3-Dimethyl-spiro(imidazolidin-5,2'-indane)-2,4-dione

Spiro[imidazolidine-4,2'-indane]-2,5-dione (2-indanone hydantoin) (200 mg, 0.989 mmol) and potassium tert-butoxide (255 mg, 2.28 mmol) were suspended in DMF (2 ml) and stirred for 20 min at room temperature. Iodomethane (323 mg, 2.28 mmol) was added and the mixture was stirred overnight. The addition of potassium tert-butoxide, stirring for 20 min, addition of iodomethane and stirring overnight at room temperature were repeated. Then the reaction mixture was partitioned between EA and 2 N hydrochloric acid, the aqueous phase extracted with EA, and the combined organic extracts were dried over sodium chloride, decanted and evaporated to dryness. Purification of the residue by silica gel chromatography gave a mixture of the mono-methylated and the di-methylated product. This mixture was dissolved in a 3:1 mixture of 0.3 N potassium hydroxide solution and dioxane and stirred overnight at room temperature. The mixture was partitioned between EA and water and the aqueous phase extracted with EA. The combined organic extracts were dried over sodium chloride, decanted and evaporated to dryness to give 90 mg of the title compound.

LC/MS (Method LC1): Rt=1.10 min; m/z=231.1 [MH$^+$]

Step 2

2-{[4-Methoxy-3-(2-m-tolyl-ethoxy)-benzoyl]-methyl-amino}-indane-2-carboxylic acid The compound of step 1 (90 mg, 0.391 mmol) was dissolved in a mixture of methanol and 50% sodium hydroxide solution and stirred in a microwave reactor at 140° C. for about 3 h until hydrolysis was complete. The mixture was evaporated to dryness and the residue suspended in a mixture of water (6 ml) and dioxane (3 ml) and cooled in an ice bath. An excess of 4-methoxy-3-(2-m-tolyl-ethoxy)-benzoyl chloride, which had been freshly prepared by dissolving the corresponding benzoic acid in thionyl chloride, stirring the mixture at 60° C. for 20 min, evaporating to dryness and dissolving the residue in dioxane, was slowly added to the mixture with stirring. The reaction mixture was stirred for 1 h in the ice bath. Then the mixture was partitioned between 2 N hydrochloric acid and EA, the aqueous phase extracted with EA, and the combined organic extracts were dried over sodium chloride, decanted and evaporated to dryness in vacuo. The residue was purified by silica gel chromatography (DCM/methanol/ammonium hydroxide gradient).

¹H-NMR: δ=12.3 (br s, 1H); 7.25-7.08 (m, 7H); 7.05-6.97 (m, 4H); 4.15 (t, 2H); 3.79 (s, 3H); 3.63 (d, 2H); 3.40 (d, 2H); 3.00 (t, 2H); 2.98 (s, 3H); 2.27 (s, 3H)

EXAMPLE 109

2-(3-Benzenesulfonyloxy-4-methoxy-benzoylamino)-indane-2-carboxylic acid

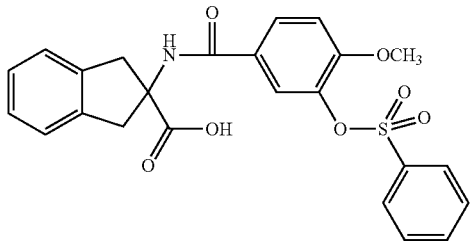 [SMILES: COc1ccc(C(=O)NC2(C(=O)O)Cc3ccccc3C2)cc1OS(=O)(=O)c1ccccc1]

The compound of step 2 of example 15 (200 mg, 0.586 mmol) was dissolved in ACN (3 ml), potassium carbonate (243 mg, 1.7 mmol) and benzenesulfonyl chloride (155 mg, 0.88 mmol) were added, and the mixture was stirred for 30 min. The mixture was partitioned between EA and saturated sodium chloride solution, the aqueous phase extracted with EA, and the combined organic extracts were dried over magnesium sulfate, filtered, and evaporated to dryness. The residue was dissolved in dioxane (0.8 ml), lithium hydroxide (0.8 ml of a 1 N aqueous solution) was added, and the mixture was stirred at room temperature for 2.5 h. The mixture was partitioned between 2 N hydrochloric acid and EA, the aqueous phase extracted with EA, and the combined organic extracts were dried over magnesium sulfate, filtered and evaporated to dryness. The residue was purified by preparative RP HPLC (water/ACN gradient) to give 115 mg of the title compound.

¹H-NMR: δ=12.4 (s, 1H); 8.77 (s, 1H); 7.87-7.77 (m, 4H); 7.72 (d, 1H); 7.67-7.61 (m, 2H); 7.76-7.71 (m, 2H); 7.21-7.16 (m, 2H); 7.10 (d, 1H); 3.57 (d, 2H); 3.48 (s, 3H); 3.38 (d, 2H)

In analogy to example 109, the example compounds of the formula In listed in table 2 were prepared. The compounds can be named as 2-[3-(R⁹¹-sulfonyloxy)-4-methoxy-benzoylamino]-indane-2-carboxylic acid, for example as 2-[3-(toluene-3-sulfonyloxy)-4-methoxy-benzoylamino]-indane-2-carboxylic acid in the case of example 111.

In

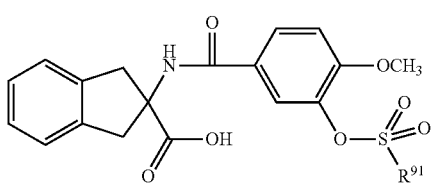

TABLE 2

Example compounds of the formula In

| Example | R⁹¹ | LC/MS Method | m/z [MH⁺] | Retention time [min] |
|---|---|---|---|---|
| 110 | 4-methyl-phenyl | LC2 | 482.0 | 1.54 |
| 111 | 3-methyl-phenyl | LC2 | 482.0 | 1.54 |
| 112 | 2-methyl-phenyl | LC2 | 482.0 | 1.55 |

EXAMPLE 113

2-[4-Methoxy-3-(2-m-tolyloxy-acetyl)-benzoylamino]-indane-2-carboxylic acid

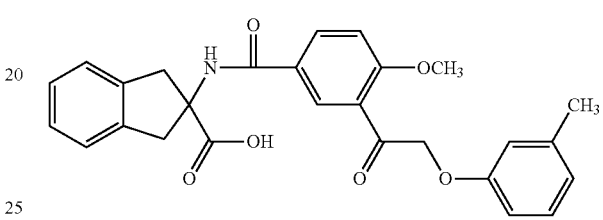

Step 1

3-(2-Bromo-acetyl)-4-methoxy-benzoic acid methyl ester

3-Acetyl-4-methoxy-benzoic acid methyl ester (T. Nagano et al., J. Am. Chem. Soc. 75 (1953), 6237-6238) (1.25 g) was dissolved in a mixture of acetic acid (7 ml) and hydrobromic acid (3 ml), the solution was cooled in an ice bath, and bromine (0.961 g) added. The mixture was allowed to slowly warm to room temperature and react for 2 h. Then the mixture was evaporated to dryness in vacuo, the residue was partitioned between EA and a saturated aqueous sodium hydrogencarbonate solution, the aqueous phase extracted with EA, and the combined organic extracts were dried over sodium sulfate, filtered and evaporated to dryness. Upon stirring with a mixture of EA and HEP, part of the title compound crystallized and was filtered off. The filtrate was evaporated to dryness and the residue purified by preparative RP HPLC (water/ACN gradient). Altogether, 1.18 g of the title compound were obtained.

LC/MS (Method LC2): Rt=1.40 min; m/z=287.0/289.0 [MH⁺]

Step 2

4-Methoxy-3-(2-m-tolyloxy-acetyl)-benzoic acid methyl ester

The compound of step 1 (1.18 g, 4.12 mmol) and potassium carbonate (1.72 g, 12.4 mmol) were suspended in DMF (10 ml), m-cresol (450 mg, 4.12 mmol) was added, and the mixture was stirred at room temperature for 2 h. The volatiles were evaporated in vacuo, the residue was partitioned between EA and water, and the aqueous phase extracted with EA. The combined organic extracts were washed with a sodium chloride solution, dried over sodium sulfate, filtered and evaporated to dryness. The residue was purified by preparative RP HPLC (water/ACN gradient) to give 0.49 g of the title compound.

¹H-NMR: δ=8.28 (d, 1H); 8.18 (dd, 1H); 7.37 (d, 1H); 7.13 (dd, 1H); 6.74 (d, 1H); 6.72 (s, 1H); 6.67 (d, 1H); 5.30 (s, 2H); 4.03 (s, 3H); 3.85 (s, 3H); 2.26 (s, 3H)

Step 3

2-[4-Methoxy-3-(2-m-tolyloxy-acetyl)-benzoylamino]-indane-2-carboxylic acid

From the compound of step 2, the title compound was obtained by hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.
¹H-NMR: δ=12.4 (s, 1H); 8.88 (s, 1H); 8.22 (d, 1H); 8.10 (dd, 1H); 7.29 (d, 1H); 7.23-7.19 (m, 2H); 7.18-7.10 (m, 3H); 6.73 (d, 1H); 6.70 (s, 1H); 6.65 (d, 1H); 5.28 (s, 2H); 3.98 (s, 3H); 3.57 (d, 2H); 3.40 (d, 2H); 2.24 (s, 3H)

EXAMPLE 114

2-[3-(1-Hydroxy-2-m-tolyloxy-ethyl)-4-methoxy-benzoylamino]-indane-2-carboxylic acid

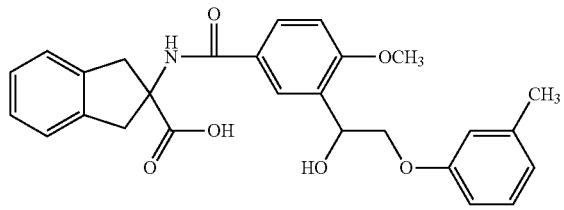 [SMILES: COc1ccc(C(=O)NC2(C(=O)O)Cc3ccccc3C2)cc1C(O)COc1cccc(C)c1]

The compound of example 113 (113 mg, 0.246 mmol) was dissolved in a mixture of methanol (2 ml) and ethanol (2 ml). With cooling in an ice bath, sodium borohydride (28 mg, 0.738 mmol) was added to the stirred solution, and the mixture was stirred in an ice bath for 2 h. The volatiles were evaporated, the residue was partitioned between diethyl ether and diluted hydrochloric acid, the aqueous phase extracted with diethyl ether, the combined organic extracts filtered over a small plug of silica gel, dried with sodium sulfate, filtered and evaporated to dryness. The residue was stirred with a mixture of EA and HEP and filtered to give 112 mg of the title compound.
LC/MS (Method LC2): Rt=1.51 min; m/z=462.1 [MH⁺]

EXAMPLE 115

2-[4-Methoxy-3-(2-m-tolyloxy-ethyl)-benzoylamino]-indane-2-carboxylic acid

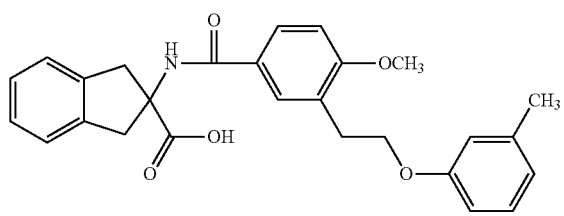 [SMILES: COc1ccc(C(=O)NC2(C(=O)O)Cc3ccccc3C2)cc1CCOc1cccc(C)c1]

The compound of example 114 (20 mg, 0.043 mmol) was dissolved in ethanol (2 ml), a 0.5 M solution of hydrogen chloride in methanol (0.2 ml) was added and the mixture was hydrogenated overnight in the presence of palladium on charcoal (10%) at room temperature at a hydrogen pressure of 5 bar (complete conversion of the starting compound). After filtration over a small plug of silica gel and evaporation, the residue was purified by preparative RP HPLC (water/ACN gradient).
LC/MS (Method LC2): Rt=1.69 min; m/z=446.0 [MH⁺]

EXAMPLE 116

2-[4-Methoxy-3-(3-m-tolyl-propyl)-benzoylamino]-indane-2-carboxylic acid

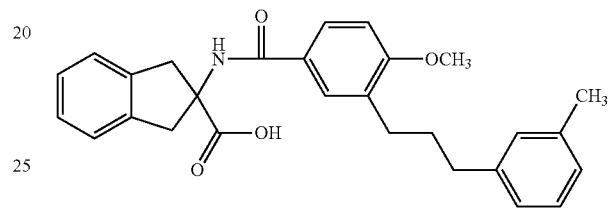

Step 1

3-(1,3-Dihydroxy-3-m-tolyl-propyl)-4-methoxy-benzoic acid methyl ester

3-Acetyl-4-methoxy-benzoic acid methyl ester (150 mg, 0.720 mmol) was dissolved in THF (3 ml), cooled to −78° C., and a freshly prepared solution of lithium diisopropylamide (obtained by addition of n-butyllithium in n-hexane (0.317 ml, 2.5 M solution) to diisopropylamine (80.1 mg, 0.792 mmol) in THF (3 ml) at 0° C. and stirring for 10 min) was slowly added with stirring. After 10 min, 3-methylbenzaldehyde (86.5 mg, 0.720 mmol) was added at −78° C. After 30 min at −78° C., 2 N hydrochloric acid and EA were added, the cooling bath was removed, the mixture was brought to room temperature. The phases were separated, the aqueous phase was extracted three times with EA, the combined organic extracts were dried over sodium chloride, decanted and evaporated to dryness. The residue was dissolved in methanol (5 ml), sodium borohydride (28.7 mg, 0.761 mmol) was added, and the mixture was stirred at room temperature for 30 min. The mixture was evaporated to dryness and the residue was purified by silica gel chromatography (HEP/EA gradient) to give 140 mg of the title compound as a mixture of diastereomers.
LC/MS (Method LC1): Rt=1.32 min; m/z=353.1 [MNa⁺], 683.2 [2MNa⁺]

Step 2

4-Methoxy-3-(3-m-tolyl-propyl)-benzoic acid methyl ester

The compound of step 1 (140 mg, 0.424 mmol) was dissolved in ethanol (10 ml) and 12 N hydrochloric acid (0.2 ml), palladium on charcoal (10%) was added, and the mixture was hydrogenated at a hydrogen pressure of 6 bar at room temperature overnight. After filtration and evaporation, the residue was purified by silica gel chromatography (HEP/EA gradient) to give 80 mg of the title compound.

$^1$H-NMR: δ=7.83 (dd, 1H); 7.72 (d, 1H); 7.16 (dd, 1H); 7.06 (d, 1H); 7.03-6.96 (m, 3H); 3.85 (s, 3H); 3.80 (s, 3H); 2.65-2.53 (m, 4H); 2.27 (s, 3H); 1.82 (m, 2H)

Step 3

2-[4-Methoxy-3-(3-m-tolyl-propyl)-benzoylamino]-indane-2-carboxylic acid

From the compound of step 2, the title compound was obtained by hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.

$^1$H-NMR: δ=12.3 (br s, 1H); 8.61 (s, 1H); 7.73 (dd, 1H); 7.66 (d, 1H); 7.25-7.20 (m, 2H); 7.19-7.12 (m, 3H); 3.81 (s, 3H); 3.57 (d, 2H); 3.38 (d, 2H); 2.61-2.52 (m, 4H); 2.26 (s, 3H); 1.86-1.78 (m, 2H)

EXAMPLE 117

2-(4-Methoxy-3-phenylacetylamino-benzoylamino)-indane-2-carboxylic acid

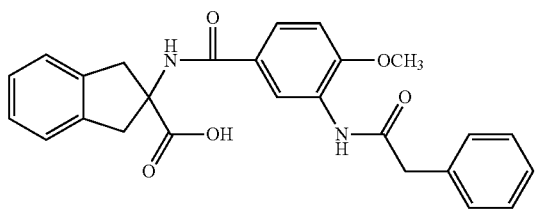 [SMILES: COc1ccc(C(=O)NC2(C(=O)O)Cc3ccccc3C2)cc1NC(=O)Cc1ccccc1]

Step 1

2-(4-Methoxy-3-nitro-benzoylamino)-indane-2-carboxylic acid methyl ester

To 2-amino-indane-2-carboxylic acid methyl ester hydrochloride (0.40 g, 1.77 mmol) and 4-methoxy-3-nitrobenzoic acid (0.35 g, 1.77 mmol) in 4 ml of DMF were added NMM (0.59 ml, 5.32 mmol), HOBT (0.31 g, 2.31 mmol) and EDC (0.44 g, 2.31 mmol). The mixture was stirred at 60° C. until LC/MS analysis showed complete conversion. The crude product was purified by silica gel chromatography (HEP/EA gradient) to give 0.43 g of the title compound.

Step 2

2-(3-Amino-4-methoxy-benzoylamino)-indane-2-carboxylic acid methyl ester

The compound of step 1 (0.43 g, 1.16 mmol) was dissolved in methanol (30 ml), 10% palladium on charcoal (200 mg) was added, and the flask flushed with argon. A balloon filled with hydrogen was connected, and the mixture was stirred at room temperature overnight. The balloon was removed, the flask flushed with argon, the catalyst filtered off over Celite, and the filtrate was evaporated in vacuo to give 0.38 g of the title compound.

Step 3

2-(4-Methoxy-3-phenylacetylamino-benzoylamino)-indane-2-carboxylic acid methyl ester The compound of step 2 (0.042 g, 0.12 mmol) and phenylacetic acid (0.013 g, 0.092 mmol) were dissolved in DCM (3 ml) and DMF (1 ml), NMM (0.031 ml, 0.28 mmol), HOBT (0.016 g, 0.12 mmol) and EDC (0.021 g, 0.12 mmol) were added, and the mixture was stirred overnight. LC/MS analysis showed complete conversion. The mixture was filtered, the filtrate subjected to preparative RP HPLC (water/ACN gradient), and the fractions containing the title compound freeze-dried. Yield: 0.042 g.

Step 4

2-(4-Methoxy-3-phenylacetylamino-benzoylamino)-indane-2-carboxylic acid

The compound of step 3 (42 mg, 0.091 mmol) was dissolved in methanol (3 ml) and water (1 ml), lithium hydroxide hydrate (5.3 mg, 0.12 mmol) was added, and the mixture was reacted at room temperature overnight. LC/MS analysis showed complete conversion. The mixture was filtered, the filtrate subjected to preparative RP HPLC (water/ACN gradient), and the fractions containing the title compound freeze-dried. Yield: 27 mg.

LC/MS (Method LC5): Rt=1.95 min; m/z=445.48 [MH$^+$]

$^1$H-NMR: δ=12.4 (br s, 1H); 9.39 (s, 1H); 8.67 (s, 1H); 8.31 (s, 1H); 7.62 (d, 1H); 7.38-7.30 (m, 4H); 7.28-7.20 (m, 3H); 7.18-7.12 (m, 2H); 7.08 (d, 1H); 3.87 (s, 3H); 3.72 (s, 2H); 3.55 (d, 2H); 3.35 (d, 2H)

In analogy to example 117, the example compounds of the formula Ip listed in table 3 were prepared. The compounds can be named as 2-[3-(R$^{92}$-carbonyl-amino)-4-methoxy-benzoylamino)-indane-2-carboxylic acid, for example as 2-[3-[3-fluoro-benzoylamino)-4-methoxy-benzoylamino)-indane-2-carboxylic acid in the case of example 120.

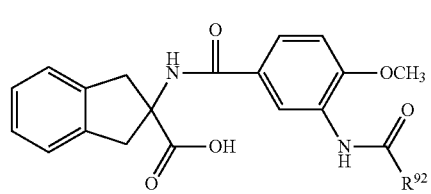

Ip

TABLE 3

Example compounds of the formula Ip

| Example | R$^{92}$ | LC/MS Method | m/z [MH$^+$] | Retention time [min] |
|---|---|---|---|---|
| 118 | 3-bromo-benzyl | LC6 | 523.04 | 1.75 |
| 119 | 3-chloro-benzyl | LC6 | 479.08 | 1.72 |
| 120 | 3-fluoro-phenyl | LC6 | 449.12 | 1.66 |

EXAMPLE 121

2-[3-(4-Fluoro-benzylamino)-4-methoxy-benzoy-lamino]-indane-2-carboxylic acid

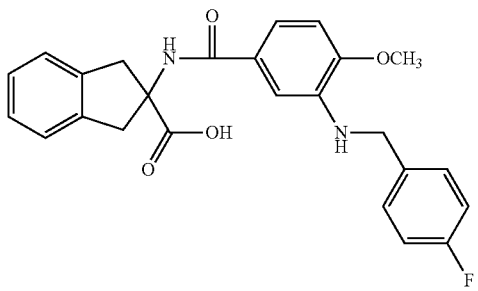 [SMILES: COc1ccc(C(=O)NC2(C(=O)O)Cc3ccccc3C2)cc1NCc1ccc(F)cc1]

Step 1

2-[3-(4-Fluoro-benzylamino)-4-methoxy-benzoy-lamino]-indane-2-carboxylic acid methyl ester The compound of example 117, step 2 (0.042 g, 0.12 mmol) and 4-fluorobenzaldehyde (0.0115 g, 0.092 mmol) were dissolved in THF (3 ml) and acetic acid (0.5 ml). Resin-bound sodium cyanoborohydride (0.2 mmol) was added, and the mixture was stirred at room temperature until LC/MS analysis showed complete conversion. The resin was filtered off, the filtrate was subjected to preparative RP HPLC (water/ACN gradient), and the fractions containing the title compound freeze-dried to give 33 mg of the title compound.

Step 2

2-[3-(4-Fluoro-benzylamino)-4-methoxy-benzoy-lamino]-indane-2-carboxylic acid

The compound of step 1 (30 mg, 0.053 mmol) was dissolved in methanol (3 ml) and water (1 ml). Lithium hydroxide hydrate (3.8 mg, 0.09 mmol) was added, and the mixture was stirred at room temperature until LC/MS analysis showed complete conversion. The mixture was filtered, the filtrate subjected to preparative RP HPLC (water/ACN gradient), and the fractions containing the title compound freeze-dried to give 19 mg of the title compound.

LC/MS (Method LC6): Rt=1.66 min; m/z=435.19 [MH$^+$]

$^1$H-NMR: δ=12.2 (br s, 1H); 8.45 (s, 1H); 7.38-7.32 (m, 2H); 7.22-7.20 (m, 2H); 7.20-7.14 (m, 3H); 7.14-7.09 (m, 2H); 6.92 (s, 1H); 6.81 (d, 1H); 4.32 (s, 2H); 3.80 (s, 3H); 3.72 (s, 2H); 3.53 (d, 2H); 3.32 (d, 2H)

In analogy to example 121, the example compounds of the formula Ir listed in table 4 were prepared. The compounds can be named as 2-[3-(R$^{93}$-amino)-4-methoxy-benzoylamino]-indane-2-carboxylic acid, for example as 2-[3-[2-phenyl-ethylamino)-4-methoxy-benzoylamino)-indane-2-carboxylic acid in the case of example 122.

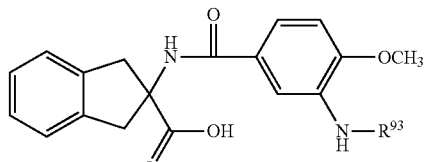

Ir

TABLE 4

Example compounds of the formula Ir

| Example | R$^{93}$ | LC/MS Method | m/z [MH$^+$] | Retention time [min] |
|---|---|---|---|---|
| 122 | 2-phenyl-ethyl | LC6 | 431.13 | 1.61 |
| 123 | 3-chloro-benzyl | LC6 | 451.07 | 1.79 |
| 124 | 2-phenyl-propyl | LC6 | 445.13 | 1.76 |

EXAMPLE 125

General Procedure for Solid Phase Synthesis 0.5 g of Polystyrene AM RAM resin with FMOC-protected linker (0.5 mmol/g or 0.75 mmol/g, respectively; Rapp Polymere GmbH, Tubingen, Germany) were treated with a 50% solution of piperidine in DMF for 20 min and washed extensively with DMF. The respective FMOC-protected 2-amino-indane-2-carboxylic acid (5 equivalents), HOBT (5 equivalents) and DIC (5 equivalents) were dissolved in DMF (5 ml) and added to the resin. The mixture was shaken overnight at room temperature. The resin was repeatedly washed with DMF and the FMOC protecting group was removed by treatment of the resin with a 50% solution of piperidine in DMF for 20 min. The resin was repeatedly washed with DMF.

For acylation of the amino group, a solution of the respective hydroxy-substituted benzoic acid (5 equivalents), HOBT (5 equivalents) and DIC (5 equivalents) in DMF (5 ml) was added to the resin and the mixture was shaken overnight at room temperature. The resin was washed with DMF and treated with a 2 N solution of dimethylamine in THF overnight, or in some cases with a 50% solution of piperidine in DMF for 2 h, for hydrolyzing the ester formed by acylation of the hydroxy group. The resin was washed extensively with DMF, DCM and THF.

For the Mitsunobu reaction on the hydroxy group, triphenylphosphine (10 equivalents) and the respective alcohol (10 equivalents) were dissolved in 5 ml of dry THF and added to the resin. The slurry was cooled to 0° C. and DIAD (10 equivalents) was added to the cooled mixture which was allowed to react overnight at room temperature. The resin was washed repeatedly with DCM.

For cleavage of the obtained compound, the resin was treated with neat TFA for 2 h. TFA was removed in vacuo, and the residue was purified by preparative RP HPLC (water/ACN gradient). In most cases the carboxylic acid was isolated after the TFA cleavage. In some cases the carboxylic acid amide was isolated which was converted into the carboxylic acid by hydrolysis in 50% aqueous TFA at 60° C. overnight, partial removal of the TFA in vacuo and lyophilization of the aqueous solution.

According to the general procedure described in example 125, the compounds of the formula Is listed in table 5 were synthesized. In the formulae of the groups R$^{95}$ in table 5 the line crossed with the symbol ~~~ represents the free bond via which the group R^95 is bonded to the oxygen atom which is attached to the 3-position of the benzoyl group depicted in formula Is. I.e., in the formula of the complete molecule the terminal endpoint of the line crossed with the said symbol ends at the oxygen atom attached to the 3-position of the benzoyl group. The compounds can be named as 2-[3-($R^{95}$-oxy)-4-$R^{94}$-benzoylamino]-indane-2-carboxylic acid, for example as 2-{4-methoxy-3-[2-(3-trifluoromethyl-phenyl)-ethoxy]-benzoylamino}-indane-2-carboxylic acid in the case of example 127.

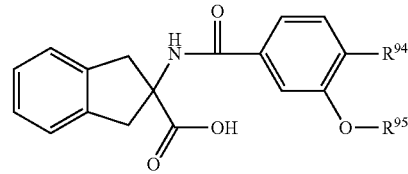

TABLE 5

Example compounds of the formula Is

| Example | $R^{94}$— | $R^{95}$ | LC/MS Method | m/z [MH$^+$] | Retention time [min] |
|---|---|---|---|---|---|
| 126 | CH$_3$O— | | LC9 | 432.2 | 4.32 |
| 127 | CH$_3$O— | | LC8 | 500.2 | 4.39 |
| 128 | Cl— | | LC8 | 504.1/ 506.1 | 4.80 |
| 129 | CH$_3$— | | LC9 | 430.2 | 5.14 |
| 130 | CH$_3$O— | | LC9 | 432.2 | 4.51 |
| 131 | CH$_3$O— | | LC9 | 450.2 | 4.58 |
| 132 | CH$_3$O— | | LC9 | 466.1/ 468.1 | 4.74 |
| 133 | CH$_3$O— | | LC9 | 462.2 | 4.48 |

TABLE 5-continued
Example compounds of the formula Is
| Example | R⁹⁴— | R⁹⁵ group | LC/MS Method | m/z [MH⁺] | Retention time [min] |
|---|---|---|---|---|---|
| 134 | CH₃O— | 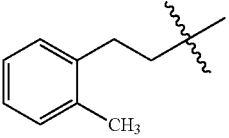 | LC9 | 446.2 | 4.65 |
| 135 | CH₃O— | 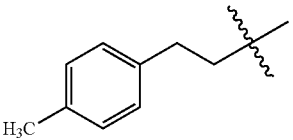 | LC9 | 446.2 | 4.69 |
| 136 | CH₃O— | 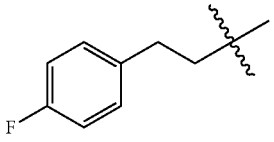 [SMILES: *CCc1ccc(F)cc1] | LC9 | 450.2 | 4.55 |
| 137 | CH₃O— | 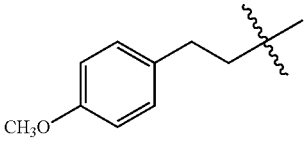 | LC9 | 462.2 | 4.48 |
| 138 | CH₃O— | 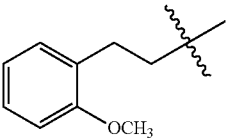 [SMILES: *CCc1ccccc1OC] | LC9 | 462.2 | 4.57 |
| 139 | CH₃O— | 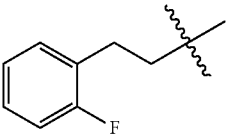 | LC9 | 450.2 | 4.55 |
| 140 | CH₃O— | 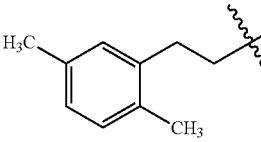 | LC9 | 460.2 | 4.91 |
| 141 | H— | 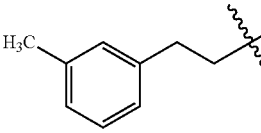 | LC7 | 416.2 | 4.50 |
| 142 | CH₃O— | 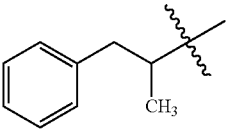 [SMILES: *C(C)Cc1ccccc1] | LC7 | 446.2 | 4.56 |

TABLE 5-continued

Example compounds of the formula Is

| Example | R⁹⁴— | R⁹⁵— | LC/MS Method | m/z [MH⁺] | Retention time [min] |
|---|---|---|---|---|---|
| 143 | CH₃O— | 3-Br-phenyl-CH₂CH₂- | LC7 | 510.1/ 512.1 | 5.28 |
| 144 | CH₃O— | PhCH(CH₃)CH₂- | LC7 | 446.2 | 5.14 |
| 145 | F— | 3-CH₃-phenyl-CH₂CH₂- | LC7 | 434.2 | 4.89 |
| 146 | CH₃O— | thiophen-3-yl-CH₂CH₂- | LC7 | 438.1 | 4.35 |
| 147 | CH₃O— | thiophen-2-yl-CH₂CH₂- | LC7 | 438.1 | 4.34 |
| 148 | CH₃O— | pyridin-2-yl-CH₂CH₂- | LC7 | 433.2 | 2.56 |
| 149 | CH₃O— | 2-Cl-phenyl-CH₂CH₂- | LC7 | 466.1/ 468.1 | 4.64 |
| 150 | CH₃O— | cyclopentyl-CH₂CH₂- | LC7 | 424.2 | 4.72 |
| 151 | CH₃O— | Ph-CH₂CH₂CH₂- | LC7 | 446.2 | 4.58 |
| 152 | CH₃O— | 2-F-6-Cl-phenyl-CH₂CH₂- | LC9 | 484.1/ 486.1 | 4.71 |

TABLE 5-continued

Example compounds of the formula Is

| Example | R⁹⁴— | R⁹⁵— | LC/MS Method | m/z [MH⁺] | Retention time [min] |
|---|---|---|---|---|---|
| 153 | CH₃O— | (3-chloro-2-fluorophenethyl) | LC9 | 484.1/ 486.1 | 4.77 |
| 154 | CH₃O— | (2-fluoro-5-trifluoromethylphenethyl) | LC9 | 518.2 | 4.86 |
| 155 | CH₃O— | (2-fluoro-3-trifluoromethylphenethyl) | LC9 | 518.2 | 8.87 |

EXAMPLE 156

5-Bromo-2-[4-methoxy-3-(2-m-tolyl-ethoxy)-benzoylamino]-indane-2-carboxylic acid

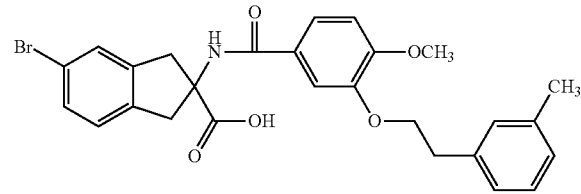 [SMILES: COc1ccc(C(=O)NC2(C(=O)O)Cc3ccc(Br)cc3C2)cc1OCCc1cccc(C)c1]

The title compound was prepared according to the general procedure described in example 125.

LC/MS (Method LC7): Rt=5.06 min; m/z=524.1/526.1 [MH⁺]

EXAMPLE 157

5-Fluoro-2-[4-methoxy-3-(2-m-tolyl-ethoxy)-benzoylamino]-indane-2-carboxylic acid

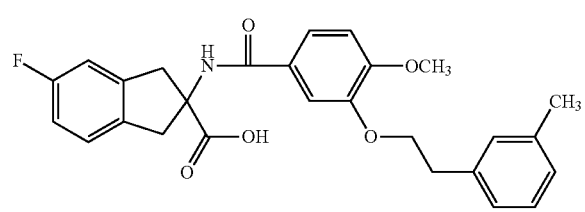 [SMILES: COc1ccc(C(=O)NC2(C(=O)O)Cc3ccc(F)cc3C2)cc1OCCc1cccc(C)c1]

The title compound was prepared according to the general procedure described in example 125.

LC/MS (Method LC7): Rt=4.74 min; m/z=464.2 [MH⁺]

EXAMPLE 158

2-[4-Methoxy-3-(2-m-tolyl-ethoxy)-benzoylamino]-5,6-dimethyl-indane-2-carboxylic acid

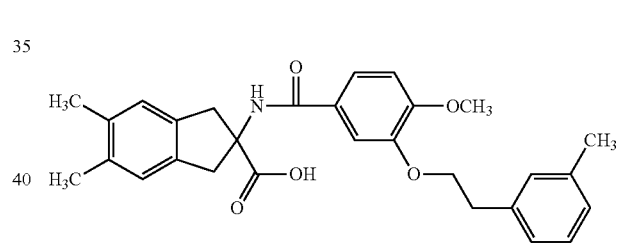

The title compound was prepared according to the general procedure described in example 125.

LC/MS (Method LC7): Rt=5.03 min; m/z=474.2 [MH⁺]

EXAMPLE 159

5-Methoxy-2-[4-methoxy-3-(2-m-tolyl-ethoxy)-benzoylamino]-indane-2-carboxylic acid

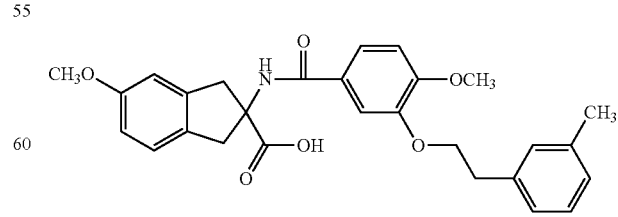

The title compound was prepared according to the general procedure described in example 125.

LC/MS (Method LC7): Rt=4.60 min; m/z=476.2 [MH⁺]

EXAMPLE 160

2-[4-Methoxy-3-(2-m-tolyl-ethoxy)-benzoylamino]-indane-2-carboxylic acid amide

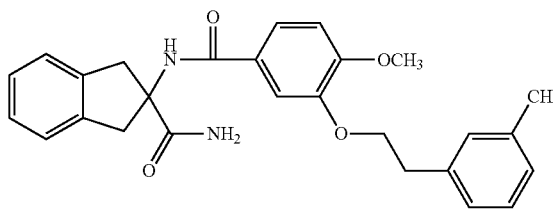

The compound of example 14 (100 mg, 0.224 mmol) was added to thionyl chloride (0.5 ml) and stirred for 30 min at 60° C. The volatiles were evaporated, dioxane (1 ml) was added and the mixture was evaporated to dryness again. The obtained raw acid chloride was dissolved in DCM and added to a stirred mixture of EA, a saturated sodium hydrogencarbonate solution and ammonia (30% in water, 0.015 ml). After stirring at room temperature for 90 min, the layers were separated and the aqueous layer was extracted with EA. The combined organic extracts were dried over sodium sulfate and evaporated to dryness. The residue was purified by preparative RP HPLC (water/ACN gradient).

LC/MS (Method LC1): Rt=1.55 min; m/z=445.1 [MH$^+$]

EXAMPLE 161

2-{4-[2-(3-Chloro-phenyl)-ethoxy]-3-methoxy-benzoylamino}-indane-2-carboxylic acid

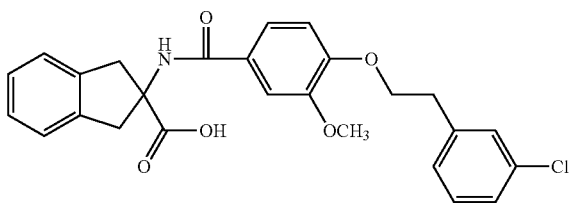 [SMILES: COc1cc(C(=O)NC2(C(=O)O)Cc3ccccc3C2)ccc1OCCc1cccc(Cl)c1]

The title compound was prepared according to the general procedure described in example 125.
LC/MS (Method LC7): Rt=4.70 min; m/z=466.1/468.1 [MH$^+$]

EXAMPLE 162

2-{4-[2-(2-Chloro-phenyl)-ethoxy]-3-methoxy-benzoylamino}-indane-2-carboxylic acid

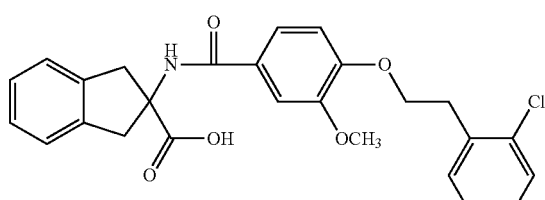

The title compound was prepared according to the general procedure described in example 125.
LC/MS (Method LC7): Rt=4.69 min; m/z=466.1/468.1 [MH$^+$]

EXAMPLE 163

2-[4-Amino-3-(2-m-tolyl-ethoxy)-benzoylamino]-indane-2-carboxylic acid

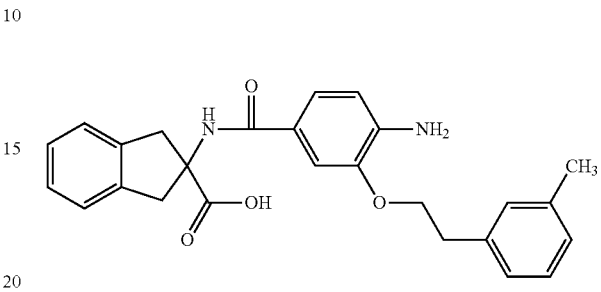

The title compound was prepared according to the general procedure described in example 125 using 0.1 g of resin (0.5 mmol/g). In the acylation step, 3-hydroxy-4-nitro-benzoic acid was employed. In the final step the nitro group was reduced with a 1 M solution of tin(II) chloride dihydrate in DMF overnight at room temperature. The resin was washed extensively with DMF, methanol, and DCM, and the product was cleaved from the resin by treatment with TFA for 2 h. TFA was removed in vacuo, and the residue was purified by preparative RP HPLC (water/ACN gradient). Yield: 12.4 mg.

LC/MS (Method LC9): Rt=4.33 min; m/z=431.2 [MH$^+$]
$^1$H-NMR (300 MHz, D$_6$-DMSO+2% TFA): δ=2.29 (s, 3H); 3.06 (t, J=6.97 Hz, 2H); 3.30-3.43 (m, 2H); 3.54-3.65 (m, 2H); 4.28 (t, J=7.06 Hz, 2H); 7.04 (d, J=7.35 Hz, 1H); 7.09-7.26 (m, 8H); 7.43-7.54 (m, 2H); 8.71 (s, 1H)

EXAMPLE 164

2-[4-Methylamino-3-(2-m-tolyl-ethoxy)-benzoylamino]-indane-2-carboxylic acid

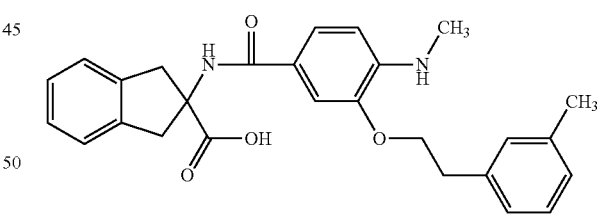

The title compound was prepared in analogy to example 163 using 0.12 g of resin (0.5 mmol/g). After reduction of the nitro group, the amino group was methylated using a 37% aqueous formaldehyde solution (10 equivalents) and sodium cyanoborohydride (8 equivalents, 1 M solution in THF) in a mixture of DCM and ACN (3:1) containing 2% of acetic acid. The mixture was shaken overnight, then the resin was washed and the procedure was repeated with fresh reagents. For cleavage, the resin was treated with TFA for 2 h, TFA was removed in vacuo and the residue was dissolved in 50% aqueous TFA. The solution was heated to 50° C. for 48 h, TFA was partially removed in vacuo and the aqueous solution was lyophilized. The residue was purified by preparative RP HPLC (water/ACN gradient). Yield: 9.8 mg.

LC/MS (Method LC7): Rt=4.41 min; m/z=445.2 [MH+]

1H-NMR (300 MHz, D6-DMSO+2% TFA): δ=2.28 (s, 3H); 2.75 (s, 3H); 3.04 (t, J=6.78 Hz, 2H); 3.30-3.41 (m, 2H); 3.52-3.63 (m, 2H); 4.21 (t, J=6.88 Hz, 2H); 6.61-6.71 (m, 1H); 7.03 (d, J=7.16 Hz, 1H); 7.10-7.25 (m, 7H); 7.37 (d, J=1.70 Hz, 1H); 7.47 (dd, J=8.19/1.79 Hz, 1H); 8.49 (br s, 1H)

EXAMPLE 165

2-[4-Dimethylamino-3-(2-m-tolyl-ethoxy)-benzoylamino]-indane-2-carboxylic acid

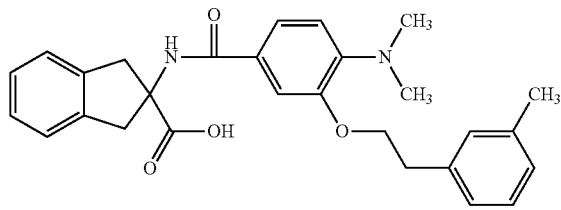 [SMILES: Cc1cccc(CCOc2cc(C(=O)NC3(C(=O)O)Cc4ccccc4C3)ccc2N(C)C)c1]

The title compound was prepared in analogy to example 164 using 0.12 g of resin (0.5 mmol/g) and repeating the methylation procedure three more times with fresh reagents for complete conversion of intermediary methylamino compound into the dimethylamino compound. Yield: 6.6 mg.

LC/MS (Method LC7): Rt=3.37 min; m/z=459.2 [MH+]

1H-NMR (300 MHz, D6-DMSO+2% TFA): δ=2.28 (s, 3H); 3.04 (s, 6H); 3.12 (t, J=6.50 Hz, 2H); 3.33-3.44 (m, 2H); 3.62 (d, J=16.77 Hz, 2H); 4.43 (t, J=6.69 Hz, 2H); 7.04 (d, J=6.97 Hz, 1H); 7.11-7.27 (m, 7H); 7.55-7.71 (m, 3H); 8.93 (s, 1H)

EXAMPLE 166

2-[4-Isopropylamino-3-(2-m-tolyl-ethoxy)-benzoylamino]-indane-2-carboxylic acid

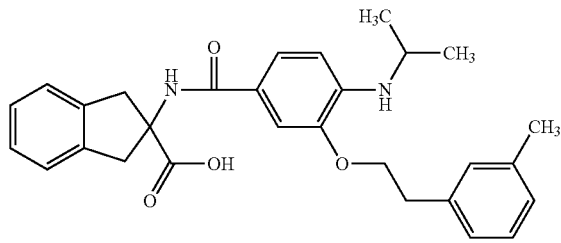

The title compound was prepared in analogy to example 163 using 0.25 g of resin (0.5 mmol/g). After reduction of the nitro group, the amino group was alkylated using 2-methoxypropene (10 equivalents) in 2 ml of a mixture of DCM and ACN (3:1) containing 2% of acetic acid and 1 ml of a 1 M solution of sodium cyanoborohydride in THF. The alkylation was repeated three times with fresh reagents. Cleavage and work-up were performed in analogy to example 164. Yield: 13.4 mg.

LC/MS (Method LC7): Rt=4.19 min; m/z=473.2 [MH+]

EXAMPLE 167

2-{3-[2-(2-Fluoro-phenyl)-2-hydroxy-ethoxy]-4-methoxy-benzoylamino}-indane-2-carboxylic acid

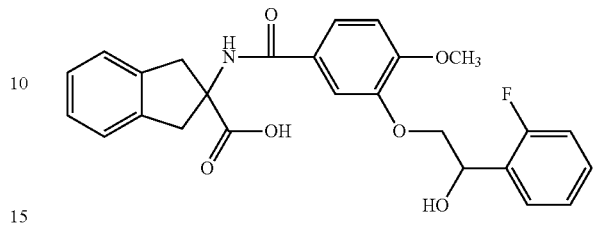

The title compound was prepared according to the general procedure described in example 125 using 0.25 g of resin (0.5 mmol/g). Attachment of the 2-amino-indane-2-carboxylic acid moiety to the resin was followed by acylation with 3-hydroxy-4-methoxy-benzoic acid and treatment with 50% piperidine in DMF for 2 h. After extensive washing with DMF and DCM the resin was reacted with 2-bromo-1-(2-fluoro-phenyl)-ethanone (3 equivalents) in the presence of 1,8-diazabicyclo[5.4.0]undec-7-ene (DBU; 3 equivalents) in 3 ml of DCM overnight at room temperature. The compound was cleaved from the resin with neat TFA for 2 h, and TFA was evaporated in vacuo. The crude intermediate product was dissolved in 4 ml of THF, 10 mg of lithium borohydride were added and the reaction mixture was shaken for 3 h. Then the reaction mixture was quenched with acetic acid, evaporated to dryness, and the residue was purified by preparative RP HPLC (water/ACN gradient). Yield: 3.7 mg.

LC/MS (Method LC7): Rt=4.01 min; m/z=466.2 [MH+]

EXAMPLE 168

2-[4-Cyano-3-(2-m-tolyl-ethoxy)-benzoylamino]-indane-2-carboxylic acid

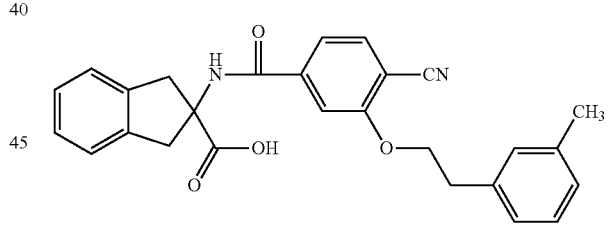

The title compound was prepared according to the general procedure described in example 125 using 0.3 g of resin (0.75 mmol/g). 3-Hydroxy-4-iodo-benzoic acid was used in the acylation step. Finally, the resin with the iodo compound was treated with zinc cyanide and tetrakis(triphenylphosphine) palladium(0) in 5 ml of DMF/EDIA (2:1) in a microwave reactor (90 W) at 150° C. for 10 min. The resin was decanted with DCM, then extensively washed with DMF and DCM, and the product was cleaved with neat TFA for 2 h. TFA was removed in vacuo, and the residue was dissolved in 50% aqueous TFA and heated at 50° C. overnight. The TFA was partially evaporated and the aqueous solution was lyophilized. The compound was purified by preparative RP HPLC (water/ACN gradient). Yield: 11.4 mg.

LC/MS (Method LC7): Rt=4.78 min; m/z=441.2 [MH+]

1H-NMR (300 MHz, D6-DMSO+2% TFA): δ=2.28 (s, 3H); 3.05 (t, J=6.69 Hz, 2H); 3.33-3.43 (m, 2H); 3.55-3.65

(m, 2H); 4.36 (t, J=6.59 Hz, 2H); 7.03 (d, J=7.16 Hz, 1H); 7.09-7.26 (m, 7H); 7.49-7.58 (m, 2H); 7.80 (d, J=7.91 Hz, 1H); 9.04 (s, 1H)

EXAMPLE 169

2-[4-Methoxy-3-(3-phenyl-propyl)-benzoylamino]-indane-2-carboxylic acid

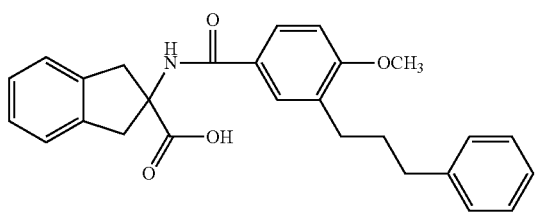

The title compound was prepared according to the general procedure described in example 125 using 0.3 g of resin (0.75 mmol/g). 3-Iodo-4-methoxy-benzoic acid was used as the acylation agent in place of the hydroxy-substituted benzoic acid. Finally, the resin with the iodo compound was reacted under Sonogashira conditions with 3-phenyl-1-propyne (10 equivalents) dissolved in 4 ml of DMF together with triethylamine (20 equivalents), copper(I) iodide (0.1 equivalents) and bis(triphenylphosphine)palladium(II) chloride (0.1 equivalents). The reaction mixture was shaken at room temperature for 48 h. The resin was washed with DMF, DCM and the intermediate product was cleaved with neat TFA for 2 h. TFA was removed in vacuo, and residue was dissolved in water/ACN (3:2) and lyophilized. The isolated intermediate product was dissolved in 6 ml of methanol, 100 mg of 10% palladium on charcoal were added, and the mixture was hydrogenated in a Parr reactor at about 3.5 bar for 2 h. After filtration, methanol was evaporated and the residue was purified by preparative RP HPLC (water/ACN gradient). Yield: 13.7 mg.

LC/MS (Method LC7): Rt=4.97 min; m/z=430.2 [MH+]
1H-NMR (300 MHz, D6-DMSO+2% TFA): δ=1.83 (dq, J=7.91, 7.66 Hz, 2H); 2.59 (q, J=7.72 Hz, 4H); 3.31-3.45 (m, 2H); 3.52-3.63 (m, 2H); 3.81 (s, 3H); 6.98 (d, J=8.67 Hz, 1H); 7.08-7.32 (m, 10H); 7.66 (d, J=2.26 Hz, 1H); 7.74 (dd, J=8.48/2.26 Hz, 1H); 8.62 (s, 1H)

EXAMPLE 170

2-[4-Acetyl-3-(2-m-tolyl-ethoxy)-benzoylamino]-indane-2-carboxylic acid

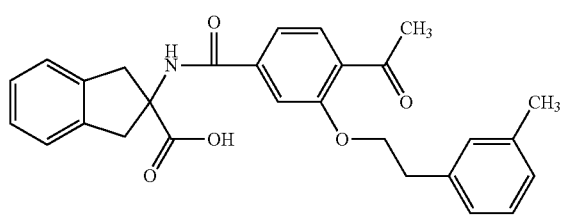 [SMILES: CC(=O)c1ccc(C(=O)NC2(C(=O)O)Cc3ccccc3C2)cc1OCCc1cccc(C)c1]

The title compound was prepared according to the general procedure described in example 125 using 0.3 g of resin (0.75 mmol/g). 3-Hydroxy-4-iodo-benzoic acid was used in the acylation step. Finally, the resin with the iodo compound was reacted with trimethylsilylacetylene (10 equivalents) dissolved in 4 ml of DMF together with triethylamine (20 equivalents), copper(I) iodide (0.1 equivalents) and bis(triphenylphosphine)palladium(II) chloride (0.1 equivalents) overnight at room temperature. The resin was washed with DMF and THF and treated with a 1 M solution of tetrabutylammonium fluoride in THF for 30 min. After extensive washing with DCM, 10% acetic acid in DCM and DCM the compound was cleaved from the resin with neat TFA for 2 h. The carboxylic acid amide was converted into the carboxylic acid as described in the general procedure in example 125 and the title compound purified by preparative RP HPLC (water/ACN gradient). Yield: 5.8 mg.

LC/MS (Method LC7): Rt=4.77 min; m/z=458.2 [MH+]

EXAMPLE 171

2-[4-Methoxy-3-(2-m-tolyl-ethylamino)-benzoylamino]-indane-2-carboxylic acid

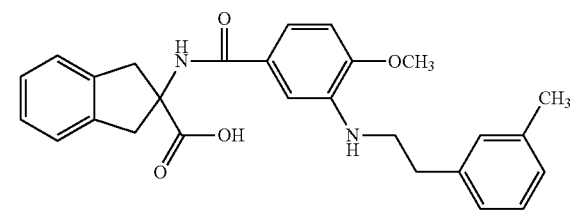 [SMILES: COc1ccc(C(=O)NC2(C(=O)O)Cc3ccccc3C2)cc1NCCc1cccc(C)c1]

The title compound was prepared according to the general procedure described in example 125 using 0.5 g of resin (0.75 mmol/g). 4-Methoxy-3-nitro-benzoic acid in place of the hydroxy-substituted benzoic acid was used in the acylation step, and the nitro group was subsequently reduced with a 1 M solution of tin(II) chloride dihydrate in DMF overnight. The resin was washed with DMF, DCM and reacted with 2,4-dinitro-benzenesulfonyl chloride (5 equivalents) and 2,6-lutidine (10 equivalents) dissolved in 5 ml of DCM for 5 h. After washing with DCM and THF, a solution of triphenylphosphine (10 equivalents) and 2-(3-methylphenyl)-ethanol (10 equivalents) in THF was added to the resin and the slurry was cooled to 0° C. DIAD was added to the cooled mixture and the reaction mixture was shaken overnight at room temperature. The resin was washed with DCM and treated with mercaptoacetic acid (5 equivalents) and triethylamine (10 equivalents) in DCM for 10 min. The step was repeated with a fresh solution. The resin was washed with DMF and DCM. The compound was cleaved from the resin with neat TFA for 2 h, the carboxylic acid amide was converted into the carboxylic acid as described in the general procedure in example 125 and the title compound purified by preparative RP HPLC (water/ACN gradient). Yield: 36.4 mg.

LC/MS (Method LC7): Rt=3.80 min; m/z=445.2 [MH+]
1H-NMR (300 MHz, D6-DMSO+2% TFA): δ=2.27 (s, 3H); 2.83-2.92 (m, 2H); 3.33-3.48 (m, 4H); 3.53-3.64 (m, 2H); 3.90 (s, 3H); 6.99-7.25 (m, 10H); 7.56 (s, 1H); 7.63 (s, 1H); 8.72 (s, 1H)

EXAMPLE 172

2-{4-Methoxy-3-[methyl-(2-m-tolyl-ethyl)-amino]-benzoylamino}-indane-2-carboxylic acid

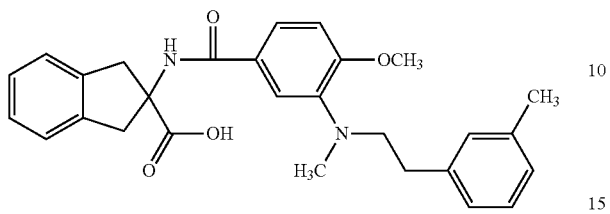

First, the synthesis was carried out as described in example 171 using 0.25 g of resin (0.75 mmol/g). Subsequently, for the N-methylation, the resin was treated with a 37% aqueous solution of formaldehyde (10 equivalents) in DCM/ACN (3:1) containing 2% of acetic acid and 1.5 ml of a 1 M sodium cyanoborohydride solution in THF overnight. The methylation reaction was repeated three times with fresh reagents. The cleavage, isolation and purification of the compound were performed as described in example 171. Yield: 21.4 mg.

LC/MS (Method LC7): Rt=3.19 min; m/z=459.2 [MH$^+$]

$^1$H-NMR (300 MHz, D$_6$-DMSO+2% TFA): δ=2.22 (s, 3H); 2.72 (t, J=7.82 Hz, 2H); 3.23 (s, 3H); 3.34-3.45 (m, 2H); 3.63 (d, J=16.95 Hz, 2H); 3.78 (t, J=8.67 Hz, 2H); 3.99 (s, 3H); 6.89-6.96 (m, 2H); 7.00 (d, J=7.91 Hz, 1H); 7.10-7.29 (m, 6H); 7.33 (d, J=8.85 Hz, 1H); 8.04 (dd, J=8.67/1.70 Hz, 1H); 8.16 (s, 1H); 8.84 (s, 1H)

EXAMPLE 173

2-[4-Cyano-3-(2-m-tolyl-ethylamino)-benzoylamino]-indane-2-carboxylic acid

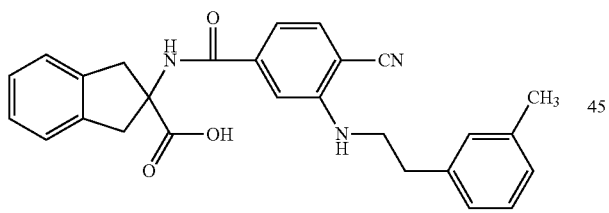

0.1 g of PL Wang resin (Polymer Laboratories, Amherst, Mass., USA; 1.7 mmol/g) was acylated with FMOC-protected 2-amino-indane-2-carboxylic acid (3 equivalents) in the presence of DIC (3 equivalents), HOBT (3 equivalents) and 1-methylimidazole in DMF overnight. The FMOC protecting group was removed by treatment with 50 piperidine in DMF, and the obtained amino acid was acylated with 4-cyano-3-fluorobenzoic acid (3 equivalents) in the presence of DIC (3 equivalents) and HOBT (3 equivalents) in DMF. The resin was treated with a 1 M solution of 2-(3-methyl-phenyl)-ethylamine in DMF overnight at room temperature. The reaction was repeated with fresh amine solution. The resin was washed with DMF and DCM and the compound was cleaved from the resin with neat TFA for 1.5 h. TFA was removed in vacuo and the compound was purified by preparative RP HPLC (water/ACN gradient). Yield: 9.7 mg.

LC/MS (Method LC7): Rt=4.66 min; m/z=440.2 [MH$^+$]

$^1$H-NMR (300 MHz, D$_6$-DMSO+2% TFA): δ=2.27 (s, 3H); 2.83 (t, J=7.44 Hz, 2H); 3.33-3.47 (m, 4H); 3.54-3.65 (m, 2H); 6.98-7.11 (m, 4H); 7.11-7.26 (m, 7H); 7.54 (d, J=8.10 Hz, 1H); 8.95 (s, 1H)

EXAMPLE 174

2-[4-Cyano-3-[3-phenyl-pyrrolidin-1-yl)-benzoylamino]-indane-2-carboxylic acid

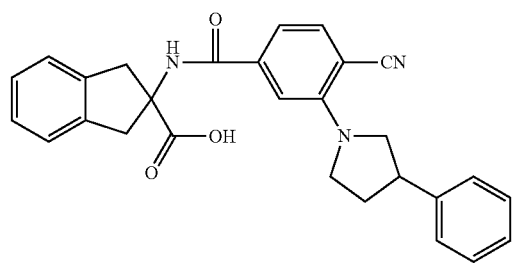 [SMILES: N#Cc1ccc(C(=O)NC2(C(=O)O)Cc3ccccc3C2)cc1N1CCC(c2ccccc2)C1]

The synthesis was carried out as described in example 174 using 0.15 g of PL Wang resin (1.7 mmol/g). Instead of with 2-(3-methyl-phenyl)-ethylamine, in the last step the resin was reacted with 3-phenyl-pyrrolidine (8 equivalents) in dimethylacetamide at 90° C. overnight. The compound was cleaved, isolated and purified as described in example 173.

Yield: 11.3 mg.

LC/MS (Method LC7): Rt=4.82 min; m/z=452.2 [MH$^+$]

EXAMPLE 175

2-{4-Cyano-3-[2-(2-fluoro-phenyl)-ethylamino]-benzoylamino}-indane-2-carboxylic acid

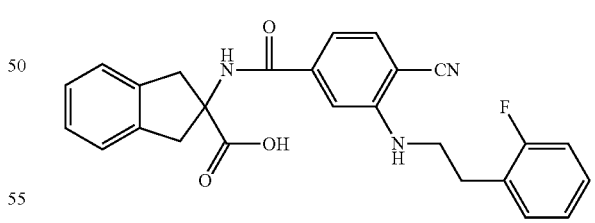

The synthesis was carried out as described in example 173 using 0.1 g of PL Wang resin (1.7 mmol/g). Instead of with 2-(3-methyl-phenyl)-ethylamine, in the last step the resin was reacted with 2-(2-fluorophenyl)-ethylamine (10 equivalents) in dimethylacetamide in a microwave reactor at 150° C. for 1 h. The compound was cleaved, isolated and purified as described in example 173.

Yield: 1.7 mg.

LC/MS (Method LC7): Rt=4.51 min; m/z=444.2 [MH$^+$]

EXAMPLE 176

2-{3-[2-(3-Chloro-phenyl)-ethoxy]-4-methyl-benzoylamino}-indane-2-carboxylic acid

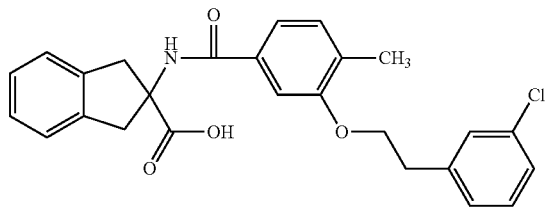 [SMILES: Cc1ccc(C(=O)NC2(C(=O)O)Cc3ccccc3C2)cc1OCCc1cccc(Cl)c1]

The synthesis was carried out on 0.15 g of PL Wang resin (1.7 mmol/g). The attachment of 2-amino-indane-2-carboxylic acid and the acylation with 3-hydroxy-4-methylbenzoic acid were performed as in described in example 173. After the acylation step, the resin was washed with THF and a solution of triphenylphosphine (10 equivalents) and 2-(3-chlorophenyl)-ethanol (10 equivalents) in THF was added to the resin. The slurry was cooled to 0° C., DIAD (10 equivalents) was added to the cooled mixture, and the reaction mixture was shaken overnight at room temperature. The resin was washed with DCM. The compound was cleaved, isolated and purified as in described in example 173. Yield: 2.3 mg.

LC/MS (Method LC7): Rt=5.11 min; m/z=450.2 [MH$^+$]

EXAMPLE 177

2-{3-[2-(2-Fluoro-phenyl)-ethoxy]-4-methyl-benzoylamino}-indane-2-carboxylic acid

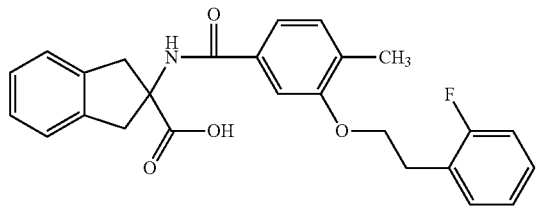 [SMILES: Cc1ccc(C(=O)NC2(C(=O)O)Cc3ccccc3C2)cc1OCCc1ccccc1F]

The title compound was prepared as described in example 176. Yield: 3.8 mg.
LC/MS (Method LC7): Rt=4.87 min; m/z=434.2 [MH$^+$]

EXAMPLE 178

2-[4-Ethoxy-3-(2-m-tolyl-ethylamino)-benzoylamino]-indane-2-carboxylic acid

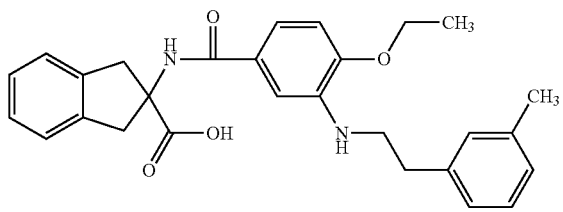 [SMILES: CCOc1ccc(C(=O)NC2(C(=O)O)Cc3ccccc3C2)cc1NCCc1cccc(C)c1]

The synthesis was carried out on 0.15 g of PL Wang resin (1.7 mmol/g). The attachment of 2-amino-indane-2-carboxylic acid and the acylation step using 4-fluoro-3-nitro-benzoic acid were performed as described in example 173. After the acylation step, the resin was shaken with ethanol (5 equivalents) in the presence of sodium bis(trimethylsilyl)amide (5 equivalents) in 3 ml of dimethylacetamide. The resin was washed with DMF, 10% acetic acid/DMF, DMF and finally with DCM. The reduction of the nitro group with tin(II) chloride, sulfonylation with 2,4-dinitro-benzenesulfonyl chloride, alkylation with 2-(3-methylphenyl)-ethanol and removal of the sulfonyl group were performed as described in example 171 and the compound purified by preparative RP HPLC (water/ACN gradient). Yield: 2.4 mg.

LC/MS (Method LC7): Rt=3.73 min; m/z=459.2 [MH$^+$]

EXAMPLE 179

2-[4-Hydroxy-3-(2-m-tolyl-ethylamino)-benzoylamino]-indane-2-carboxylic acid

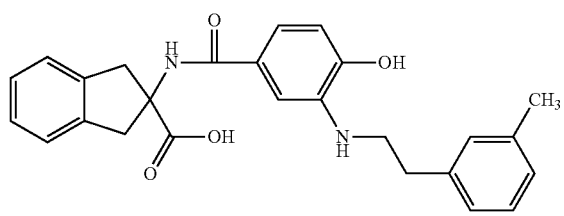

10 mg of the compound of example 171 were dissolved in DCM and treated with 200 µl of a 1 M solution of boron tribromide in DCM for 5 h. A 2 M solution of sodium carbonate was added, and the mixture was evaporated in vacuo. The product was purified by preparative RP HPLC (water/ACN gradient).

LC/MS (Method LC7): Rt=3.34; m/z=431.2 [MH$^+$]
$^1$H-NMR (300 MHz, D$_6$-DMSO+2% TFA): δ=2.21 (s, 3H); 2.81-2.92 (m, 2H); 3.24-3.37 (m, 2H); 3.37-3.48 (m, 2H); 3.48-3.60 (m, 2H); 6.88-7.04 (m, 5H); 7.04-7.21 (m, 6H); 7.66-7.79 (m, 2H); 8.66 (s, 1H)

EXAMPLE 180

2-[4-Methoxy-3-(2-m-tolyl-ethylsulfanyl)-benzoylamino]-indane-2-carboxylic acid

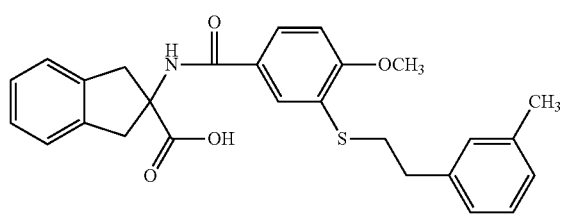

Step 1

3-(5-Carboxy-2-methoxy-phenyldisulfanyl)-4-methoxy-benzoic acid 45 g (179.5 mmol) of 3-chlorosulfonyl-4-methoxy-benzoic acid were suspended in 200 ml of acetic acid and warmed to 40° C. Then a solution of 85.1 g (448.8 mmol) tin(II) chloride in 100 ml of hydrochloric acid was added within 15 min and the mixture was stirred for 2 h under reflux. The hot solution was added dropwise to 2000 ml of ice/water. The formed precipitate was collected by suction, washed with water and dried. 32.8 g of the title compound were obtained.

Step 2

4-Methoxy-3-(2-m-tolyl-ethylsulfanyl)-benzoic acid 732.8 mg (2 mmol) of the compound of step 1 were dissolved in 30 ml of absolute methanol and 151.3 mg (4 mmol) of sodium borohydride were added slowly in portions. After stirring overnight, a solution of 796.4 mg (4 mmol) of 1-(2-bromo-ethyl)-3-methyl-benzene in 10 ml of DCM was added and the mixture was stirred overnight. Then 202.4 mg (4 mmol) of triethylamine were added and stirring was continued for 2 h at room temperature and for 2 h at 40° C. After cooling, the mixture was extracted with a sodium hydrogencarbonate solution and the organic phase was dried and evaporated. The residue was used in the subsequent step without further purification.

Step 3

2-[4-Methoxy-3-(2-m-tolyl-ethylsulfanyl)-benzoylamino]-indane-2-carboxylic acid 700 mg of the crude compound of step 2 were dissolved in 5 ml of DMF and 598 mg (4.63 mmol) of EDIA and 968 mg (2.55 mmol) of O-(7-azabenzotriazol-1-yl)-N,N,N',N'-tetramethyluronium hexafluorophosphate were added. Then a solution of 527 mg (2.32 mmol) of 2-amino-indane-2-carboxylic acid methyl ester hydrochloride in 5 ml of DMF was added. After stirring overnight, EA and an aqueous solution of lithium chloride (4%) were added, the organic phase was separated, washed once with a solution of lithium chloride and twice with a solution of sodium hydrogencarbonate, dried and evaporated. The solid residue was dissolved in 10 ml of a 9:1 mixture of THF and water, and 131 mg (5.47 mmol) of lithium hydroxide were added. After stirring overnight, the mixture was evaporated to dryness. The residue was purified by preparative RP HPLC (water/ACN gradient) to give 222 mg of the title compound.

LC/MS (Method LC3): Rt=1.97 min; m/z=462.23 [MH⁺]
¹H-NMR: δ=12.45 (br s, 1H); 8.87 (s, 1H); 7.78 (s, 1H); 7.74 (d, 1H); 7.20-7.26 (m, 2H); 7.13-7.20 (m, 3H); 7.09 (s, 1H); 6.98-7.08 (m, 3H); 3.87 (s, 3H); 3.60 (d, 2H); 3.18 (d, 2H); 2.82 (t, 2H); 2.29 (s, 3H)

EXAMPLE 181

2-{3-[2-(3-Chloro-phenyl)-ethylsulfanyl]-4-methoxy-benzoylamino}-indane-2-carboxylic acid

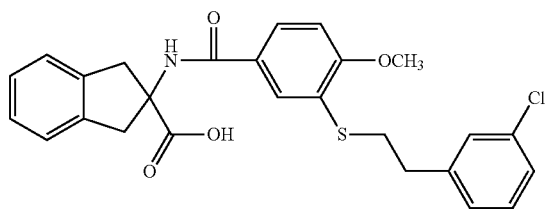 [SMILES: COc1ccc(C(=O)NC2(C(=O)O)Cc3ccccc3C2)cc1SCCc1cccc(Cl)c1]

The title compound was obtained in analogy to example 180 by using 1-(2-bromo-ethyl)-3-chloro-benzene instead of 1-(2-bromo-ethyl)-3-methyl-benzene in step 2.
LC/MS (Method LC3): Rt=1.97 min; m/z=482.19 [MH⁺]

EXAMPLE 182

2-(3-Benzylsulfanyl-4-methoxy-benzoylamino)-indane-2-carboxylic acid

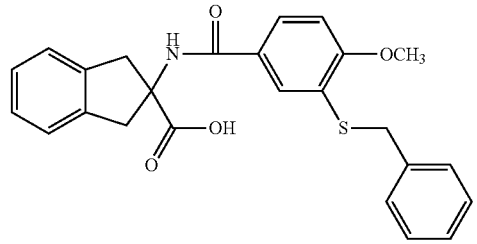 [SMILES: COc1ccc(C(=O)NC2(C(=O)O)Cc3ccccc3C2)cc1SCc1ccccc1]

The title compound was obtained in analogy to example 180 by using benzyl bromide instead of 1-(2-bromo-ethyl)-3-methyl-benzene in step 2.
LC/MS (Method LC3): Rt=1.80 min; m/z=434.26 [MH⁺]

EXAMPLE 183

2-[4-Methoxy-3-(2-m-tolyl-ethanesulfonyl)-benzoylamino]-indane-2-carboxylic acid

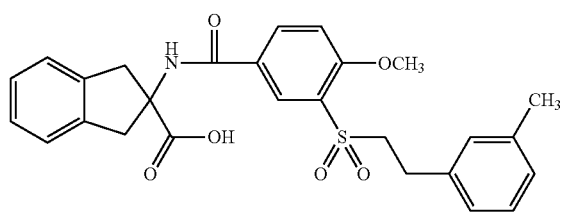 [SMILES: COc1ccc(C(=O)NC2(C(=O)O)Cc3ccccc3C2)cc1S(=O)(=O)CCc1cccc(C)c1]

55 mg (119.2 mmol) of the compound of example 180 were dissolved in 5 ml of DCM and treated with a solution of 88.2 mg (357.6 mmol) of 3-chloroperbenzoic acid in 5 ml of DCM. After stirring at room temperature overnight, the solvent was evaporated and the residue was purified by preparative RP HPLC (water/ACN gradient) to give 28 mg of the title compound.

LC/MS (Method LC3): Rt=1.68 min; m/z=494.25 [MH⁺]
¹H-NMR: δ=12.45 (br s, 1H); 9.00 (s, 1H); 8.30 (s, 1H); 7.21-7.28 (m, 3H); 7.13-7.20 (m, 2H); 7.08 (t, 1H); 6.90-6.95 (m, 2H); 6.88 (s, 1H); 3.94 (s, 3H); 3.70 (t, 2H); 3.60 (d, 2H); 3.42 (d, 2H); 2.82 (t, 2H); 2.18 (s, 3H)

EXAMPLE 184

2-{3-[2-(3-Chloro-phenyl)-ethanesulfonyl]-4-methoxy-benzoylamino}-indane-2-carboxylic acid

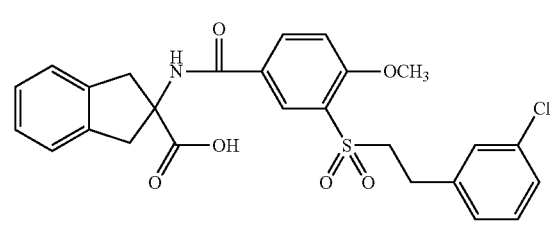 [SMILES: COc1ccc(C(=O)NC2(C(=O)O)Cc3ccccc3C2)cc1S(=O)(=O)CCc1cccc(Cl)c1]

The title compound was obtained in analogy to example 183, starting from the compound of example 181.
LC/MS (Method LC3): Rt=1.69 min; m/z=514.20 [MH⁺]

EXAMPLE 185

2-[3-(2-m-Tolyl-ethoxy)-4-trifluoromethyl-benzoylamino]-indane-2-carboxylic acid

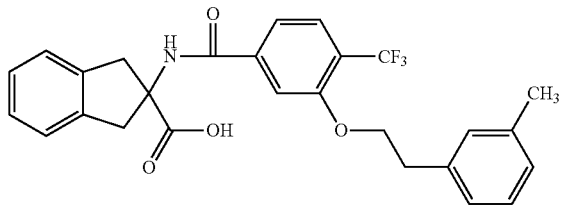 [SMILES: Cc1cccc(CCOc2cc(C(=O)NC3(C(=O)O)Cc4ccccc4C3)ccc2C(F)(F)F)c1]

Step 1

3-Acetoxy-4-trifluoromethyl-benzoic acid 3.5 g (17 mmol) of 3-hydroxy-4-trifluoromethyl-benzoic acid (prepared as described in WO 2006/128184) were dissolved in 35 ml of acetic acid anhydride and heated to reflux for 3 h. 60 ml of water were added and heating to reflux was continued for 10 min. After cooling and stirring overnight, the formed precipitate was collected by suction and dried to give 3.0 g of the title compound.

Step 2

2-(3-Acetoxy-4-trifluoromethyl-benzoylamino)-indane-2-carboxylic acid methyl ester To a solution of 2.7 g (10.9 mmol) of the compound of step 1 in 16.3 ml of a 2 M solution of oxalyl chloride in DCM (32.6 mmol), 80 mg of DMF were added and the mixture was stirred for 30 min at room temperature. The solvent was evaporated, 20 ml of DCM were added and the mixture was evaporated again. The residue was dissolved in 20 ml of DCM and the solution added within 5 min at 0° C. to a solution of 2.48 g (10.9 mmol) of 2-amino-indane-2-carboxylic acid methyl ester hydrochloride in 50 ml of DCM and 30 ml of a saturated sodium hydrogencarbonate solution. After stirring overnight, the phases were separated, the organic phase was dried over sodium sulfate, evaporated, and the residue was purified by silica gel chromatography (HEP/EA gradient). 1.1 g of the title compound were obtained.

Step 3

2-[3-(2-m-Tolyl-ethoxy)-4-trifluoromethyl-benzoylamino]-indane-2-carboxylic acid methyl ester 200 mg (0.48 mmol) of the compound of step 2 were dissolved in 5 ml of methanol, 13.1 mg (0.1 mmol) of potassium carbonate were added and the mixture was stirred for 30 min. The mixture was acidified with 1 N hydrochloric acid and extracted three times with 20 ml portions of EA. The combined organic phases were dried and evaporated. The residue was dissolved in 5 ml of THF, 96.9 mg (0.71 mmol) of 2-(3-methylphenyl)-ethanol and 186.7 mg (0.71 mmol) of triphenylphosphine were added, the mixture was cooled in an ice bath, and 191.9 mg (0.95 mmol) of DIAD were added. After stirring overnight, the mixture was evaporated to dryness and the residue was purified by preparative RP HPLC (water/ACN gradient). 104 mg of the title compound were obtained.

Step 4

2-[3-(2-m-Tolyl-ethoxy)-4-trifluoromethyl-benzoylamino]-indane-2-carboxylic acid The title compound was obtained from the compound of step 3 by hydrolysis with lithium hydroxide in analogy to example 180, step 3.

LC/MS (Method LC3): Rt=2.15 min; m/z=484.19 [MH$^+$]

$^1$H-NMR: δ=12.50 (br s, 1H); 9.00 (s, 1H); 7.69 (d, 1H); 7.59 (s, 1H); 7.55 (d, 1H); 7.20-7.26 (m, 2H); 7.13-7.20 (m, 4H); 7.11 (d, 1H); 7.03 (d, 1H); 4.35 (t, 2H); 3.60 (d, 2H); 3.39 (d, 2H); 3.02 (t, 2H); 2.29 (s, 3H)

In analogy to example 185, the example compounds of the formula It listed in table 6 were prepared by using the respective 2-(substituted phenyl)-ethanol instead of 2-(3-methylphenyl)-ethanol in step 3. The compounds can be named as 2-{3-[2-(R$^{96}$)-ethoxy]-4-trifluoromethyl-benzoylamino}-indane-2-carboxylic acid, for example as 2-{3-[2-(3-chlorophenyl)-ethoxy]-4-trifluoromethyl-benzoylamino}-indane-2-carboxylic acid in the case of example 186.

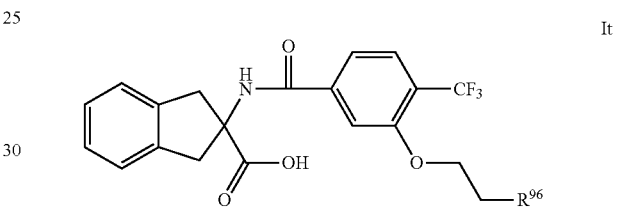

It

TABLE 6

Example compounds of the formula It

| Example | R$^{96}$ | LC/MS Method | m/z [MH$^+$] | Retention time [min] |
|---|---|---|---|---|
| 186 | 3-chloro-phenyl | LC3 | 504.24 | 2.15 |
| 187 | 2-chloro-6-fluoro-phenyl | LC3 | 522.04 | 2.10 |
| 188 | 2,5-difluoro-phenyl | LC3 | 506.07 | 2.03 |
| 189 | 5-chloro-2-fluoro-phenyl | LC3 | 522.06 | 2.12 |
| 190 | 3-methyl-pyrazin-2-yl | LC3 | 486.23 | 1.67 |
| 191 | 2-fluoro-5-trifluoromethyl-phenyl | LC3 | 556.26 | 2.14 |
| 192 | 2-fluoro-5-methyl-phenyl | LC4 | 502.17 | 2.67 |

EXAMPLE 193

2-{3-[2-(5-Chloro-2-fluoro-phenyl)-ethoxy]-4-methoxy-benzoylamino}-indane-2-carboxylic acid

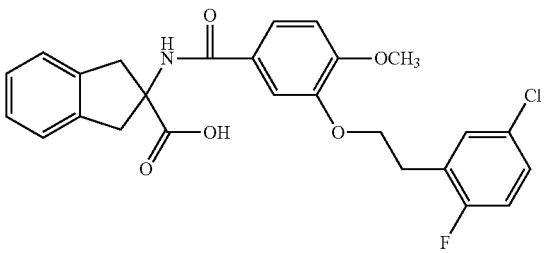 [SMILES: COc1ccc(C(=O)NC2(C(=O)O)Cc3ccccc3C2)cc1OCCc1cc(Cl)ccc1F]

Step 1

2-(5-Chloro-2-fluoro-phenyl)-ethanol

A solution of 5 g (26.51 mmol) of 5-chloro-2-fluoro-phenylacetic acid in 60 ml of THF was added dropped to a suspension of 2.012 g (53.02 mmol) of lithium aluminium hydride in 26.5 ml of THF. 30 ml of THF were added, and the mixture was heated under reflux for 3 h. After cooling to 0° C., a solution of 929.7 mg (16.57 mmol) of potassium hydroxide in 4 ml of water was cautiously added and the mixture was stirred overnight at room temperature. The formed precipitate was filtered off with suction and washed with THF. The combined filtrates were dried over sodium sulfate, filtered and evaporated to dryness. The residue was purified by silica gel chromatography (DCM/methanol 98:2) to give 3.8 g of the title compound.

Step 2

2-{3-[2-(5-Chloro-2-fluoro-phenyl)-ethoxy]-4-methoxy-benzoylamino}-indane-2-carboxylic acid The title compound was obtained in analogy to example 185 by using in 2-(5-chloro-2-fluoro-phenyl)-ethanol instead of 2-(3-methylphenyl)-ethanol in step 3.

LC/MS (Method LC4): Rt=2.35 min; m/z=484.13 [MH$^+$]
$^1$H-NMR: δ=12.45 (br s, 1H); 8.61 (s, 1H); 7.55 (m, 1H) 7.50 (d, 1H); 7.45 (s, 1H); 7.30-7.37 (m, 1H); 7.18-7.26 (m, 3H); 7.11-7.19 (m, 2H); 7.00 (d, 1H); 4.21 (t, 2H); 3.80 (s, 3H); 3.59 (d, 2H); 3.35 (d, 2H); 3.06 (t, 2H)

EXAMPLE 194

2-[4-Methoxy-3-(4-trifluoromethyl-phenylethynyl)-benzoylamino]-indane-2-carboxylic acid

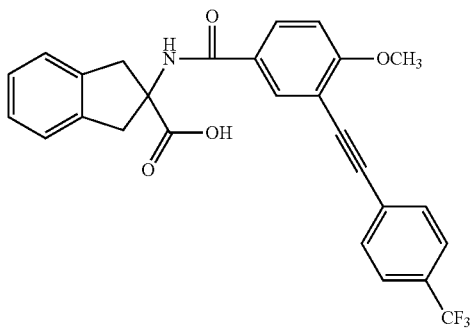 [SMILES: COc1ccc(C(=O)NC2(C(=O)O)Cc3ccccc3C2)cc1C#Cc1ccc(C(F)(F)F)cc1]

Step 1

2-(3-Bromo-4-methoxy-benzoylamino)-indane-2-carboxylic acid methyl ester

3-Bromo-4-methoxybenzoic acid (22.8 g, 98.8 mmol) was dissolved in thionyl chloride (42 ml) and stirred at 60° C. for 30 min. The volatiles were evaporated in vacuo and the residue was stripped with dioxane. The obtained acid chloride was dissolved in DCM (50 ml). 2-Amino-indane-2-carboxylic acid methyl ester hydrochloride (15.0 g, 65.9 mmol) was suspended in DCM (100 ml), EDIA (10.2 g, 79.1 mmol) was added, the mixture was cooled in an ice bath, and the solution of the acid chloride was slowly added. The mixture was stirred overnight at room temperature and evaporated to dryness. The residue was purified by silica gel chromatography (DCM/methanol gradient) and subsequent crystallization from EA to give 21.8 g of the title compound.

LC/MS (Method LC3): Rt=1.495 min; m/z=404.0/406.0 [MH$^+$]

Step 2

2-[4-Methoxy-3-(4-trifluoromethyl-phenylethynyl)-benzoylamino]-indane-2-carboxylic acid methyl ester 300 mg (0.74 mmol) of the compound of step 1 and 90.1 mg (0.89 mmol) of triethylamine were dissolved in 10 ml of dry toluene. 171.5 mg (148 µmol) of tetrakis(triphenylphosphine)palladium(0) and 14.1 mg (74 µmol) of copper(I) iodide were added, and the mixture was stirred for 30 min. Subsequently 126.2 mg (0.74 mmol) of 1-ethynyl-4-trifluoromethyl-benzene were added and the mixture was heated to 100° C. for 10 h. The mixture was filtered, the solvent was evaporated and the residue was purified by preparative RP HPLC (water/ACN gradient) to give 40 mg of the title compound.

Step 3

2-[4-Methoxy-3-(4-trifluoromethyl-phenylethynyl)-benzoylamino]-indane-2-carboxylic acid From the compound of step 2, the title compound was obtained by hydrolysis with lithium hydroxide in analogy to example 180, step 3, and purification by silica gel chromatography (DCM/methanol 98:2). Yield: 32 mg.

LC/MS (Method LC4): Rt=2.57 min; m/z=480.17 [MH$^+$]
$^1$H-NMR: δ=12.45 (br s, 1H); 8.80 (s, 1H); 8.09 (s, 1H); 7.94 (d, 1H); 7.80 (d, 2H); 7.74 (d, 2H); 7.60-7.65 (m, 1H); 7.13-7.25 (m, 4H); 3.91 (s, 3H); 3.57 (d, 2H); 3.40 (d, 2H)

EXAMPLE 195

2-[3-(4-tert-Butyl-phenylethynyl)-4-methoxy-benzoylamino]-indane-2-carboxylic acid

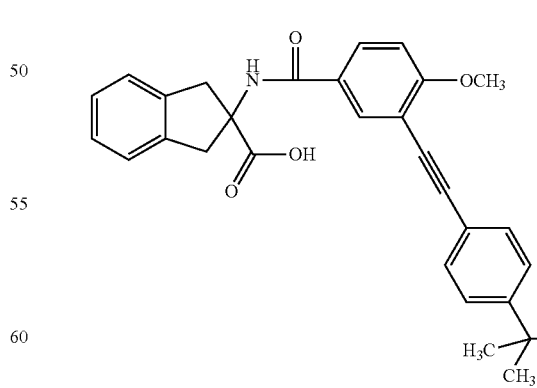

The title compound was obtained in analogy to example 194 by using 1-tert-butyl-4-ethynyl-benzene instead of 1-ethynyl-4-trifluoromethyl-benzene.

LC/MS (Method LC4): Rt=2.79 min; m/z=486.24 [MH$^+$]

EXAMPLE 196

2-[(3'-Isopropyl-6-methoxy-biphenyl-3-carbonyl)-amino]-indane-2-carboxylic acid

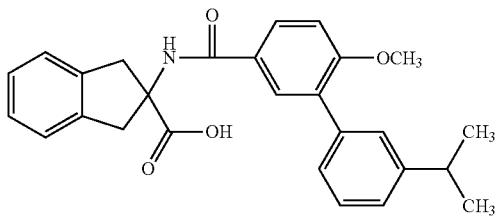 [SMILES: COc1ccc(C(=O)NC2(C(=O)O)Cc3ccccc3C2)cc1-c1cccc(C(C)C)c1]

250 mg (0.62 mmol) of the compound of example 194, step 1, and 152.1 mg (0.93 mmol) of 3-isopropylphenylboronic acid were dissolved in 5 ml of DMF and 5 ml of toluene under an argon atmosphere. 187.9 mg (1.24 mmol) of cesium fluoride and 35.73 mg (0.05 mmol) of tetrakis(triphenylphosphine)palladium(0) were added, and the mixture was stirred overnight at 100° C. After cooling, the mixture was filtered and the solvent was evaporated. The obtained 2-[(3'-isopropyl-6-methoxy-biphenyl-3-carbonyl)-amino]-indane-2-carboxylic acid methyl ester was dissolved in 10 ml of a mixture of THF and water (9:1), 42.2 mg (1.80 mmol) of lithium hydroxide were added and the mixture was stirred overnight. The solvent was evaporated and the residue was purified by preparative RP HPLC (water/ACN gradient). 71 mg of the title compound were obtained.

LC/MS (Method LC4): Rt=2.50 min; m/z=430.30 [MH$^+$]

$^1$H-NMR: δ=12.5 (br s, 1H); 8.72 (s, 1H); 7.89 (d, 1H); 7.80 (s, 1H); 7.13-7.37 (m, 9H); 3.81 (s, 3H); 3.60 (d, 2H); 2.92 (m, 1H); 1.24 (d, 6H)

In analogy to example 196, the example compounds of the formula Iu listed in table 7 were prepared by using the respective substituted phenylboronic acid instead of 3-isopropylphenylboronic acid. In the case of examples 198 and 199, the intermediary 2-[(substituted biphenyl-3-carbonyl)-amino]-indane-2-carboxylic acid methyl ester was purified by preparative RP HPLC (water/ACN gradient) before hydrolysis. The compounds can be named as 2-[(substituted biphenyl-3-carbonyl)-amino]-indane-2-carboxylic acid, for example as 2-[(3'-cyanomethyl-6-methoxy-biphenyl-3-carbonyl)-amino]-indane-2-carboxylic acid in the case of example 199 in which the group R$^{97}$ is 3-cyanomethyl-phenyl and, in view of the rules of nomenclature, the group 3-(R$^{97}$)-4-methoxy-phenyl-C(O) depicted in formula Iu thus is named 3'-cyanomethyl-6-methoxy-biphenyl-3-carbonyl.

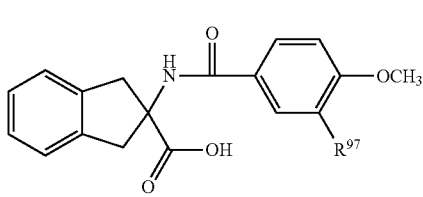

Iu

TABLE 7

Example compounds of the formula Iu

| Example | R$^{97}$ | LC/MS Method | m/z [MH$^+$] | Retention time [min] |
|---|---|---|---|---|
| 197 | 4-isobutyl-phenyl | LC4 | 444.32 | 2.70 |
| 198 | 3-chloro-phenyl | LC4 | 422.22 | 2.32 |
| 199 | 3-cyanomethyl-phenyl | LC4 | 427.27 | 1.99 |
| 200 | 3-trifluoromethyl-phenyl | LC4 | 456.24 | 2.38 |
| 201 | 4-tert-butyl-phenyl | LC4 | 444.32 | 2.63 |
| 202 | 3-ethyl-phenyl | LC3 | 416.32 | 1.95 |
| 203 | 3-dimethylaminosulfonyl-amino-phenyl | LC10 | 510.22 | 2.30 |

EXAMPLE 204

2-{3-[2-(2,5-Difluoro-phenyl)-ethoxy]-4-methoxy-benzoylamino}-indane-2-carboxylic acid

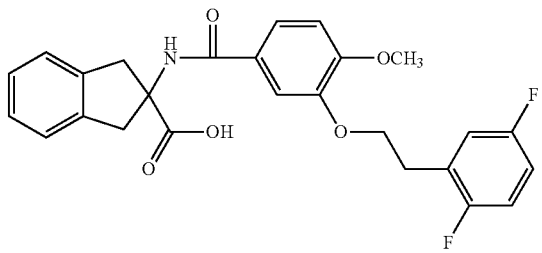 [SMILES: COc1ccc(C(=O)NC2(C(=O)O)Cc3ccccc3C2)cc1OCCc1cc(F)ccc1F]

Step 1

2-{3-[2-(2,5-Difluoro-phenyl)-ethoxy]-4-methoxy-benzoylamino}-indane-2-carboxylic acid methyl ester 300.1 mg (0.88 mmol) of 2-(3-hydroxy-4-methoxy-benzoylamino)-indane-2-carboxylic acid methyl ester, 208.6 mg (1.32 mmol) of 2-(2,5-difluoro-phenyl)-ethanol and 346 mg (1.32 mmol) of triphenylphosphine were dissolved in 10 ml of THF. The mixture was cooled in an ice bath, and 355.5 mg (1.76 mmol) of DIAD were added. After stirring overnight, the mixture was evaporated to dryness and the residue was purified by preparative RP HPLC (water/ACN gradient). 340 mg of the title compound were obtained.

Step 2

2-{3-[2-(2,5-Difluoro-phenyl)-ethoxy]-4-methoxy-benzoylamino}-indane-2-carboxylic acid From the compound of step 1, the title compound was obtained by hydrolysis with lithium hydroxide in analogy to example 180, step 3, and purification by preparative RP HPLC (water/ACN gradient). Yield: 260 mg.

LC/MS (Method LC3): Rt=1.81 min; m/z=468.11 [MH$^+$]

$^1$H-NMR: δ=12.5 (br s, 1H); 8.63 (s, 1H); 7.51 (d, 1H); 7.44 (s, 1H); 7.30-7.10 (m, 6H); 7.00 (d, 1H); 4.22 (t, 2H); 3.79 (s, 3H); 3.59 (d, 2H); 3.38 (d, 2H); 3.08 (t, 2H)

EXAMPLE 205

2-{3-[2-(5-Ethyl-pyridin-2-yl)-ethoxy]-4-methoxy-benzoylamino}-indane-2-carboxylic acid

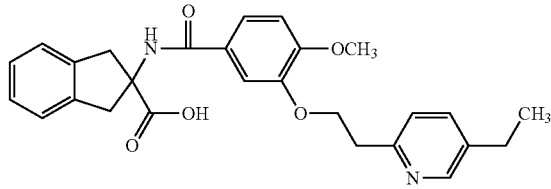 [SMILES: CCc1ccc(CCOc2cc(C(=O)NC3(C(=O)O)Cc4ccccc4C3)ccc2OC)nc1]

The title compound was obtained in analogy to example 204 by using 2-(5-ethyl-pyridin-2-yl)-ethanol instead 2-(2,5-difluoro-phenyl)-ethanol in step 1.
LC/MS (Method LC3): Rt=1.22 min; m/z=461.34 [MH$^+$]

EXAMPLE 206

2-{4-Methoxy-3-[2-(4-methyl-thiazol-5-yl)-ethoxy]-benzoylamino}-indane-2-carboxylic acid

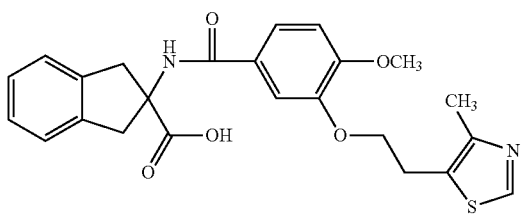 [SMILES: COc1ccc(C(=O)NC2(C(=O)O)Cc3ccccc3C2)cc1OCCc1scnc1C]

The title compound was obtained in analogy to example 204 using 2-(4-methyl-thiazol-5-yl)-ethanol instead 2-(2,5-difluoro-phenyl)-ethanol in step 1.
LC/MS (Method LC4): Rt=2.70 min; m/z=453.11 [MH$^+$]

EXAMPLE 207

6-[4-Methoxy-3-(2-m-tolyl-ethoxy)-benzoylamino]-6,7-dihydro-5H-cyclopentapyrazine-6-carboxylic acid

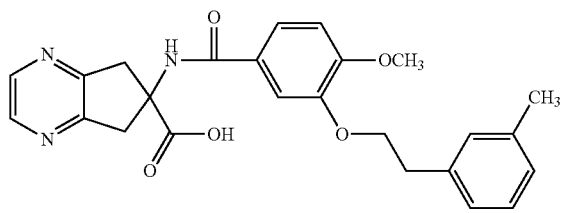

The title compound was obtained from 2,3-bis-chloromethyl-pyrazine (K. Yoshiizumi et al., Bioorg. Med. Chem. 11 (2003), 433-450) in analogy to examples 97 and 98, using N-methylpyrrolidone instead of DMF as solvent in the initial cyclization step. The intermediary amino acid ester was not purified, but used as raw material. LC/MS (Method LC1): Rt=1.32 min; m/z=448.0 [MH$^+$]

EXAMPLE 208

2-{[6-Methoxy-5-(2-m-tolyl-ethoxy)-pyridine-3-carbonyl]-amino}-indane-2-carboxylic acid

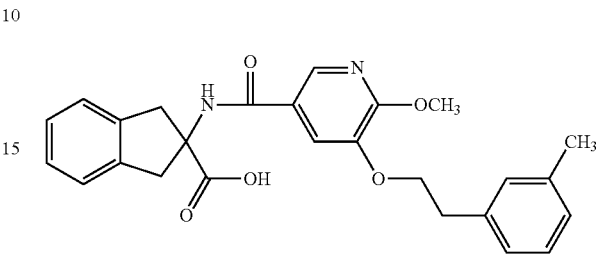

6-Chloro-5-nitro-nicotinic acid methyl ester was prepared according to the procedure described in WO 2005/021544 and transformed into 5-hydroxy-6-methoxy-nicotinic acid methyl ester according to the procedure described in WO 95/04045, which was then transformed into the title compound by etherification with 2-m-tolyl-ethanol in analogy to step 1 of example 1, hydrolysis of the ester group in analogy to example 2, reaction of the obtained carboxylic acid with 2-amino-indane-2-carboxylic acid methyl ester hydrochloride in analogy to step 1 of example 15, and hydrolysis of the ester group in analogy to example 2.
$^1$H-NMR: δ=12.5 (s, 1H); 8.75 (s, 1H); 8.21 (d, 1H); 7.63 (d, 1H); 7.75-7.13 (m, 6H); 7.11 (d, 1H); 7.02 (d, 1H); 4.21 (t, 2H); 3.91 (s, 3H); 3.61 (d, 2H); 3.37 (d, 2H); 3.01 (t, 2H); 2.28 (s, 3H)

EXAMPLE 209

2-[4-Methoxy-3-(2-m-tolyl-ethoxy)-benzoylamino]-1-methyl-indane-2-carboxylic acid

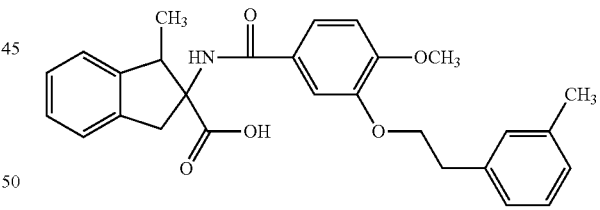

Step 1

1-(1-Chloro-ethyl)-2-chloromethyl-benzene 1-(2-Hydroxymethyl-phenyl)-ethanol (prepared according to the procedure described in P. Canorme et al., Tetrahedron 44 (1988), 2903-2912) (0.376 g, 2.47 mmol) was dissolved in DCM. Thionyl chloride (2.94 g, 24 mmol) was added and allowed to react for 1 h. The mixture was partitioned between EA and an excess of an aqueous sodium hydrogencarbonate solution. The combined organic extracts were dried over sodium sulfate, filtered and evaporated to dryness in vacuo. The residue was purified by silica gel chromatography with HEP to yield 0.228 g of the title compound.

$^1$H-NMR: δ=7.68 (dd, 1H); 7.46-7.41 (m, 2H); 7.35 (dd, 1H); 5.66 (q, 1H); 4.95 (d, 1H); 4.90 (d, 1H); 1.82 (d, 3H)

Step 2

2-[4-Methoxy-3-(2-m-tolyl-ethoxy)-benzoylamino]-1-methyl-indane-2-carboxylic acid The title compound was obtained from the compound of step 1 in analogy to examples 97 and 98, using N-methylpyrrolidone instead of DMF as solvent in the initial cyclization step. The intermediary amino acid ester was not purified, but used as raw material.

LC/MS (Method LC1): Rt=1.66 min; m/z=460.2 [MH$^+$]

EXAMPLE 210

2-(3-{2-[3-(2-Hydroxy-1-hydroxymethyl-1-methylethyl)-phenyl]-ethoxy}-4-methoxy-benzoylamino)-indane-2-carboxylic acid

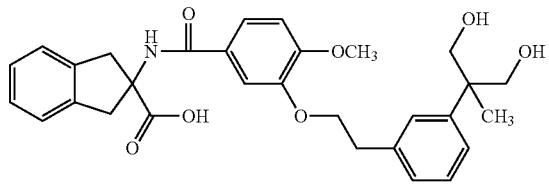 [SMILES: COc1ccc(C(=O)NC2(C(=O)O)Cc3ccccc3C2)cc1OCCc1cccc(C(C)(CO)CO)c1]

Step 1

2-(3-Methoxycarbonylmethyl-phenyl)-malonic acid dimethyl ester

Tris(dibenzylideneacetone)dipalladium(0) (0.104 g, 0.113 mmol), tri-(tert-butyl)phosphonium tetrafluoroborate (65.8 mg, 0.227 mmol) and sodium hydride (295 mg, 60% dispersion in mineral oil) were charged into a flask under an argon atmosphere. (3-Bromophenyl)acetic acid methyl ester (1.30 g, 5.67 mmol) was dissolved in THF (10 ml) and added to the mixture. Subsequently, dimethyl malonate (0.995 g, 7.37 mmol) was added and the mixture stirred under reflux overnight. The mixture was filtered over a small plug of silica gel, evaporated to dryness and the residue purified by silica gel chromatography (HEP/EA gradient) to yield 0.704 g of the title compound.

LC/MS (Method LC1): Rt=1.28 min; m/z=281.1 [MH$^+$]

Step 2

2-(3-Methoxycarbonylmethyl-phenyl)-2-methyl-malonic acid dimethyl ester

The compound of step 1 (0.353 g, 1.26 mmol) was dissolved in DMF (1.5 ml), potassium tert-butoxide (151 mg, 1.32 mmol) was added, the mixture stirred at room temperature for 10 min, and then iodomethane (0.542 g, 3.78 mmol) was added. The mixture was stirred at room temperature for 3 h and partitioned between EA and 2 N hydrochloric acid. The combined extracts were washed with a saturated aqueous sodium chloride solution, dried over sodium sulfate and evaporated to dryness. The residue was purified by preparative RP HPLC (water/ACN gradient) to yield 0.128 g of the title compound.

LC/MS (Method LC1): Rt=1.36 min; m/z=295.0 [MH$^+$]

Step 3

2-[3-(2-Hydroxy-ethyl)-phenyl]-2-methyl-propane-1,3-diol

The compound of step 2 (0.128 g, 0.435 mmol) was dissolved in 2 ml of THF and cautiously added to an ice-cold suspension of lithium aluminium hydride (174 mg, 4.35 mmol) in THF. After a few minutes, diethyl ether (12 ml) was added and thereafter 200 µl of EA. Subsequently, water was added slowly and cautiously until the alumina salts formed a light grey mass at the bottom of the flask. The supernatant was decanted and the residue washed with EA. The combined extracts were dried over sodium sulfate and evaporated to dryness. The residue was used in the next step without further purification.

LC/MS (Method LC1): Rt=0.69 min; m/z=228.1 [MNH$_4^+$]

Step 4

2-(3-{2-[3-(2-Hydroxy-1-hydroxymethyl-1-methylethyl)-phenyl]-ethoxy}-4-methoxy-benzoylamino)-indane-2-carboxylic acid The compound of step 3 was reacted with methyl 3-hydroxy-4-methoxybenzoate in analogy to step 1 of example 94. From the obtained intermediate the title compound was prepared in analogy to step 1 of example 15.

LC/MS (Method LC1): Rt=1.28 min; m/z=520.1 [MH$^+$]

EXAMPLE 211

2-[4-Methoxy-3-(2-m-tolyl-ethoxy)-benzoylamino]-octahydro-indene-2-carboxylic acid

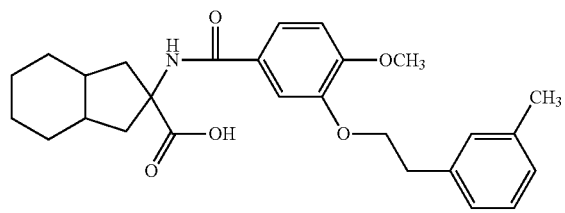 [SMILES: COc1ccc(C(=O)NC2(C(=O)O)CC3CCCCC3C2)cc1OCCc1cccc(C)c1]

Acetyl chloride (22 mg, 0.282 mmol) was cautiously dissolved in ethanol (2 ml). 2-Amino-indane-2-carboxylic acid (50 mg, 0.282 mmol) and platinum dioxide (25 mg) were added, and the mixture was hydrogenated at room temperature at a hydrogen pressure of 5 bar for 5 h. The solution was filtered over a small plug of celite and evaporated to dryness. For conversion into 2-amino-octahydroindene-2-carboxylic acid methyl ester, the residue was suspended in methanol (2 ml), thionyl chloride (0.5 ml) was added and the mixture was stirred overnight at room temperature. The mixture was evaporated to dryness to yield 99 mg of raw material which was used in the next step without further purification. From the obtained intermediate, the title compound was prepared in analogy to step 1 of example 15 and hydrolysis of the ester group in analogy to example 2.

$^1$H-NMR: δ=12.0 (s, 1H); 8.40 (s, 1H); 7.48 (dd, 1H); 7.41 (dd, 1H); 7.22-7.16 (m, 2H); 7.11 (d, 1H); 7.04 (d, 1H); 7.00

(d, 1H); 4.18 (t, 2H); 3.80 (s, 3H); 3.01 (t, 2H); 2.29 (s, 3H); 2.20-2.00 (m, 6H); 1.53-1.40 (m, 6H); 1.32-1.20 (m, 2H)

EXAMPLE 212

2-{3-[2-(3-Chloro-phenyl)-2,2-difluoro-ethoxy]-4-methoxy-benzoylamino}-indane-2-carboxylic acid

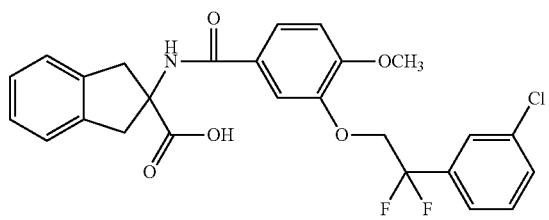 [SMILES: COc1ccc(C(=O)NC2(C(=O)O)Cc3ccccc3C2)cc1OCC(F)(F)c1cccc(Cl)c1]

Step 1

2-(3-Chloro-phenyl)-2,2-difluoro-ethanol 1.00 g (4.26 mmol) (3-chloro-phenyl)-difluoro-acetic acid ethyl ester (prepared according to the procedure described in WO 2006/122788) were dissolved in 100 ml of methanol and treated in an ice bath with 120 mg (0.75 mmol) of sodium borohydride. After stirring overnight the mixture was evaporated and the residue was purified by silica gel chromatography (DCM/methanol 98:2) to give 700 mg of the title compound.

Step 2

Trifluoromethanesulfonic acid 2-(3-chloro-phenyl)-2,2-difluoro-ethyl ester 700 mg (3.64 mmol) of the compound of step 1 were dissolved in 10 ml of DCM and treated at 0° C. with 78 μl (4.36 mmol) of EDIA and 1.23 g (4.36 mmol) of trifluoromethanesulfonic acid anhydride. After completion of the reaction (monitored by thin layer chromatography (DCM/methanol 98:2), the mixture was poured on water and the phases were separated. The organic phase was washed once with a saturated sodium chloride solution, dried over sodium sulfate and evaporated to dryness. The residue was purified by silica gel chromatography (DCM) to give 450 mg of the title compound.

Step 3

2-{3-[2-(3-Chloro-phenyl)-2,2-difluoro-ethoxy]-4-methoxy-benzoylamino}-indane-2-carboxylic acid methyl ester To a mixture of 230 mg (0.67 mmol) of 2-(3-hydroxy-4-methoxy-benzoylamino)-indane-2-carboxylic acid methyl ester and 227 mg (1.62 mmol) of potassium carbonate in 6 ml of acetone and 1.7 ml of DMF was added slowly a solution of 437 mg (1.65 mmol) of the compound of step 2. The reaction mixture was stirred for 3 d at room temperature and then evaporated. The residue was purified by preparative RP HPLC (water/ACN gradient) to give 20 mg of the title compound.

Step 4

2-{3-[2-(3-Chloro-phenyl)-2,2-difluoro-ethoxy]-4-methoxy-benzoylamino}-indane-2-carboxylic acid 20 mg of the compound of step 3 were dissolved in 5 ml of a mixture of THF and water (9:1), and 1.9 mg (77.5 μmol) of lithium hydroxide were added. After stirring at room temperature for 3 d, the mixture was acidified with 1 M hydrochloric acid and evaporated. The residue was purified by silica gel chromatography (DCM/methanol 95:5) and RP HPLC (water/ACN gradient) to give 8 mg of the title compound.

LC/MS (Method LC1): Rt=1.64 min; m/z=502.10 [MH$^+$]
$^1$H-NMR: δ=12.45 (br s, 1H); 8.62 (s, 1H); 7.75 (s, 1H); 7.50-7.65 (m, 4H); 7.48 (s, 1H); 7.23 (m, 2H) 7.17 (m, 2H); 7.04 (d, 1H); 4.65 (t, 2H); 3.80 (s, 3H); 3.59 (d, 2H); 3.38 (d, 2H)

EXAMPLE 213

2-[3-(2,2-Difluoro-2-phenyl-ethoxy)-4-methoxy-benzoylamino]-indane-2-carboxylic acid

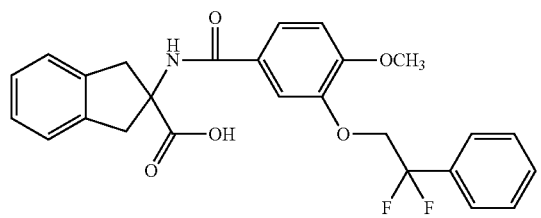 [SMILES: COc1ccc(C(=O)NC2(C(=O)O)Cc3ccccc3C2)cc1OCC(F)(F)c1ccccc1]

The title compound was obtained in analogy to example 212, starting from 2,2-difluoro-2-phenyl-ethanol.

LC/MS (Method LC1): Rt=1.53 min; m/z=468.15 [MH$^+$]
$^1$H-NMR: δ=12.45 (br s, 1H); 8.62 (s, 1H); 7.64 (d, 2H); 7.46-7.59 (m, 5H); 7.22 (m, 2H) 7.17 (m, 2H); 7.04 (d, 1H); 4.60 (t, 2H); 3.80 (s, 3H); 3.58 (d, 2H); 3.38 (d, 2H)

EXAMPLE 214

4,7-Difluoro-2-[4-methoxy-3-(2-m-tolyl-ethoxy)-benzoylamino]-indane-2-carboxylic acid

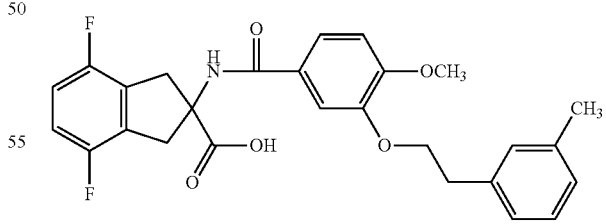

Step 1

(3,6-Difluoro-2-hydroxymethyl-phenyl)-methanol

Lithium aluminium hydride (792 mg, 19.8 mmol) was suspended in THF (6 ml) and cooled in an ice bath. A solution of 4,7-difluoro-isobenzofuran-1,3-dione (730 mg, 3.97 mmol) in THF (6 ml) was added during 5 min. After completion of the reaction (5 min), diethyl ether (30 ml) was added. Subsequently, 2 ml of EA were added in order to decompose excess of lithium aluminium hydride, and thereafter water was slowly added until the alumina salts precipitated. The supernatant was decanted and the precipitate washed twice with EA. The combined extracts were dried over sodium sulfate, filtered and evaporated to dryness to yield 360 mg of the title compound.

$^1$H-NMR: δ=7.16 (t, 2H); 5.13 (t, 2H); 4.60 (d, 4H)

Step 2

2,3-Bis-chloromethyl-1,4-difluoro-benzene

The compound of step 1 (360 mg, 2.07 mmol) was dissolved in acetyl chloride (2.3 ml) in a vial. After 10 min, zinc chloride (843 mg, 6.21 mmol) was added and the mixture was heated to 130° C. in a microwave reactor for 30 min. After cooling, the mixture was partitioned between diethyl ether and saturated sodium hydrogencarbonate solution and the aqueous phase extracted with diethyl ether. The combined organic phases were dried over sodium sulfate, filtered and evaporated to dryness to yield 200 mg of the title compound.

$^1$H-NMR: δ=7.40 (t, 2H); 4.90 (s, 4H)

Step 3

4,7-Difluoro-2-[4-methoxy-3-(2-m-tolyl-ethoxy)-benzoylamino]-indane-2-carboxylic acid The compound of step 2 was transformed into the title compound in analogy to examples 97 and 98.

LC/MS (Method LC13): Rt=2.60 min; m/z=482.2 [MH$^+$]

EXAMPLE 215

4-Fluoro-2-[4-methoxy-3-(2-m-tolyl-ethoxy)-benzoylamino]-indane-2-carboxylic acid

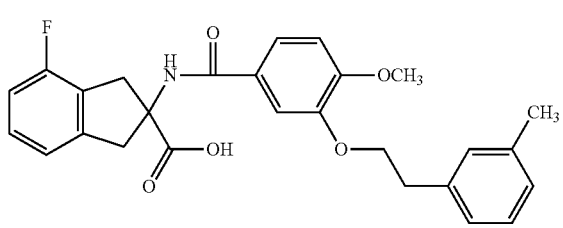 [SMILES: COc1ccc(C(=O)NC2(C(=O)O)Cc3cccc(F)c3C2)cc1OCCc1cccc(C)c1]

The title compound was prepared in analogy to example 214, starting from (3-fluoro-2-hydroxymethyl-phenyl)-methanol.

LC/MS (Method LC11): Rt=1.91 min; m/z=464.2 [MH$^+$]

EXAMPLE 216

2-[4-Methoxy-3-(2-m-tolyl-ethoxy)-benzoylamino]-4-methyl-indane-2-carboxylic acid

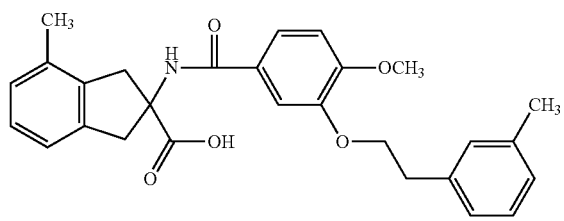

The title compound was prepared in analogy to example 214, starting from 4-methyl-isobenzofuran-1,3-dione.

LC/MS (Method LC12): Rt=3.74 min; m/z=460.2 [MH$^+$]

EXAMPLE 217

4-Chloro-2-[4-methoxy-3-(2-m-tolyl-ethoxy)-benzoylamino]-indane-2-carboxylic acid

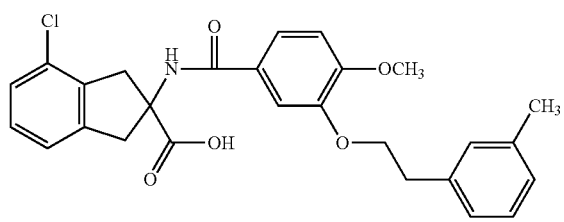

The title compound was prepared in analogy to example 214, starting from 4-chloro-isobenzofuran-1,3-dione.

LC/MS (Method LC13): Rt=2.67 min; m/z=480.2 [MH$^+$]

EXAMPLE 218

5-Cyano-2-[4-methoxy-3-(2-m-tolyl-ethoxy)-benzoylamino]-indane-2-carboxylic acid

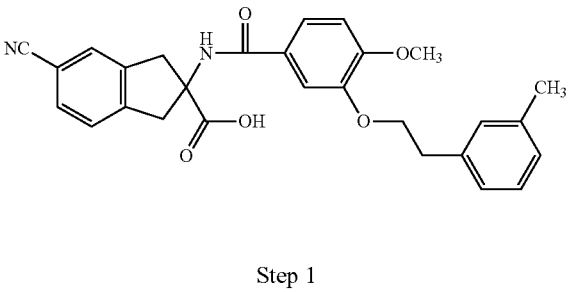

Step 1

5-Bromo-2-[4-methoxy-3-(2-m-tolyl-ethoxy)-benzoylamino]-indane-2-carboxylic acid ethyl ester Starting from 5-bromo-3H-isobenzofuran-1-one, the intermediate 4-bromo-1,2-bis-chloromethyl-benzene was prepared in analogy to steps 1 and 2 of example 214.

This intermediate was transformed into the title compound in analogy to example 97. LC/MS (Method LC13): Rt=3.03 min; m/z=552.2 [MH⁺]

Step 2

5-Cyano-2-[4-methoxy-3-(2-m-tolyl-ethoxy)-benzoylamino]-indane-2-carboxylic acid ethyl ester The compound of step 1 (50 mg, 0.091 mmol) was added to a mixture of zinc cyanide (10.6 mg, 0.091 mmol) and tetrakis (triphenylphosphine)palladium(0) (5.2 mg, 0.004 mmol) in DMF (0.16 ml) at 150° C. and stirred for 2 h. After cooling, tert-butyl methyl ether was added and the mixture was filtered over celite. The filtrate was washed with water, the organic phase dried over magnesium sulfate, filtered and evaporated to dryness to yield the title compound which was used without further purification.

Step 3

5-Cyano-2-[4-methyl-3-(2-m-tolyl-ethoxy)-benzoylamino]-indane-2-carboxylic acid

The compound of step 2 was transformed into the title compound by hydrolysis in analogy to step 3 of example 94.
LC/MS (Method LC13): Rt=2.54 min; m/z=471.3 [MH⁺]

EXAMPLE 219

5-Carbamoyl-2-[4-methoxy-3-(2-m-tolyl-ethoxy)-benzoylamino]-indane-2-carboxylic acid

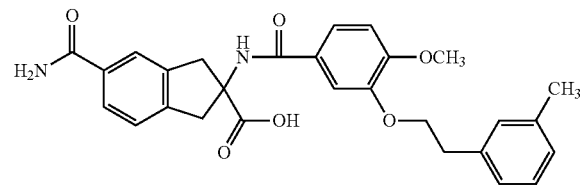 [SMILES: COc1ccc(C(=O)NC2(C(=O)O)Cc3ccc(C(N)=O)cc3C2)cc1OCCc1cccc(C)c1]

The compound of step 2 of example 218 was transformed into the title compound by hydrolysis in analogy to example 98 (hydrolysis time 3 h).
LC/MS (Method LC14): Rt=3.68 min; m/z=489.3 [MH⁺]

EXAMPLE 220

1-Hydroxy-2-[4-methoxy-3-(2-m-tolyl-ethoxy)-benzoylamino]-indane-2-carboxylic acid

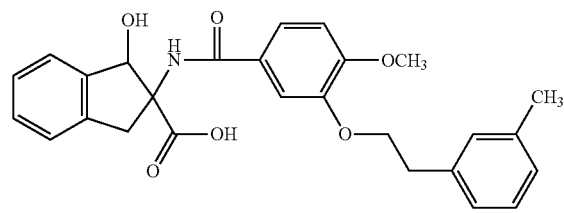 [SMILES: COc1ccc(C(=O)NC2(C(=O)O)Cc3ccccc3C2O)cc1OCCc1cccc(C)c1]

Step 1

2-[4-Methoxy-3-(2-m-tolyl-ethoxy)-benzoylamino]-1-oxo-indane-2-carboxylic acid ethyl ester 2-Amino-1-oxo-indane-2-carboxylic acid ethyl ester (L. Benati et al., J. Org. Chem. 64 (1999), 7836-7841) (460 mg, 2.10 mmol) was reacted with 4-methoxy-3-(2-m-tolyl-ethoxy)-benzoic acid in analogy to step 2 of example 13 to yield 0.331 g of the title compound.
LC/MS (Method LC12): Rt=4.09 min; m/z=488.2 [MH⁺]

Step 2

1-Hydroxy-2-[4-methoxy-3-(2-m-tolyl-ethoxy)-benzoylamino]-indane-2-carboxylic acid ethyl ester The compound of step 1 (0.439 g, 0.900 mmol) was dissolved in THF (4 ml). The mixture was cooled to −30° C. and sodium borohydride (35 mg, 0.90 mmol) was added followed by dropwise addition of methanol. After 30 min, the mixture was partitioned between diethyl ether and 2 N hydrochloric acid, the aqueous phase was extracted with diethyl ether, the combined organic phases were dried over sodium sulfate and evaporated to dryness. The residue was purified by silica gel chromatography (HEP/EA gradient) to yield the title compound as a mixture of stereoisomers.
LC/MS (Method LC12): Rt=3.77 min; m/z=490.3 [MH⁺]

Step 3

1-Hydroxy-2-[4-methoxy-3-(2-m-tolyl-ethoxy)-benzoylamino]-indane-2-carboxylic acid The compound of step 2 was hydrolyzed in analogy to example 2. Purification by RP HPLC (water/ACN gradient) gave one of the diastereomers (diastereomer A) of the title compound in pure form (as the racemate) and a mixture of the other diastereomer with diastereomer A (relative stereochemistry of the diastereomers unknown).
Diastereomer A:
LC/MS (Method LC12): Rt=3.43 min; m/z=462.2 [MH⁺]
¹H-NMR: δ=12.1 (br s, 1H); 8.43 (s, 1H); 7.48 (dd, 1H); 7.41 (d, 1H); 7.32 (dd, 1H); 7.28-7.13 (m, 5H); 7.10 (d, 1H); 7.02 (d, 1H); 7.00 (d, 1H); 5.70 (br s, 1H); 5.40 (s, 1H); 4.16 (t, 2H); 3.90 (d, 1H); 3.09 (d, 1H); 3.00 (t, 2H); 2.28 (s, 3H)

EXAMPLE 221

2-{[5-(3-Isopropyl-phenyl)-6-methoxy-pyridine-3-carbonyl]-amino}-indane-2-carboxylic acid

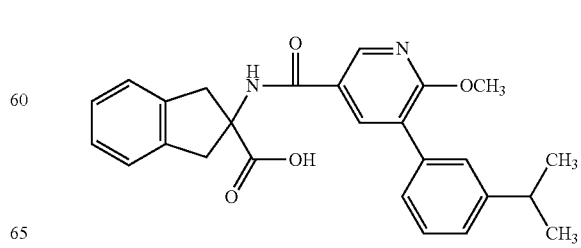

Step 1

5-(3-Isopropyl-phenyl)-6-methoxy-nicotinic acid methyl ester

Under an atmosphere of argon, a mixture of 5-bromo-6-methoxy-nicotinic acid methyl ester (W. J. Thompson and J. Gaudino, J. Org. Chem. 49 (1984), 5237-5243) (100 mg, 0.406 mmol), 3-isopropylphenylboronic acid (73 mg, 0.447 mmol), tri-(tert-butyl)phosphonium tetrafluoroborate (7 mg, 0.024 mmol), tris(dibenzylideneacetone)dipalladium(0) (11 mg, 0.012 mmol) and potassium fluoride (78 mg, 1.34 mmol) in a flask was suspended in dioxane (1.5 ml) and heated to 45° C. for 3 h. After cooling, it was filtered over a small plug of silica gel and evaporated to dryness. Purification of the residue by silica gel chromatography (HEP/EA gradient) and subsequent RP HPLC (water/ACN gradient) yielded 63 mg of the title compound.

LC/MS (Method LC13): Rt=2.95 min; m/z=286.1 [MH$^+$]

Step 2

5-(3-Isopropyl-phenyl)-6-methoxy-nicotinic acid

The compound of step 1 (60 mg, 0.63 mmol) was hydrolyzed in analogy to step 3 of example 94 to yield 57 mg of the title compound.

LC/MS (Method LC13): Rt=2.48 min; m/z=272.1 [MH$^+$]

Step 3

2-{[5-(3-Isopropyl-phenyl)-6-methoxy-pyridine-3-carbonyl]-amino}-indane-2-carboxylic acid The compound of step 2 was reacted with 2-amino-indane-2-carboxylic acid methyl ester hydrochloride in analogy to step 2 of example 13, and the obtained ester hydrolyzed in analogy to example 2.

LC/MS (Method LC14): Rt=3.52 min; m/z=431.2 [MH$^+$]

EXAMPLE 222

2-{[6-Methoxy-5-(3-methylsulfanyl-phenyl)-pyridine-3-carbonyl]-amino}-indane-2-carboxylic acid

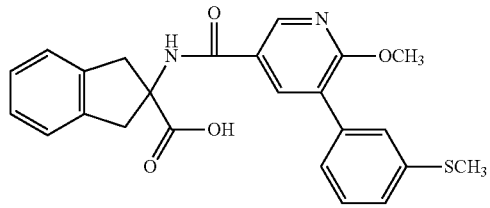 [SMILES: COc1ncc(C(=O)NC2(C(=O)O)Cc3ccccc3C2)cc1-c1cccc(SC)c1]

Step 1

2-[(5-Bromo-6-methoxy-pyridine-3-carbonyl)-amino]-indane-2-carboxylic acid methyl ester 5-Bromo-6-methoxy-nicotinic acid methyl ester (W. J. Thompson and J. Gaudino, J. Org. Chem. 49 (1984), 5237-5243) (2.00 g, 8.13 mmol) was hydrolyzed in analogy to example 2. The obtained acid was reacted with 2-amino-indane-2-carboxylic acid methyl ester hydrochloride in analogy to step 2 of example 13.

LC/MS (Method LC14): Rt=3.28 min; m/z=405.0 [MH$^+$]

Step 2

2-{[6-Methoxy-5-(3-methylsulfanyl-phenyl)-pyridine-3-carbonyl]-amino}-indane-2-carboxylic acid The compound of step 1 was reacted with 3-methylsulfanyl-phenylboronic acid in analogy to step 1 of example 221. The intermediate ester was hydrolyzed in analogy to example 2.

LC/MS (Method LC14): Rt=3.30 min; m/z=435.1 [MH$^+$]

In analogy to example 221 and example 222, respectively, the example compounds of the formula Iv listed in table 8 were prepared by using the respective substituted phenylboronic acid. If the initial palladium coupling reaction in the preparation analogously to example 221 did not proceed satisfactorily, it was repeated once more. The compounds can be named as 2-{[5-(substituted phenyl)-6-methoxy-pyridine-3-carbonyl]-amino}-indane-2-carboxylic acid, for example as 2-{[6-methoxy-5-(3-methyl-phenyl)-pyridine-3-carbonyl]-amino}-indane-2-carboxylic acid in the case of example 224.

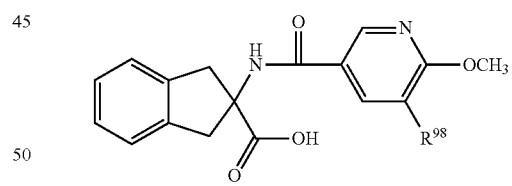

Iv

TABLE 8

| | Example compounds of the formula Iv | | | |
|---|---|---|---|---|
| Example | R$^{98}$ | Preparation | LC/MS Method | m/z [MH$^+$] | Retention time [min] |
| 223 | 3-chloro-phenyl | (a) | LC14 | 423.1 | 3.00 |
| 224 | 3-methyl-phenyl | (a) | LC12 | 403.1 | 3.57 |
| 225 | 2-chloro-phenyl | (a) | LC12 | 423.0 | 3.49 |
| 226 | 4-chloro-phenyl | (a) | LC17 | 423.3 | 4.79 |
| 227 | 2-chloro-3-trifluoromethyl-phenyl | (a) | LC14 | 457.1 | 3.43 |
| 228 | 2,3-dichloro-phenyl | (a) | LC12 | 457.1 | 3.65 |
| 229 | 3,4,5-trifluoro-phenyl | (b) | LC12 | 443.2 | 3.68 |
| 230 | 2-fluoro-3-trifluoromethyl-phenyl | (b) | LC14 | 475.1 | 3.46 |

TABLE 8-continued

Example compounds of the formula Iv

| Example | R$^{98}$ | Preparation | LC/MS Method | m/z [MH$^+$] | Retention time [min] |
|---|---|---|---|---|---|
| 231 | 3-dimethylaminosulfonylamino-phenyl | (b) | LC14 | 511.2 | 2.94 |
| 232 | 3-chloro-4-trifluoromethyl-phenyl | (b) | LC16 | 978.9(c) | 4.99 |
| 233 | 3-ethylsulfanyl-phenyl | (b) | LC12 | 449.2 | 3.70 |
| 234 | 3-trifluoromethoxy-phenyl | (b) | LC17 | 473.2 | 4.89 |
| 235 | 3-chloro-5-trifluoromethyl-phenyl | (b) | LC14 | 491.2 | 3.71 |
| 236 | 3-cyano-phenyl | (b) | LC12 | 414.2 | 3.30 |

(a) preparation in analogy to example 221
(b) preparation in analogy to example 222
(c) [(2M − H)$^-$] instead of [MH$^+$]

EXAMPLE 237

2-{[5-(3-Ethanesulfonyl-phenyl)-6-methoxy-pyridine-3-carbonyl]-amino}-indane-2-carboxylic acid

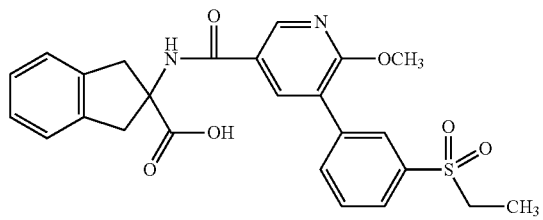

The compound of example 233 (50 mg, 0.11 mmol) was dissolved in acetic acid (3.8 ml). Hydrogen peroxide (30% solution in water, 0.034 ml, 0.33 mmol) was added and the mixture was reacted at room temperature for 72 h. The mixture was partitioned between EA and an aqueous solution of sodium sulfite (about 1 strength). The organic phase was dried over magnesium sulfate, filtered and evaporated to dryness. The residue was purified by RP HPLC (water/ACN gradient). After evaporation of the product fraction, the residue was stirred with a mixture of diethyl ether/HEP, filtered and dried in vacuo.

LC/MS (Method LC14): Rt=3.88 min; m/z=481.2 [MH$^+$]

EXAMPLE 238

2-(4-Methoxy-3-o-tolyloxy-benzoylamino)-indane-2-carboxylic acid

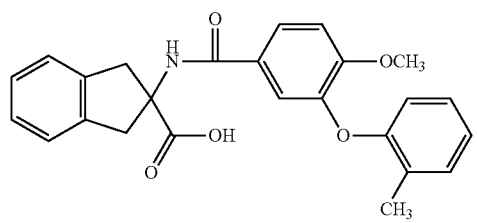 [SMILES: COc1ccc(C(=O)NC2(C(=O)O)Cc3ccccc3C2)cc1Oc1ccccc1C]

Step 1

4-Methoxy-3-o-tolyloxy-benzoic acid

Potassium carbonate (1.20 g, 8.66 mmol), o-cresol (468 mg, 4.33 mmol), copper powder (28 mg, 0.43 mmol) and 3-bromo-4-methoxybenzoic acid (1.00 g, 4.33 mmol) were suspended in DMF (5 ml) and heated to 165° C. overnight. Potassium carbonate (1.20 g, 8.66 mmol) and o-cresol (468 mg, 4.33 mmol) were added once again and heating was continued for another 2 h. The crude mixture was partitioned between EA and 2 N hydrochloric acid, the aqueous phase extracted with EA, and the combined organic phases were dried over magnesium sulfate, filtered and evaporated to dryness. The residue was purified by silica gel chromatography (HEP/EA gradient) to yield 600 mg of the title compound.

LC/MS (Method LC14): Rt=3.00 min; m/z=300.1 [(M+CH$_3$CN+H)$^+$]

Step 2

2-(4-Methoxy-3-o-tolyloxy-benzoylamino)-indane-2-carboxylic acid

The compound of step 1 was reacted with 2-amino-indane-2-carboxylic acid methyl ester hydrochloride in analogy to step 2 of example 13. The obtained ester was hydrolyzed in analogy to example 2.

LC/MS (Method LC12): Rt=3.57 min; m/z=418.1 [MH$^+$]

EXAMPLE 239

2-(4-Methoxy-3-m-tolyloxy-benzoylamino)-indane-2-carboxylic acid

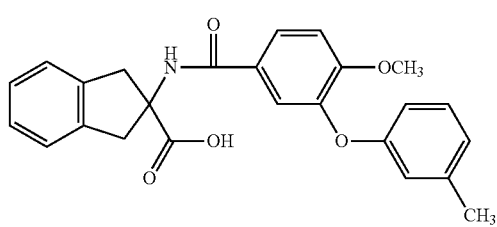 [SMILES: COc1ccc(C(=O)NC2(C(=O)O)Cc3ccccc3C2)cc1Oc1cccc(C)c1]

The title compound was prepared in analogy to example 238 using m-cresol instead of o-cresol.

LC/MS (Method LC12): Rt=3.54 min; m/z=418.1 [MH$^+$]

EXAMPLE 240

2-[4-Methoxy-3-(2-methyl-benzoyl)-benzoylamino]-indane-2-carboxylic acid

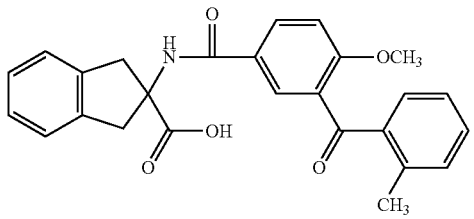

Step 1

4-Methoxy-3-(2-methyl-benzoyl)-benzoic acid methyl ester

4-Methoxybenzoic acid methyl ester (5.00 g, 30.1 mmol) and 2-methylbenzoyl chloride (4.88 g, 31.6 mmol) were dissolved in chlorobenzene (10 ml), tin(IV) chloride (9.41 g, 36.1 mmol) was added cautiously, and the mixture was heated to 140° C. for 3 h. The addition of the acid chloride and tin tetrachloride was repeated twice, and the mixture subsequently heated to 140° C. for 3 h each time. The mixture was poured onto 300 ml of ice/water and extracted with DCM. The combined extracts were dried over magnesium sulfate, filtered and evaporated to dryness. The residue was purified by silica gel chromatography (HEP/EA gradient) and subsequently by RP HPLC (water/ACN gradient) to yield 200 mg of the title compound.

$^1$H-NMR: δ=8.12 (dd, 1H); 7.91 (d, 1H); 7.71 (d, 1H); 7.50-7.41 (m, 1H); 7.31-7.22 (m, 2H); 7.06 (d, 1H); 3.81 (s, 3H); 3.72 (s, 3H); 2.42 (s, 3H)

Step 2

2-[4-Methoxy-3-(2-methyl-benzoyl)-benzoylamino]-indane-2-carboxylic acid

The compound of step 1 was hydrolyzed in analogy to example 2 and the obtained acid reacted with 2-amino-indane-2-carboxylic acid methyl ester hydrochloride in analogy to step 2 of example 13. The obtained ester was hydrolyzed in analogy to example 2.

LC/MS (Method LC14): Rt=3.16 min; m/z=430.1 [MH$^+$]

EXAMPLE 241

2-[3-(Hydroxy-o-tolyl-methyl)-4-methoxy-benzoylamino]-indane-2-carboxylic acid

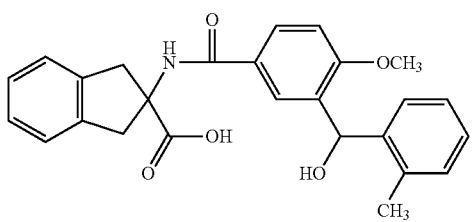 [SMILES: COc1ccc(C(=O)NC2(C(=O)O)Cc3ccccc3C2)cc1C(O)c1ccccc1C]

The compound of example 240 (70 mg, 0.163 mmol) was dissolved in a mixture of methanol (1.5 ml) and ethanol (1.5 ml) and cooled in an ice bath. Sodium borohydride (18.9 mg, 0.49 mmol) was added in two batches and the mixture reacted with ice cooling until completion (3 h). The volatiles were evaporated and the residue was partitioned between diethyl ether and 1 N hydrochloric acid. The aqueous phase was extracted with diethyl ether, and the combined organic phases were dried and evaporated. The residue was purified by RP HPLC (water/ACN gradient) to yield 13 mg of the title compound.

LC/MS (Method LC12): Rt=3.22 min; m/z=432.2 [MH$^+$]

EXAMPLE 242

2-[4-Methoxy-3-(2-methyl-benzyl)-benzoylamino]-indane-2-carboxylic acid

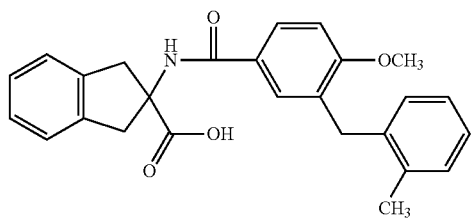

The compound of example 241 (32 mg, 0.074 mmol) was dissolved in ethanol (10 ml), palladium (10%) on charcoal (10 mg) was added, and the mixture was hydrogenated at room temperature for 1 h at a hydrogen pressure of 5 bar. After completion of the reaction, the mixture was filtered over silica gel and evaporated to dryness. The residue was triturated with diethyl ether, filtered and dried in vacuo to yield 25 mg of the title compound.

LC/MS (Method LC14): Rt=3.45 min; m/z=416.3 [MH$^+$]

EXAMPLE 243

2-[4-Methoxy-3-benzyl-benzoylamino]-indane-2-carboxylic acid

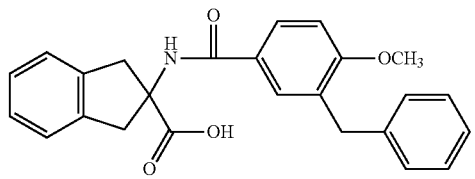 [SMILES: COc1ccc(C(=O)NC2(C(=O)O)Cc3ccccc3C2)cc1Cc1ccccc1]

The title compound was prepared in analogy to examples 240, 241 and 242. LC/MS (Method LC14): Rt=3.33 min; m/z=402.2 [MH$^+$]

EXAMPLE 244

2-[4-Methoxy-3-(3-methyl-benzyl)-benzoylamino]-indane-2-carboxylic acid

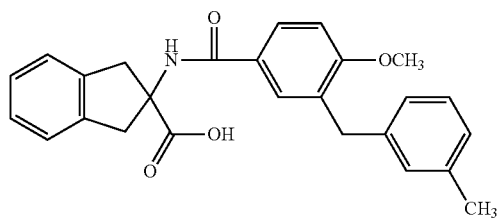 [SMILES: COc1ccc(C(=O)NC2(C(=O)O)Cc3ccccc3C2)cc1Cc1cccc(C)c1]

The title compound was prepared in analogy to examples 240, 241 and 242. LC/MS (Method LC12): Rt=3.74 min; m/z=416.1 [MH+]

EXAMPLE 245

2-[4-Methoxy-3-(4-methyl-benzyl)-benzoylamino]-indane-2-carboxylic acid

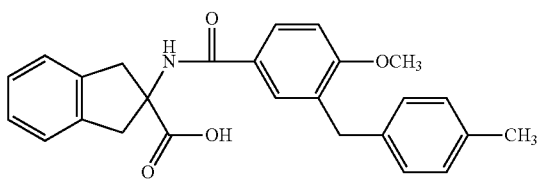 [SMILES: COc1ccc(C(=O)NC2(C(=O)O)Cc3ccccc3C2)cc1Cc1ccc(C)cc1]

The title compound was prepared in analogy to examples 240, 241 and 242. LC/MS (Method LC12): Rt=3.68 min; m/z=416.2 [MH+]

EXAMPLE 246

2-(3-{2-[3-(2-Amino-ethyl)-phenyl]-ethoxy}-4-methoxy-benzoylamino)-indane-2-carboxylic acid

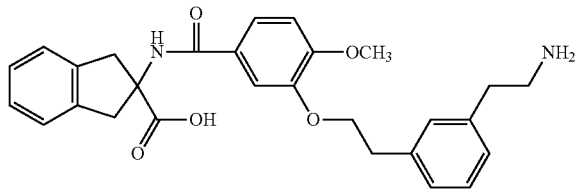 [SMILES: COc1ccc(C(=O)NC2(C(=O)O)Cc3ccccc3C2)cc1OCCc1cccc(CCN)c1]

Step 1

2-(3-{2-[3-(2-Azido-ethyl)-phenyl]-ethoxy}-4-methoxy-benzoylamino)-indane-2-carboxylic acid methyl ester 300 mg (0.613 mmol) of 2-(3-{2-[3-(2-hydroxy-ethyl)-phenyl]-ethoxy}-4-methoxy-benzoylamino)-indane-2-carboxylic acid methyl ester (methyl ester intermediate of example 27) and triphenylphosphine (0.241 g, 0.920 mmol) were dissolved in THF (5 ml) and cooled in an ice bath. Diphenylphosphoryl azide (0.258 g, 0.920 mmol) and DIAD (0.198 g, 0.920 mmol) were added sequentially, the ice bath was removed and the mixture was stirred for 2 h at room temperature. The mixture was evaporated to dryness and purified by silica gel chromatography (HEP/EA gradient) to yield 0.188 g of the title compound.

LC/MS (Method LC14): Rt=3.68 min; m/z=515.3 [MH+]

Step 2

2-(3-{2-[3-(2-Amino-ethyl)-phenyl]-ethoxy}-4-methoxy-benzoylamino)-indane-2-carboxylic acid methyl ester The compound of step 1 (0.185 g, 0.360 mmol) and triphenylphosphine (0.149 g, 0.539 mmol) were dissolved in a mixture of 3 ml of THF and 3 ml of water, and the solution was stirred overnight at room temperature. The mixture was evaporated to dryness and purified by silica gel chromatography (DCM/methanol/28% ammonia gradient, 70:30:0 to 0:100:0 to 0:90:10) to yield 0.17 g of the title compound.

LC/MS (Method LC14): Rt=2.68 min; m/z=489.2 [MH+]

Step 3

2-(3-{2-[3-(2-Amino-ethyl)-phenyl]-ethoxy}-4-methoxy-benzoylamino)-indane-2-carboxylic acid The compound of step 2 (85 mg, 0.174 mmol) was hydrolyzed in analogy to example 2 to yield 31 mg of the title compound.

LC/MS (Method LC12): Rt=2.68 min; m/z=475.2 [MH+]

EXAMPLE 247

2-(3-{2-[3-(2-Acetylamino-ethyl)-phenyl]-ethoxy}-4-methoxy-benzoylamino)-indane-2-carboxylic acid

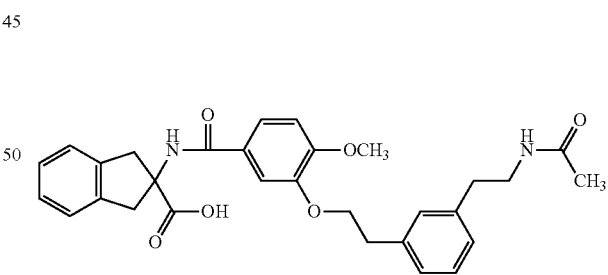

The compound of Step 2 of example 246 (85 mg, 0.174 mmol) was dissolved in acetic anhydride and stirred under reflux for 30 min. Water was added in excess and the mixture was refluxed for 10 min. After cooling, the mixture was extracted with EA, the combined extracts were dried over sodium sulfate and evaporated to dryness. The residue was purified by RP HPLC (water/ACN gradient) to yield the methyl ester of the title compound. Hydrolysis of this ester in analogy to example 2 yielded 17 mg of the title compound.

EXAMPLE 248

2-{3-[2-(3-Carbamoylmethyl-phenyl)-ethoxy]-4-methoxy-benzoylamino}-indane-2-carboxylic acid

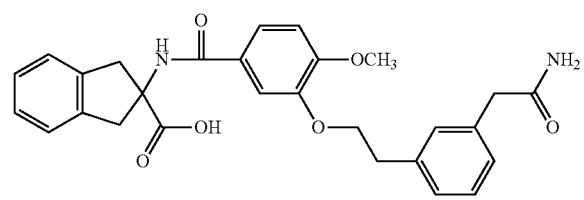 [SMILES: COc1ccc(C(=O)NC2(C(=O)O)Cc3ccccc3C2)cc1OCCc1cccc(CC(N)=O)c1]

Step 1

(3-Methoxycarbonylmethyl-phenyl)-acetic acid (3-Carboxymethyl-phenyl)-acetic acid (7.4 g, 38.1 mmol) was suspended in methanol (20 ml). Thionyl chloride (4.5 g, 38 mmol) was added at about −30° C. (vigorous reaction), and the mixture subsequently stirred at room temperature for 90 min. After completion of the reaction, the mixture was evaporated to dryness to yield the diester as a yellow oil. This material was dissolved in methanol (20 ml), solid lithium hydroxide (0.948 g, 1 equivalent) was added and the mixture stirred at room temperature for 1 h. After evaporation of the methanol, the residue was partitioned between 2 N hydrochloric acid and EA and the aqueous phase extracted with EA. The combined organic phases were dried over sodium sulfate and evaporated to dryness. The crude mixture of diester, monoester and dicarboxylic acid was purified by RP HPLC (water/ACN gradient) to yield 3.1 g of the title compound.

LC/MS (Method LC16): Rt=3.18 min; m/z=415.3 [(2M−H)⁻]

Step 2

(3-Carbamoylmethyl-phenyl)-acetic acid methyl ester

The compound of step 1 (0.4 g, 1.92 mmol) was dissolved in thionyl chloride (2.7 ml) and stirred at 60° C. for 1 h. The volatiles were evaporated, and the residue was dissolved in DCM and added to a stirred mixture of EA and 28% aqueous ammonia. After completion of the reaction, the mixture was partitioned between water and EA and the aqueous phase extracted with EA. The combined organic phases were dried over sodium sulfate and evaporated to dryness to yield 0.278 g of the title compound.

LC/MS (Method LC16): Rt=2.56 min; m/z=252.0 [(M+HCOOH−H)⁻]

Step 3

2-[3-(2-Hydroxy-ethyl)-phenyl]-acetamide

The compound of step 2 (0.151 g, 0.729 mmol) was dissolved in 0.5 ml of THF and added to a suspension of lithium aluminium hydride (58 mg, 1.46 mmol) in THF (1.5 ml) at −78° C. After 2 min, diethyl ether (6 ml) was added, followed by EA (0.2 ml). After warming to room temperature, water was added slowly until the alumina salts formed a thick slurry from which the supernatant could be decanted easily. The slurry was washed repeatedly with EA. The combined extracts were dried with sodium sulfate and evaporated to dryness to yield 0.101 g of the title compound.

LC/MS (Method LC15): Rt=2.40 min; m/z=180.2 [MH⁺]

Step 4

2-{3-[2-(3-Carbamoylmethyl-phenyl]-ethoxy}-4-methoxy-benzoylamino)-indane-2-carboxylic acid The compound of step 3 was transformed into the title compound in analogy to step 3 of example 15, followed by hydrolysis in analogy to example 2.

LC/MS (Method LC12): Rt=2.93 min; m/z=489.3 [MH⁺]

EXAMPLE 249

2-(3-{2-[3-(2-Hydroxy-2-methyl-propyl)-phenyl]-ethoxy}-4-methoxy-benzoylamino)-indane-2-carboxylic acid

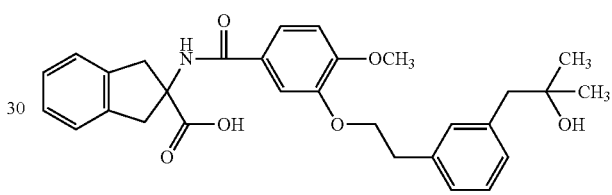

Step 1

[3-(2-Hydroxy-2-methyl-propyl)-phenyl]-acetic acid (3-Methoxycarbonylmethyl-phenyl)-acetic acid (500 mg, 2.40 mmol) was dissolved in THF (3.5 ml) and methylmagnesium chloride (2.8 ml, 3 M solution in THF) was added slowly at room temperature. After stirring for 30 min the reaction was completed. Water was added cautiously and the mixture was partitioned between EA and 2 N hydrochloric acid. The aqueous phase was extracted with EA and the combined organic phases were dried over sodium sulfate and evaporated to dryness. The residue was purified by RP HPLC (water/ACN gradient) to yield 0.34 g of the title compound.

LC/MS (Method LC16): Rt=2.92 min; m/z=415.2 [(2M−H)⁻]

Step 2

1-[3-(2-Hydroxy-ethyl)-phenyl]-2-methyl-propan-2-ol

The compound of step 1 (0.132 g, 0.634 mmol) was dissolved in THF (0.5 ml) and added to a refluxing suspension of lithium aluminium hydride (122 mg, 3.1 mmol) in THF (1 ml). The mixture was stirred for 1 h under reflux and cooled to room temperature. Diethyl ether (6 ml) was added, followed by EA (0.4 ml). Subsequently, water was added slowly until the alumina salts formed a thick slurry from which the supernatant could be decanted easily. The slurry was repeatedly washed with EA, the combined extracts were dried with sodium sulfate and evaporated to dryness.

The residue was purified by RP HPLC (water/ACN gradient) to yield 49 mg of the title compound.
$^1$H-NMR: δ=7.15 (t, 1H); 7.06-7.00 (m, 3H); 4.59 (t, 1H); 4.23 (s, 1H); 3.58 (dt, 2H); 2.69 (t, 2H); 2.60 (s, 2H); 1.04 (s, 6H)

Step 3

2-(3-{2-[3-(2-Hydroxy-2-methyl-propyl)-phenyl]-ethoxy}-4-methoxy-benzoylamino)-indane-2-carboxylic acid The compound of step 2 was transformed into the title compound in analogy to step 3 of example 15, followed by hydrolysis in analogy to example 2.
LC/MS (Method LC14): Rt=3.05 min; m/z=504.2 [MH$^+$]

EXAMPLE 250

2-[4-Methoxy-3-(3-phenyl-oxetan-3-ylmethoxy)-benzoylamino]-indane-2-carboxyl is acid

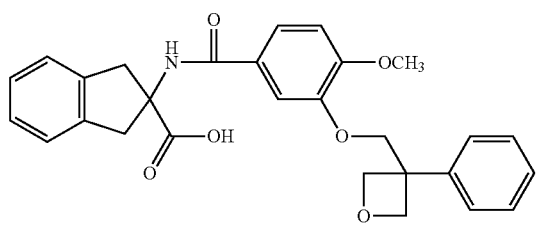 [SMILES: COc1ccc(C(=O)NC2(C(=O)O)Cc3ccccc3C2)cc1OCC1(c2ccccc2)COC1]

The compound of step 2 of example 15 and (3-phenyl-oxetan-3-yl)-methanol (S. Kanoh et al., Tetrahedron 58 (2002), 7065-7074) were reacted in analogy to step 3 of example 15, and the obtained methyl ester was hydrolyzed in analogy to example 16.
LC/MS (Method LC14): Rt=3.10 min; m/z=474.4 [MH$^+$]

EXAMPLE 251

2-{3-[2-(3-Hydroxy-phenyl)-ethoxy]-4-methoxy-benzoylamino}-indane-2-carboxylic acid

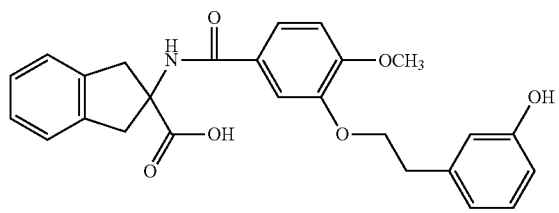 [SMILES: COc1ccc(C(=O)NC2(C(=O)O)Cc3ccccc3C2)cc1OCCc1cccc(O)c1]

Step 1

Acetic acid 3-(2-hydroxy-ethyl)-phenyl ester 2-(3-Hydroxyphenyl)ethanol (400 mg, 2.90 mmol) was dissolved in a mixture of 4 ml of dioxane and 4 ml of water, and sodium hydrogencarbonate (2.43 g, 29 mmol) was added followed by acetic anhydride (2.96 g, 29 mmol) with ice cooling. The mixture was stirred overnight at room temperature and then partitioned between 2 N hydrochloric acid and EA. The aqueous phase was extracted with EA, the combined organic phases were dried over sodium sulfate and evaporated to dryness to yield the crude title compound which was used without further purification.

Step 2

2-{3-[2-(3-Hydroxy-phenyl)-ethoxy]-4-methoxy-benzoylamino}-indane-2-carboxylic acid The compound of step 1 and the compound of step 2 of example 15 were reacted in analogy to step 3 of example 15 and the obtained ester hydrolyzed in analogy to example 16.
LC/MS (Method LC12): Rt=3.17 min; m/z=448.2 [MH$^+$]

EXAMPLE 252

2-[3-Methoxy-4-(2-m-tolyl-ethoxy)-benzoylamino]-indane-2-carboxylic acid

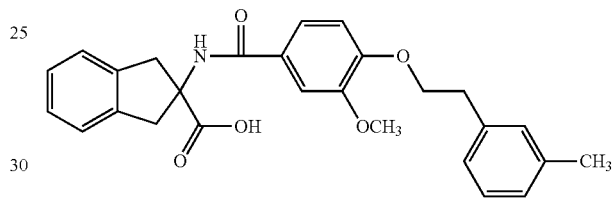

Step 1

3-Acetoxy-4-hydroxy-benzoic acid ethyl ester 3,4-Dihydroxy-benzoic acid ethyl ester (550 mg, 3.02 mmol) was dissolved in DMF (5 ml), potassium tert-butoxide (210 mg, 2.87 mmol) was added and the mixture stirred for 10 min. Acetic anhydride (339 mg, 3.32 mmol) was added and stirring continued for 10 min. The mixture was partitioned between EA and 2 N hydrochloric acid, and the aqueous phase extracted with EA. The combined organic phases were dried over sodium chloride, decanted and evaporated to dryness. The residue was purified by RP HPLC (water/ACN gradient).
LC/MS (Method LC15): Rt=3.97 min; m/z=225.2 [MH$^+$]

Step 2

3-Acetoxy-4-(2-m-tolyl-ethoxy)-benzoic acid ethyl ester

The compound of step 1 (350 mg, 1.56 mmol) was reacted with 2-m-tolyl-ethanol in analogy to step 3 of example 15 to yield 450 mg of the title compound.
LC/MS (Method LC14): Rt=3.86 min; m/z=343.2 [MH$^+$]

Step 3

3-Methoxy-4-(2-m-tolyl-ethoxy)-benzoic acid methyl ester

The compound of step 2 (150 mg, 0.438 mmol) was dissolved in methanol (3 ml), potassium tert-butoxide (73 mg, 0.657 mmol) was added and the mixture was stirred overnight under reflux. Potassium carbonate (60 mg, 0.44 mmol) and iodomethane (124 mg, 0.876 mmol) were then added repeatedly, at intervals of 1 h, with stirring under reflux until completion of the reaction. The volatiles were evaporated in vacuo, the residue was partitioned between EA and 2 N hydrochloric acid, and the aqueous phase was extracted with EA. The combined organic phases were dried over sodium chloride, decanted and evaporated to dryness to yield the title compound.

LC/MS (Method LC15): Rt=5.27 min; m/z=301.2 [MH+]

Step 4

2-[3-Methoxy-4-(2-m-tolyl-ethoxy)-benzoylamino]-indane-2-carboxylic acid

The compound of step 3 was hydrolyzed in analogy to example 2, the obtained carboxylic acid reacted with 2-amino-indane-2-carboxylic acid methyl ester in analogy to step 1 of example 15, and the obtained ester hydrolyzed in analogy to example 2.

LC/MS (Method LC14): Rt=3.41 min; m/z=446.1 [MH+]

EXAMPLE 253

2-[4-Benzyloxy-3-(2-m-tolyl-ethoxy)-benzoylamino]-indane-2-carboxylic acid

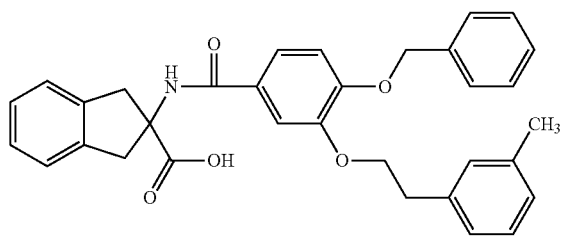 [SMILES: Cc1cccc(CCOc2cc(C(=O)NC3(C(=O)O)Cc4ccccc4C3)ccc2OCc2ccccc2)c1]

Step 1

3-Acetoxy-4-benzyloxy-benzoic acid ethyl ester

The compound of step 1 of example 252 (20 g, 89.2 mmol) was dissolved in DMF (100 ml) and cooled in an ice bath. Potassium carbonate (18.4 g, 134 mmol) and, immediately thereafter, benzyl bromide (15.2 g, 89.2 mmol) were added. The mixture was stirred for 30 min at room temperature, filtered into a mixture of 2 N hydrochloric acid and diethyl ether. The solid was washed repeatedly with diethyl ether. The combined ethereal phases were washed with water, dried over sodium chloride, decanted and evaporated to dryness. The residue was purified by silica gel chromatography (HEP/EA gradient) to yield 21 g of the title compound.

LC/MS (Method LC14): Rt=3.68 min; m/z=315.1 [MH+]

Step 2

4-Benzyloxy-3-hydroxy-benzoic acid ethyl ester

The compound of step 1 (10 g, 31.8 mmol) was dissolved in methanol, potassium carbonate (88 mg, 0.636 mmol) was added and the mixture was stirred for 2 h under reflux. After evaporation to dryness, the residue was used without further purification in the subsequent step.

LC/MS (Method LC14): Rt=3.32 min; m/z=273.1 [MH+]

Step 3

2-[4-Benzyloxy-3-(2-m-tolyl-ethoxy)-benzoylamino]-indane-2-carboxylic acid methyl ester The compound of step 2 was reacted with 2-m-tolyl-ethanol in analogy to step 1 of example 1, and the obtained ester was hydrolyzed in analogy to example 2. The obtained carboxylic acid was reacted with 2-amino-indane-2-carboxylic acid methyl ester in analogy to step 2 of example 13.

LC/MS (Method LC14): Rt=4.05 min; m/z=536.3 [MH+]

Step 4

2-[4-Benzyloxy-3-(2-m-tolyl-ethoxy)-benzoylamino]-indane-2-carboxylic acid

The compound of step 3 was hydrolyzed in analogy to example 2. LC/MS (Method LC14): Rt=3.79 min; m/z=522.2 [MH+]

EXAMPLE 254

2-[4-Hydroxy-3-(2-m-tolyl-ethoxy)-benzoylamino]-indane-2-carboxylic acid

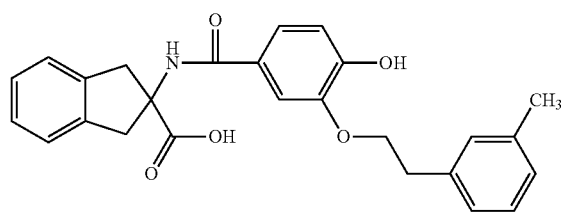

Step 1

2-[4-Hydroxy-3-(2-m-tolyl-ethoxy)-benzoylamino]-indane-2-carboxylic acid methyl ester The compound of step 3 of example 253 (800 mg, 1.49 mmol) was dissolved in EA (15 ml) and hydrogenated in the presence of palladium (10%) on charcoal (200 mg) at a hydrogen pressure of 5 bar and room temperature for 6 h. The mixture was filtered over silica gel and evaporated to dryness. The residue was purified by RP HPLC (water/ACN gradient) to yield 300 mg of the title compound.

LC/MS (Method LC14): Rt=3.47 min; m/z=446.2 [MH+]

Step 2

2-[4-Hydroxy-3-(2-m-tolyl-ethoxy)-benzoylamino]-indane-2-carboxylic acid

The compound of step 1 was hydrolyzed in analogy to example 2. LC/MS (Method LC14): Rt=3.22 min; m/z=432.2 [MH+]

EXAMPLE 255

2-[4-Isopropoxy-3-(2-m-tolyl-ethoxy)-benzoylamino]-indane-2-carboxylic acid

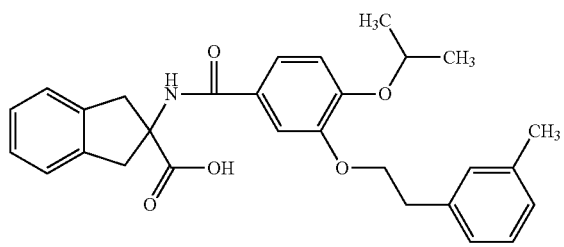 [SMILES: Cc1cccc(CCOc2cc(C(=O)NC3(C(=O)O)Cc4ccccc4C3)ccc2OC(C)C)c1]

The compound of step 1 of example 254 was reacted with 2-propanol in analogy to step 1 of example 1 and the obtained ester hydrolyzed in analogy to example 2.

LC/MS (Method LC14): Rt=3.71 min; m/z=474.2 [MH+]

In analogy to example 255, the following example compounds of the formula Iw listed in table 9 were prepared by using the respective alcohol instead of 2-propanol. In the formulae of the groups $R^{99}$ in table 9 the line crossed with the symbol ~~~ represents the free bond via which the group $R^{99}$ is bonded to the oxygen atom which is attached to the 4-position of the benzoyl group depicted in formula Iw. I.e., in the formula of the complete molecule the terminal endpoint of the line crossed with the said symbol ends at the oxygen atom attached to the 4-position of the benzoyl group. The compounds can be named as 2-[4-($R^{99}$-oxy)-3-(2-m-tolyl-ethoxy)-benzoylamino]-indane-2-carboxylic acid, for example as 2-[4-cyclopropylmethoxy-3-(2-m-tolyl-ethoxy)-benzoylamino]-indane-2-carboxylic acid in the case of example 266.

Iw

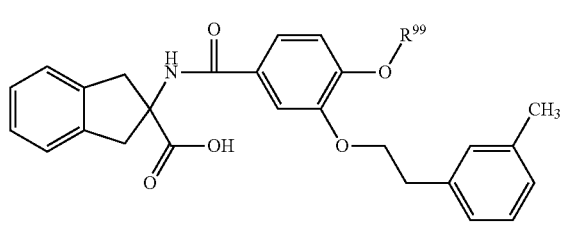

TABLE 9

Example compounds of the formula Iw

| Example | $R^{99}$ | LC/MS Method | m/z [MH+] | Retention time [min] |
|---|---|---|---|---|
| 256 | CH3O-~~~ | LC21 | 488.3 (a) | 4.67 |
| 257 | cyclohexyl-CH2-~~~ | LC21 | 526.4 (a) | 5.15 |

TABLE 9-continued

Example compounds of the formula Iw

| Example | $R^{99}$ | LC/MS Method | m/z [MH+] | Retention time [min] |
|---|---|---|---|---|
| 258 | tetrahydrofuranyl-CH2-~~~ | LC21 | 514.3 (a) | 4.69 |
| 259 | (CH3)3C-O-CH2-CH2-~~~ | LC21 | 530.3 (a) | 4.88 |
| 260 | F3C-CH2-~~~ | LC21 | 526.2 (a) | 4.82 |
| 261 | (CH3)3C-CH2-~~~ | LC2 | 516.2 | 4.42 |
| 262 | cyclobutyl-~~~ | LC2 | 500.2 | 4.29 |
| 263 | H3C-(CH2)4-~~~ | LC12 | 502.2 | 4.35 |
| 264 | tetrahydropyranyl-CH2-~~~ | LC12 | 530.2 | 3.95 |
| 265 | (CH3)2N-CH2-CH2-~~~ | LC12 | 503.2 | 2.87 |
| 266 | cyclopropyl-CH2-~~~ | LC12 | 486.2 | 3.93 |
| 267 | CH3S-CH2-CH2-~~~ | LC12 | 506.2 | 3.97 |
| 268 | F-CH2-CH2-~~~ | LC20 | 478.2 | 11.26 |
| 269 | H2C=CH-CH2-~~~ | LC12 | 472.2 | 3.93 |

(a) [(M − H)−] instead of [MH+]

EXAMPLE 270

2-[4-(2-Hydroxy-ethoxy)-3-(2-m-tolyl-ethoxy)-benzoylamino]-indane-2-carboxylic acid

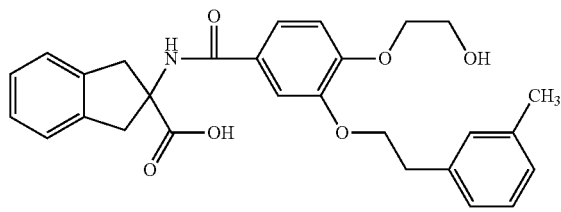 [SMILES: Cc1cccc(CCOc2cc(C(=O)NC3(C(=O)O)Cc4ccccc4C3)ccc2OCCO)c1]

Step 1

2-[4-(2-Acetoxy-ethoxy)-3-(2-m-tolyl-ethoxy)-benzoylamino]-indane-2-carboxylic acid The compound of step 1 of example 254 (70 mg, 0.157 mmol) was dissolved in DMF (1 ml). Potassium carbonate (108 mg, 0.786 mmol) was added and subsequently 2-bromoethyl acetate (39 mg, 0.235 mmol). The mixture was stirred at room temperature for 2 h and then partitioned between EA and water. The aqueous phase was extracted with EA, and the combined organic phases were dried over sodium sulfate and evaporated to dryness. The residue was purified by RP HPLC (water/ACN gradient).

LC/MS (Method LC18): Rt=2.59 min; m/z=532.2 [MH$^+$]

Step 2

2-[4-(2-Hydroxy-ethoxy)-3-(2-m-tolyl-ethoxy)-benzoylamino]-indane-2-carboxylic acid The compound of step 1 was hydrolyzed in analogy to example 2 using 6 equivalents lithium hydroxide.

LC/MS (Method LC18): Rt=2.21 min; m/z=476.2 [MH$^+$]

EXAMPLE 271

2-[4-Carboxymethoxy-3-(2-m-tolyl-ethoxy)-benzoylamino]-indane-2-carboxylic acid

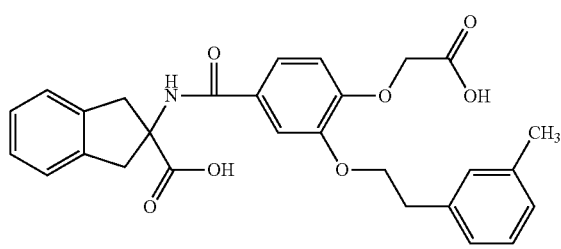 [SMILES: Cc1cccc(CCOc2cc(C(=O)NC3(C(=O)O)Cc4ccccc4C3)ccc2OCC(=O)O)c1]

The title compound was prepared in analogy to example 270 from the compound of step 1 of example 254 and 2-bromo-acetamide. In the final hydrolysis step, 6 equivalents of lithium hydroxide were used, resulting in the hydrolysis of the ester moiety and the acetamide moiety.

LC/MS (Method LC18): Rt=2.23 min; m/z=490.1 [MH$^+$]

EXAMPLE 272

2-[4-Cyclopropoxy-3-(2-m-tolyl-ethoxy)-benzoylamino]-indane-2-carboxylic acid

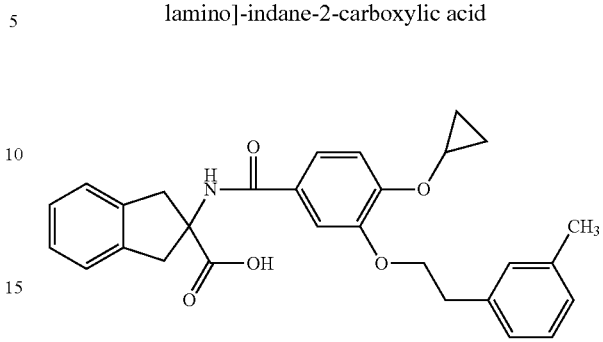

Step 1

2-[4-(1-Phenylsulfanyl-cyclopropoxy)-3-(2-m-tolylethoxy)-benzoylamino]-indane-2-carboxylic acid The compound of step 1 of example 254 (50 mg, 0.116 mmol), (1-iodo-cyclopropylsulfanyl)-benzene (G. J. Hollingworth et al., Tetrahedron Lett. 40 (1999), 2633-2636) (64 mg, 0.232 mmol) and silver carbonate (64 mg, 0.232 mmol) in toluene (1 ml) were stirred overnight at 50° C. The mixture was filtered, the filtrate evaporated to dryness and the residue purified by silica gel chromatography (HEP/EA gradient) to yield 44 mg of the title compound.

LC/MS (Method LC14): Rt=4.23 min; m/z=594.2 [MH$^+$]

Step 2

2-[4-Cyclopropoxy-3-(2-m-tolyl-ethoxy)-benzoylamino]-indane-2-carboxylic acid

3-Chloroperbenzoic acid (43 mg, 0.177 mmol) was added to the compound of step 1 (35 mg, 0.059 mmol) in DCM (2 ml) and saturated aqueous sodium hydrogencarbonate solution (2 ml). The mixture was stirred for 30 min at room temperature and then partitioned between EA and a sodium carbonate solution. The aqueous phase was extracted with EA and the combined organic phases were dried over sodium sulfate and evaporated to dryness. The residue (44 mg) was dissolved in a mixture of 0.5 ml of THF and 1 ml of methanol. Disodium hydrogenphosphate (40 mg, 0.28 mmol) and sodium mercury amalgam (5% sodium) (250 mg) were added and the mixture was stirred for 30 min at room temperature and stored for 6 days at 5° C. Then the mixture was partitioned between 2 N hydrochloric acid and EA, the aqueous phase extracted with EA, and the combined organic extracts were dried over sodium chloride, decanted and evaporated to dryness. The residue was purified by silica gel chromatography (DCM/methanol/28% ammonia gradient, 90:10:1 to 85:15: 1.5). The product fractions were evaporated to dryness and the residue partitioned between 2 N hydrochloric acid and EA. The aqueous phase was extracted with EA, and the combined organic extracts were dried over sodium chloride, decanted and evaporated to dryness.

LC/MS (Method LC14): Rt=3.60 min; m/z=472.2 [MH$^+$]

EXAMPLE 273

2-{[5-Ethyl-4-(2-m-tolyl-ethoxy)-thiazole-2-carbonyl]-amino}-indane-2-carboxylic acid

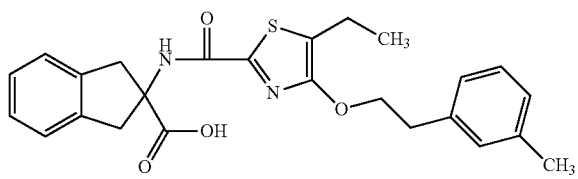 [SMILES: CCc1sc(C(=O)NC2(C(=O)O)Cc3ccccc3C2)nc1OCCc1cccc(C)c1]

5-Ethyl-4-hydroxy-thiazole-2-carboxylic acid ethyl ester (F. A. J. Kerdesky et al., J. Med. Chem. 34 (1991), 2158-2165) (100 mg, 0.497 mmol) was reacted with 2-m-tolyl-ethanol in analogy to step 1 of example 1 and subsequently the ester moiety hydrolyzed in analogy to example 2. The obtained carboxylic acid was reacted with 2-amino-indane-2-carboxylic acid methyl ester hydrochloride in analogy to step 2 of example 13 and the obtained ester hydrolyzed in analogy to example 2.

LC/MS (Method LC12): Rt=4.17 min; m/z=451.2 [MH+]

EXAMPLE 274

2-({5-[2-(2-Fluoro-5-methyl-phenyl)-ethoxy]-6-methoxy-pyridine-3-carbonyl}-amino)-indane-2-carboxylic acid

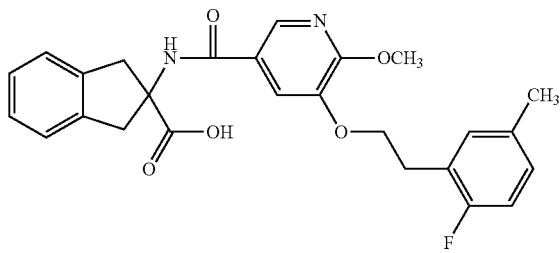 [SMILES: COc1ncc(C(=O)NC2(C(=O)O)Cc3ccccc3C2)cc1OCCc1cc(C)ccc1F]

The title compound was prepared in analogy to example 208 using 2-(2-fluoro-5-methyl-phenyl)-ethanol instead of 2-m-tolyl-ethanol.

LC/MS (Method LC12): Rt=3.64 min; m/z=465.2 [MH+]

EXAMPLE 275

2-[(5-{2-[3-(2-Hydroxy-ethyl)-phenyl]-ethoxy}-6-methoxy-pyridine-3-carbonyl)-amino]-indane-2-carboxylic acid

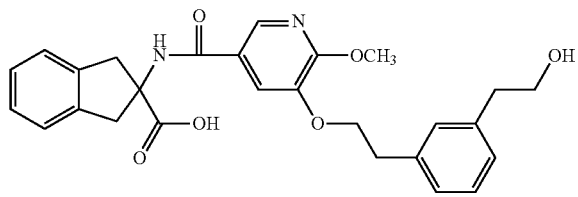 [SMILES: COc1ncc(C(=O)NC2(C(=O)O)Cc3ccccc3C2)cc1OCCc1cccc(CCO)c1]

6-Chloro-5-nitro-nicotinic acid methyl ester was prepared according to the procedure described in WO 2005/021544 and transformed into 5-hydroxy-6-methoxy-nicotinic acid methyl ester according to the procedure described in WO 95/04045. The latter compound was transformed into the title compound by etherification with 2-[3-(2-hydroxy-ethyl)-phenyl]-ethanol in analogy to step 1 of example 1, hydrolysis of the ester group in analogy to example 2, reaction of the obtained carboxylic acid with 2-amino-indane-2-carboxylic acid methyl ester hydrochloride in analogy to step 3 of example 1, and hydrolysis of the ester group in analogy to example 2.

LC/MS (Method LC14): Rt=2.90 min; m/z=477.2 [MH+]

EXAMPLE 276

2-(3-Fluoro-5-{2-[3-(2-hydroxy-ethyl)-phenyl]-ethoxy}-4-methoxy-benzoylamino)-indane-2-carboxylic acid

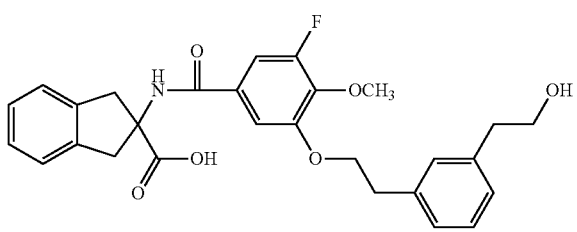 [SMILES: COc1c(F)cc(C(=O)NC2(C(=O)O)Cc3ccccc3C2)cc1OCCc1cccc(CCO)c1]

Step 1

Acetic acid 2-[3-(2-hydroxy-ethyl)-phenyl]-ethyl ester

2-[3-(2-Hydroxy-ethyl)-phenyl]-ethanol (2.49 g, 15.0 mmol) was dissolved in ACN (5 ml) and acetic anhydride (3.06 g, 30 mmol) added. The mixture was stirred under reflux for 1 h and then evaporated to dryness. Silica gel chromatography (HEP/EA gradient) of the residue yielded 1.30 g of the title compound (mono-acetylated product).

$^1$H-NMR: δ=7.20 (t, 1H); 7.10-7.05 (m, 3H); 4.61 (t, 1H); 4.19 (t, 2H); 3.59 (dt, 2H); 2.82 (t, 2H); 2.69 (t, 2H); 1.98 (s, 3H)

Step 2

2-Fluoro-3-hydroxy-4-methoxybenzoic acid methyl ester and 3-fluoro-5-hydroxy-4-methoxybenzoic acid methyl ester 3-Acetoxy-4-methoxy-benzoic acid methyl ester (WO 2005/009389) (3.58 g, 16.0 mmol) and 1-chloromethyl-4-fluoro-1.4-diazoniabicyclo[2.2.2]octane bis(tetrafluoroborate) (Selectfluor®) (14.1 g, 39.9 mmol) in ACN were batchwise (7 batches) heated to 170° C. for 7 min in a microwave reactor. The combined batches were partitioned between 2 N hydrochloric acid and diethyl ether. The aqueous phase was extracted with diethyl ether, the combined organic phases were dried over sodium sulfate, filtered and evaporated to dryness. The residue was purified by silica gel chromatography (HEP/EA gradient) to yield 0.7 g of a mixture of the isomeric fluorinated compounds with and without an acetyl group. This mixture was dissolved in methanol (5 ml) and, after addition of potassium carbonate (80 mg), heated under reflux for 3 h. After evaporation to dryness, the residue was partitioned between 2 N hydrochloric acid and EA, the aqueous phase extracted with EA, and the combined extracts were dried over sodium sulfate and evaporated to dryness. The residue was separated by RP HPLC (water/ACN gradient) to yield 0.14 g of 2-fluoro-3-hydroxy-4-methoxybenzoic acid methyl ester and 0.27 g of 3-fluoro-5-hydroxy-4-methoxybenzoic acid methyl ester.

2-Fluoro-3-hydroxy-4-methoxybenzoic acid methyl ester:
$^1$H-NMR: δ=10.55 (s, 1H); 7.61 (dd, 1H); 6.80 (dd, 1H); 3.90 (s, 3H); 3.88 (s, 3H)

3-Fluoro-5-hydroxy-4-methoxybenzoic acid methyl ester $^1$H-NMR: δ=10.25 (s, 1H); 7.30 (br s, 1H); 7.21 (dd, 1H); 3.87 (s, 3H); 3.81 (s, 3H)

Step 3

2-(3-Fluoro-5-{2-[3-(2-hydroxy-ethyl)-phenyl]-ethoxy}-4-methoxy-benzoylamino)-indane-2-carboxylic acid The title compound was prepared from 3-fluoro-5-hydroxy-4-methoxybenzoic acid methyl ester by etherification with the compound of step 1 in analogy to step 1 of example 1, hydrolysis of both ester moieties of the obtained compound with 6 equivalents of lithium hydroxide in analogy to example 2, reaction of the obtained carboxylic acid with 2-amino-indane-2-carboxylic acid methyl ester hydrochloride in analogy to step 3 of example 1, and hydrolysis of the methyl ester in analogy to example 2.

LC/MS (Method LC14): Rt=3.11 min; m/z=494.2 [MH$^+$]

EXAMPLE 277

2-[2-Fluoro-4-methoxy-3-(2-m-tolyl-ethoxy)-benzoylamino]-indane-2-carboxylic acid

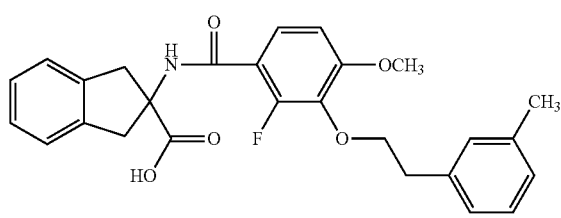 [SMILES: COc1ccc(C(=O)NC2(C(=O)O)Cc3ccccc3C2)c(F)c1OCCc1cccc(C)c1]

2-Fluoro-3-hydroxy-4-methoxybenzoic acid methyl ester was etherified with 2-m-tolyl-ethanol in analogy to step 1 of example 1, the obtained ester hydrolyzed in analogy to example 2, the obtained carboxylic acid reacted with 2-amino-indane-2-carboxylic acid methyl ester hydrochloride in analogy to step 3 of example 1, and the methyl ester hydrolyzed in analogy to example 2.

LC/MS (Method LC14): Rt=3.92 min; m/z=464.2 [MH$^+$]

EXAMPLE 278

2-{4-Methoxy-3-[2-(3-methyl-cyclohexyl)-ethoxy]-benzoylamino}-indane-2-carboxylic acid

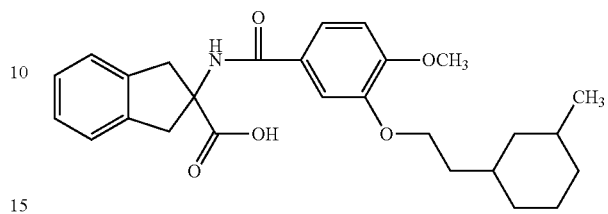

Step 1

4-Methoxy-3-[2-(3-methyl-cyclohexyl)-ethoxy]-benzoic acid

The compound of step 1 of example 13 (100 mg) was dissolved in ethanol (5 ml). Platinum(IV) oxide (12 mg) was added, the mixture was hydrogenated for 1 h at room temperature at a hydrogen pressure of 1 bar, filtered over celite and evaporated to dryness to yield 99 mg of the title compound.

LC/MS (Method LC12): Rt=3.87 min; m/z=334.2 [(M+CH$_3$CN+H)$^+$]

Step 2

2-{4-Methoxy-3-[2-(3-methyl-cyclohexyl)-ethoxy]-benzoylamino}-indane-2-carboxylic acid The compound of step 1 was reacted with 2-amino-indane-2-carboxylic acid methyl ester hydrochloride in analogy to step 4 of example 3 and the obtained ester hydrolyzed in analogy to example 2.

LC/MS (Method LC18): Rt=2.72 min; m/z=452.2 [MH$^+$]

EXAMPLE 279

2-[4-Methoxy-3-(3-methyl-benzyloxymethyl)-benzoylamino]-indane-2-carboxylic acid

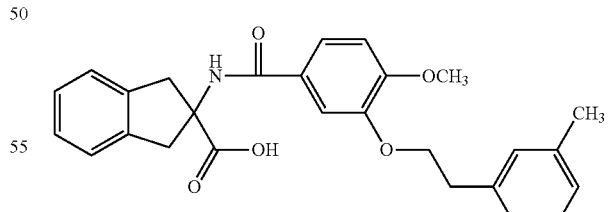

Step 1

2-(3-Formyl-4-methoxy-benzoylamino)-indane-2-carboxylic acid methyl ester

3-Formyl-4-methoxy-benzoic acid (F. D. Chattaway and F. Calvet, J. Chem. Soc. (1928), 2913-2918) (1.017 g, 5.65 mmol) was reacted with 2-amino-indane-2-carboxylic acid methyl ester hydrochloride in analogy to step 4 of example 3. The obtained product (1.895 g) was dissolved in acetic acid (20 ml), sodium acetate (0.57 g, 6.96 mmol) was added and the mixture was stirred under reflux for 24 h. The volatiles were evaporated in vacuo, the residue partitioned between a saturated sodium hydrogencarbonate solution and EA, and the aqueous phase extracted with EA. The combined organic phases were dried over sodium sulfate and evaporated to dryness to yield 1.52 g of the title compound.

LC/MS (Method LC14): Rt=3.00 min; m/z=354.1 [MH$^+$]

Step 2

2-(3-Hydroxymethyl-4-methoxy-benzoylamino)-indane-2-carboxylic acid methyl ester The compound of step 1 (0.500 g, 1.42 mmol) was dissolved in THF (5 ml) and cooled in an ice bath. Sodium borohydride (0.164 g, 4.25 mmol) was added. Subsequently methanol (2 ml) was added dropwise. After 1 h, the volatiles were evaporated, the residue was partitioned between diethyl ether and a saturated sodium hydrogencarbonate solution, and the aqueous phase extracted with diethyl ether. The combined organic phases were dried over sodium sulfate and evaporated to dryness.

LC/MS (Method LC14): Rt=2.74 min; m/z=356.1 [MH$^+$]

Step 3

2-[4-Methoxy-3-(3-methyl-benzyloxymethyl)-benzoylamino]-indane-2-carboxylic acid The compound of step 2 (50 mg, 0.14 mmol)) was dissolved in DMF (3 ml) and sodium hydride (60% dispersion in mineral oil, 6.2 mg, 0.15 mmol) was added followed by 1-bromomethyl-3-methyl-benzene (27 mg, 0.14 mmol). The mixture was stirred overnight. Then lithium hydroxide (1 M solution in water, 0.42 ml) and dioxane (1 ml) were added and the mixture heated to 60° C. for 1 h. The residue was partitioned between 2 N hydrochloric acid and EA and the aqueous phase was extracted with EA. The combined organic phases were dried over sodium sulfate and evaporated to dryness. The residue was purified by RP HPLC (water/ACN gradient) to yield 5 mg of the title compound.

LC/MS (Method LC14): Rt=3.44 min; m/z=446.2 [MH$^+$]

In analogy to example 196, the example compounds of the formula Iu listed in table 10 were prepared by using the respective substituted phenylboronic acid instead of 3-isopropylphenylboronic acid. In the case of examples 282, 283 and 284, the intermediary 2-[3-($R^{97}$)-4-methoxy-benzoylamino]-indane-2-carboxylic acid methyl ester was purified by preparative RP HPLC (water/ACN gradient) before hydrolysis. The compounds can be named as 2-[3-($R^{97}$)-4-methoxy-benzoylamino]-indane-2-carboxylic acid, for example as 2-[3-(5-chloro-pyridin-3-yl)-4-methoxy-benzoylamino]-indane-2-carboxylic acid in the case of example 282.

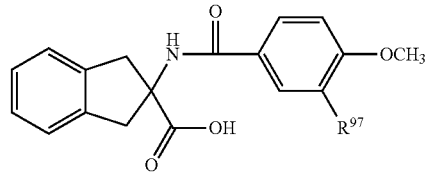

TABLE 10

Example compounds of the formula Iu

| Example | $R^{97}$ | LC/MS Method | m/z [MH$^+$] | Retention time [min] |
|---|---|---|---|---|
| 280 | 4-chloro-phenyl | LC22 | 422.22 | 2.37 |
| 281 | 2-chloro-phenyl | LC22 | 422.22 | 2.17 |
| 282 | 5-chloro-pyridin-3-yl | LC14 | 423.08 | 2.93 |
| 283 | 6-cyano-pyridin-2-yl | LC12 | 414.19 | 3.17 |
| 284 | 5-cyano-pyridin-3-yl | LC14 | 414.15 | 2.85 |

EXAMPLE 285

General procedure for the preparation of 2-(3-aryl-4-methoxy-benzoylamino)-indane-2-carboxylic acids 0.3 mmol of the respective boronic acid were weighed into a microwave reaction vial. 0.2 mmol of 2-(3-bromo-4-methoxy-benzoylamino)-indane-2-carboxylic acid methyl ester in 2 ml of 1,2-dimethoxyethane and 0.4 mmol of cesium fluoride in 1 ml of methanol were added, followed by 0.01 mmol of tetrakis(triphenylphosphine)palladium(0) in 0.5 ml of methanol. The vial was closed with a crimp cap and irradiated in a microwave reactor at 130° C. for 5 min. The cooled solution was treated with 0.25 ml of 4 N aqueous sodium hydroxide and irradiated for another 5 min at 130° C. in a microwave reactor. The cooled solution was neutralized with 0.25 ml of 4 N aqueous hydrochloric acid and evaporated. The residue was dissolved in 2 ml of DMF, filtered and submitted to preparative RP HPLC (water/ACN gradient).

According to the general procedure described in example 285, the compounds of the formula Iu listed in table 11 were prepared. They can be named as 2-[3-($R^{97}$)-4-methoxy-benzoylamino]-indane-2-carboxylic acid, for example as 2-[(3'-ethanesulfonyl-6-methoxy-biphenyl-3-carbonyl)-amino]-indane-2-carboxylic acid in the case of example 312 in which the group $R^{97}$ is 3-ethanesulfonyl-phenyl and, in view of the rules of nomenclature, the group 3-($R^{97}$)-4-methoxy-phenyl-C(O) depicted in formula Iu thus is named 3'-ethanesulfonyl-6-methoxy-biphenyl-3-carbonyl.

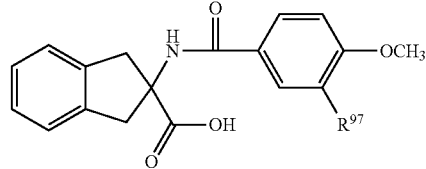

TABLE 11

Example compounds of the formula Iu

| Example | R97 | LC/MS Method | m/z [MH+] | Retention time [min] |
|---|---|---|---|---|
| 286 | 3-methyl-phenyl | LC13 | 402.21 | 2.55 |
| 287 | 3-acetylamino-phenyl | LC13 | 445.23 | 2.14 |
| 288 | 3-ethoxy-phenyl | LC13 | 432.21 | 2.55 |
| 289 | 2-chloro-5-trifluoromethyl-phenyl | LC13 | 490.12 | 2.70 |
| 290 | 4-propyl-phenyl | LC13 | 430.22 | 2.80 |
| 291 | 3,4-dimethyl-phenyl | LC13 | 416.22 | 2.63 |
| 292 | 3,4-dichloro-phenyl | LC13 | 456.12 | 2.75 |
| 293 | 2,3-dichloro-phenyl | LC13 | 456.12 | 2.61 |
| 294 | 4-methoxy-3,5-dimethyl-phenyl | LC13 | 446.22 | 2.57 |
| 295 | benzo[b]thiophen-3-yl | LC12 | 444.2 | 3.65 |
| 296 | 5-chloro-2-methoxy-phenyl | LC13 | 452.17 | 2.53 |
| 297 | 3-cyano-phenyl | LC13 | 413.19 | 2.39 |
| 298 | 3-dimethylamino-phenyl | LC13 | 472.27 | 1.88 |
| 299 | 2-dimethylaminomethyl-phenyl | LC13 | 445.22 | 1.87 |
| 300 | 4-methyl-thiophen-2-yl | LC13 | 408.16 | 2.54 |
| 301 | 3-methylsulfanyl-phenyl | LC13 | 434.18 | 2.56 |
| 302 | 3-trifluoromethoxy-phenyl | LC13 | 472.14 | 2.70 |
| 303 | 2,5-dichloro-phenyl | LC13 | 456.12 | 2.64 |
| 304 | 5-fluoro-2-methoxy-phenyl | LC13 | 436.18 | 2.43 |
| 305 | 3-benzyloxy-phenyl | LC13 | 494.24 | 2.76 |
| 306 | 3,4,5-trifluoro-phenyl | LC13 | 442.14 | 2.63 |
| 307 | 3-methanesulfonylamino-phenyl | LC13 | 481.19 | 2.20 |
| 308 | 3-ethylsulfanyl-phenyl | LC13 | 448.19 | 2.67 |
| 309 | 3-methanesulfonyl-phenyl | LC13 | 466.18 | 2.21 |
| 310 | 4-chloro-3-trifluoromethyl-phenyl | LC13 | 490.12 | 2.79 |
| 311 | 3-(pyrrolidin-1-yl)-phenyl | LC13 | 498.27 | 2.22 |
| 312 | 3-ethanesulfonyl-phenyl | LC13 | 480.19 | 2.28 |
| 313 | 3-tert-butyl-5-methyl-phenyl | LC13 | 458.25 | 2.91 |
| 314 | 5-chloro-2-methyl-phenyl | LC12 | 436.19 | 3.74 |
| 315 | 3-methoxymethyl-phenyl | LC13 | 432.21 | 2.40 |
| 316 | 2-methoxymethyl-phenyl | LC12 | 432.25 | 3.34 |
| 317 | 2,4,5-trimethyl-phenyl | LC13 | 430.22 | 2.69 |
| 318 | 3-propoxy-phenyl | LC13 | 446.23 | 2.68 |
| 319 | 3-isopropoxy-phenyl | LC13 | 446.18 | 2.58 |
| 320 | 2-fluoro-5-trifluoromethyl-phenyl | LC13 | 474.01 | 2.60 |
| 321 | 3-chloro-4-propoxy-phenyl | LC13 | 480.08 | 2.76 |
| 322 | 3-chloro-4-trifluoromethyl-phenyl | LC13 | 490.01 | 2.75 |
| 323 | 3-methylcarbamoyl-phenyl | LC13 | 445.12 | 2.08 |
| 324 | 3-cyclopropylmethoxy-phenyl | LC13 | 458.12 | 2.61 |
| 325 | 3-chloro-4-methoxy-phenyl | LC13 | 452.12 | 2.49 |
| 326 | benzofuran-5-yl | LC13 | 428.14 | 2.46 |
| 327 | 3-chloro-2-methyl-phenyl | LC13 | 436.12 | 2.61 |
| 328 | 3-(2-carboxy-ethyl)-phenyl | LC13 | 460.22 | 2.21 |
| 329 | 2-chloro-thiophen-3-yl | LC13 | 428.09 | 2.45 |
| 330 | 1-methyl-1H-indol-5-yl | LC13 | 441.21 | 2.44 |
| 331 | 2-ethoxy-naphthalen-1-yl | LC13 | 482.21 | 2.58 |
| 332 | 5-chloro-2-fluoro-phenyl | LC13 | 440.11 | 2.53 |
| 333 | 5-chloro-2-fluoro-3-methyl-phenyl | LC13 | 454.12 | 2.63 |
| 334 | 3-(pyrazol-1-yl)-phenyl | LC13 | 454.16 | 2.37 |
| 335 | 5-fluoro-2-isopropoxy-phenyl | LC13 | 464.19 | 2.56 |
| 336 | 2-fluoro-5-isopropoxy-phenyl | LC13 | 464.16 | 2.57 |
| 337 | 5-fluoro-3-trifluoromethyl-phenyl | LC13 | 474.09 | 2.68 |
| 338 | 3-dimethylaminomethyl-phenyl | LC13 | 445.18 | 1.84 |
| 339 | 3-(acetylamino-methyl)-phenyl | LC13 | 459.23 | 2.11 |
| 340 | 4-ethoxy-3-methyl-phenyl | LC13 | 446.23 | 2.69 |
| 341 | 4-isopropoxy-3-methyl-phenyl | LC13 | 460.24 | 2.78 |
| 342 | 3-chloro-5-fluoro-phenyl | LC13 | 440.13 | 2.66 |
| 343 | 5-fluoro-3-isopropoxy-phenyl | LC13 | 464.21 | 2.71 |
| 344 | 5-fluoro-3-isobutoxy-phenyl | LC13 | 478.22 | 2.88 |
| 345 | 4-fluoro-3-trifluoromethyl-phenyl | LC13 | 474.17 | 2.68 |
| 346 | 3-(2,2,2-trifluoro-ethoxy)-phenyl | LC12 | 486.22 | 3.68 |
| 347 | 5-chloro-3-trifluoromethyl-phenyl | LC13 | 490.13 | 2.83 |
| 348 | 2-fluoro-3-trifluoromethyl-phenyl | LC13 | 474.13 | 2.63 |
| 349 | 5-methoxy-3-trifluoromethyl-phenyl | LC13 | 486.16 | 2.69 |
| 350 | 3-isobutyrylamino-phenyl | LC12 | 473.28 | 3.30 |
| 351 | 5-chloro-2-trifluoromethyl-phenyl | LC13 | 490.12 | 2.68 |

In analogy to the examples listed in table 1, the example compounds of the formula Im listed in table 12 were prepared. In the formulae of the groups R90 in table 12 the line crossed with the symbol  represents the free bond via which the group R90 is bonded to the oxygen atom which is attached to the 3-position of the benzoyl group depicted in formula Im. I.e., in the formula of the complete molecule the terminal endpoint of the line crossed with the said symbol ends at the oxygen atom attached to the 3-position of the benzoyl group. The compounds can be named as 2-[3-(R90-oxy)-4-methoxy-benzoylamino]-indane-2-carboxylic acid, for example as 2-{3-[2-(2-fluoro-5-trifluoromethoxy-phenyl)-ethoxy]-4-methoxy-benzoylamino}-indane-2-carboxylic acid in the case of example 355.

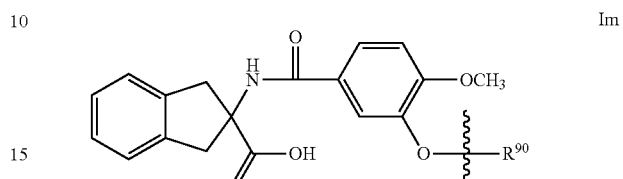

Im

TABLE 12

Example compounds of the formula Im

| Example | R90 | LC/MS Method | m/z [MH+] | Retention time [min] |
|---|---|---|---|---|
| 352 | 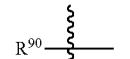 | LC13 | 500.04 | 2.77 |
| 353 | 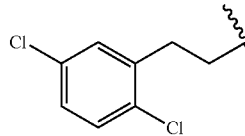 | LC13 | 438.13 | 2.25 |
| 354 | 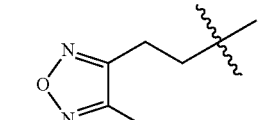 | LC13 | 473.18 | 2.37 |
| 355 | 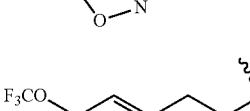 | LC12 | 534.07 | 3.84 |

EXAMPLE 356

Starting Compound 2-(2-Fluoro-5-trifluoromethoxy-phenyl)-ethanol 3.00 g (12.6 mmol) of 2-(2-fluoro-5-trifluoromethoxy-phenyl)-acetic acid were dissolved in 50 ml of dry THF and dropped at 0° C. into a suspension of 956 mg (25.2 mmol) of lithium aluminium hydride in 11 ml of THF. After stirring overnight, 150 ml of THF were added followed by 3 ml of EA. 15 ml water were added dropwise and the supernatant decanted from the resulting slurry. The slurry was extracted three times with 20 ml of EA. The combined organic phases were dried over sodium sulfate and evaporated. The remaining oil (2.5 g) was used for the next step without further purification.

In analogy to example 356, the starting compounds 2-(benzo[d]isoxazol-3-yl)-ethanol and 2-(4-methyl-furazan-3-yl)-ethanol were prepared from 2-(benzo[d]isoxazol-3-yl)-acetic acid and 2-(4-methyl-furazan-3-yl)-acetic acid, respectively.

EXAMPLE 357

2-[(3'-Ethanesulfonyl-5-fluoro-6-methoxy-biphenyl-3-carbonyl)-amino]-indane-2-carboxylic acid

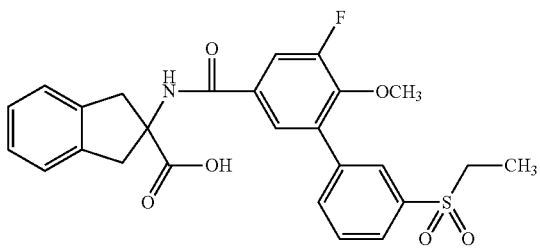 [SMILES: CCS(=O)(=O)c1cccc(-c2cc(C(=O)NC3(C(=O)O)Cc4ccccc4C3)cc(F)c2OC)c1]

Step 1

3-Bromo-5-fluoro-4-hydroxy-benzoic acid methyl ester

During 30 min, 5.64 g (35.27 mmol) of bromine were added to a solution of 5.00 g (29.39 mmol) of 3-fluoro-4-hydroxy-benzoic acid methyl ester in 30 ml of DCM and 30 ml of acetic acid at 0° C. After stirring overnight, 200 ml of methyl acetate were added. The resulting solution was extracted with a solution of 7.56 g (60 mmol) of sodium sulfite in 50 ml of water, a saturated sodium chloride solution and water. The organic phase was dried over sodium sulfate, filtered and evaporated. The resulting white solid (7.2 g) was used in the next step without further purification.

Step 2

3-Bromo-5-fluoro-4-methoxy-benzoic acid methyl ester 6 g (24.09 mmol) of the product obtained in step 1 were dissolved in 60 ml of acetone, 10.13 g (2.270 mmol) of potassium carbonate and 6.84 g (48.18 mmol) of iodomethane were added, and the mixture was stirred for 4 days. Then is was filtered and evaporated. The resulting product (5.8 g) was used in the next step without further purification.

Step 3

3-Bromo-5-fluoro-4-methoxy-benzoic acid 5.8 g of the product obtained in step 2 were dissolved in 100 ml of a mixture of THF and water (9:1), 1.06 g (44.1 mmol) of lithium hydroxide were added and the mixture was stirred for 3 days. The solvent was evaporated and the residue was purified by preparative RP HPLC (water/ACN gradient). 2.9 g of the title compound were obtained.

Step 4

2-(3-Bromo-5-fluoro-4-methoxy-benzoylamino)-indane-2-carboxylic acid methyl ester 2.4 g (9.64 mmol) of the compound of step 3 were dissolved in 40 ml of DMF and 2.49 g (19.27 mmol) of EDIA and 4.03 g (10.60 mmol) of O-(7-azabenzotriazol-1-yl)-N,N,N',N'-tetramethyluronium hexafluorophosphate were added. Then a solution of 2.19 g (9.64 mmol) of 2-amino-indane-2-carboxylic acid methyl ester hydrochloride in 10 ml of DMF was added. After stirring overnight, the mixture was evaporated to dryness and the residue purified by preparative RP HPLC (water/ACN gradient). 3.6 g of the title compound were obtained.

Step 5

2-[(3'-Ethanesulfonyl-5-fluoro-6-methoxy-biphenyl-3-carbonyl)-amino]-indane-2-carboxylic acid 300 mg (0.71 mmol) of the compound of step 4 and 175 mg (1.07 mmol) of 3-ethanesulfonylphenylboronic acid were dissolved in 4 ml of DMF and 4 ml of 1,2-dimethoxyethane under an argon atmosphere. 216 mg (1.42 mmol) of cesium fluoride and 41.08 mg (0.04 mmol) of tetrakis(triphenylphosphine)palladium(0) were added, and the mixture was heated to 130° C. in a microwave reactor for 15 min. After cooling, the solvent was evaporated and the residue purified by preparative RP HPLC (water/ACN gradient) to yield the methyl ester of the title compound. 135.1 mg (0.26 mmol) methyl ester were dissolved in 5 ml of a mixture of THF and water (9:1), 12.65 mg (0.53 mmol) of lithium hydroxide were added and the mixture was stirred for 3 days. The solvent was evaporated and the residue was purified by preparative RP HPLC (water/ACN gradient). 123 mg of the title compound were obtained.

LC/MS (Method LC14): Rt=3.07 min; m/z=498.19 [MH$^+$]
1H-NMR: δ=12.5 (br s, 1H); 8.90 (s, 1H); 7.98 (s, 1H); 7.75-7.95 (m, 6H); 7.28 (d, 4H); 3.30-3.64 (m, 6H); 1.13 (t, 3H)

In analogy to example 357, the example compounds of the formula Ix listed in table 13 were prepared by using the respective substituted phenylboronic acid instead of 3-ethanesulfonylphenylboronic acid. They can be named as 2-[3-(R$^{100}$)-5-fluoro-4-methoxy-benzoylamino]-indane-2-carboxylic acid, for example as 2-[(5-fluoro-3'-isopropyl-6-methoxy-biphenyl-3-carbonyl)-amino]-indane-2-carboxylic acid in the case of example 360 in which the group R$^{100}$ is 3-isopropyl-phenyl and, in view of the rules of nomenclature, the group 3-(R$^{100}$)-5-fluoro-4-methoxy-phenyl-C(O) depicted in formula Ix thus is named 5-fluoro-3'-isopropyl-6-methoxy-biphenyl-3-carbonyl.

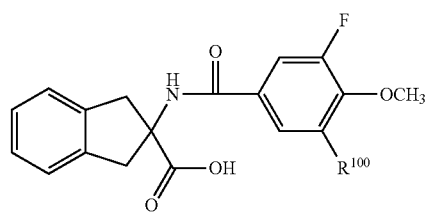

Ix

TABLE 13

Example compounds of the formula Ix

| Example | R[100] | LC/MS Method | m/z [MH+] | Retention time [min] |
|---|---|---|---|---|
| 358 | 4-chloro-phenyl | LC14 | 440.15 | 3.53 |
| 359 | 3-methanesulfonylamino-phenyl | LC14 | 499.19 | 2.96 |
| 360 | 3-isopropyl-phenyl | LC14 | 448.22 | 4.08 |
| 361 | 3-dimethylaminosulfonylamino-phenyl | LC14 | 528.21 | 3.28 |

EXAMPLE 362

2-{3-[2-(2,5-Dichloro-phenyl)-ethoxy]-4-trifluoromethyl-benzoylamino}-indane-2-carboxylic acid

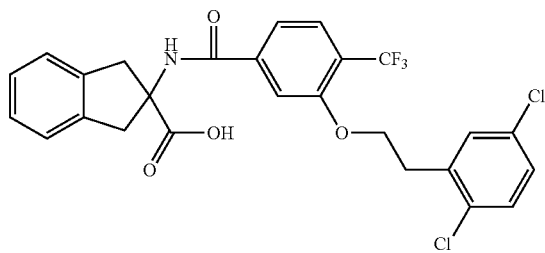 [SMILES: O=C(NC1(C(=O)O)Cc2ccccc2C1)c1ccc(C(F)(F)F)c(OCCc2cc(Cl)ccc2Cl)c1]

The title compound was synthesized in analogy to example 185 by using 2,5-dichloro-phenyl-ethanol instead of 2-(3-methyl-phenyl)-ethanol in step 3.

LC/MS (Method LC13): Rt=538,01 min; m/z=3.06 min [MH+]

Pharmacological Tests

A) Determination of Edg-2 receptor inhibition by fluorescence imaging plate reader (FLIPR) measurements The inhibition of the Edg-2 receptor (LPA$_1$ receptor) by the compounds of the invention was quantified by the inhibitory effect on the LPA-mediated calcium liberation in a cell-based calcium fluorescence assay by use of Chinese hamster ovarian (CHO) cells in which the human Edg-2 receptor was stably overexpressed (Flp-In system, Invitrogen). In order to enforce G-Protein coupling and to direct signaling towards Ca$^{2+}$ liberation, the overexpressed receptor additionally had a C-terminal sequence of a modified G-protein (G$_{\alpha i4qi4}$) (WO 02/04665). Changes in intracellular calcium were determined by fluorescence measurement with the calcium-sensitive dye fluo-4 (Invitrogen) in a fluorescence imaging plate reader (FLIPR, Molecular Dynamics).

CHO cells stably overexpressing the human Edg-2 receptor were seeded (40.000 per well) in black clear-bottomed poly-D-lysine-coated 96 well plates (Becton Dickinson, Biocoat cellware) approximately 18-24 h prior to the experiments. Cells were grown in an incubator at 37° C., 5% carbon dioxide and 95% humidity in cell culture media based on F-12 glutamax media (Gibco, #31765) supplemented with 1% (vol/vol) penicilline/streptomycine (PAN, #P06-07100), 10% (vol/vol) fetal calf serum (FCS, PAA, #A15-151) and hygromycin B (Invitrogen, #10687-010) 300 mg/l (final concentrations).

Prior to the FLIPR experiment, cells were loaded with fluo-4 acetoxymethyl ester (fluo-4 AM, Invitrogen, #F14202) for 60 min in an incubator at 37° C., 5% carbon dioxide and 95% humidity in dye-loading buffer consisting of Hanks' Balanced Salt Solution (HBSS, Invitrogen, #14065049) supplemented with fluo-4 AM at 2 µM (all data given for final concentration), Pluronic® F-127 0.05% (vol/vol) (Invitrogen, #P-3000 MP), HEPES 20 mM (Gibco, #15630), probenecid 2.5 mM (Sigma, #P-8761) and bovine serum albumin 0.05% (BSA, Sigma, #A-6003), adjusted to pH 7.5 with sodium hydroxide. During cell loading, fluo-4 AM is cleaved by intracellular esterase resulting in trapping of the dye fluo-4 within the cells. Loading was terminated by washing of the cells in a cell washer (Tecan Power washer) three times with the buffer specified afore but without fluo-4 AM and BSA. This latter buffer was also used as the buffer in the subsequent cell fluorescence measurements.

The dye-loaded and washed cells were pre-incubated for approximately 5 min with various concentrations of the test compound added as a solution in DMSO (0.3 vol/vol maximum final concentration of DMSO), or with DMSO in the respective concentration only (positive control). Subsequent addition of LPA (18:1,1-oleoyl-sn-glycerol 3-phosphate; 100 nM final concentration) leads to liberation of intracellular calcium from internal stores resulting in a large transient increase of the fluo-4 fluorescence signal which was monitored over approximately 3 min. The percent inhibition caused by the test compound was determined from the maximum fluorescence response after LPA addition to cells pre-incubated with the compound as compared to the maximum fluorescence response after LPA addition to cells pre-incubated with DMSO only. All fluorescence values were corrected for the baseline fluorescence values obtained with cells which were pre-incubated with DMSO only and were not treated with LPA (baseline control). All measurements were performed in triplicate. From the percent inhibitions the inhibitory concentration IC$_{50}$ was determined.

Inhibitory concentrations IC$_{50}$ of various example compounds are given in table 14, wherein "a" denotes an IC$_{50}$ of less than 0.1 µM, "b" denotes an IC$_{50}$ between 0.1 µM and 1 µM, and "c" denotes an IC$_{50}$ between 1 µM and 30 µM.

TABLE 14

Inhibitory concentrations IC$_{50}$ for inhibition of the Edg-2 receptor

| Example | IC$_{50}$ |
|---|---|
| 2 | a |
| 4 | a |
| 5 | c |
| 6 | c |
| 8 | b |
| 9 | b |
| 10 | a |
| 11 | a |
| 12 | a |
| 14 | a |
| 16 | a |
| 17 | c |
| 18 | c |
| 19 | a |
| 20 | a |
| 21 | a |
| 22 | c |
| 23 | a |
| 24 | a |
| 25 | a |
| 26 | c |
| 27 | a |
| 28 | c |
| 29 | c |
| 30 | c |
| 31 | c |
| 32 | c |
| 33 | c |
| 34 | c |
| 35 | c |

TABLE 14-continued

Inhibitory concentrations $IC_{50}$ for inhibition of the Edg-2 receptor

| Example | $IC_{50}$ |
|---|---|
| 36 | c |
| 37 | c |
| 38 | c |
| 39 | c |
| 40 | c |
| 41 | c |
| 42 | c |
| 43 | c |
| 44 | c |
| 45 | c |
| 46 | b |
| 47 | c |
| 48 | c |
| 49 | c |
| 50 | b |
| 51 | c |
| 52 | c |
| 53 | c |
| 54 | c |
| 55 | c |
| 56 | c |
| 57 | c |
| 58 | c |
| 59 | c |
| 60 | c |
| 61 | c |
| 62 | c |
| 63 | c |
| 64 | c |
| 65 | c |
| 66 | c |
| 67 | c |
| 68 | c |
| 69 | c |
| 70 | c |
| 71 | c |
| 72 | c |
| 73 | c |
| 74 | c |
| 75 | c |
| 76 | c |
| 77 | c |
| 78 | c |
| 79 | c |
| 80 | c |
| 81 | a |
| 82 | c |
| 83 | c |
| 84 | c |
| 85 | c |
| 86 | c |
| 87 | c |
| 88 | c |
| 89 | c |
| 90 | c |
| 91 | c |
| 94 | a |
| 95 | c |
| 96 | c |
| 98 | a |
| 99 | a |
| 100 | a |
| 101 | c |
| 102 | b |
| 103 | c |
| 104 | c |
| 105 | b |
| 106 | a |
| 107 | c |
| 108 | b |
| 109 | c |
| 110 | c |
| 111 | c |
| 112 | c |
| 113 | c |
| 114 | c |
| 115 | c |
| 116 | a |
| 117 | b |
| 118 | c |
| 119 | c |
| 120 | c |
| 121 | c |
| 122 | b |
| 123 | c |
| 124 | b |
| 126 | c |
| 127 | a |
| 128 | b |
| 129 | b |
| 130 | a |
| 131 | a |
| 132 | a |
| 133 | b |
| 134 | c |
| 135 | c |
| 136 | c |
| 137 | c |
| 138 | c |
| 139 | b |
| 140 | c |
| 141 | c |
| 142 | c |
| 143 | a |
| 144 | a |
| 145 | b |
| 146 | b |
| 147 | b |
| 148 | c |
| 149 | a |
| 150 | c |
| 151 | c |
| 152 | a |
| 153 | b |
| 154 | a |
| 155 | c |
| 156 | a |
| 157 | a |
| 158 | b |
| 159 | a |
| 161 | c |
| 162 | c |
| 163 | b |
| 164 | a |
| 165 | b |
| 166 | b |
| 167 | c |
| 168 | a |
| 169 | b |
| 171 | a |
| 172 | c |
| 173 | c |
| 174 | c |
| 175 | c |
| 176 | a |
| 177 | b |
| 178 | c |
| 179 | b |
| 180 | a |
| 181 | a |
| 182 | c |
| 183 | c |
| 184 | c |
| 185 | a |
| 186 | a |
| 187 | a |
| 188 | a |
| 189 | a |
| 190 | c |
| 191 | a |
| 192 | a |
| 193 | a |

TABLE 14-continued

Inhibitory concentrations $IC_{50}$ for inhibition of the Edg-2 receptor

| Example | $IC_{50}$ |
|---|---|
| 194 | c |
| 195 | b |
| 196 | a |
| 197 | c |
| 198 | a |
| 199 | a |
| 200 | a |
| 201 | c |
| 202 | a |
| 203 | a |
| 204 | a |
| 205 | c |
| 206 | c |
| 207 | c |
| 208 | a |
| 209 | a |
| 210 | b |
| 211 | a |
| 212 | a |
| 213 | a |
| 214 | a |
| 215 | a |
| 216 | a |
| 217 | a |
| 218 | a |
| 219 | c |
| 220 | a |
| 221 | a |
| 222 | a |
| 223 | a |
| 224 | a |
| 225 | b |
| 226 | a |
| 227 | a |
| 228 | a |
| 229 | a |
| 230 | a |
| 231 | a |
| 232 | a |
| 233 | a |
| 234 | a |
| 235 | a |
| 236 | a |
| 237 | b |
| 238 | b |
| 239 | c |
| 240 | c |
| 241 | c |
| 242 | b |
| 243 | c |
| 244 | b |
| 245 | a |
| 246 | c |
| 247 | b |
| 248 | a |
| 249 | a |
| 250 | a |
| 251 | c |
| 252 | b |
| 253 | a |
| 254 | c |
| 255 | a |
| 256 | a |
| 257 | a |
| 258 | a |
| 259 | a |
| 260 | b |
| 261 | b |
| 262 | a |
| 263 | a |
| 264 | a |
| 265 | b |
| 266 | a |
| 267 | a |
| 268 | a |
| 269 | a |

TABLE 14-continued

Inhibitory concentrations $IC_{50}$ for inhibition of the Edg-2 receptor

| Example | $IC_{50}$ |
|---|---|
| 270 | a |
| 271 | b |
| 272 | b |
| 273 | b |
| 274 | a |
| 275 | a |
| 276 | a |
| 277 | c |
| 278 | c |
| 279 | b |
| 280 | b |
| 281 | c |
| 282 | b |
| 283 | c |
| 284 | a |
| 286 | a |
| 287 | b |
| 288 | b |
| 289 | b |
| 290 | c |
| 291 | b |
| 292 | a |
| 293 | a |
| 294 | a |
| 295 | a |
| 296 | a |
| 297 | a |
| 298 | b |
| 299 | c |
| 300 | b |
| 301 | a |
| 302 | a |
| 303 | a |
| 304 | a |
| 305 | b |
| 306 | a |
| 307 | a |
| 308 | a |
| 309 | b |
| 310 | b |
| 311 | c |
| 312 | b |
| 313 | a |
| 314 | a |
| 315 | a |
| 316 | b |
| 317 | b |
| 318 | a |
| 319 | b |
| 320 | a |
| 321 | c |
| 322 | a |
| 323 | c |
| 324 | c |
| 325 | a |
| 326 | b |
| 327 | a |
| 328 | b |
| 329 | c |
| 330 | c |
| 331 | b |
| 332 | b |
| 333 | a |
| 334 | b |
| 335 | a |
| 336 | c |
| 337 | a |
| 338 | c |
| 339 | b |
| 340 | b |
| 341 | c |
| 342 | a |
| 343 | a |
| 344 | b |
| 345 | a |
| 346 | b |

TABLE 14-continued

Inhibitory concentrations IC$_{50}$ for inhibition of the Edg-2 receptor

| Example | IC$_{50}$ |
|---|---|
| 347 | a |
| 348 | a |
| 349 | a |
| 350 | c |
| 351 | a |
| 352 | a |
| 353 | c |
| 354 | c |
| 355 | a |
| 357 | a |
| 358 | a |
| 359 | a |
| 360 | a |
| 361 | a |
| 362 | a |

B) In Vivo Antihypertrophic and Renoprotective Activity

The in vivo pharmacological activity of the compounds of the invention can be investigated, for example, in the model of DOCA-salt sensitive rats with unilateral nephrectomy. Briefly, in this model unilateral nephrectomy of the left kidney (UNX) is performed on Sprague Dawley rats of 150 g to 200 g of body weight. After the operation as well as at the beginning of each of the following weeks 30 mg/kg of body weight of DOCA (desoxycorticosterone acetate) are administered to the rats by subcutaneous injection. The nephrectomized rats treated with DOCA are supplied with drinking water containing 1% of sodium chloride (UNX/DOCA rats). The UNX/DOCA rats develop high blood pressure, endothelial dysfunction, myocardial hypertrophy and fibrosis as well as renal dysfunction. In the test group (UNX/DOCA Test) and the placebo group (UNX/DOCA Placebo), which consist of randomized UNX/DOCA rats, the rats are treated orally by gavage in two part administrations at 6 a.m. and 6 p.m. with the daily dose of the test compound (for example 10 mg/kg of body weight dissolved in vehicle) or with vehicle only, respectively. In a control group (control), which consists of animals which have not been subjected to UNX and DOCA administration, the animals receive normal drinking water and are treated with vehicle only. After five weeks of treatment, systolic blood pressure (SBP) and heart rate (HR) are measured non-invasively via the tail cuff method. For determination of albuminuria and creatinine, 24 h urine is collected on metabolic cages. Endothelial function is assessed in excised rings of the thoracic aorta as described previously (W. Linz et al., JRAAS (Journal of the renin-angiotensin-aldosterone system) 7 (2006), 155-161). As a measure of myocardial hypertrophy and fibrosis, heart weight, left ventricular weight and the relation of hydroxyproline and proline are determined in excised hearts.

We claim:

1. A compound of formula I,

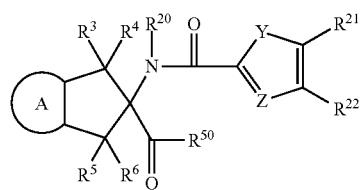

wherein ring A is a monocyclic 5-membered or 6-membered aromatic heterocyclic ring which comprises 1 or 2 identical or different hetero ring members chosen from the series consisting of N, N(R$^o$), O and S, wherein the heterocyclic ring is optionally substituted by one or more identical or different substituents chosen from the series consisting of halogen, R$^1$, HO—, R$^1$—O—, R$^1$—C(O)—O—, R$^1$—S(O)$_2$—O—, R$^1$—S(O)$_m$—, H$_2$N—, R$^1$—NH—, R$^1$—N(R$^1$)—, R$^1$—C(O)—NH—, R$^1$—C(O)—N(R$^{71}$)—, R$^1$—S(O)$_2$—NH—, R$^1$—S(O)$_2$—N(R$^{71}$)—, R$^1$—C(O)—, HO—C(O)—, R$^1$—O—C(O)—, H$_2$N—C(O)—, R$^1$—NH—C(O)—, R$^1$—N(R$^1$)—C(O)—, H$_2$N—S(O)$_2$—, R$^1$—NH—S(O)$_2$—, R$^1$—N(R$^1$)—S(O)$_2$—, NC—, O$_2$N—, phenyl and Het;

Y is C(R$^{12}$)=C(R$^{13}$);

Z is C(R$^{16}$);

R$^o$ is chosen from the series consisting of hydrogen and R$^2$;

R$^1$, R$^2$, R$^{30}$, R$^{33}$, R$^{35}$, R$^{54}$, R$^{55}$, R$^{57}$ and R$^{58}$ are, independently of each other group R$^1$, R$^2$, R$^{11}$, R$^{30}$, R$^{33}$, R$^{35}$, R$^{54}$, R$^{55}$, R$^{57}$ and R$^{58}$, chosen from the series consisting of (C$_1$-C$_6$)-alkyl, (C$_2$-C$_6$)-alkenyl, (C$_2$-C$_6$)-alkynyl, (C$_3$-C$_7$)-cycloalkyl and (C$_3$-C$_7$)-cycloalkyl-(C$_1$-C$_4$)-alkyl- which are all optionally substituted by one or more identical or different substituents R$^{70}$;

R$^3$ and R$^5$ are independently of each other chosen from the series consisting of hydrogen, (C$_1$-C$_4$)-alkyl, phenyl-(C$_1$-C$_4$)-alkyl-, phenyl and hydroxy;

R$^4$ and R$^6$ are independently of each other chosen from the series consisting of hydrogen and (C$_1$-C$_4$)-alkyl;

R$^{12}$, R$^{13}$ and R$^{16}$ are independently of each other chosen from the series consisting of hydrogen, halogen, (C$_1$-C$_4$)-alkyl, HO—(C$_1$-C$_4$)-alkyl-, (C$_1$-C$_4$)-alkyl-O-, (C$_1$-C$_4$)-alkyl-S(O)$_m$-, H$_2$N—, (C$_1$-C$_4$)-alkyl-NH—, (C$_1$-C$_4$)-alkyl-N((C$_1$-C$_4$)-alkyl)-, (C$_1$-C$_4$)-alkyl-C(O)—, NC— and O$_2$N—;

R$^{20}$ is chosen from the series consisting of hydrogen and (C$_1$-C$_4$)-alkyl;

one of the groups R$^{21}$ and R$^{22}$ is a group of the formula II $$R^{24}\text{-}R^{23}\text{-} \qquad \qquad II$$

and the other of the groups R$^{21}$ and R$^{22}$ is chosen from the series consisting of hydrogen, halogen, R$^{30}$, HO—, R$^{30}$—O—, R$^{30}$—C(O)—O—, R$^{30}$—S(O)$_2$—O—, R$^{30}$—S(O)$_m$—, H$_2$N—, R$^{30}$—NH—, R$^{30}$—N(R$^{30}$)—, R$^{30}$—C(O)—NH—, R$^{30}$—C(O)—N(R$^{71}$)—, R$^{30}$—S(O)$_2$—NH—, R$^{30}$—S(O)$_2$—N(R$^{71}$)—, R$^{30}$—C(O)—, HO—C(O)—, R$^{30}$—O—C(O)—, H$_2$N—C(O)—, R$^{30}$—NH—C(O)—, R$^{30}$—N(R$^{30}$)—C(O)—, H$_2$N—S(O)$_2$—, R$^{30}$—NH—S(O)$_2$—, R$^{30}$—N(R$^{30}$)—S(O)$_2$—, NC—, O$_2$N— and Het$^1$;

R$^{23}$ is a direct bond or a chain consisting of 1 to 5 chain members of which 0, 1 or 2 chain members are identical or different hetero chain members chosen from the series consisting of N(R$^{25}$), O, S, S(O) and S(O)$_2$, but two hetero chain members can be present in adjacent positions only if one of them is chosen from the series consisting of S(O) and S(O)$_2$ and the other is chosen from the series consisting of N(R$^{25}$), O and S, and the other chain members are identical or different groups C(R$^{26}$)(R$^{26}$), wherein two adjacent groups C(R$^{26}$)(R$^{26}$) can be connected to each other by a double bond or a triple bond;

R$^{24}$ is chosen from the series consisting of hydrogen, R$^{31}$, HO—, R$^{31}$—O—, R$^{31}$—C(O)—O—, R$^{31}$—S(O)$_m$—, H$_2$N—, R$^{31}$—NH—, R$^{31}$—N(R$^{31}$)—, R$^{31}$—C(O)—NH—, R$^{31}$—C(O)—N(R$^{71}$)—, R$^{31}$—S(O)$_2$—NH—, R$^{31}$—S(O)$_2$—N(R$^{71}$)—, R$^{31}$—C(O)—, HO—C(O)—, R$^{31}$—O—C(O)—, H$_2$N—C(O)—, R$^{31}$—NH—C(O)—, R$^{31}$—N(R$^{31}$)—C(O)—, H$_2$N—S(O)$_2$—, R$^{31}$—NH—S(O)$_2$—, R$^{31}$—N(R$^{31}$)—S(O)$_2$—, NC— and a 3-membered to 10-membered, monocyclic, bicyclic or tricyclic ring which is saturated or unsaturated and contains 0, 1, 2 or 3 identical or different hetero ring members chosen from the series consisting of N, N($R^{32}$), O, S, S(O) and S(O)$_2$, which ring is optionally substituted on ring carbon atoms by one or more identical or different substituents chosen from the series consisting of halogen, $R^{33}$, HO—, $R^{33}$—O—, $R^{33}$—C(O)—O—, $R^{33}$—S(O)$_2$—O—, $R^{33}$—S(O)$_m$—, H$_2$N—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, H$_2$N—S(O)$_2$—NH—, $R^{33}$—NH—S(O)$_2$—NH—, $R^{33}$—N($R^{33}$)—S(O)$_2$—NH—, H$_2$N—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, $R^{33}$—C(O)—, HO—C(O)—, $R^{33}$—O—C(O)—, H$_2$N—C(O)—, $R^{33}$—NH—C(O)—, $R^{33}$—N($R^{33}$)—C(O)—, H$_2$N—S(O)$_2$—, $R^{33}$—NH—S(O)$_2$—, $R^{33}$—N($R^{33}$)—S(O)$_2$—, NC—, O$_2$N—, oxo, phenyl and Het,
provided that the total number of C, N, O and S atoms which is present in the two groups $R^{23}$ and $R^{24}$, is at least 5;
$R^{25}$ is chosen from the series consisting of hydrogen and (C$_1$-C$_4$)-alkyl;
$R^{26}$, independently of each other group $R^{26}$, is chosen from the series consisting of hydrogen, fluorine, (C$_1$-C$_4$)-alkyl and HO—, or two groups $R^{26}$ bonded to the same carbon atom together are oxo, or two of the groups $R^{26}$ or one group $R^{25}$ and one group $R^{26}$, together with the comprised chain members, form a 3-membered to 7-membered monocyclic ring which is saturated and contains 0, 1 or 2 identical or different hetero ring members chosen from the series consisting of N, N($R^{34}$), O, S, S(O) and S(O)$_2$, which ring is optionally substituted on ring carbon atoms by one more identical or different substituents chosen from the series consisting of fluorine and (C$_1$-C$_4$)-alkyl;
$R^{31}$ is chosen from the series consisting of (C$_1$-C$_6$)-alkyl, (C$_2$-C$_6$)-alkenyl and (C$_2$-C$_6$)-alkynyl which are all optionally substituted by one or more identical or different substituents $R^{70}$;
$R^{32}$ and $R^{34}$ are independently of each other chosen from the series consisting of hydrogen, $R^{35}$, $R^{35}$—S(O)$_2$—, $R^{35}$—C(O)—, $R^{35}$—O—C(O)—, phenyl and Het;
$R^{50}$ is chosen from the series consisting of $R^{51}$—O— and $R^{52}$—N($R^{53}$)—;
$R^{51}$ is chosen from the series consisting of hydrogen and $R^{54}$;
$R^{52}$ is chosen from the series consisting of hydrogen, $R^{55}$, NC— and $R^{56}$—S(O)$_2$—;
$R^{53}$ is chosen from the series consisting of hydrogen and $R^{57}$;
$R^{56}$ is chosen from the series consisting of $R^{58}$ and phenyl;
$R^{60}$, independently of each other group $R^{60}$, is chosen from the series consisting of hydrogen and (C$_1$-C$_4$)-alkyl;
$R^{70}$ is chosen from the series consisting of HO—, $R^{71}$—O—, $R^{71}$—C(O)—O—, $R^{71}$—S(O)$_m$—, H$_2$N—, $R^{71}$—NH—, $R^{71}$—N($R^{71}$)—, $R^{71}$—C(O)—NH—, $R^{71}$—C(O)—N($R^{71}$)—, $R^{71}$—S(O)$_2$—NH—, $R^{71}$—S(O)$_2$—N($R^{71}$)—, HO—C(O)—, $R^{71}$—O—C(O)—, H$_2$N—C(O)—, $R^{71}$—NH—C(O)—, $R^{71}$—N($R^{71}$)—C(O)—, H$_2$N—S(O)$_2$—, $R^{71}$—NH—S(O)$_2$—, $R^{71}$—N($R^{71}$)—S(O)$_2$—, NC—, oxo, phenyl and Het$^2$;
$R^{71}$, independently of each other group $R^{71}$, is chosen from (C$_1$-C$_4$)-alkyl, (C$_3$-C$_4$)-cycloalkyl and (C$_3$-C$_4$)-cycloalkyl-(C$_1$-C$_2$)-alkyl-;
Het, independently of each other group Het, is a monocyclic 4-membered to 7-membered heterocyclic ring which comprises 1, 2 or 3 identical or different hetero ring members chosen from the series consisting of N, N($R^{60}$), O, S, S(O) and S(O)$_2$, which ring is saturated or unsaturated and is optionally substituted by one or more identical or different substituents chosen from the series consisting of halogen, (C$_1$-C$_4$)-alkyl and $R^{70}$;
Het$^1$ is a monocyclic 4-membered to 7-membered heterocyclic ring which comprises 1 or 2 identical or different hetero ring members chosen from the series consisting of N, N($R^{60}$), O, S, S(O) and S(O)$_2$, which ring is saturated and is optionally substituted by one or more identical or different substituents chosen from the series consisting of fluorine and (C$_1$-C$_4$)-alkyl;
Het$^2$ is a monocyclic 5-membered or 6-membered heterocyclic ring which comprises 1, 2 or 3 identical or different hetero ring members chosen from the series consisting of N, N($R^{60}$), O and S, which ring is aromatic and is optionally substituted by one or more identical or different substituents chosen from the series consisting of halogen, (C$_1$-C$_4$)-alkyl, (C$_1$-C$_4$)-alkyl-O— and NC—;
m, independently of each other number m, is an integer chosen from the series consisting of 0, 1 and 2;
phenyl, independently of each other group phenyl, is optionally substituted by one or more identical or different substituents chosen from the series consisting of halogen, (C$_1$-C$_4$)-alkyl, (C$_1$-C$_4$)-alkyl-O— and NC—, unless specified otherwise;
cycloalkyl, independently of each other group cycloalkyl, and independently of any other substituents on cycloalkyl, is optionally substituted by one or more identical or different substituents chosen from fluorine and (C$_1$-C$_4$)-alkyl; and
alkyl, alkenyl and alkynyl, independently of each other group alkyl, alkenyl and alkynyl, and independently of any other substituents on alkyl, alkenyl and alkynyl, is optionally substituted by one or more fluorine substituents;
in any of its stereoisomeric forms or a mixture of stereoisomeric forms in any ratio, or a physiologically acceptable salt thereof, or a physiologically acceptable solvate of any of them.

2. The compound according to claim 1, wherein:
$R^3$ and $R^5$ are independently of each other chosen from the series consisting of hydrogen, (C$_1$-C$_4$)-alkyl, phenyl-(C$_1$-C$_4$)-alkyl- and phenyl;
in any of its stereoisomeric forms or a mixture of stereoisomeric forms in any ratio, or a physiologically acceptable salt thereof, or a physiologically acceptable solvate of any of them.

3. The compound according to claim 1, wherein:
ring A is a pyridine ring, a pyridazine ring or a thiophene ring, wherein the pyridine ring, the pyridazine ring and the thiophene ring are optionally substituted by one or more identical or different substituents chosen from the series consisting of halogen, $R^1$, HO—, $R^1$—O—, $R^1$—C(O)—O—, $R^1$—S(O)$_2$—O—, $R^1$—S(O)$_m$—, H$_2$N—, $R^1$—NH—, $R^1$—N($R^1$)—, $R^1$—C(O)—NH—, $R^1$—C(O)—N($R^{71}$)—, $R^1$—S(O)$_2$—NH—, $R^1$—S(O)$_2$—N($R^{71}$)—, $R^1$—C(O)—, HO—C(O)—, $R^1$—O—C(O)—, H$_2$N—C(O)—, $R^1$—NH—C(O)—, $R^1$—N($R^1$)—C(O)—, H$_2$N—S(O)$_2$—, $R^1$—NH—S(O)$_2$—, $R^1$—N($R^1$)—S(O)$_2$—, NC— and O$_2$N—;
in any of its stereoisomeric forms or a mixture of stereoisomeric forms in any ratio, or a physiologically acceptable salt thereof, or a physiologically acceptable solvate of any of them.

4. The compound according to claim 1, wherein:

ring A is a pyridine ring, a pyrazine or a thiophene ring which rings are all optionally substituted by one or two identical or different substituents chosen from the series consisting of halogen, $(C_1-C_4)$-alkyl and $(C_1-C_4)$-alkyl-O—;

$R^3$ and $R^5$ are independently of each other chosen from the series consisting of hydrogen and $(C_1-C_4)$-alkyl;

$R^4$ and $R^6$ are hydrogen;

$R^{12}$, $R^{13}$, and $R^{16}$ are independently of each other chosen from the series consisting of hydrogen, halogen $(C_1-C_4)$-alkyl, $(C_1-C_4)$-alkyl-O— and NC—; and $R^{20}$ is hydrogen;

in any of its stereoisomeric forms or a mixture of stereoisomeric forms in any ratio, or a physiologically acceptable salt thereof, or a physiologically acceptable solvate of any of them.

5. The compound according to claim 1, wherein:

$R^{21}$ is chosen from the series consisting of hydrogen, halogen, $(C_1-C_4)$-alkyl, HO—$(C_1-C_4)$-alkyl-, $(C_1-C_4)$-alkyl-O—, $(C_1-C_4)$-alkyl-S(O)$_m$—, $H_2N$—, $(C_1-C_4)$-alkyl-NH—, di(($C_1-C_4$)-alkyl)N—, $(C_1-C_4)$-alkyl-C(O)— and NC—;

$R^{22}$ is a group of the formula II;

$$R^{24}\text{-}R^{23}\text{-} \qquad \qquad \text{II}$$

$R^{23}$ is a direct bond or a chain consisting of 2, 3 or 4 chain members of which 0 or 1 chain members are hetero chain members chosen from the series consisting of $N(R^{25})$, O, S, S(O) and $S(O)_2$, and the other chain members are identical or different groups $C(R^{26})(R^{26})$, wherein two adjacent groups $C(R^{26})(R^{26})$ can be connected to each other by a double bond or a triple bond;

in any of its stereoisomeric forms or a mixture of stereoisomeric forms in any ratio, or a physiologically acceptable salt thereof, or a physiologically acceptable solvate of any of them.

6. The compound according to claim 1, wherein:

$R^{24}$ is a 3-membered to 7-membered monocyclic ring or a 7-membered to 10-membered bicyclic ring, which rings are saturated or unsaturated and contain 0, 1 or 2 identical or different hetero ring members chosen from the series consisting of N, $N(R^{32})$, O, S, S(O) and $S(O)_2$, and which rings are optionally substituted on ring carbon atoms by one or more identical or different substituents chosen from the series consisting of halogen, $R^{33}$, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, $H_2N$—S(O)$_2$—NH—, $R^{33}$—NH—S(O)$_2$—NH—, $R^{33}$—N($R^{33}$)—S(O)$_2$—NH—, $H_2N$—S(O)$_2$—N($R^{71}$)—, $R^{33}$—NH—S(O)$_2$—N($R^{71}$)—, $R^{33}$—N($R^{33}$)—S(O)$_2$—N($R^{71}$)—, HO—C(O)—, $R^{33}$—O—C(O)—, $H_2N$—C(O)—, $R^{33}$—NH—C(O)—, $R^{33}$—N($R^{33}$)—C(O)—, NC—, oxo, phenyl and Het; and $R^{32}$ is chosen from the series consisting of hydrogen, $R^{35}$, $R^{35}$—C(O)—, $R^{35}$—O—C(O)— and phenyl;

in any of its stereoisomeric forms or a mixture of stereoisomeric forms in any ratio, or a physiologically acceptable salt thereof, or a physiologically acceptable solvate of any of them.

7. The compound according to claim 1, wherein:

ring A is a pyridine ring, a pyrazine or a thiophene ring which rings are all optionally substituted by one or two identical or different substituents chosen from the series consisting of halogen, $(C_1-C_4)$-alkyl and $(C_1-C_4)$-alkyl-O—;

$R^3$ and $R^5$ are independently of each other chosen from the series consisting of hydrogen and $(C_1-C_4)$-alkyl;

$R^4$ and $R^6$ are hydrogen;

$R^{12}$, $R^{13}$, and $R^{16}$ are independently of each other chosen from the series consisting of hydrogen, halogen $(C_1-C_4)$-alkyl, $(C_1-C_4)$-alkyl-O— and NC—;

$R^{20}$ is hydrogen;

$R^{21}$ is chosen from the series consisting of hydrogen, halogen, $(C_1-C_4)$-alkyl, HO—$(C_1-C_4)$-alkyl-, $(C_1-C_4)$-alkyl-O—, $(C_1-C_4)$-alkyl-S(O)$_m$—, $H_2N$—, $(C_1-C_4)$-alkyl-NH—, di(($C_1-C_4$)-alkyl)N—, $(C_1-C_4)$-alkyl-C(O)— and NC—;

$R^{22}$ is a group of the formula II;

$$R^{24}\text{-}R^{23}\text{-} \qquad \qquad \text{II}$$

$R^{23}$ is a direct bond or a chain consisting of 2, 3 or 4 chain members of which 0 or 1 chain members are hetero chain members chosen from the series consisting of $N(R^{25})$, O, S, S(O) and $S(O)_2$, and the other chain members are identical or different groups $C(R^{26})(R^{26})$, wherein two adjacent groups $C(R^{26})(R^{26})$ can be connected to each other by a double bond or a triple bond;

$R^{24}$ is a 3-membered to 7-membered monocyclic ring or a 7-membered to 10-membered bicyclic ring, which rings are saturated or unsaturated and contains 0, 1 or 2 identical or different hetero ring members chosen from the series consisting of N, $N(R^{32})$, O, S, S(O) and $S(O)_2$, which ring is optionally substituted on ring carbon atoms by one or more identical or different substituents chosen from the series consisting of halogen, $R^{33}$, HO—, $R^{33}$—O—, $R^{33}$—S(O)$_m$—, $H_2N$—, $R^{33}$—NH—, $R^{33}$—N($R^{33}$)—, $R^{33}$—C(O)—NH—, $R^{33}$—C(O)—N($R^{71}$)—, $R^{33}$—S(O)$_2$—NH—, $R^{33}$—S(O)$_2$—N($R^{71}$)—, HO—C(O)—, $R^{33}$—O—C(O)—, $H_2N$—C(O)—, $R^{33}$—NH—C(O)—, $R^{33}$—N($R^{33}$)—C(O)—, NC—, oxo, phenyl and Het; and $R^{32}$ is chosen from the series consisting of hydrogen, $R^{35}$, $R^{35}$—C(O)—, $R^{35}$—O—C(O)— and phenyl;

in any of its stereoisomeric forms or a mixture of stereoisomeric forms in any ratio, or a physiologically acceptable salt thereof, or a physiologically acceptable solvate of any of them.

8. The compound according to claim 1, which is in any of its stereoisomeric forms or a mixture of stereoisomeric forms in any ratio, or a physiologically acceptable salt thereof, or a physiologically acceptable solvate of any of them.

9. A process for preparing the compound according to claim 1, comprising reacting a compound of formula III with a compound of the formula IV,

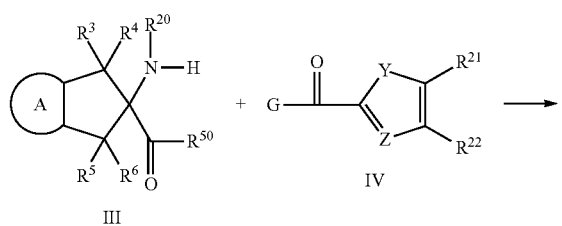

-continued

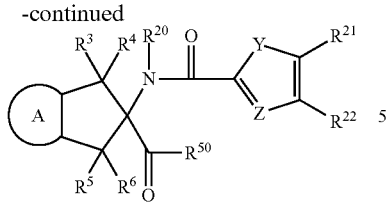

I wherein the ring A and the groups Y, Z, $R^3$ to $R^6$, $R^{20}$ to $R^{22}$ and $R^{50}$ in the compounds of the formulae III and IV are defined as in claim 1 and additionally functional groups can be present in protected form or in the form of a precursor group, and the group G in the compound of the formula IV is HO—, $(C_1\text{-}C_4)$-alkyl-O— or halogen.

10. A pharmaceutical composition comprising the compound according to claim 1, in any of its stereoisomeric forms or a mixture of stereoisomeric forms in any ratio, or a physiologically acceptable salt thereof, or a physiologically acceptable solvate of any of them, and a pharmaceutically acceptable carrier.

11. A pharmaceutical composition comprising the compound according to claim 8, in any of its stereoisomeric forms or a mixture of stereoisomeric forms in any ratio, or a physiologically acceptable salt thereof, or a physiologically acceptable solvate of any of them, and a pharmaceutically acceptable carrier.

\* \* \* \* \*